(12) United States Patent
Sammons et al.

(10) Patent No.: US 9,988,634 B2
(45) Date of Patent: *Jun. 5, 2018

(54) POLYNUCLEOTIDE MOLECULES FOR GENE REGULATION IN PLANTS

(71) Applicant: Monsanto Technology LLC, St. Louis, MO (US)

(72) Inventors: Robert D Sammons, New Melle, MO (US); Sergey Ivashuta, Ballwin, MO (US); Hong Liu, St. Louis, MO (US); Dafu Wang, St. Louis, MO (US); Paul C. C. Feng, Wildwood, MO (US); Andrei Y Kouranov, Chesterfield, MO (US); Scott E Andersen, Manchester, MO (US)

(73) Assignee: Monsanto Technology LLC, St. Louis, MO (US)

( * ) Notice: Subject to any disclaimer, the term of this patent is extended or adjusted under 35 U.S.C. 154(b) by 886 days.

This patent is subject to a terminal disclaimer.

(21) Appl. No.: 14/015,785

(22) Filed: Aug. 30, 2013

(65) Prior Publication Data

US 2014/0057789 A1 Feb. 27, 2014

Related U.S. Application Data

(62) Division of application No. 13/042,856, filed on Mar. 8, 2011, now Pat. No. 9,121,022.

(60) Provisional application No. 61/311,762, filed on Mar. 8, 2010, provisional application No. 61/349,087, filed on May 28, 2010, provisional application No. 61/381,556, filed on Sep. 10, 2010.

(51) Int. Cl.

| C12N 15/113 | (2010.01) |
| C12N 15/87 | (2006.01) |
| A01P 13/00 | (2006.01) |
| A01N 25/30 | (2006.01) |
| A01N 57/16 | (2006.01) |
| A01N 63/02 | (2006.01) |
| C12N 15/82 | (2006.01) |

(52) U.S. Cl.
CPC .......... *C12N 15/1137* (2013.01); *A01N 57/16* (2013.01); *A01N 63/02* (2013.01); *C12N 15/113* (2013.01); *C12N 15/8206* (2013.01); *C12N 15/8207* (2013.01); *C12N 15/8218* (2013.01)

(58) Field of Classification Search
None
See application file for complete search history.

(56) References Cited

U.S. PATENT DOCUMENTS

| 3,687,808 A | 8/1972 | Merigan et al. |
| 3,791,932 A | 2/1974 | Schuurs et al. |
| 3,839,153 A | 10/1974 | Schuurs et al. |
| 3,850,578 A | 11/1974 | McConnell |
| 3,850,752 A | 11/1974 | Schuurs et al. |
| 3,853,987 A | 12/1974 | Dreyer |
| 3,867,517 A | 2/1975 | Ling |
| 3,879,262 A | 4/1975 | Schuurs et al. |
| 3,901,654 A | 8/1975 | Gross |
| 3,935,074 A | 1/1976 | Rubenstein et al. |
| 3,984,533 A | 10/1976 | Uzgiris |
| 3,996,345 A | 12/1976 | Ullman et al. |
| 4,034,074 A | 7/1977 | Miles |
| 4,098,876 A | 7/1978 | Piasio et al. |
| 4,469,863 A | 9/1984 | Ts'o et al. |
| 4,476,301 A | 10/1984 | Imbach et al. |
| 4,535,060 A | 8/1985 | Comai |
| 4,581,847 A | 4/1986 | Hibberd et al. |
| 4,666,828 A | 5/1987 | Gusella |
| 4,683,202 A | 7/1987 | Mullis |
| 4,761,373 A | 8/1988 | Anderson et al. |
| 4,769,061 A | 9/1988 | Comai |
| 4,801,531 A | 1/1989 | Frossard |
| 4,810,648 A | 3/1989 | Stalker |
| 4,879,219 A | 11/1989 | Wands et al. |
| 4,940,835 A | 7/1990 | Shah et al. |
| 4,971,908 A | 11/1990 | Kishore et al. |
| 5,004,863 A | 4/1991 | Umbeck |
| 5,011,771 A | 4/1991 | Bellet et al. |
| 5,013,659 A | 5/1991 | Bedbrook et al. |
| 5,015,580 A | 5/1991 | Christou et al. |
| 5,023,243 A | 6/1991 | Tullis |
| 5,034,506 A | 7/1991 | Summerton et al. |
| 5,094,945 A | 3/1992 | Comai |
| 5,141,870 A | 8/1992 | Bedbrook et al. |
| 5,145,783 A | 9/1992 | Kishore et al. |

(Continued)

FOREIGN PATENT DOCUMENTS

| AU | 2008258254 B2 | 7/2014 |
| CN | 101279950 A | 10/2008 |

(Continued)

OTHER PUBLICATIONS

Wiesman et al (J. Biotechnology, 2007, 130: 85-94).*
Sun et al (Plant J, 2005, 44: 128-138).*
Orbovic et al (J. Amer. Soc. Hort. Sci., 2001, 126(4): 486-490).*
Widholm et al (Phyisologia Plantarum, 2001, 112: 540-545).*
Pasloske (2001, Ribonuclease Inhibitors. In: Schein C.H. (eds) Nuclease Methods and Protocols. Methods in Molecular Biology, vol. 160. Humana Press) (Year: 2001).*
Tenllado et al (BMC Biotechnology, 2003, 3:3).*
Tenllado et al (Virus Research, 2004, 102: 85-96).*
Communication pursuant to Article 94(3) EPC dated Mar. 24, 2016, in European Patent Application No. 12 831 684.1.

(Continued)

*Primary Examiner* — Stephen Uyeno
(74) *Attorney, Agent, or Firm* — Arnold & Porter Kaye Scholer LLP; David R. Marsh; Amanda Carmany-Rampey

(57) ABSTRACT

This invention provides polynucleotide molecules and methods for regulating genes in plants, e. g., by providing RNA for systemic regulation of genes. Various aspects of the invention provide polynucleotide molecules and methods for regulating endogenous genes and transgenes in a plant cell and polynucleotide molecules.

19 Claims, 42 Drawing Sheets

(56) References Cited

U.S. PATENT DOCUMENTS

| | | |
|---|---|---|
| 5,159,135 A | 10/1992 | Umbeck |
| 5,166,315 A | 11/1992 | Summerton et al. |
| 5,177,196 A | 1/1993 | Meyer, Jr. et al. |
| 5,185,444 A | 2/1993 | Summerton et al. |
| 5,188,642 A | 2/1993 | Shah et al. |
| 5,188,897 A | 2/1993 | Suhadolnik et al. |
| 5,192,659 A | 3/1993 | Simons |
| 5,214,134 A | 5/1993 | Weis et al. |
| 5,216,141 A | 6/1993 | Benner |
| 5,235,033 A | 8/1993 | Summerton et al. |
| 5,264,423 A | 11/1993 | Cohen et al. |
| 5,264,562 A | 11/1993 | Matteucci |
| 5,264,564 A | 11/1993 | Matteucci |
| 5,272,057 A | 12/1993 | Smulson et al. |
| 5,276,019 A | 1/1994 | Cohen et al. |
| 5,281,521 A | 1/1994 | Trojanowski et al. |
| 5,286,634 A | 2/1994 | Stadler et al. |
| 5,286,717 A | 2/1994 | Cohen et al. |
| 5,304,732 A | 4/1994 | Anderson et al. |
| 5,310,667 A | 5/1994 | Eichholtz et al. |
| 5,312,910 A | 5/1994 | Kishore et al. |
| 5,321,131 A | 6/1994 | Agrawal et al. |
| 5,331,107 A | 7/1994 | Anderson et al. |
| 5,339,107 A | 8/1994 | Henry et al. |
| 5,346,107 A | 9/1994 | Bouix et al. |
| 5,378,824 A | 1/1995 | Bedbrook et al. |
| 5,390,667 A | 2/1995 | Kumakura et al. |
| 5,392,910 A | 2/1995 | Bell et al. |
| 5,393,175 A | 2/1995 | Courville |
| 5,399,676 A | 3/1995 | Froehler |
| 5,405,938 A | 4/1995 | Summerton et al. |
| 5,405,939 A | 4/1995 | Suhadolnik et al. |
| 5,416,011 A | 5/1995 | Hinchee et al. |
| 5,453,496 A | 9/1995 | Caruthers et al. |
| 5,455,233 A | 10/1995 | Spielvogel et al. |
| 5,459,127 A | 10/1995 | Feigner et al. |
| 5,460,667 A | 10/1995 | Moriyuki et al. |
| 5,462,910 A | 10/1995 | Ito et al. |
| 5,463,174 A | 10/1995 | Moloney et al. |
| 5,463,175 A | 10/1995 | Barry et al. |
| 5,466,677 A | 11/1995 | Baxter et al. |
| 5,470,967 A | 11/1995 | Huie et al. |
| 5,476,925 A | 12/1995 | Letsinger et al. |
| 5,489,520 A | 2/1996 | Adams et al. |
| 5,489,677 A | 2/1996 | Sanghvi et al. |
| 5,491,288 A | 2/1996 | Chaubet et al. |
| 5,510,471 A | 4/1996 | Lebrun et al. |
| 5,518,908 A | 5/1996 | Corbin et al. |
| 5,519,126 A | 5/1996 | Hecht |
| 5,536,821 A | 7/1996 | Agrawal et al. |
| 5,538,880 A | 7/1996 | Lundquist et al. |
| 5,541,306 A | 7/1996 | Agrawal et al. |
| 5,541,307 A | 7/1996 | Cook et al. |
| 5,550,111 A | 8/1996 | Suhadolnik et al. |
| 5,550,318 A | 8/1996 | Adams et al. |
| 5,550,398 A | 8/1996 | Kocian et al. |
| 5,550,468 A | 8/1996 | Häberlein et al. |
| 5,558,071 A | 9/1996 | Ward et al. |
| 5,561,225 A | 10/1996 | Maddry et al. |
| 5,561,236 A | 10/1996 | Leemans et al. |
| 5,563,253 A | 10/1996 | Agrawal et al. |
| 5,569,834 A | 10/1996 | Hinchee et al. |
| 5,571,799 A | 11/1996 | Tkachuk et al. |
| 5,587,361 A | 12/1996 | Cook et al. |
| 5,591,616 A | 1/1997 | Hiei et al. |
| 5,593,874 A | 1/1997 | Brown et al. |
| 5,596,086 A | 1/1997 | Matteucci et al. |
| 5,597,717 A | 1/1997 | Guerineau et al. |
| 5,602,240 A | 2/1997 | De Mesmaeker et al. |
| 5,605,011 A | 2/1997 | Bedbrook et al. |
| 5,608,046 A | 3/1997 | Cook et al. |
| 5,610,289 A | 3/1997 | Cook et al. |
| 5,618,704 A | 4/1997 | Sanghvi et al. |
| 5,623,070 A | 4/1997 | Cook et al. |
| 5,625,050 A | 4/1997 | Beaton et al. |
| 5,627,061 A | 5/1997 | Barry et al. |
| 5,633,360 A | 5/1997 | Bischofberger et al. |
| 5,633,435 A | 5/1997 | Barry et al. |
| 5,633,448 A | 5/1997 | Lebrun et al. |
| 5,639,024 A | 6/1997 | Mueller et al. |
| 5,646,024 A | 7/1997 | Leemans et al. |
| 5,648,477 A | 7/1997 | Leemans et al. |
| 5,663,312 A | 9/1997 | Chaturvedula |
| 5,677,437 A | 10/1997 | Teng et al. |
| 5,677,439 A | 10/1997 | Weis et al. |
| 5,719,046 A | 2/1998 | Guerineau et al. |
| 5,721,138 A | 2/1998 | Lawn |
| 5,731,180 A | 3/1998 | Dietrich |
| 5,739,180 A | 4/1998 | Taylor-Smith |
| 5,746,180 A | 5/1998 | Jefferson et al. |
| 5,767,361 A | 6/1998 | Dietrich |
| 5,767,373 A | 6/1998 | Ward et al. |
| 5,780,708 A | 7/1998 | Lundquist et al. |
| 5,804,425 A | 9/1998 | Barry et al. |
| 5,824,877 A | 10/1998 | Hinchee et al. |
| 5,837,848 A | 11/1998 | Ely et al. |
| 5,859,347 A | 1/1999 | Brown et al. |
| 5,866,775 A | 2/1999 | Eichholtz et al. |
| 5,874,265 A | 2/1999 | Adams et al. |
| 5,879,903 A | 3/1999 | Strauch et al. |
| 5,914,451 A | 6/1999 | Martinell et al. |
| 5,919,675 A | 7/1999 | Adams et al. |
| 5,928,937 A | 7/1999 | Kakefuda et al. |
| 5,939,602 A | 8/1999 | Volrath et al. |
| 5,969,213 A | 10/1999 | Adams et al. |
| 5,981,840 A | 11/1999 | Zhao et al. |
| 5,985,793 A | 11/1999 | Sandbrink et al. |
| RE36,449 E | 12/1999 | Lebrun et al. |
| 6,040,497 A | 3/2000 | Spencer et al. |
| 6,056,938 A | 5/2000 | Unger et al. |
| 6,069,115 A | 5/2000 | Pallett et al. |
| 6,084,089 A | 7/2000 | Mine et al. |
| 6,084,155 A | 7/2000 | Volrath et al. |
| 6,118,047 A | 9/2000 | Anderson et al. |
| 6,121,513 A | 9/2000 | Zhang et al. |
| 6,130,366 A | 10/2000 | Herrera-Estrella et al. |
| 6,140,078 A | 10/2000 | Sanders et al. |
| 6,153,812 A | 11/2000 | Fry et al. |
| 6,160,208 A | 12/2000 | Lundquist et al. |
| 6,177,616 B1 | 1/2001 | Bartsch et al. |
| 6,194,636 B1 | 2/2001 | McElroy et al. |
| 6,225,105 B1 | 5/2001 | Sathasivan et al. |
| 6,225,114 B1 | 5/2001 | Eichholtz et al. |
| 6,232,526 B1 | 5/2001 | McElroy et al. |
| 6,245,968 B1 | 6/2001 | Boudec et al. |
| 6,248,876 B1 | 6/2001 | Barry et al. |
| 6,252,138 B1 | 6/2001 | Karimi et al. |
| RE37,287 E | 7/2001 | Lebrun et al. |
| 6,268,549 B1 | 7/2001 | Sailland et al. |
| 6,271,359 B1 | 8/2001 | Norris et al. |
| 6,282,837 B1 | 9/2001 | Ward et al. |
| 6,288,306 B1 | 9/2001 | Ward et al. |
| 6,288,312 B1 | 9/2001 | Christou et al. |
| 6,294,714 B1 | 9/2001 | Matsunaga et al. |
| 6,326,193 B1 | 12/2001 | Liu et al. |
| 6,329,571 B1 | 12/2001 | Hiei |
| 6,348,185 B1 | 2/2002 | Piwnica-Worms |
| 6,365,807 B1 | 4/2002 | Christou et al. |
| 6,384,301 B1 | 5/2002 | Martinell et al. |
| 6,385,902 B1 | 5/2002 | Schipper et al. |
| 6,399,861 B1 | 6/2002 | Anderson et al. |
| 6,403,865 B1 | 6/2002 | Koziel et al. |
| 6,414,222 B1 | 7/2002 | Gengenbach et al. |
| 6,421,956 B1 | 7/2002 | Boukens et al. |
| 6,426,446 B1 | 7/2002 | McElroy et al. |
| 6,433,252 B1 | 8/2002 | Kriz et al. |
| 6,437,217 B1 | 8/2002 | McElroy et al. |
| 6,453,609 B1 | 9/2002 | Soll et al. |
| 6,479,291 B2 | 11/2002 | Kumagai et al. |
| 6,506,559 B1 | 1/2003 | Fire et al. |
| 6,642,435 B1 | 11/2003 | Antoni et al. |
| 6,644,341 B1 | 11/2003 | Chemo et al. |
| 6,645,914 B1 * | 11/2003 | Woznica ............ A01N 25/30 504/206 |

(56) References Cited

U.S. PATENT DOCUMENTS

| | | |
|---|---|---|
| 6,768,044 B1 | 7/2004 | Boudec et al. |
| 6,992,237 B1 | 1/2006 | Habben et al. |
| 7,022,896 B1 | 4/2006 | Weeks et al. |
| 7,026,528 B2 | 4/2006 | Cheng et al. |
| RE39,247 E | 8/2006 | Barry et al. |
| 7,105,724 B2 | 9/2006 | Weeks et al. |
| 7,297,541 B2 | 11/2007 | Moshiri et al. |
| 7,304,209 B2 | 12/2007 | Zink et al. |
| 7,312,379 B2 | 12/2007 | Andrews et al. |
| 7,323,310 B2 | 1/2008 | Peters et al. |
| 7,371,927 B2 | 5/2008 | Yao et al. |
| 7,392,379 B2 | 6/2008 | Le Pennec et al. |
| 7,405,347 B2 | 7/2008 | Hammer et al. |
| 7,406,981 B2 | 8/2008 | Hemo et al. |
| 7,462,379 B2 | 12/2008 | Fukuda et al. |
| 7,485,777 B2 | 2/2009 | Nakajima et al. |
| 7,525,013 B2 | 4/2009 | Hildebrand et al. |
| 7,550,578 B2 | 6/2009 | Budworth et al. |
| 7,622,301 B2 | 11/2009 | Ren et al. |
| 7,657,299 B2 | 2/2010 | Huizenga et al. |
| 7,671,254 B2 | 3/2010 | Tranel et al. |
| 7,714,188 B2 | 5/2010 | Castle et al. |
| 7,738,626 B2 | 6/2010 | Weese et al. |
| 7,807,791 B2 | 10/2010 | Sekar et al. |
| 7,838,263 B2 | 11/2010 | Dam et al. |
| 7,838,733 B2 | 11/2010 | Wright et al. |
| 7,842,856 B2 | 11/2010 | Tranel et al. |
| 7,884,262 B2 | 2/2011 | Clemente et al. |
| 7,910,805 B2 | 3/2011 | Duck et al. |
| 7,935,869 B2 | 5/2011 | Pallett et al. |
| 7,943,819 B2 | 5/2011 | Baum et al. |
| 7,973,218 B2 | 7/2011 | McCutchen et al. |
| 8,090,164 B2 | 1/2012 | Bullitt et al. |
| 8,143,480 B2 | 3/2012 | Axtell et al. |
| 8,548,778 B1 | 10/2013 | Hart et al. |
| 8,554,490 B2 | 10/2013 | Tang et al. |
| 9,121,022 B2 | 9/2015 | Sammons et al. |
| 9,445,603 B2 | 9/2016 | Baum et al. |
| 2001/0006797 A1 | 7/2001 | Kumagai et al. |
| 2001/0042257 A1 | 11/2001 | Connor-Ward et al. |
| 2002/0069430 A1 | 6/2002 | Kiaska et al. |
| 2002/0114784 A1 | 8/2002 | Li et al. |
| 2003/0150017 A1 | 8/2003 | Mesa et al. |
| 2003/0154508 A1 | 8/2003 | Stevens et al. |
| 2003/0167537 A1 | 9/2003 | Jiang |
| 2004/0029275 A1 | 2/2004 | Brown et al. |
| 2004/0053289 A1 | 3/2004 | Allen et al. |
| 2004/0055041 A1 | 3/2004 | Labate et al. |
| 2004/0072692 A1 | 4/2004 | Hoffman et al. |
| 2004/0082475 A1 | 4/2004 | Hoffman et al. |
| 2004/0123347 A1 | 6/2004 | Hinchey et al. |
| 2004/0126845 A1 | 7/2004 | Eenennaam et al. |
| 2004/0133944 A1 | 7/2004 | Hake et al. |
| 2004/0147475 A1 | 7/2004 | Li et al. |
| 2004/0177399 A1 | 9/2004 | Hammer et al. |
| 2004/0216189 A1 | 10/2004 | Houmard et al. |
| 2004/0244075 A1 | 12/2004 | Cal et al. |
| 2004/0250310 A1 | 12/2004 | Shukla et al. |
| 2005/0005319 A1 | 1/2005 | della-Cioppa et al. |
| 2005/0044591 A1 | 2/2005 | Yao et al. |
| 2005/0215435 A1 | 9/2005 | Menges et al. |
| 2005/0250647 A1 | 11/2005 | Hills et al. |
| 2006/0009358 A1 | 1/2006 | Kibler et al. |
| 2006/0021087 A1 | 1/2006 | Baum et al. |
| 2006/0040826 A1 | 2/2006 | Eaton et al. |
| 2006/0111241 A1 | 5/2006 | Gerwick, III et al. |
| 2006/0130172 A1 | 6/2006 | Whaley et al. |
| 2006/0135758 A1 | 6/2006 | Wu |
| 2006/0200878 A1 | 9/2006 | Lutfiyya et al. |
| 2006/0223708 A1 | 10/2006 | Hoffman et al. |
| 2006/0223709 A1 | 10/2006 | Helmke et al. |
| 2006/0247197 A1 | 11/2006 | Van De Craen et al. |
| 2006/0272049 A1 | 11/2006 | Waterhouse et al. |
| 2006/0276339 A1 | 12/2006 | Windsor et al. |
| 2007/0011775 A1 | 1/2007 | Allen et al. |
| 2007/0021360 A1 | 1/2007 | Nyce et al. |
| 2007/0050863 A1 | 3/2007 | Tranel et al. |
| 2007/0124836 A1 | 5/2007 | Baum et al. |
| 2007/0199095 A1 | 8/2007 | Allen et al. |
| 2007/0250947 A1 | 10/2007 | Boukharov et al. |
| 2007/0259785 A1 | 11/2007 | Heck et al. |
| 2007/0269815 A1 | 11/2007 | Rivory et al. |
| 2007/0281900 A1 | 12/2007 | Cui et al. |
| 2007/0300329 A1 | 12/2007 | Allen et al. |
| 2008/0022423 A1 | 1/2008 | Roberts et al. |
| 2008/0050342 A1 | 2/2008 | Fire et al. |
| 2008/0092256 A1 | 4/2008 | Kohn |
| 2008/0113351 A1 | 5/2008 | Naito et al. |
| 2008/0155716 A1 | 6/2008 | Sonnewald et al. |
| 2008/0214443 A1 | 9/2008 | Baum et al. |
| 2009/0011934 A1 | 1/2009 | Zawierucha et al. |
| 2009/0018016 A1 | 1/2009 | Duck et al. |
| 2009/0036311 A1 | 2/2009 | Witschel et al. |
| 2009/0054240 A1 | 2/2009 | Witschel et al. |
| 2009/0075921 A1 | 3/2009 | Ikegawa et al. |
| 2009/0098614 A1 | 4/2009 | Zamore et al. |
| 2009/0118214 A1 | 5/2009 | Paldi et al. |
| 2009/0137395 A1 | 5/2009 | Chicoine et al. |
| 2009/0165153 A1 | 6/2009 | Wang et al. |
| 2009/0165166 A1 | 6/2009 | Feng et al. |
| 2009/0172838 A1 | 7/2009 | Axtell et al. |
| 2009/0188005 A1 | 7/2009 | Boukharov et al. |
| 2009/0205079 A1 | 8/2009 | Kumar et al. |
| 2009/0215628 A1 | 8/2009 | Witschel et al. |
| 2009/0285784 A1 | 11/2009 | Raemaekers et al. |
| 2009/0293148 A1 | 11/2009 | Ren et al. |
| 2009/0298787 A1 | 12/2009 | Raemaekers et al. |
| 2009/0306189 A1 | 12/2009 | Raemaekers et al. |
| 2009/0307803 A1 | 12/2009 | Baum et al. |
| 2010/0005551 A1 | 1/2010 | Roberts et al. |
| 2010/0048670 A1 | 2/2010 | Biard et al. |
| 2010/0068172 A1 | 3/2010 | Van De Craen |
| 2010/0071088 A1 | 3/2010 | Sela et al. |
| 2010/0099561 A1 | 4/2010 | Selby et al. |
| 2010/0100988 A1 | 4/2010 | Tranel et al. |
| 2010/0152443 A1 | 6/2010 | Hirai et al. |
| 2010/0154083 A1 | 6/2010 | Ross et al. |
| 2010/0192237 A1 | 7/2010 | Ren et al. |
| 2010/0247578 A1 | 9/2010 | Salama |
| 2011/0015084 A1 | 1/2011 | Christian et al. |
| 2011/0015284 A1 | 1/2011 | Dees et al. |
| 2011/0028412 A1 | 2/2011 | Cappello et al. |
| 2011/0035836 A1 | 2/2011 | Eudes et al. |
| 2011/0041400 A1 | 2/2011 | Trias Vila et al. |
| 2011/0053226 A1 | 3/2011 | Rohayem |
| 2011/0098180 A1 | 4/2011 | Michel et al. |
| 2011/0105327 A1 | 5/2011 | Nelson |
| 2011/0105329 A1 | 5/2011 | Song et al. |
| 2011/0112570 A1 | 5/2011 | Mannava et al. |
| 2011/0126310 A1 | 5/2011 | Feng et al. |
| 2011/0126311 A1 | 5/2011 | Velcheva et al. |
| 2011/0152339 A1 | 6/2011 | Brown et al. |
| 2011/0152346 A1 | 6/2011 | Karleson et al. |
| 2011/0152353 A1 | 6/2011 | Koizumi |
| 2011/0160082 A1 | 6/2011 | Woo et al. |
| 2011/0166022 A1 | 7/2011 | Israels et al. |
| 2011/0166023 A1 | 7/2011 | Nettleton-Hammond et al. |
| 2011/0171176 A1 | 7/2011 | Baas et al. |
| 2011/0171287 A1 | 7/2011 | Saarma et al. |
| 2011/0177949 A1 | 7/2011 | Krapp et al. |
| 2011/0185444 A1 | 7/2011 | Li et al. |
| 2011/0185445 A1 | 7/2011 | Bogner et al. |
| 2011/0191897 A1 | 8/2011 | Poree et al. |
| 2011/0201501 A1 | 8/2011 | Song et al. |
| 2011/0296555 A1 | 12/2011 | Ivashuta et al. |
| 2011/0296556 A1 | 12/2011 | Sammons et al. |
| 2012/0036594 A1 | 2/2012 | Cardoza et al. |
| 2012/0107355 A1 | 5/2012 | Harris et al. |
| 2012/0108497 A1 | 5/2012 | Paldi et al. |
| 2012/0137387 A1 | 5/2012 | Baum et al. |
| 2012/0150048 A1 | 6/2012 | Kang et al. |
| 2012/0156784 A1 | 6/2012 | Adams, Jr. et al. |
| 2012/0164205 A1 | 6/2012 | Baum et al. |
| 2012/0185967 A1 | 7/2012 | Sela et al. |

(56) References Cited

U.S. PATENT DOCUMENTS

| | | | |
|---|---|---|---|
| 2012/0198586 A1 | 8/2012 | Narva et al. | |
| 2012/0230565 A1 | 9/2012 | Steinberg et al. | |
| 2012/0258646 A1 | 10/2012 | Sela et al. | |
| 2013/0003213 A1 | 1/2013 | Kabelac et al. | |
| 2013/0041004 A1 | 2/2013 | Drager et al. | |
| 2013/0047297 A1 | 2/2013 | Sammons et al. | |
| 2013/0047298 A1 | 2/2013 | Tang | |
| 2013/0060133 A1 | 3/2013 | Kassab et al. | |
| 2013/0067618 A1 | 3/2013 | Ader et al. | |
| 2013/0084243 A1 | 4/2013 | Goetsch et al. | |
| 2013/0096073 A1 | 4/2013 | Sidelman | |
| 2013/0097726 A1 | 4/2013 | Ader et al. | |
| 2013/0212739 A1 | 8/2013 | Giritch et al. | |
| 2013/0226003 A1 | 8/2013 | Edic et al. | |
| 2013/0247247 A1 | 9/2013 | Ader et al. | |
| 2013/0254940 A1 | 9/2013 | Ader et al. | |
| 2013/0254941 A1 | 9/2013 | Ader et al. | |
| 2013/0288895 A1 | 10/2013 | Ader et al. | |
| 2013/0318657 A1 | 11/2013 | Avniel et al. | |
| 2013/0318658 A1 | 11/2013 | Ader et al. | |
| 2013/0324842 A1 | 12/2013 | Mittal et al. | |
| 2013/0326731 A1 | 12/2013 | Ader et al. | |
| 2014/0018241 A1 | 1/2014 | Sammons et al. | |
| 2014/0057789 A1 | 2/2014 | Sammons et al. | |
| 2014/0109258 A1 | 4/2014 | Van De Craen et al. | |
| 2014/0230090 A1 | 8/2014 | Avniel et al. | |
| 2014/0274712 A1 | 9/2014 | Finnessy et al. | |
| 2014/0275208 A1 | 9/2014 | Hu et al. | |
| 2014/0296503 A1 | 10/2014 | Avniel et al. | |
| 2015/0096079 A1 | 4/2015 | Avniel et al. | |
| 2015/0143580 A1 | 5/2015 | Beattie et al. | |
| 2015/0159156 A1 | 6/2015 | Inberg et al. | |
| 2015/0203867 A1 | 7/2015 | Beattie et al. | |
| 2015/0240258 A1 | 8/2015 | Beattie et al. | |
| 2016/0015035 A1 | 1/2016 | Tao | |
| 2016/0029644 A1 | 2/2016 | Tao | |
| 2017/0159064 A1* | 6/2017 | Carbonell | C12N 15/8218 |
| 2017/0211085 A1* | 7/2017 | Kotchoni | C12N 15/8261 |

FOREIGN PATENT DOCUMENTS

| | | |
|---|---|---|
| CN | 101279951 A | 10/2008 |
| CN | 101914540 A | 12/2010 |
| CN | 102822350 A | 12/2012 |
| DE | 288618 A5 | 4/1991 |
| DE | 10000600 A1 | 7/2001 |
| DE | 10116399 A1 | 10/2002 |
| DE | 10256353 A1 | 6/2003 |
| DE | 10256354 A1 | 6/2003 |
| DE | 10256367 A1 | 6/2003 |
| DE | 10204951 A1 | 8/2003 |
| DE | 10234875 A1 | 2/2004 |
| DE | 10234876 A1 | 2/2004 |
| DE | 102004054666 A1 | 5/2006 |
| DE | 102005014638 A1 | 10/2006 |
| DE | 102005014906 A1 | 10/2006 |
| DE | 102007012168 A1 | 9/2008 |
| DE | 102010042866 A1 | 5/2011 |
| EP | 0 804 600 A1 | 11/1997 |
| EP | 1 157 991 A2 | 11/2001 |
| EP | 1 238 586 A1 | 9/2002 |
| EP | 1 416 049 A1 | 5/2004 |
| EP | 2 147 919 A1 | 1/2010 |
| EP | 2 160 098 B1 | 11/2010 |
| EP | 2 530 159 A1 | 3/2011 |
| EP | 2 305 813 A2 | 4/2011 |
| EP | 2 545 182 A1 | 1/2013 |
| JP | 2001253874 A | 9/2001 |
| JP | 2002080454 A | 3/2002 |
| JP | 2002138075 A | 5/2002 |
| JP | 2002145707 A | 5/2002 |
| JP | 2002220389 A | 8/2002 |
| JP | 2003064059 A | 3/2003 |
| JP | 2003096059 A | 4/2003 |
| JP | 2004051628 A | 2/2004 |
| JP | 2004107228 A | 4/2004 |
| JP | 2005008583 A | 1/2005 |
| JP | 2005239675 A | 9/2005 |
| JP | 2005314407 A | 11/2005 |
| JP | 2006232824 A | 9/2006 |
| JP | 2006282552 A | 10/2006 |
| JP | 2007153847 A | 6/2007 |
| JP | 2007161701 A | 6/2007 |
| JP | 2007182404 A | 7/2007 |
| JP | 2008074840 A | 4/2008 |
| JP | 2008074841 A | 4/2008 |
| JP | 2008133207 A | 6/2008 |
| JP | 2008133218 A | 6/2008 |
| JP | 2008169121 A | 7/2008 |
| JP | 2009067739 A | 4/2009 |
| JP | 2009114128 A | 5/2009 |
| JP | 2009126792 A | 6/2009 |
| JP | 2009137851 A | 6/2009 |
| WO | WO 89/11789 A1 | 12/1989 |
| WO | WO 95/34659 A1 | 12/1995 |
| WO | WO 95/34668 A2 | 12/1995 |
| WO | WO 96/005721 A1 | 2/1996 |
| WO | WO 96/033270 A1 | 10/1996 |
| WO | WO 96/038567 A2 | 12/1996 |
| WO | WO 96/040964 A2 | 12/1996 |
| WO | WO 97/49816 A1 | 12/1997 |
| WO | WO 99/024585 A1 | 5/1999 |
| WO | WO 99/26467 A1 | 6/1999 |
| WO | WO 99/27116 A2 | 6/1999 |
| WO | WO 99/32619 A1 | 7/1999 |
| WO | WO 99/61631 A1 | 12/1999 |
| WO | WO 99/67367 A1 | 12/1999 |
| WO | WO 00/32757 A2 | 6/2000 |
| WO | WO 00/044914 A1 | 8/2000 |
| WO | WO 01/07601 A2 | 2/2001 |
| WO | WO 02/14472 A2 | 2/2002 |
| WO | WO 02/066660 A2 | 8/2002 |
| WO | WO 03/000679 A2 | 1/2003 |
| WO | WO 03/006422 A1 | 1/2003 |
| WO | WO 03/012052 A2 | 2/2003 |
| WO | WO 03/013247 A1 | 2/2003 |
| WO | WO 03/016308 A1 | 2/2003 |
| WO | WO 03/020704 A1 | 3/2003 |
| WO | WO 03/022051 A1 | 3/2003 |
| WO | WO 03/022831 A1 | 3/2003 |
| WO | WO 03/022843 A1 | 3/2003 |
| WO | WO 03/029243 A2 | 4/2003 |
| WO | WO 03/037085 A1 | 5/2003 |
| WO | WO 03/037878 A1 | 5/2003 |
| WO | WO 03/045878 A2 | 6/2003 |
| WO | WO 03/050087 A2 | 6/2003 |
| WO | WO 03/051823 A1 | 6/2003 |
| WO | WO 03/051824 A1 | 6/2003 |
| WO | WO 03/051846 A2 | 6/2003 |
| WO | WO 03/064625 A2 | 8/2003 |
| WO | WO 03/076409 A1 | 9/2003 |
| WO | WO 03/077648 A2 | 9/2003 |
| WO | WO 03/087067 A1 | 10/2003 |
| WO | WO 03/090539 A2 | 11/2003 |
| WO | WO 03/091217 A1 | 11/2003 |
| WO | WO 03/093269 A2 | 11/2003 |
| WO | WO 03/104206 A2 | 12/2003 |
| WO | WO 2004/002947 A1 | 1/2004 |
| WO | WO 2004/002981 A2 | 1/2004 |
| WO | WO 2004/005485 A2 | 1/2004 |
| WO | WO 2004/009761 A2 | 1/2004 |
| WO | WO 2004/011429 A1 | 2/2004 |
| WO | WO 2004/022771 A2 | 3/2004 |
| WO | WO 2004/029060 A1 | 4/2004 |
| WO | WO 2004/035545 A2 | 4/2004 |
| WO | WO 2004/035563 A1 | 4/2004 |
| WO | WO 2004/035564 A1 | 4/2004 |
| WO | WO 2004/037787 A1 | 5/2004 |
| WO | WO 2004/049806 A1 | 6/2004 |
| WO | WO 2004/062351 A2 | 7/2004 |
| WO | WO 2004/067518 A1 | 8/2004 |
| WO | WO 2004/067527 A1 | 8/2004 |
| WO | WO 2004/074443 A2 | 9/2004 |
| WO | WO 2004/077950 A1 | 9/2004 |

(56) References Cited

FOREIGN PATENT DOCUMENTS

| | | |
|---|---|---|
| WO | WO 2005/000824 A1 | 1/2005 |
| WO | WO 2005/003362 A2 | 1/2005 |
| WO | WO 2005/007627 A1 | 1/2005 |
| WO | WO 2005/007860 A1 | 1/2005 |
| WO | WO 2005/040152 A1 | 5/2005 |
| WO | WO 2005/047233 A1 | 5/2005 |
| WO | WO 2005/047281 A1 | 5/2005 |
| WO | WO 2005/061443 A2 | 7/2005 |
| WO | WO 2005/061464 A1 | 7/2005 |
| WO | WO 2005/068434 A1 | 7/2005 |
| WO | WO 2005/070889 A1 | 8/2005 |
| WO | WO 2005/089551 A1 | 9/2005 |
| WO | WO 2005/095335 A1 | 10/2005 |
| WO | WO 2005/107437 A2 | 11/2005 |
| WO | WO 2005/110068 A2 | 11/2005 |
| WO | WO 2006/006569 A1 | 1/2006 |
| WO | WO 2006/024820 A1 | 3/2006 |
| WO | WO 2006/029828 A1 | 3/2006 |
| WO | WO 2006/029829 A1 | 3/2006 |
| WO | WO 2006/037945 A1 | 4/2006 |
| WO | WO 2006/050803 A1 | 5/2006 |
| WO | WO 2006/074400 A2 | 7/2006 |
| WO | WO 2006/090792 A1 | 8/2006 |
| WO | WO 2006/123088 A2 | 11/2006 |
| WO | WO 2006/125687 A1 | 11/2006 |
| WO | WO 2006/125688 A1 | 11/2006 |
| WO | WO 2006/138638 A1 | 12/2006 |
| WO | WO 2007/003294 A1 | 1/2007 |
| WO | WO2007/007316 A1 | 1/2007 |
| WO | WO 2007/024783 | 3/2007 |
| WO | WO 2007/026834 A1 | 3/2007 |
| WO | WO 2007/035650 A2 | 3/2007 |
| WO | WO 2007/039454 A1 | 4/2007 |
| WO | WO 2007/050715 A2 | 5/2007 |
| WO | WO 2007/051462 A2 | 5/2007 |
| WO | WO 2007/070389 A2 | 6/2007 |
| WO | WO 2007/071900 A1 | 6/2007 |
| WO | WO 2007070389 * 6/2007 | ......... C12N 15/8279 |
| WO | WO 2007/074405 A2 | 7/2007 |
| WO | WO 2007/077201 A1 | 7/2007 |
| WO | WO 2007/077247 A1 | 7/2007 |
| WO | WO 2007/080126 A2 | 7/2007 |
| WO | WO 2007/080127 A2 | 7/2007 |
| WO | WO 2007/083193 A2 | 7/2007 |
| WO | WO 2007/096576 A1 | 8/2007 |
| WO | WO 2007/051462 A1 | 10/2007 |
| WO | WO 2007/051462 A3 | 10/2007 |
| WO | WO 2007/119434 A1 | 10/2007 |
| WO | WO 2007/134984 A1 | 11/2007 |
| WO | WO 2008/007100 A2 | 1/2008 |
| WO | WO 2008/009908 A1 | 1/2008 |
| WO | WO 2008/029084 A1 | 3/2008 |
| WO | WO 2008/042231 A2 | 4/2008 |
| WO | WO 2008/059948 A1 | 5/2008 |
| WO | WO 2008/063203 A2 | 5/2008 |
| WO | WO 2008/071918 A1 | 6/2008 |
| WO | WO 2008/074991 A1 | 6/2008 |
| WO | WO 2008/084073 A1 | 7/2008 |
| WO | WO 2008/100426 A2 | 8/2008 |
| WO | WO 2008/102908 A1 | 8/2008 |
| WO | WO 2008/148223 A1 | 12/2008 |
| WO | WO 2008/152072 A2 | 12/2008 |
| WO | WO 2008/152073 A2 | 12/2008 |
| WO | WO 2009/000757 A1 | 12/2008 |
| WO | WO 2009/005297 A2 | 1/2009 |
| WO | WO 2009/035150 A2 | 3/2009 |
| WO | WO 2009/046384 A1 | 4/2009 |
| WO | WO 2009/063180 A2 | 5/2009 |
| WO | WO 2009/068170 A2 | 6/2009 |
| WO | WO 2009/068171 A2 | 6/2009 |
| WO | WO 2009/086041 A1 | 7/2009 |
| WO | WO 2009/090401 A2 | 7/2009 |
| WO | WO 2009/090402 A2 | 7/2009 |
| WO | WO 2009/115788 A1 | 9/2009 |
| WO | WO 2009/116558 A1 | 9/2009 |
| WO | WO 2009/125401 A2 | 10/2009 |
| WO | WO 2009/152995 A1 | 12/2009 |
| WO | WO 2009/158258 A1 | 12/2009 |
| WO | WO 2010/012649 A1 | 2/2010 |
| WO | WO 2010/026989 A1 | 3/2010 |
| WO | WO 2010/034153 A1 | 4/2010 |
| WO | WO 2010/049270 A1 | 5/2010 |
| WO | WO 2010/049369 A1 | 5/2010 |
| WO | WO 2010/049405 A1 | 5/2010 |
| WO | WO 2010/049414 A1 | 5/2010 |
| WO | WO 2010/056519 A1 | 5/2010 |
| WO | WO 2010/063422 A1 | 6/2010 |
| WO | WO 2010/069802 A1 | 6/2010 |
| WO | WO 2010/078906 A2 | 7/2010 |
| WO | WO 2010/078912 A1 | 7/2010 |
| WO | WO 2010/104217 A1 | 9/2010 |
| WO | WO 2010/108611 A1 | 9/2010 |
| WO | WO 2010/112826 A2 | 10/2010 |
| WO | WO 2010/116122 A2 | 10/2010 |
| WO | WO 2010/119906 A1 | 10/2010 |
| WO | WO 2010/130970 A1 | 11/2010 |
| WO | WO 2011/001434 A1 | 1/2011 |
| WO | WO 2011/003776 A2 | 1/2011 |
| WO | WO 2011/035874 A1 | 3/2011 |
| WO | WO 2011/045796 A1 | 4/2011 |
| WO | WO 2011/065451 A1 | 6/2011 |
| WO | WO 2011/067745 A2 | 6/2011 |
| WO | WO 2011/080674 A2 | 7/2011 |
| WO | WO 2011/112570 A1 | 9/2011 |
| WO | WO 2011/132127 A1 | 10/2011 |
| WO | WO 2012/001626 A1 | 1/2012 |
| WO | WO 2012/056401 A1 | 5/2012 |
| WO | WO 2012/092580 A2 | 7/2012 |
| WO | WO 2013/010691 A1 | 1/2013 |
| WO | WO 2013/025670 A1 | 2/2013 |
| WO | WO 2013/025670 A1 | 3/2013 |
| WO | WO 2013/039990 A1 | 3/2013 |
| WO | WO 2013/040005 A1 | 3/2013 |
| WO | WO 2013/040021 A1 | 3/2013 |
| WO | WO 2013/040033 A1 | 3/2013 |
| WO | WO 2013/040049 A1 | 3/2013 |
| WO | WO 2013/040057 A1 | 3/2013 |
| WO | WO 2013/040116 A9 | 3/2013 |
| WO | WO 2013/040117 A9 | 3/2013 |
| WO | WO 2013/153553 A2 | 10/2013 |
| WO | WO 2013/175480 A1 | 11/2013 |
| WO | WO 2014/022739 A2 | 2/2014 |
| WO | WO 2014/106837 A2 | 7/2014 |
| WO | WO 2014/106838 A2 | 7/2014 |
| WO | WO 2014/151255 A1 | 9/2014 |
| WO | WO 2014/164761 A1 | 10/2014 |
| WO | WO 2014/164797 A1 | 10/2014 |
| WO | WO 2014/164797 A2 | 10/2014 |
| WO | WO 2015/010026 A2 | 1/2015 |

OTHER PUBLICATIONS

Communication pursuant to Article 94(3) EPC dated Mar. 24, 2016, in European Patent Application No. 12 830 932.5.
Communication pursuant to Article 94(3)EPC dated Mar. 9, 2016, in European Patent Application No. 12 831 166.9.
Communication pursuant to Article 94(3) EPC dated Mar. 18, 2016, in European Patent Application No. 12 832 160.1.
Communication pursuant to Article 94(3) EPC dated Jan. 14, 2016, in European Patent Application No. 12 832 415.9.
Database Accession No. HD315444, "Sequence 192160 from Patent EP2213738," (2010).
Extended European Search Report dated Jan. 20, 2016, in European Patent Application No. 13 794 339.5.
First Office Action dated Feb. 2, 2016, in Chinese Patent Application No. 201380039346.6.
GenBank Accession No. GU120406, "Chrysomela tremulae ribosomal protein L7 (RpL7) mRNA, complete cds," (2009) Retrieved from the internet, U RL: <http://www.ncbi.nlm.nih.gov/nuccore/GU120406>.
GenBank Accession No. Q4GXM3_BIPLU, "Ribosomal protein L7e" (2006) [Retrieved on Feb. 5, 2016] Retrieved from the internet, URL: <http://www.ncbi.nlm.nih.gov/protein/Q4GXM3>.

(56) References Cited

OTHER PUBLICATIONS

Gudkov, "Minireview: The L7/L12 ribosomal domain of the ribosome: structural and functional studies," *FEBS Letters*, 407:253-256 (1997).
Heffer et al., "Rapid isolation of gene homologs across taxa: Efficient identification and isolation of gene orthologs from non-model organism genomes, a technical report," *EvoDevo Journal*, 2(7):1-5 (2011).
Knudsen, "Promoter2.0: for the recognition of PolI promoter sequences," *Bioniformatics*, 15(5):356-361 (1999).
Migge et al., "Greenhouse-grown conditionally lethal tobacco plants obtained by expression of plastidic glutamine synthetase antisense RNA may contribute to biological safety," *Plant Science* 153:107-112 (2000).
Office Action dated Apr. 13, 2016, in Chinese Patent Application No. 201280053985.3.
Patent Examination Report No. 1 dated Feb. 8, 2016, in Australian Patent Application No. 2014262189.
Promoter Prediction for SEQ ID No. 1702 from 13/612929/MK/, Promoter 2.0 Prediction Results, pp. 1-4 (2016).
Salanenka et al.,"Seedcoat Permeability: Uptake and Post-germination Transport of Applied Model Tracer Compounds," *HortScience*, 46(4):622-626 (2011).
Scott et al., Botanical Insecticides for Controlling Agricultural Pests: Piperamides and the Colorado Potato Beetle *Leptinotarsa decemlineata* Say (Coleoptera: Chrysomelidae), *Archives of Insect Biochemistry and Physiology*, 54:212-225 (2003).
Second Office Action dated Mar. 4, 2016, in Chinese Patent Application No. 201280054820.8.
Second Office Action dated Feb. 25, 2016, in Chinese Patent Application No. 201280054179.8.
Shintani et al., "Antisense Expression and Overexpression of Biotin Carboxylase in Tobacco Leaves," *Plant Physiol.*, 114:881-886 (1997).
Written Opinion dated Apr. 7, 2016, in Singapore Patent Application No. 201206152-9.
Zhang et al., "Development and Validation of Endogenous Reference Genes for Expression Profiling of Medaka (*Oryzias latipes*) Exposed to Endocrine Disrupting Chemicals by Quantitative Real-Time RT-PCR," *Toxicological Sciences*, 95(2):356-368 (2007).
Alarcón-Reverte et al., "Resistance to ACCase-inhibiting herbicides in the weed *Lolium multiflorum*," *Comm. Appl. Biol. Sci.*, 73(4):899-902 (2008).
Amarzguioui et al., "An algorithm for selection of functional siRNA sequences," *Biochemical and Biophysical Research Communications*, 316:1050-1058 (2004).
Ambrus et al., "The Diverse Roles of RNA Helicases in RNAi," *Cell Cycle*, 8(21):3500-3505 (2009).
Anonymous, "A handbook for high-level expression and purification of 6xHis-tagged proteins," *The QUIexpressionist*, (2003).
An et al., "Transient RNAi Induction against Endogenous Genes in *Arabidopsis* Protoplasts Using in Vitro-Prepared Double-Stranded RNA," *Biosci Biotechnol Biochem*, 69(2):415-418 (2005).
Aoki et al., "In Vivo Transfer Efficiency of Antisense Oligonucleotides into the Myocardium Using HVJ—Liposome Method," *Biochem Biophys Res Commun*, 231:540-545 (1997).
Arpaia et al., "Production of transgenic eggplant (*Solanum melongena* L.) resistant to Colorado Potato Beetle (*Leptinotarsa decemlineata* Say)," (1997) *Theor. Appl. Genet.*, 95:329-334 (1997).
Artmyovich, "Using RNA interference to increase crop yield and decrease pest damage," *MMG 445 Basic Biotech.*, 5(1):7-12 (2009).
Australian Patent Examination report No. 1 dated Nov. 11, 2013, in Australian Application No. 2011224570.
Axtell et al., "A Two-Hit Trigger for siRNA Biogenesis in Plants," *Cell*, 127:565-577 (2006).
Baerson et al., "Glyphosate-Resistant Goosegrass. Identification of a Mutation in the Target Enzyme 5-Enolpyruvylshikimate-3-Phosphate Synthase," *Plant Physiol.*, 129(3):1265-1275 (2002).

Baulcombe, "RNA silencing and heritable epigenetic effects in tomato and *Arabidopsis*," Abstract 13th Annual Fall Symposium, Plant Genomes to Phenomes, Donald Danforth Plant Science Center, 28-30 (2011).
Bannerjee et al., "Efficient production of transgenic potato (*S. tuberosum* L. ssp. *andigena*) plants via *Agrobacterium tumefaciens*-mediated transformation," *Plant Sci.*, 170:732 738 (2006).
Bayer et al., "Programmable ligand-controlled riboregulators of eukaryotic gene expression," *Nature Biotechnol.*, 23(3):337-343 (2005).
Beal, et al., "Second Structural Motif for Recognition of DNA by Oligonucleotide-Directed Triple-Helix Formation," *Science*, 251:1360-1363 (1992).
Becker et al., "Fertile transgenic wheat from microprojectile bombardment of scutellar tissue," *The Plant Journal*, 5(2):299-307 (1994).
Bhargava et al., "Long double-stranded RNA-mediated RNA interference as a tool to achieve site-specific silencing of hypothalamic neuropeptides," *Brain Research Protocols*, 13:115-125 (2004).
Boletta et al., "High Efficient Non-Viral Gene Delivery to the Rat Kidney by Novel Polycationic Vectors," *J. Am Soc. Nephrol.*, 7:1728 (1996).
Bolognesi et al., "Characterizing the Mechanism of Action of Double-Stranded RNA Activity against Western Corn Rootworm(*Diabrotica virgifera virgifera* LeConte)," PLoS ONE 7(10):e47534 (2012).
Bolter et al., "A chloroplastic inner envelope membrane protease is essential for plant development," *FEBS Letters*, 580:789-794 (2006).
Breaker et al., "A DNA enzyme with $Mg2^+$-dependent RNA phosphoesterase activity," *Chemistry and Biology*, 2:655-660 (1995).
Butler et al., "Priming and re-drying improve the survival of mature seeds of *Digitalis purpurea* during storage," *Annals of Botany*, 103:1261-1270 (2009).
Bytebier et al., "T-DNA organization in tumor cultures and transgenic plants of the monocotyledon *Asparagus officinalis*," *Proc. Natl. Acad. Sci. U.S.A.*, 84:5345-5349 (1987).
Chabbouh et al., "Cucumber mosaic virus in artichoke," *FAO Plant Protection Bulletin*, 38:52-53 (1990).
Chakravarty et al., "Genetic Transformation in Potato: Approaches and Strategies," *Amer J Potato Res*, 84:301 311 (2007).
Chee et al., "Transformation of Soybean (*Glycine max*) by Infecting Germinating Seeds with *Agrobacterium tumefaciens*," *Plant Physiol.*, 91:1212-1218 (1989).
Chen et al., "In Vivo Analysis of the Role of atTic20 in Protein Import into Chloroplasts," *The Plant Cell*, 14:641-654 (2002).
Cheng et al., "Production of fertile transgenic peanut (*Arachis hypogaea* L.) plants using *Agrobacterium tumefaciens*," *Plant Cell Reports*, 15:653-657 (1996).
Chi et al., "The Function of RH22, a DEAD RNA Helicase, in the Biogenesis of the 50S Ribosomal Subunits of *Arabidopsis* Chloroplasts," *Plant Physiology*, 158:693-707 (2012).
Chinese Office Action dated Aug. 28, 2013 in Chinese Application No. 201180012795.2.
Clough et al., "Floral dip: a simplified method for Agrobacterium-mediated transformation of *Arabidopsis thaliana*," *The Plant Journal*, 16(6):735-743 (1998).
CN101914540 Patent Diclosure, "Introduction of RNA into plant by interference," (2010).
Colombian Office Action dated Aug. 2, 2013 in Application No. 12 152898.
Colombian Office Action dated Feb. 21, 2014 in Application No. 12 152898.
Cooney et al., "Site-Specific Oligonucleotide Binding Represses Transcription of the Human c-myc Gene in Vitro," *Science* ,241:456-459 (1988).
Colbourne et al., "The Ecoresponsive Genome of Daphnia pulex," *Science*, 331(6017):555-561 (2011).
COST Action FA0806 progress report "Plant virus control employing RNA-based vaccines: A novel non-transgenic strategy" (2010).

(56) References Cited

OTHER PUBLICATIONS

Dalmay et al., "An RNA-Depenedent RNA Polymerase Gene in *Arabidopsis* is Required for Posttranscriptional Gene Silencing Mediated by a Transgene but Not by a Virus," *Cell*, 101:543-553 (2000).
Datebase EMBL CBIB Daphnia—XP-002732239 (2011).
Davidson et al., "Engineering regulatory RNAs," *TRENDS in Biotechnology*, 23(3):109-112 (2005).
De Block, et al. "Engineering herbicide resistance in plants by expression of a detoxifying enzyme," *EMBO J.* 6(9):2513-2519 (1987).
De Framond, "MINI-Ti: A New Vector Strategy for Plant Genetic Engineering," *Nature Biotechnology*, 1:262-269 (1983).
Della-Cioppa et al., "Import of a precursor protein into chloroplasts is inhibited by the herbicide glyphosate," *The EMBO Journal*, 7(5):1299-1305 (1988).
"Devgen, The mini-Monsanto," KBC Securities (2006).
Diallo et al., "Long Endogenous dsRNAs Can Induce Complete Gene Silencing in Mammalian Cells and Primary Cultures," *Oligonucleotides*, 13:381-392 (2003).
Du et al., "A systematic analysis of the silencing effects of an active siRNA at all single-nucleotide mismatched target sites," *Nucleic Acids Research*, 33(5):1671-1677 (2005).
Dunoyer et al., "Small RNA Duplexes Function as Mobile Silencing Signals Between Plant Cells," *Science*, 328:912-916 (2010).
Ellington et al., "In vitro selection of RNA molecules that bind specific ligands," *Nature*, 346:818-822 (1990).
Eurasian Office Action dated Feb. 24, 2014, in Application No. 201201264.
European Cooperation in the field of Scientific and Technical Research—Memorandum of Understanding for COST Action FA0806 (2008).
European Supplemental Search Report dated Oct. 8, 2013 in Application No. 11753916.3.
Farooq et al., "Rice seed priming," *IPRN*, 30(2):45-48 (2005).
Fire et al., "Potent and specific genetic interference by double-stranded RNA in *Caenorhabditis elegans*," *Nature*, 391:806-811 (1998).
Fukuhara et al., "Enigmatic Double-Stranded RNA in Japonica Rice," *Plant Molecular Biology*, 21:1121-1130 (1993).
Fukuhara et al., "The Unusual Structure of a Novel RNA Replicon in Rice," *The Journal of Biological Chemistry*, 270(30):18147-18149 (1995).
Fukuhara et al., "The wide distribution of endornaviruses, large double-stranded RNA replicons with plasmid-like properties," *Archives of Virology*, 151:995-1002 (2006).
Further Examination Report issued in New Zealand Patent Application No. 601784 dated May 16, 2014.
Gaines et al., "Gene amplification confers glyphosate resistance in *Amaranthus palmeri*," *Proc. Natl. Acad. Sci. USA*, 107(3):1029-1034 (2010).
Gallie et al., "Identification of the motifs within the tobacco mosaic virus 5'-leader responsible for enhancing translation," *Nucleic Acids Res.*, 20(17):4631-4638 (1992).
Gan et al., "Bacterially expressed dsRNA protects maize against SCMV infection," *Plant Cell Rep*, 11:1261-1268 (2010).
Ge et al., "Rapid vacuolar sequestration: the horseweed glyphosate resistance mechanism," *Pest Management Sci.*, 66:345-348 (2010).
GenBank accession No. AY545657.1, published 2004.
GenBank Accession No. DY640489, PU2_plate27_F03 PU2 Prunus persica cDNA similar to expressed mRNA inferred from Prunus persica hypothetical domain/motif containing IPR011005:Dihydropteroate synthase-like, MRNA sequence (2006) [Retrieved on Feb. 4, 2013]. Retrieved from the internet <URL: http://www.ncbi.nlm.nih.gov/nucest/DY640489>.
GenBank Accession No. EU24568—"Amaranthus hypochondriacus acetolactate synthase (ALS) gene," (2007).
GenBank Accession No. FJ972198, Solanum lycopersicum cultivar Ailsa Craig dihydropterin pyrophosphokinase-dihydropteroate synthase (HPPK-DHPS) gene, complete cds (2010) [Retrieved on Nov. 26, 2012]. Retrieved from the internet ,URL: http://www.ncbi.nlm.nih.gov/nuccore/FJ972198>.
GenBank accession No. GI:186478573, published Jan. 22, 2014.
GenEmbl FJ861243, published Feb. 3, 2010.
Gutensohn et al., "Functional analysis of the two *Arabidopsis* homologues of Toc34, a component of the chloroplast protein import apparatus," *The Plant Journal*, 23(6):771-783 (2000).
Haigh, "The Priming of Seeds: Investigation into a method of priming large quantities of seeds using salt solution," Thesis submitted to Macquarie University (1983).
Hamilton et al. "Guidelines for the Identification and Characterization of Plant Viruses," *J. gen. Virol.*, 54:223-241 (1981).
Hamilton et al., "Two classes of short interfering RNA in RNA silencing," *EMBO J.*, 21(17):4671-4679 (2002).
Han et al., "Molecular Basis for the Recognition of Primary microRNAs by the Drosha-DGCR8 Complex," *Cell*, 125(5):887-901 (2006).
Hannon, "RNA interference," *Nature*,481:244-251 (2002).
Hardegree, "Drying and storage effects on germination of primed grass seeds," *Journal of Range Management*, 47(3):196-199 (1994).
Herman et al., "A three-component dicamba O-demethylase from *Pseudomonas maltophilia*, strain DI-6: gene isolation, characterization, and heterologous expression," J. Biol. Chem., 280: 24759-24767 (2005).
Hidayat et al., "Enhanced Metabolism of Fluazifop Acid in a Biotype of *Digitaria sanguinalis* Resistant to the Herbicide Fluazifop-P-Butyl," *Pesticide Biochem. Physiol.*, 57:137-146 (1997).
Himber et al., "Transitivity-dependant and—independent cell-to-cell movement of RNA silencing," *The EMBO Journal*, 22(17):4523-4533 (2003).
Hirschberg et al., "Molecular Basis of Herbicide Resistance in *Amaranthus hybridus*," *Science*, 222:1346-1349 (1983).
Hoekema et al., "A binary plant vector strategy based on separation of vir- and T-region of the *Agrobacterium tumefaciens* Ti-plasmid," *Nature*, 303:179-180 (1983).
Hofgen et al., "Repression of Acetolactate Synthase Activity through Antisense Inhibition: Molecular and Biochemical Analysis of Transgenic Potato (*Solanum tuberosum* L. cv Desiree) Plants," *Plant Physiol.*, 107(2):469-477 (1995).
Hsieh et al., "A library of siRNA duplexes targeting the phosphoinositide 3-kinase pathway: determinants of gene silencing for use in cell-based screens," *Nucleic Acids Res.*, 32(3):893-901 (2004).
Huesken et al., "Design of a genome-wide siRNA library using an artificial neural network," *Nature Biotechnology*, 23(8): 995-1001 (2005).
Hunter et al., "RNA Interference Strategy to suppress Psyllids & Leafhoppers," *International Plant and Animal Genome XIX*, 15-19 (2011).
Ichihara et al., "Thermodynamic instability of siRNA duplex is a prerequisite for dependable prediction of siRNA activities," *Nucleic Acids Res.*, 35(18):e123 (2007).
International Preliminary Report on Patentability dated Sep. 11, 2014, in International Application No. PCT/IL13/50447.
International Search Report dated Mar. 12, 2013 in International Application No. PCT/US 12/54789.
International Search Report and the Written Opinion dated May 10, 2011, in International Application No. PCT/US 11/27528.
International Search Report and the Written Opinion dated Feb. 25, 2013, in International Application No. PCT/US 12/54883.
International Search Report and the Written Opinion dated Feb. 27, 2013, in International Application No. PCT/US 12/54814.
International Search Report and the Written Opinion dated Feb. 27, 2013, in International Application No. PCT/US 12/54842.
International Search Report and the Written Opinion dated Feb. 27, 2013, in International Application No. PCT/US 12/54862.
International Search Report and the Written Opinion dated Feb. 27, 2013, in International Application No. PCT/US 12/54894.
International Search Report and the Written Opinion dated Feb. 27, 2013, in International Application No. PCT/US 12/54974.

(56) References Cited

OTHER PUBLICATIONS

International Search Report and the Written Opinion dated Feb. 27, 2013, in International Application No. PCT/US 12/54980.
International Search Report and the Written Opinion dated Jul. 15, 2014, International Application No. PCT/US2014/025305.
Invitation to Pay Additional Fees dated May 6, 2014, in International Application No. PCT/IL2013/051083.
Invitation to Pay Additional Fees dated May 6, 2014, in International Application No. PCT/IL2013/051085.
Invitation to Pay Additional Fees dated Nov. 25, 2014, in International Application No. PCT/US2014/047204.
Isaacs et al., "Engineered riboregulators enable post-transcriptional control of gene expression," *Nature Biotechnology*, 22(7):841-847 (2004).
Ji et al., "Regulation of small RNA stability: methylation and beyond," *Cell Research*, 22:624-636 (2012).
Jones-Rhoades et al., "MicroRNAs and Their Regulatory Roles in Plants," *Annu. Rev. Plant Biol.*, 57:19-53 (2006).
Josse et al., "A DELLA in Disguise: SPATULA Restrains the Growth of the Developing *Arabidopsis* Seedling," *Plant Cell*, 23:1337-1351 (2011).
Kam et al., "Nanotube Molecular Transporters: Internalization of Carbon Nanotube—Protein Conjugates into Mammalian Cells," *J Am. Chem. Soc.*, 126(22):6850-6851 (2004).
Katoh et al., "Specific residues at every third position of siRNA shape its efficient RNAi activity," *Nucleic Acids Res.*, 35(4): e27 (2007).
Kertbundit et al. "In vivo random β-glucuronidase gene fusions in *Arabidopsis thaliana*," *Proc. Natl. Acad. Sci. USA.*, 88:5212-5216 (1991).
Khachigian, "DNAzymes: Cutting a path to a new class of therapeutics," *Curr Opin Mol Ther* 4(2):119-121 (2002).
Khodakovskaya et al., "Carbon Nanotubes are Able to Penetrate Plant Seed Coat and Dramatically Affect Seed Germination and Plant Growth," *ACS Nano*, 3(10):3221-3227 (2009).
Kirkwood, "Use and Mode of Action of Adjuvants for Herbicides: A Review of some Current Work," *Pestic Sci.*, 38:93-102 (1993).
Klahre et al., "High molecular weight RNAs and small interfering RNAs induce systemic posttranscriptional gene silencing in plants," *Proc. Natl. Acad. Sci. USA*, PNAS, 99(18):11981-11986 (2002).
Kronenwett et al., "Oligodeoxyribonucleotide Uptake in Primary Human Hematopoietic Cells is Enhanced by Cationic Lipids and Depends on the Hematopoietic Cell Subset," *Blood*, 91(3):852-862 (1998).
Kumar et al., "Sequencing, De Novo Assembly and Annotation of the Colorado Potato Beetle, *Leptinotarsa decemlineata*,Transcriptome," *PLoS One*, 9(1):e86012 (2014).
Kusaba et al., "*Low glutelin content1*: A Dominant Mutation That Suppresses the Glutelin Multigene Family via RNA Silencing ni Rice," *The Plant Cell*, 15(6):1455-1467 (2003).
Kusaba, "RNA interference in crop plants," *Curr Opin Biotechnol*, 15(2):139-143 (2004).
Lavigne et al., "Enhanced antisense inhibition of human immunodeficiency virus type 1 in cell cultures by DLS delivery system," *Biochem Biophys Res Commun*, 237:566-571 (1997).
Lesnik et al., "Prediction of rho-independent transcriptional terminators in *Escherichia coli*," *Nucleic Acids Research*, 29(17):3583-3594 (2001).
Li et al., "Establishment of a highly efficient transformation system for pepper (*Capsicum annuum* L.)," *Plant Cell Reports*, 21: 785-788 (2003).
Li et al., "The FAST technique: a simplified Agrobacterium-based transformation method for transient gene expression analysis in seedlings of *Arabidopsis* and other plant species," *Plant Methods*, 5(6):1-15 (2009).
Liu et al., "Comparative study on the interaction of DNA with three different kinds of surfactants and the formation of multilayer films," *Bioelectrochemistry*, 70:301-307 (2007).
Liu et al., "Carbon Nanotubes as Molecular Transporters for Walled Plant Cells," *Nano Letters*, 9(3):1007-1010 (2009).
Llave et al., "Endogenous and Silencing-Associated Small RNAs in Plants," *The Plant Cell*, 14:1605-1619 (2002).
Lu et al., "RNA silencing in plants by the expression of siRNA duplexes," *Nucleic Acids Res.*, 32(21):e171 (2004).
Lu et al., "OligoWalk: an online siRNA design tool utilizing hybridization thermodynamics," *Nucleic Acids Research*, 36:W104-W108 (2008).
Luft, "Making sense out of antisense oligodeoxynucleotide delivery: getting there is half the fun," *J Mol Med*, 76:75-76 (1998).
Maas et al., "Mechanism and optimized conditions for PEG mediated DNA transfection into plant protoplasts," *Plant Cell Reports*, 8:148-149 (1989).
Maher III et al., "Inhibition of DNA binding proteins by oligonucleotide-directed triple helix formation," *Science*, 245(4919):725-730 (1989).
Makkouk et al., "Virus Diseases of Peas, Beans, and Faba Bean in the Mediterranean region," *Adv Virus Res*, 84:367-402 (2012).
Mandal et al., "Adenine riboswitches and gene activation by disruption of a transcription terminator," *Nature Struct. Mol. Biol.*, 11(1):29-35 (2004).
Mandal et al., "Gene Regulation by Riboswitches," *Nature Reviews | Molecular Cell Biology*, 5:451-463 (2004).
Masoud et al., "Constitutive expression of an inducible β-1,3-glucanase in alfalfa reduces disease severity caused by the oomycete pathogen *Phytophthora megasperma* f. sp *medicaginis*, but does not reduce disease severity of chitincontaining fungi," *Transgenic Research*, 5:313-323 (1996).
Matveeva et al., "Prediction of antisense oligonucleotide efficacy by in vitro methods," *Nature Biotechnology*, 16:1374-1375 (1998).
Meinke, et al., "Identifying essential genes in *Arabidopsis thaliana*," *Trends Plant Sci.*, 13(9):483-491 (2008).
Meins et al., "RNA Silencing Systems and Their Relevance to Plant Development," *Annu. Rev. Cell Dev. Biol.*, 21:297-318 (2005).
Melnyk et al., "Intercellular and systemic movement of RNA silencing signals," *The EMBO Journal*, 30:3553-3563 (2011).
Misawa et al., "Functional expression of the *Erwinia uredovora* carotenoid biosynthesis gene crtI in transgenic plants showing an increase of β-carotene biosynthesis activity and resistance to the bleaching herbicide norflurazon," *The Plant Journal*, 4(5):833-840 (1993).
Molnar et al., "Plant Virus-Derived Small Interfering RNAs Originate redominantly from Highly Structured Single-Stranded Viral RNAs," *Journal of Virology*, 79(12):7812-7818 (2005).
Molnar et al., "Small Silencing RNAs in Plants are Mobile and Direct Epigenetic Modification in Recipient Cells," *Science*, 328:872-875 (2010).
Moriyama et al., "Double-stranded RNA in rice: a novel RNA replicon in plants," *Molecular & General Genetics*, 248(3):364-369 (1995).
Moriyama et al., "Stringently and developmentally regulated levels of a cytoplasmic double-stranded RNA and its high-efficiency transmission via egg and pollen in rice," *Plant Molecular Biology*, 31:713-719 (1996).
Morrissey et al., "Potent and persistent in vivo anti-HBV activity of chemically modified siRNAs," *Nat Biotechnol.* 23(8):1002-1007 (2005).
Moser et al., "Sequence-Specific Cleavage of Double Helical DNA by Triple Helix Formation," *Science*, 238:645-646 (1987).
Nowak et al., "A new and efficient method for inhibition of RNA viruses by DNA interference," *The FEBS Journal*, 276:4372-4380 (2009).
Office Action dated Feb. 17, 2014, in Mexican Patent Application No. MX/a/2012/010479.
Office Action dated Nov. 19, 2014, in Eurasian Patent Application No. 201201264/28.
Office Action dated Jan. 6, 2015, in Japanese Patent Application No. 2012-557165.
Ongvarrasopone et al., "A Simple and Cost Effective Method to Generate dsRNA for RNAi Studies in Invertebrates," *Science Asia*, 33:35-39 (2007).
Paddison et al., "Stable suppression of gene expression by RNAi in mammalian cells," *Proc. Natl Acad. Sci. USA*, 99(3):1443-1448 (2002).

(56) References Cited

OTHER PUBLICATIONS

Palauqui et al., "Activation of systemic acquired silencing by localised introduction of DNA," *Current Biology*, 9:59-66 (1999).
Paungfoo-Lonhienne et al., "DNA uptake by *Arabidopsis* induces changes in the expression of CLE peptides which control root morphology," *Plant Signaling & Behavior*, 5(9):1112-1114 (2010).
Paungfoo-Lonhienne et al., "DNA is Taken up by Root Hairs and Pollen, and Stimulates Root and Pollen Tube Growth," *Plant Physiology*, 153:799-805 (2010).
Pei et al., "On the art of identifying effective and specific siRNAs," *Nature Methods*, 3(9):670-676 (2006).
Peretz et al., "A Universal Expression/Silencing Vector in Plants," *Plant Physiology*, 145:1251-1263 (2007).
Pormprom et al., "Glutamine synthetase mutation conferring target-site-based resistance to glufosinate in soybean cell selections," *Pest Manag Sci*, 2009; 65(2):216-222 (2009).
Qiwei, "Progress in DNA interference," *Progress in Veterinary Medicine*, 30(1):71-75 (2009).
Rajur et al., "Covalent Protein—Oligonucleotide Conjugates for Efficient Delivery of Antisense Molecules," *Bioconjug Chem.*, 8:935-940 (1997).
Reddy et al "Organosilicone Adjuvants Increased the Efficacy of Glyphosate for Control of Weeds in Citrus (*Citrus* spp.)" HortScience (1992) 27(9):1003-1005.
Reddy et al., "Aminomethylphosphonic Acid Accumulation in Plant Species Treated with Glyphosate," *J Agric. Food Chem.*, 56(6):2125-2130 (2008).
Rey et al., "Diversity of Dicotyledenous-Infecting Geminiviruses and Their Associated DNA Molecules in Southern Africa, Including the South-West Indian Ocean Islands," *Viruses*, 4:1753-1791 (2012).
Reynolds et al., "Rational siRNA design for RNA interference," *Nat Biotechnol*, 22(3):326-330 (2004).
Reynolds et al., "Rational siRNA design for RNA interference," *Nature Biotechnology*, 22:326-330 (2004).
Ryabov et al., "Cell-to-Cell, but Not Long-Distance, Spread of RNA Silencing That is Induced in Individual Epidermal Cells," *Journal of Virology*, 78(6):3149-3154 (2004).
Santoro et al., "A general purpose RNA-cleaving DNA enzyme," *Proc. Natl. Acad. Sci. USA*, 94:4262-4266 (1997).
Sathasivan et al., "Nucleotide sequence of a mutant acetolactate synthase gene from an imidazolinone-resistant *Arabidopsis thaliana* var. Columbia," *Nucleic Acids Research*, 18(8):2188-2193 (1990).
Schwab et al., "RNA silencing amplification in plants: Size matters," *PNAS*, 107(34):14945-14946 (2010).
Schwember et al., "Drying Rates following Priming Affect Temperature Sensitivity of Germination and Longevity of Lettuce Seeds," *HortScience*, 40(3):778-781 (2005).
Second Chinese Office Action issued in Chinese Patent Application No. 201180012795.2, dated Jun. 10, 2014.
Seidman et al., "The potential for gene repair via triple helix formation," *J Clin Invest.*, 112(4):487-494 (2003).
Selvarani et al., "Evaluation of seed priming methods to improve seed vigour of onion (*Allium cepa* cv. *Aggregatum*) and carrot (*Daucus carota*)," *Journal of Agricultural Technology*, 7(3):857-867 (2011).
Sharma et al., "A simple and efficient *Agrobacterium*-mediate procedure for transformation of tomato," *J. Biosci.*, 34(3):423 433 (2009).
Sijen et al., "On the Role of RNA Amplification in dsRNA-Triggered Gene Silencing," *Cell*, 107:465-476 (2001).
Silwet L-77 Spray Adjuvant for agricultural applications, product description from Momentive Performance Materials, Inc. (2003).
Singh et al., "Absorption and translocation of glyphosate with conventional and organosilicone adjuvants," *Weed Biology and Management*, 8:104-111 (2008).
Steeves et al., "Transgenic soybeans expressing siRNAs specific to a major sperm protein gene suppress *Heterodera glycines* reproduction," *Funct. Plant Biol.*, 33:991-999 (2006).
Stock et al., "Possible Mechanisms for Surfactant-Induced Foliar Uptake of Agrochemicals," *Pestic. Sci.*, 38:165-177 (1993).
Strat et al., "Specific and nontoxic silencing in mammalian cells with expressed long dsRNAs," *Nucleic Acids Research*, 34(13):3803-3810 (2006).
Sudarsan et al., "Metabolite-binding RNA domains are present in the genes of eukaryotes," *RNA*, 9:644-647 (2003).
Sun et al., "Antisense oligodeoxynucleotide inhibition as a potent strategy in plant biology: identification of SUSIBA2 as a transcriptional activator in plant sugar signalling," *The Plant Journal*, 44:128-138 (2005).
Sun et al., "A Highly efficient Transformation Protocol for Micro-Tom, a Model Cultivar for Tomato Functional Genomics," *Plant Cell Physiol.*, 47(3):426-431 (2006).
Sun et al., "Sweet delivery—sugar translocators as ports of entry for antisense oligodeoxynucleotides in plant cells," *The Plant Journal*, 52:1192-1198 (2007).
Takasaki et al., "An Effective Method for Selecting siRNA Target Sequences in Mammalian Cells," *Cell Cycle*, 3:790-795 (2004).
Templeton et al., "Improved DNA: liposome complexes for increased systemic delivery and gene expression," *Nature Biotechnology*, 15:647-652 (1997).
Tenllado et al., "Crude extracts of bacterially expressed dsRNA can be used to protect plants against virus infection," *BMC Biotechnology*, 3(3):1-11 (2003).
Tenllado et al., "RNA interference as a new biotechnological tool for the control of virus diseases in plants," *Virus Research*, 102:85-96 (2004).
Tepfer, "Risk assessment of virus resistant transgenic plants," *Annual Review of Phytopathology*, 40:467-491 (2002).
The Seed Biology Place, Website Gerhard Leubner Lab Royal Holloway, University of London, <http://www.seedbiology.de/seedtechnology.asp.
Third Party Submission filed on Nov. 29, 2012 in U.S. Appl. No. 13/042,856.
Thompson, et al., "Clustal W: improving the sensitivity of progressive multiple sequence alignment through sequence weighting, position-specific gap penalties and weight matrix choice," *Nucl. Acids Res.*, 22(22):4673-4680 (1994).
Timmons et al., "Specific interference by ingested dsRNA," *Nature*, 395:854 (1998).
Tomari et al., "Perspective: machines for RNAi," *Genes & Dev.*, 19:517-529 (2005).
Töpfer et al., "Uptake and Transient Expression of Chimeric Genes in Seed-Derived Embryos," *Plant Cell*, 1:133-139 (1989).
Toriyama et al., "Transgenic Rice Plants After Direct Gene Transfer Into Protoplasts," *Bio/Technology*, 6:1072-1074 (1988).
Tran et al., "Control of specific gene expression in mammalian cells by co-expression of long complementary RNAs," *FEBS Lett.*;573(1-3):127-134 (2004).
Tuschl, "RNA Interference and Small Interfering RNAs," *ChemBiochem*. 2(4):239-245 (2001).
Tuschl, "Expanding small RNA interference," *Nature Biotechnol.*, 20: 446-448 (2002).
Ui-Tei et al., "Guidelines for the selection of highly effective siRNA sequences for mammalian and chick RNA interference," *Nucleic Acids Res.*, 32(3): 936-948 (2004).
Unnamalai et al., "Cationic oligopeptide-mediated delivery of dsRNA for post-transcriptional gene silencing in plant cells," *FEBS Letters*, 566:307-310 (2004).
Urayama et al., "Knock-down of OsDCL2 in Rice Negatively Affects Maintenance of the Endogenous dsRNA Virus, *Oryza sativa* Endornavirus," *Plant and Cell Physiology*, 51(1):58-67 (2010).
Van de Wetering et al., "Specific inhibition of gene expression using a stably integrated, inducible small-interfering-RNA vector," *EMBO Rep.*, 4(6):609-615 (2003).
Vasil et al., "Herbicide Resistant Fertile Transgenic Wheat Plants Obtained by Microprojectile Bombardment of Regenerable Embryogenic Callus," *Bio/Technology*,10:667-674 (1992).
Vaucheret, "Post-transcriptional small RNA pathways in plants: mechanisms and regulations," *Genes Dev.*, 20:759-771 (2006).
Vencill et al., "Resistance of Weeds to Herbicides," *Herbicides and Environment*, 29:585-594 (2011).

(56) References Cited

OTHER PUBLICATIONS

Verma et al., "Modified oligonucleotides: synthesis and strategy for users," *Annu. Rev. Biochem.*, 67:99-134 (1998).
Vert et al., "An accurate and interpretable model for siRNA efficacy prediction," *BMC Bioinformatics*, 7:520 (2006).
Vionnet et al., "Systemic Spread of Sequence-Specific Transgene RNA Degradation in Plants is Initiated by Localized Introduction of Ectopic Promoterless DNA," *Cell*, 95:177-187 (1998).
Wakelin et al., "A target-site mutation is present in a glyphosate-resistant *Lolium rigidum* population," *Weed Res. (Oxford)*, 46(5):432-440 (2006).
Walton et al., "Prediction of antisense oligonucleotide binding affinity to a structured RNA target," *Biotechnol Bioeng* 65(1):1-9 (1999).
Wan et al., "Generation of Large Numbers of Independently Transformed Fertile Barley Plants," *Plant Physiol.*, 104:37-48 (1994).
Wardell,"Floral Activity in Solutions of Deoxyribonucleic Acid Extracted from Tobacco Stems," *Plant Physiol*, 57:855-861 (1976).
Wardell, "Floral Induction of Vegetative Plants Supplied a Purified Fraction of Deoxyribonucleic Acid from Stems of Flowering Plants," *Plant Physiol*, 60:885-891 (1977).
Waterhouse et al., "Virus resistance and gene silencing in plants can be induced by simultaneous expression of sense and antisense RNA," *Proc Natl Acad Sci USA*, 95 13959-13964 (1998).
Welch et al., "Expression of ribozymes in gene transfer systems to modulate target RNA levels," *Curr Opin Biotechnol.* 9(5):486-496 (1998).
Wilson, et al., "Transcription termination at intrinsic terminators: The role of the RNA hairpin," *Proc. Natl. Acad. Sci. USA*, 92:8793-8797 (1995).
Winkler et al., "Thiamine derivatives bind messenger RNAs directly to regulate bacterial gene expression," *Nature*, 419:952-956 (2002).
Written Opinion dated May 8, 2014, in International Application No. PCT/IL2013/050447.
Written Opinion dated Sep. 1, 2014, in Singapore Patent Application No. 201206152-9.
Yin et al., "Production of double-stranded RNA for interference with TMV infection utilizing a bacterial prokaryotic expression system," *Appl. Microbiol. Biotechnol.*, 84(2):323-333 (2009).
YouTube video by General Electric Company "Silwet Surfactants," screen shot taken on Jan. 11, 2012 of video of www.youtube.com/watch?v=WBw7nXMqHk8 (uploaded Jul. 13, 2009).
Zagnitko, "Lolium regidum clone LS1 acetyl-CoA carboxylase mRNA, partial cds; nuclear gene for plastid product," GenBank: AF359516.1, 2 pages (2001).
Zagnitko, et al., "An isoleucine/leucine residue in the carboxyltransferase domain of acetyl-CoA carboxylase is critical for interaction with aryloxyphenoxypropionate and cyclohexanedione inhibitors," *PNAS*, 98(12):6617-6622 (2001).
Zhang et al., "*Agrobacterium*-mediated transformation of *Arabidopsis thaliana* using the floral dip method," *Nature Protocols*, 1(2):1-6 (2006).
Zhang et al., "Cationic lipids and polymers mediated vectors for delivery of siRNA," *Journal of Controlled Release*, 123:1-10 (2007).
Zhang et al., "A novel rice gene, NRR responds to macronutrient deficiency and regulates root growth," *Mol Plant*, 5(1):63-72 (2012).
Zhao et al., "*Phyllotreta striolata* (Coleoptera: Chrysomelidae):Arginine kinase cloning and RNAi-based pest control," *European Journal of Entomology*, 105(5):815-822 (2008).
Zhu et al., "Ingested RNA interference for managing the populations of the Colorado potato beetle, *Leptinotarsa decemlineata*," *Pest Manag Sci*, 67:175-182 (2010).
Andersen et al., "Delivery of siRNA from lyophilized polymeric surfaces," *Bomaterials*, 29:506-512 (2008).
Anonymous, "A handbook for high-level expression and purification of 6xHis-tagged proteins," *The QiaEpressionist*, (2003).
Anonymous, "Devgen, The mini-Monsanto," KBC Securities (2006).

Artymovich, "Using RNA interference to increase crop yield and decrease pest damage," *MMG 445 Basic Biotech.*, 5(1):712 (2009).
Brodersen et al., "The diversity of RNA silencing pathways in plants," *Trends in Genetics*, 22(5):268-280 (2006).
Chabannes et al., "In situ analysis of lignins in transgenic tobacco reveals a differential impact of individual transformations on the spatial patterns of lignin deposition at the cellular and subcellular levels," *The Plant Journal*, 28(3):271-282 (2001).
Communication pursuant to Article 94(3) EPC dated Jun. 26, 2015, in European Patent Application No. 11 753 916.3.
Communication pursuant to Article 94(3) EPC dated Oct. 23, 2015, in European Patent Application No. 12 831 945.6.
Dalakouras et al., "Induction of Silencing in Plants by High-Pressure Spraying of In vitro-Synthesized Small RNAs," *Frontiers in Plant Science*, 7(1327):1-5 (2016).
Extended European Search Report dated Oct. 8, 2013, in European Patent Application No. 11753916.3.
Extended European Search Report dated Sep. 29, 2016, in European Patent Application No. 14778840.0.
First Examination Report dated Apr. 23, 2013, in New Zealand Patent Application No. 601784.
First Examination Report dated Jul. 28, 2014, in New Zealand Patent Application No. 627060.
Fukunaga el al., "dsRNA with 5' overhangs v contributes to endogenous and antiviral RNA silencing pathways in plants," *The EMBO Journal*, 28(5):545-555 (2009).
Further Examination Report dated May 16, 2014, in New Zealand Patent Application No. 601784.
GenBank Accession No. AY545657.1 (2004).
GenBank Accession No. DY640489, "PU2_plate27_F03_PU2 Prunus persica cDNA similar to expressed mRNA inferred from Prunus persica hypothetical domain/motif cont aining IPR011005:Dihydropteroate synthase-like, MRNA sequence" (2006).
GenBank Accession No. EU024568, "Amaranthus hypochondriacus acetolactate synthase (ALS) gene" (2007).
GenBank Accession No. FJ972198, "Solanum lycopersicum cultivar Ailsa Craig dihydropterin pyrophosphokinase-dihydropteroate synthase (HPPK-DHPS) gene, complete cds" (2010).
GenBank Accession No. GI:186478573 (2014).
GenBank Accession No. GU120406, "Chrysomela tremulae ribosomal protein L7 (RpL7) mRNA, complete cds" (2009).
GenBank Accession No. HD 5444, "Sequence 192160 from Patent EP2213738" (2010).
GenBank Accession No. Q4GXM3_BIPLU, "Ribosomal protein L7e" (2006).
GenEmbl Accession No. FJ861243 (2010).
Gong et al., "Silencing of Rieske iron-sulfur protein using chemically synthesised siRNA as a potential biopesticide against Plutella xylostella," *Pest Manag Sci*, 67:514-520 (2011).
Hewezi et al., "Local infiltration of high- and low-molecular-weight RNA from silenced sunflower (*Helianthus annuus* L.) plants triggers post-transcriptional gene silencing in non-silenced plants," *Plant Biotechnology Journal*, 3:81-89 (2005).
Ichihara et al., "Thermodynamic instability of siRNA duplex is a prerequisite for dependable prediction of siRNA activities," *Nucleic Acids Res.*, 35(18):e 123 (2007).
International Preliminary Report on Patentability dated Sep. 11, 2014, in International Application No. PCT/IL2013/050447.
International Search Report and the Written Opinion dated Feb. 25, 2013, in International Application No. PCT/US2012/054883.
International Search Report and the Written Opinion dated Feb. 27, 2013, in International Application No. PCT/US2012/054814.
International Search Report and the Written Opinion dated Feb. 27, 2013, in International Application No. PCT/US2012/054842.
International Search Report and the Written Opinion dated Feb. 27, 2013, in International Application No. PCT/US2012/054862.
International Search Report and the Written Opinion dated Feb. 27, 2013, in International Application No. PCT/US2012/054894.
International Search Report and the Written Opinion dated Feb. 27, 2013, in International Application No. PCT/US2012/054974.

(56) References Cited

OTHER PUBLICATIONS

International Search Report and the Written Opinion dated Feb. 27, 2013, in International Application No. PCT/US2012/054980.
International Search Report and the Written Opinion dated Jul. 15, 2014, in International Application No. PCT/US2014/025305.
International Search Report and the Written Opinion dated Jul. 22, 2014, in International Application No. PCT/IL2013/051083.
International Search Report and the Written Opinion dated Jul. 22, 2014, in International Application No. PCT/IL2013/051085.
International Search Report and the Written Opinion dated Jul. 24, 2014, in International Application No. PCT/US2014/026036.
International Search Report and the Written Opinion dated May 10, 2011, in International Application No. PCT/US2011/027528.
International Search Report and the Written Opinion dated Oct. 1, 2013, in International Application No. PCT/IL2013/050447.
International Search Report and Written Opinion dated Aug. 25, 2014, in International Application No. PCT/US2014/023503.
International Search Report and Written Opinion dated Aug. 27, 2014, in International Application No. PCT/US2014/023409.
International Search Report dated Mar. 12, 2013, in International Application No. PCT/US2012/054789.
Lee et al., "Aptamer Database," *Nucleic Acids Research*, 32:D95-D100 (2004).
Leopold et al., "Chapter 4: Moisture as a Regulator of Physiological Reaction in Seeds," *Seed Moisture*, 14:51-69 (1989).
Liu et al., "DNAzyme-mediated recovery of small recombinant RNAs from a 5S rRNA-derived chimera expressed in *Escherichia coli*," *BMC Biotechnology*, 10:85 (2010).
Liu, "Influence of Sugars on the Foliar Uptake of Bentazone and Glyphosate," *New Zealand Plant Protection*, 55:159-162 (2002).
Luque et al., "Water Permeability of Isolated Cuticular Membranes: A Structural Analysis," *Archives of Biochemistry and Biophysics*, 317(2):417-422 (1995).
Manoharan, "Oligonucleotide Conjugates as Potential Antisense Drugs with Improved Uptake, Biodistribution, Targeted Delivery, and Mechanism of Action," *Antisense & Nucleic Acid Drug Development*, 12:103-128 (2002).
Misawa et al., "Expression of an *Erwinia* phytoene desaturase gene not only confers multiple resistance to herbicides interfering with carotenoid biosynthesis but also alters xanthophyll metabolism in transgenic plants," *The Plant Journal*, 6(4):481-489 (1994).
Miura et al., "The Balance between Protein Synthesis and Degradation in Chloroplasts Determines Leaf Variegation in *Arabidopsis* yellow variegated Mutants," *The Plant Cell*, 19:1313-1328 (2007).
Non-Final Office Action dated Nov. 9, 2016, in U.S. Appl. No. 14/901,003.
Office Action dated Sep. 5, 2016, in Ukrainian Patent Application No. a 2014 03846.
Office Action dated Nov. 15, 2016, in Mexican Patent Application. No. MX/a/2014/003068.
Office Action dated Nov. 3, 2014, in Chinese Patent Application No. 201180012795.2.
Parera et al., "Dehydration Rate after Solid Matrix Priming Alters Seed Performance of Shrunken-2 Corn," *J. Amer. Soc. Hort. Sci.*, 119(3):629-635 (1994).
Pornprom et al., "Glutamine synthetase mutation conferring target-site-based resistance to glufosinate in soybean cell selections," *Pest Manag Sci*, 2009; 65(2):216-222 (2009).
Preston et al., "Multiple effects of a naturally occurring proline to threonine substitution within acetolactate synthase in two herbicide-resistant populations of *Lactuca serriola*," *Pesticide Biochem. Physiol.*, 84(3):227-235 (2006).
Qiwei, "Advance in DNA interference," *Progress in Veterinary Medicine*, 30(1):71-75 (2009).
Reddy et al "Organosilicone Adjuvants Increased the Efficacy of Glyphosate for Control of Weeds in Citrus (*Citrus* spp.)" *HortScience* 27(9):1003-1005 (1992).

Schönherr, "Water Permeability of Isolated Cuticular Membranes: The Effect of pH and Cations on Diffusion, Hydrodynamic Permeability and Size of Polar Pores in the Cutin Matrix," *Planta*, 128:113-126 (1976).
Shaoquan, "The action target of herbicide and the innovation of a new variety," *Chemical Industry Press*, 23-24 (2001).
Second Chinese Office Action dated Jun. 10, 2014, in Chinese Patent Application No. 201180012795.2.
Unniraman et al., "Alternate Paradigm for Intrinsic Transcription Termination in Eubacteria," *The Journal of Biological Chemistry*, 276(45)(9):41850-41855 (2001).
Voinnet et al., "Systemic Spread of Sequence-Specific Transgene RNA Degradation in Plants is Initiated by Localized Introduction of Ectopic Promoterless DNA," *Cell*, 95:177-187 (1998).
Waterhouse et al., "Virus resistance and gene silencing in plants can be induced by simultaneous expression of sense and antisense RNA," *Proc. Natl Acad Sci USA*, 95 13959-13964 (1998).
Wiesman et al., "Novel cationic vesicle platform derived from vernonia oil for efficient delivery of DNA through plant cuticle membranes," *Journal of Biotechnology*, 130:85-94 (2007).
Agricultural Chemical Usage 2006 Vegetables Summary, Agricultural Statistics Board, NASS, USDA, pp. 1-372 (2007).
Al-Kaff et al., "Plants rendered herbicide-susceptible by cauliflower mosaic virus-elicited suppression of a 35S promoter-regulated transgene," *Nature Biotechnology*, 18:995-999 (2000).
Balibrea et al., "Extracellular Invertase is an Essential Component of Cytokinin-Mediated Delay of Senescence," *The Plant Cell*, 16(5):1276-1287 (2004).
Bart et al., "A novel system for gene silencing using siRNAs in rice leaf and stem-derived protoplasts," *Plant Methods*, 2(13):1-9 (2006).
Basu et al., "Weed genomics: new tools to understand weed biology," *TRENDS in Plant Science*, 9(8):391-398 (2004).
Busch et al., "RNAi for discovery of novel crop protection products," *Pflanzenschutz-Nachrichten Bayer*, 58(1):34-50 (2005).
Chen et al., "Transfection and Expression of Plasmid DNA in Plant Cells by an Arginine-Rich Intracellular Delivery Peptide without Protoplast Preparation," *FEBS Letters 581*, pp. 1891-1897 (2007).
Colliver et al., "Differential modification of flavonoid and isoflavonoid biosynthesis with an antisense chalcone synthase construct in transgenic *Lotus corniculatus*," *Plant Molecular Biology*, 35:509-522 (1997).
Concise Descriptions of Relevance filed by a third party on Nov. 29, 2012, in U.S. Appl. No. 13/042,856.
Dawson et al., "cDNA cloning of the complete genome of tobacco mosaic virus and production of infectious transcripts," *Proc. Natl. Acad. Sci. USA*, 83:1832-1836 (1986).
Feuillet et al., "Crop genome sequencing: lessons and rationales," *Trends Plant Sci.*, 16:77-88 (2011).
Final Office Action dated Apr. 7, 2016, in U.S. Appl. No. 13/619,980.
Final Office Action dated Dec. 17, 2015, in U.S. Appl. No. 14/335,135.
Final Office Action dated Feb. 17, 2016, in U.S. Appl. No. 13/612,929.
Final Office Action dated Feb. 4, 2016, in U.S. Appl. No. 13/612,936.
Final Office Action dated Jun. 30, 2016, in U.S. Appl. No. 13/901,326.
Final Office Action dated Mar. 2, 2016, in U.S. Appl. No. 13/612,995.
Final Office Action dated Mar. 21, 2016, in U.S. Appl. No. 13/612,925.
Final Office Action dated May 26, 2016, in U.S. Appl. No. 14/532,596.
Final Office Action dated Sep. 9, 2016, in U.S. Appl. No. 13/612,954.
Final Office Action dated Nov. 19, 2015, in U.S. Appl. No. 13/612,941.
Final Office Action dated Sep. 9, 2016, in U.S. Appl. No. 14/608,951.
Final Office Action dated Sep. 9, 2016, in U.S. Appl. No. 14/603,347.

(56) References Cited

OTHER PUBLICATIONS

Final Office Action dated Oct. 20, 2016, in U.S. Appl. No. 14/480,199.
Final Office Action dated Oct. 22, 2015, in U.S. Appl. No. 14/608,951.
Fraley et al., "Liposome-mediated delivery of tobacco mosaic virus RNA into tobacco protoplasts: A sensitive assay for monitoring liposome-protoplast interactions," *Proc Natl Acad Sci U S A.*, 79(6):1859-1863 (1982).
Gan et al., "Inhibition of Leaf Senescence by Autoregulated Production of Cytokinin," *Science*, 270:1986-1988 (1995).
Gao et al., "Nonviral Methods for siRNA Delivery," *Molecular Pharmaceutics*, 6(3):651-658 (2008).
GenBank Accession No. CB377464, "CmaE1_37_J02_T3 Cowpea weevil larvae Lambda Zap Express Library *Callosobruchus maculatus* cDNA, mRNA sequence," (2007).
GenBank Accession No. EW765249, "STO20010B10C12 Normalized and subtracted western corn rootwonn female head cDNA library *Diabrotica virgifera virgifera* cDNA clone STO20010B10C12 5-, mRNA sequence," (2007).
GenBank Accession No. EW771198, "STO20010B10C12 Normalized and subtracted western corn rootworm female head cDNA library *Diabrotica virgifera virgifera* cDNA clone STO20010B10C12 5-, mRNA sequence," (2007).
GenBank Accession No. FE348695, "CBIB7954.fwd CBIB_Daphnia_pulex_Chosen_One_Library_2 Daphnia pulex cDNA clone CBIB7954 5', mRNA sequence" (2011).
GenBank Accession No. U87257.1, "Daucus carota 4-hydroxyphenylpyruvate dioxygenase mRNA, complete cds" (1997).
GenBank Accession No. XM_014456745.1, Predicted: Myotis lucifugus ribonucleoprotein, PTB-binding 2 (RAVER2), transcript variant X3, mRNA,: (2015).
GenBank Accession No. Y08611.1, "P.sativum mRNA for dihydropterin pyrophosphokinase/dihydropteroate synthase." (2006).
Gossamer Threads, Compendium of Herbicide Adjuvants: Organo-Silicone Surfactant, p. 1-4 (1998).
Hajirezaei et al., "Impact of elevated cytosolic and apoplastic invertase activity on carbon metabolism during potato tuber development," *Journal of Experimental Botany*, 51:439-445 (2000).
Holtra et al., "Assessment of the Physiological Condition of *Salvinia natans* L. Exposed to Copper(II) Ions," *Environ. Protect. Eng.*, 41:147-158 (2015).
International Preliminary Report on Patentability dated Sep. 11, 2012, in International Application No. PCT/US2011/027528.
International Rice Genome Sequencing Project, The map-based sequence of the rice genome, *Nature*, 436(11):793-800 (2005).
International Search Report and Written Opinion dated May 26, 2016, in International Application No. PCT/US2016/014344.
Jin et al., "Posttranslational Elevation of Cell Wall Invertase Activity by Silencing its Inhibitor in Tomato Delays Leaf Senescence and Increases Seed Weight and Fruit Hexose Level," *The Plant Cell*, 21:2072-2089 (2009).
Kaloumenos et al., "Identification of a Johnsongrass (*Sorghum halepense*) Biotype Resistant to ACCase-Inhibiting Herbicides in Northern Greece," *Weed Technol*, 23:470-476 (2009).
Kambiranda et al., "Relationship Between Acid Invertase Activity and Sugar Content in Grape Species," *Journal of Food Biochemistry*, 35:1646-1652 (2011).
Kim et al., "Optimization of Conditions for Transient Agrobacterium-Mediated Gene Expression Assays in *Arabidopsis*," *Plant Cell Reports*, 28:1159-1167 (2009).
Kirkwood, "Herbicides and Plants," *Botanical Journal of Scotland*, 46(3):447-462 (1993).
Liu et al., "Identification and Application of a Rice Senescence-Associated Promoter," *Plant Physiology*, 153:1239-1249 (2010).
Mora et al., "How Many Species Are There on Earth and in the Ocean?," *PLOS Biol.*, 9(8):e100127, p. 1-8 (2011).

Mount et al., "Gene and Metabolite Regulatory Network Analysis of Early Developing Fruit Tissues Highlights New Candidate Genes for the Control of Tomato Fruit Composition and Development," *Plant Physiology*, 149:1505-1528 (2009).
Non-Final Office Action dated Aug. 19, 2016, in U.S. Appl. No. 13/612,925.
Non-Final Office Action dated Aug. 19, 2016, in U.S. Appl. No. 13/612,929.
Non-Final Office Action dated Apr. 29, 2016, in U.S. Appl. No. 13/583,302.
Non-Final Office Action dated Aug. 10, 2016, in U.S. Appl. No. 13/612,995.
Non-Final Office Action dated Aug. 3, 2016, in U.S. Appl. No. 14/015,715.
Non-Final Office Action dated Aug. 8, 2016, in U.S. Appl. No. 13/612,936.
Non-Final Office Action dated Dec. 17, 2015, in U.S. Appl. No. 14/532,596.
Non-Final Office Action dated Feb. 10, 2016, in U.S. Appl. No. 13/901,326.
Non-Final Office Action dated Feb. 23, 2016, in U.S. Appl. No. 14/603,347.
Non-Final Office Action dated Feb. 23, 2016, in U.S. Appl. No. 14/608,951.
Non-Final Office Action dated Sep. 6, 2016, in U.S. Appl. No. 14/335,135.
Non-Final Office Action dated Mar. 1, 2016, in U.S. Appl. No. 13/612,954.
Non-Final Office Action dated Oct. 3, 2016, in U.S. Appl. No. 14/403,491.
Non-Final Office Action dated Sep. 1, 2015, in U.S. Appl. No. 13/612,954.
Non-Final Office Action dated Sep. 11, 2015, in U.S. Appl. No. 13/612,925.
Non-Final Office Action dated Sep. 4, 2015, in U.S. Appl. No. 13/612,995.
Nookaraju et al., "Molecular approaches for enhancing sweetness in fruits and vegetables," *Scientia Horticulture*, 127:1-15 (2010).
Notice of Allowance dated Apr. 11, 2016, in U.S. Appl. No. 13/612,985.
Notice of Allowance dated Apr. 19, 2016, in U.S. Appl. No. 13/612,941.
Notice of Allowance dated Apr. 20, 2016, in U.S. Appl. No. 13/612,948.
Notice of Allowance dated Feb. 23, 2015, in U.S. Appl. No. 13/042,856.
Notice of Allowance dated Jun. 2, 2015, in U.S. Appl. No. 13/042,856.
Office Action dated Aug. 28, 2013, in Chinese Patent Application No. 201180012795.2.
Office Action dated Jul. 18, 2016, in Indonesian Patent Application No. W00201203610.
Office Action dated Aug. 25, 2016, in Eurasian Patent Application No. 201201264.
Office Action dated Feb. 24, 2014, in Eurasian Patent Application No. 201201264.
Office Action dated Jun. 20, 2016, in Chinese Patent Application No. 201280054819.5.
Office Action dated Jun. 24, 2016, in Chinese Patent Application No. 201280053984.9.
Patent Examination Report No. 1 dated Jun. 17, 2016, in Australian Patent Application No. 2012308659.
Patent Examination Report No. 1 dated Jun. 17, 2016, in Australian Patent Application No. 2012308660.
Patent Examination Report No. 1 dated Nov. 11, 2013, in Australian Patent Application No. 2011224570.
Promoter Prediction for SEQ ID No. 4 from U.S. Appl. No. 13/612,995/MK/, Promoter 2.0 Prediction Results, pp. 1-3 (2016).
Promoter Prediction for SEQ ID No. 7 from U.S. Appl. No. 13/612,936/MK/, Promoter 2.0 Prediction Results, pp. 1-2 (2016).
Promoter Prediction for SEQ ID No. 8 from U.S. Appl. No. 13/612,925/MK/, Promoter 2.0 Prediction Results, pp. 1-6 (2016).

(56) References Cited

OTHER PUBLICATIONS

Restriction Requirement dated Jul. 15, 2016, in U.S. Appl. No. 14/143,748.
Restriction Requirement dated Jul. 18, 2016, in U.S. Appl. No. 14/143,836.
Restriction Requirement dated Oct. 13, 2016, in U.S. Appl. No. 14/206,707.
Restriction Requirement dated Oct. 28, 2015, in U.S. Appl. No. 14/603,347.
Restriction Requirement dated Sep. 2, 2015, in U.S. Appl. No. 14/532,596.
Roberts, "Fast-track applications: The potential for direct delivery of proteins and nucleic acids to plant cells for the discovery of gene function," *Plant Methods*, 1(12):1-3 (2005).
Robson et al., "Leaf senescence is delayed in maize expressing the Agrobacterium IPT gene under the control of a novel maize senescence-enhanced promoter," *Plant Biotechnology Journal*, 2:101-112 (2004).
Roitsch et al., "Extracellular invertase: key metabolic enzyme and PR protein," *Journal of Experimental Botany*, 54(382):513-524 (2003).
Roitsch et al., "Function and regulation of plant invertases: sweet sensations," *Trades in Plant Science*, 9(12):606-613 (2004).
Ruan et al., "Suppression of Sucrose Synthase Gene Expression Represses Cotton Fiber Cell Initiation, Elongation, and Seed Development," *The Plant Cell*, 15:952-964 (2003).
Showalter, "Structure and Function of Plant Cell Wall Proteins," *The Plant Cell*, 5:9-23 (1993).
Song et al., "Herbicide," *New Heterocyclic Pesticide*, Chemical Industry Press, 354-356 (2011).
Stevens, "Organosilicone Surfactants as Adjuvants for Agrochemicals," *Journal of Pesticide Science*, 38:103-122 (1993).
Tang et al., "Efficient delivery of small interfering RNA to plant cells by a nanosecond pulsed laser-induced stress wave for post-transcriptional gene silencing," *Plant Science*, 171:375-381 (2006).
Tenllado et al., "Double-Stranded RNA-Mediated Interference with Plant Virus Infection," *Journal of Virology*, 75(24):12288-12297 (2001).
Thomas et al., "Size constraints for targeting post-transcriptional gene silencing and for RNA-directed methylation in *Nicotiana benthamiana* using a potato virus X vector," *The Plant Journal*, 25(4):417-425 (2001).
Tomlinson et al., "Evidence that the hexose-to-sucrose ratio does not control the switch to storage product accumulation in oilseeds: analysis of tobacco seed development and effects of overexpressing apoplastic invertase," *Journal of Experimental Botany*, 55(406):2291-2303 (2004).
Widholm et al., "Glyphosate selection of gene amplification in suspension cultures of 3 plant species," *Phyisologia plantarum*, 112:540-545 (2001).
Wild Carrot, Noxious Weed Control Board (NWCB) of Washington State (2010) <www.nwcb.wa.gov/detail.asp?weed=46>.
Zhang et al., "Chapter 10: New Characteristics of Pesticide Research & Development," *New Progress of the world agriculture chemicals*, p. 209 (2010).
Agrios, *Plant Pathology* (Second Edition), 2:466-470 (1978).
Andersson et al., "A novel selection system for potato transformation using a mutated AHAS gene," *Plant Cell Reports*, 22(4):261-267 (2003).
Anonymous, "Agronomy Facts 37: Adjuvants for enhancing herbicide performance," n.p., 1-8, (Jan. 26, 2000), Web, (Jan. 21, 2014).
Anonymous, "Do Monsanto have the next big thing?," *Austalian Herbicide Resistance Initiative (AHRI)*, (Apr. 23, 2013) Web. (Jan. 19, 2015).
Bai et al., "Naturally Occurring Broad-Spectrum Powdery Mildew Resistance in a Central American Tomato Accession is Caused by Loss of Mlo Function," *MPMI*, 21(1):30-39 (2008).
Bourgeois et al., "Field and producer survey of ACCase resistant wild oat in Manitoba," *Canadian Journal of Plant Science*, 709-715 (1997).
Brugière et al., "Glutamine Synthetase in the Phloem Plays a Major Role in Controlling Proline Production," *The Plant Cell*, 11:1995-2011 (1999).
Busi et al., "Gene flow increases the initial frequency of herbicide resistance alleles in unselectedpopulations," *Agriculture, Ecosystems and Environments*, Elsevier, Amsterdam, NL, 142(3):403-409 (2011).
Campbell et al., "Gene-knockdown in the honey bee mite *Varroa destructor* by a non-invasive approach: studies on a glutathione S-transferase," *Parasites & Vectors*, 3(1):73, pp. 1-10 (2010).
Chang et al., "Cellular Internalization of Fluorescent Proteins via Arginine-rich Intracellular Delivery Peptide in Plant Cells," *Plant Cell Physiol.*, 46(3):482-488 (2005).
Chupp et al., "Chapter 8: White Rust," *Vegetable Diseases and Their Control*, The Ronald Press Company, New York, pp. 267-269 (1960).
Communication pursuant to Article 94(3) EPC dated Jun. 26, 2015, as received in European Patent Application No. 11 753 916.3.
Communication pursuant to Article 94(3) EPC dated Oct. 23, 2015, as received in European Patent Application No. 12 831 945.6.
Coticchia et al., "Calmodulin modulates Akt activity in human breast cancer cell lines," *Breast Cancer Res. Treat*, 115:545-560 (2009).
Desai et al., "Reduction in deformed wing virus infection in larval and adult honey bees (*Apis mellifera* L.) by double-stranded RNA ingestion," *Insect Molecular Biology*, 21(4):446-455 (2012).
Dietemann et al., "*Varroa destructor*: research avenues towards sustainable control," *Journal of Apicultural Research*, 51(1):125-132 (2012).
Emery et al., "Radial Patterning of *Arabidopsis* Shoots by Class III HD-ZIP and KANADI Genes," *Current Biology*, 13:1768-1774 (2003).
Extended European Search Report dated Feb. 2, 2015, in European Patent Application No. 12 830 932.5.
Extended European Search Report dated Feb. 27, 2015, in European Patent Application No. 12 832 160.1.
Extended European Search Report dated Feb. 3, 2015, in European Patent Application No. 12 831 945.6.
Extended European Search Report dated Jan. 21, 2015, in European Patent Application No. 12 832 415.9.
Extended European Search Report dated Jan. 29, 2015, in European Patent Application No. 12 831 567.8.
Extended European Search Report dated Jun. 29, 2015, in European Patent Application No. 12 831 494.5.
Extended European Search Report dated Mar. 17, 2015, in European Patent Application No. 12 831 684.1.
Extended European Search Report dated Mar. 3, 2015, in European Patent Application No. 12 831 166.9.
Final Office Action dated Nov. 10, 2015, in U.S. Appl. No. 13/612,985.
Final Office Action dated Nov. 7, 2013, in U.S. Appl. No. 13/042,856.
Final Office Action dated Nov. 30, 2015, in U.S. Appl. No. 13/612,948.
First Office Action dated Sep. 9, 2015, in Chinese Patent Application No. 201280055409.2.
First Office Action dated Mar. 12, 2015, in Chinese Patent Application No. 201280053984.9.
First Office Action dated Mar. 2, 2015, in Chinese Patent Application No. 201280054819.5.
First Office Action dated May 27, 2015, in Chinese Patent Application No. 201280054179.8.
First Office Action dated Jul. 7, 2015, in Chinese Patent Application No. 201280054820.8.
First Office Action dated Aug. 31, 2015, in Chinese Patent Application No. 201280053985.3.
Fukunaga et al., "dsRNA with 5' overhangs contributes to endogenous and antiviral RNA silencing pathways in plants," *The EMBO Journal*, 28(5):545-555 (2009).
Gao et al., "Down-regulation of acetolactate synthase compromises 01-1-mediated resistance to powdery mildew in tomato," *BMC Plant Biology*, 14 (2014).

(56) References Cited

OTHER PUBLICATIONS

Garbian et al., "Bidirectional Transfer of RNAi between Honey Bee and *Varroa destructor: Varroa* Gene Silencing Reduces *Varroa* Population," 8(12):1-9:e1003035 (2012).
Gressel et al., "A strategy to provide long-term control of weedy rice while mitigating herbicide resistance transgene flow, and its potential use for other crops with related weeds," *Pest Manag Sci*, 65(7):723-731 (2009).
Harrison et al., "Does Lowering Glutamine Synthetase Activity in Nodules Modigy Nitrogen Metabolism and Growth of *Lotus japonicus?*," *Plant Physiology*, 133:253-262 (2003).
International Preliminary Report on Patentability (Chapter II) dated Jul. 24, 2015, in International Application No. PCT/US2014/047204.
International Search Report and Written Opinion dated Feb. 23, 2015, in International Application No. PCT/US2014/063832.
International Search Report and Written Opinion dated Jul. 8, 2015, in International Application No. PCT/US2015/011408.
International Search Report and Written Opinion dated Mar. 26, 2015, in International Application No. PCT/U82014/069353.
International Search Report and Written Opinion dated Nov. 24, 2015, in International Application No. PCT/US2015/037522.
International Search Report and Written Opinion dated Nov. 27, 2015, in International Application No. PCT/US2015/037015.
Invitation to Pay Additional Fees dated Sep. 8, 2015, in International Application No. PCT/US2015/037015.
Invitation to Pay Additional Fees dated Sep. 9, 2015, in International Application No. PCT/US2015/037522.
Jofre-Garfias et al., "*Agrobacterium*-mediated transformation of Amaranthus *hypochondriacus*: light- and tissue-specific expression of a pea chlorophyll a/b-binding protein promoter," *Plant Cell Reports*, 16:847-852 (1997).
Khan et al., "Matriconditioning of Vegetable Seeds to Improve Stand Establishment in Early Field Plantings," *J. Amer. Soc. Hort. Sci.*, 117(1):41-47 (1992).
Kim et al., "Synthetic dsRNA Dicer substrates enhance RNAi potency and efficacy," *Nature Biotechnology*, 23(2):222-226 (2005).
Lein et al., "Target-based discovery of novel herbicides," *Current Opinion in Plant Biology*, 7:219-225 (2004).
Leopold et al., "Chapter 4: Moisture as a Regulator of Physiological Reaction in Seeds," *Seed Moisture, CSSA Special Publication* No. 14, pp. 51-69 (1989).
Lermontova et al., "Reduced activity of plastid protoporphyrinogen oxidase causes attenuated photodynamic damage during high-light compared to low-light exposure," *The Plant Journal*, 48(4):499-510 (2006).
MacKenzie et al., "Transgenic *Nicotiana debneyii* expressing viral coat protein are resistant to potato virus S infection," *Journal of General Virology*, 71:2167-2170 (1990).
Maori et al., "IAPV, a bee-affecting virus associated with Colony Collapse Disorder can be silenced by dsRNA ingestion," *Insect Molecular Biology*, 18(1):55-60 (2009).
Molina et al., "Inhibition of protoporphyrinogen oxidase expression in *Arabidopsis* causes a lesion-mimic phenotype that induces systemic acquired resistance," *The Plant Journal*, 17(6):667-678 (1999).
Non-Final Office Action dated Apr. 11, 2013, in U.S. Appl. No. 13/042,856.
Non-Final Office Action dated Aug. 12, 2015, in U.S. Appl. No. 13/612,936.
Non-Final Office Action dated Aug. 13, 2015, in U.S. Appl. No. 13/612,929.
Non-Final Office Action dated Jul. 23, 2015, in U.S. Appl. No. 14/335,135.
Non-Final Office Action dated Jul. 30, 2014, in U.S. Appl. No. 13/042,856.
Non-Final Office Action dated Jun. 5, 2015, in U.S. Appl. No. 13/612,948.
Non-Final Office Action dated Jun. 8, 2015, in U.S. Appl. No. 13/612,941.
Non-Final Office Action dated Mar. 30, 2015, in U.S. Appl. No. 13/583,302.
Non-Final Office Action dated May 15, 2015, in U.S. Appl. No. 14/608,951.
Non-Final Office Action dated May 22, 2015, in U.S. Appl. No. 13/612,985.
Nord-Larsen et al., "Cloning, characterization and expression analysis of tonoplast intrinsic proteins and glutamine synthetase in ryegrass (*Lolium perenne* L.)," *Plant Cell Reports*, 28(10):1549-1562 (2009).
Notice of Allowance dated Oct. 5, 2015, in U.S. Appl. No. 13/583,302.
Office Action dated Jul. 23, 2015, in Ukrainian Patent Application No. 201211548.
Office Action dated Oct. 5, 2015, in Eurasian Patent Application No. 201201264/28.
Orbović et al., "Foliar-Applied Surfactants and Urea Temporarily Reduce Carbon Assimilation of Grapefruit Leaves," *J. Amer. Soc. Hort. Sci.*, 126(4):486-490 (2001).
Ouellet et al., "Members of the Acetohydroxyacid Synthase Muligene Family of Brassica Napus Have Divergent Patterns of Expression," *The Plant Journal*, Blackwell Scientific Publications, Oxford, GB, 2(3):321-330 (1992).
Partial Supplementary European Search Report dated Mar. 2, 2015, in European Patent Application No. 12 831 494.5.
Pratt et al., "*Amaranthus rudis* and *A. tuberculatus*, One Species or Two?," *Journal of the Torrey Botanical Society*, 128(3):282-296 (2001).
Restriction Requirement dated Apr. 21, 2015, in U.S. Appl. No. 13/612,954.
Restriction Requirement dated Feb. 12, 2015, in U.S. Appl. No. 13/612,985.
Restriction Requirement dated Mar. 12, 2015, in U.S. Appl. No. 13/612,948.
Restriction Requirement dated Mar. 4, 2015, in U.S. Appl. No. 13/612,941.
Restriction Requirement dated May 4, 2015, in U.S. Appl. No. 13/612,929.
Restriction Requirement dated May 5, 2015, in U.S. Appl. No. 13/612,936.
Restriction Requirement dated May 7, 2015, in U.S. Appl. No. 13/612,925.
Restriction Requirement dated May 7, 2015, in U.S. Appl. No. 13/612,995.
Restriction Requirement dated Oct. 2, 2012, in U.S. Appl. No. 13/042,856.
Restriction Requirement dated Oct. 21, 2014, in U.S. Appl. No. 13/583,302.
Riggin et al., "Characterization of de novo transcriptome for waterhemp (*Amaranthus tuberculatus*) using GS-FLX 454 pyrosequencing and its application for studies of herbicide target-site genes," *Pest Manag. Sci.*, 66:1042-1052 (2010).
Rose et al., "Functional polarity is introduced by Dicer processing of short substrate RNAs," *Nucleic Acids Research*, 33(13):4140-4156 (2005).
Rothnie et al., Pararetroviruses and Retroviruses: A Comparative Review of Viral Structure and Gene Expression Strategies, *Advances in Virus Research*, 44:1-67 (1994).
Schweizer et al., "Double-stranded RNA interferes with gene function at the single-cell level in cereals," *The Plant Journal*, 24(6):895-903 (2000).
Senthil-Kumar et al., "A systematic study to determine the extent of gene silencing in *Nicotiana benthamiana* and other Solanaceae species when heterologous gene sequences are used for virus-induced gene silencing," *New Phytologist*, 176:782-791 (2007).
Snead et al., "Molecular basis for improved gene silencing by Dicer substrate interfering RNA compared with other siRNA variants," *Nucleic Acids Research*, 41(12):6209-6221 (2013).
Stevens et al., "New Formulation Technology—SILWET® Organosilicone Surfactants Have Physical and Physiological Properties Which Enhance the Performance of Sprays," *Proceedings of the 9th Australian Weeds Conference*, pp. 327-331 (1990).

(56) References Cited

OTHER PUBLICATIONS

Street, "Why is DNA (and not RNA) a stable storage form for genetic information?," *Biochemistry Revisited*, pp. 1-4 (2008).
Sutton et al., "Activity of mesotrione on resistant weeds in maize," *Pest Manag. Sci.*, 58:981-984 (2002).
Tank Mixing Chemicals Applied to Peanut Crops: Are the Chemicals Compatible?, College of Agriculture & Life Sciences, NC State University, AGW-653, pp. 1-11 (2004).
Taylor, "Seed Storage, Germination and Quality," *The Physiology of Vegetable Crops*, pp. 1-36 (1997).
Temple et al., "Can glutamine synthetase activity levels be modulated in transgenic plants by the use of recombinant DNA technology?" *Transgenic Plants and Plant Biochemistry*, 22(4):915-920 (1994).
Temple et al., "Down-regulation of specific members of the glutamine synthetase gene family in Alfalfa by antisense RNA technology," *Plant Molecular Biology*, 37:535-547 (1998).
Tranel et al., "Resistance of weeds to ALS-inhibiting herbicides: what have we learned?," *Weed Science*, 50:700-712 (2002).
Tsugawa et al., "Efficient transformation of rice protoplasts mediated by a synthetic polycationic amino polymer," *Theor Appl Genet*, 97:1019-1026 (1998).
Vermeulen et al., "The contributions of dsRNA structure to Dicer specificity and efficiency," *RNA*, 11(5):674-682 (2005).
Wang et al., "Foliar uptake of pesticides—Present status and future challenge," *ScienceDirect*, 87:1-8 (2007).
Xu et al., Characterization and Functional Analysis of the Calmodulin-Binding Domain of Rac1 GTPase, *Plos One*, 7(8)1-12:e42975 (2012).
Ascencio-Ibanez et al., "DNA abrasion onto plants is an effective method for geminivirus infection and virus-induced gene silencing," 6*Journal of Virological Methods*, 142:198-203 (2007).
Bachman et al., "Characterization of the spectrum of insecticidal activity of a double-stranded RNA with targeted activity against Western Corn Rootworm (*Diabrotica virgifera virgifera* LeConte)," Transgenic Res., pp. 1-16 (2013).
Bedell et al., "Sorghum Genome Sequencing by Methylation Filtration," PLOS Biology, 3(1):E13/104-115 (2005).
Burgos et al., "Review: Confirmation of Resistance to Herbicides and Evaluation of Resistance Levels," Weed Science, 61 (1):4-20 (2013).
Eamens et al., "RNA Silencing in Plants: Yesterday, Today, and Tomorrow," Plant Physiology, 147(2):456-468 (2008).
Fernandez et al., "Uptake of Hydrophilic Solutes Through Plant Leaves: Current State of Knowledge and Perspectives of Foliar Fertilization," Critical Reviews in Plant Sciences, 28:36-38 (2009).
Final Office Action dated Nov. 10, 2016, in U.S. Appl. No. 13/583,302.
Friedberg, "Automated protein function prediction—the genomic challenge," Briefings in Bioinformatics, 7(3):225-242 (2006).
Funke et al., "Molecular basis for herbicide resistance in Roundup Ready crops," PNAS, 103:13010-13015 (2006).
Gaskin et al., "Novel organosilicone adjuvants to reduce agrochemical spray volumes on row crops," New Zealand Plant Protection, 53:350-354 (2000).
GenBank Accession No. EF143582 (2007).
Hagio, "Chapter 25: Direct Gene Transfer into Plant Mature Seeds via Electroporation After Vacuum Treatment," Electroporation and Sonoporation in Developmental Biology, p. 285-293 (2009).
Hess, "Surfactants and Additives," 1999 Proceedings of the California Weed Science Society, 51:156-172 (1999).
Huang et al., "In Vivo Analyses of the Roles of Essential Omp85-Related Proteins in the Chloroplast Outer Envelope Membrane," Plant Physiol., 157:147-159 (2011).
Jacque et al., "Modulation of HIV-1 replication by RNA interference," Nature, 418, 435-438 (2002).
Jang et al., "Resistance to herbicides caused by single amino acid mutations in acetyl-CoA carboxylase in resistant populations of grassy weeds," New Phytologist, 197(4):1110-1116 (2013).
Kikkert et al., "Stable Transformation of Plant Cells by Particle Bombardment/Biolistics," Methods in Molecular Biology, 286:61-78 (2005).
Li et al., "A Simplified Seed Transformation Method for Obtaining Transgenic Brassica napus Plants," Agricultural Sciences in China, 8(6):658-663 (2009).
Liu et al, "The Helicase and RNaseIIIa Domains of *Arabidopsis* Dicer-Like 1 Modulate Catalytic Parameters during MicroRNA Biogenesis," Plant Physiology, 159:748-758 (2012).
McGinnis, "RNAi for functional genomics in plants," Brief Funct Genomics, 9(2):111-7 (2010).
Office Action dated Aug. 1, 2017, in European Patent Application No. 12 830 932.5.
Office Action dated Aug. 14, 2017, in Israeli Patent Application No. 235878.
Office Action dated Aug. 22, 2017, in Korean Patent Application No. 10-2012-7023415.
Office Action dated Aug. 3, 2017, in Chinese Patent Application No. 201480014392.5 (with English translation).
Office Action dated Aug. 3, 2017, in European Patent Application No. 12 831 684.1.
Office Action dated Aug. 8, 2017, in Chilean Patent Application No. 201501874.
Office Action dated Dec. 13, 2016, in Ukrainian Patent Application No. a 2014 03843.
Office Action dated Dec. 14, 2016, in Ukrainian Patent Application No. a 2014 03850.
Office Action dated Dec. 15, 2016, in Ukrainian Patent Application No. a 2014 03845.
Office Action dated Dec. 15, 2016, in Ukrainian Patent Application No. a 2014 03852.
Office Action dated Dec. 15, 2016, in Ukrainian Patent Application No. a 2014 03849.
Office Action dated Dec. 27, 2016, in Ukrainian Patent Application No. a 2012 11548.
Office Action dated Jul. 11, 2017, in Mexican Patent Application No. MX/a/2015/013118 (with English translation).
Office Action dated Jul. 3, 2017, in Mexican Patent Application No. MX/a/2015/012632 (with English translation).
Office Action dated Jul. 6, 2017, in Mexican Patent Application No. MX/a/2015/013103 (with English translation).
Office Action dated Mar. 16, 2017, in Chinese Patent Application No. 201280054819.5.
Office Action dated May 3, 2016, in Chilean Patent Application No. 201601057.
Patent Examination Report No. 1 dated Jun. 8, 2017, in Australian Patent Application No. 2012308686.
Powles et al., "Evolution in Action: Plants Resistant to Herbicides," Annual Review of Plant Biology, 61(1):317-347 (2010).
Protoplasts, Bio/Technology, 6:1072-1074 (1988).
Rakoczy-Trojanowska, "Alternative Methods of Plant Transformation—a short review," Cellular & Molecular Biology Letters, 7:849-858 (2002).
Regalado, "The Next Great GMO Debate," MIT Technology Review,pp. 1-19 (2015).
Reither et al., "Specificity of DNA triple helix formation analyzed by a FRET assay," BMC Biochemistry, 3:27 (2002).
Ryan, "Human endogenous retroviruses in health and disease: a symbiotic perspective," Journal of the Royal Society of Medicine, 97:560-565 (2004).
Small, "RNAi for revealing and engineering plant gene functions," Current Opinion in Biotechnology, 18:148-153 (2007).
Statement of Grounds and Particulars dated Sep. 1, 2017, in Australian U.S. Patent No. 2014262189.
Stevens, "Formulation of Sprays to Improve the Efficacy of Foliar Fertilisers," New Zealand Journal of Forestry Science, 24(1):27-34 (1994).
Stevens, "Organosilicone Surfactants as Adjuvants for Agrochemicals," New Zealand Journal of Forestry Science, 24:27-34 (1994).
Trucco et al., "Amaranthus hybridus can be pollinated frequently by A. tuberculatus under filed conditions," Heredity, 94:64-70 (2005).

(56) References Cited

OTHER PUBLICATIONS

Turina et al., "Tospoviruses in the Mediterranean Area," Advances in Virus Research, 84:403-437 (2012).
Unniraman et al., "Conserved Economics of Transcription Termination in Eubacteria," Nucleic Acids Research, 30(3):675-684 (2002).
Voinnet, "Origin, Biogenesis, and Activity of Plant MicroRNAs," Cell, 136:669-687 (2009).
Wild Carrot, Noxious Weed Control Board (NWCB) of Washington State (2010).
Written Opinion dated Mar. 6, 2017, in Singaporean Patent Application No. 2012061529.
Zhang et al., "DEG: a database of essential genes," Nucleic Acids Res., 32:D271-D272 (2004).
Zhang et al., "Transgenic rice plants produced by electroporation-mediated plasmid uptake into protoplasts," The Plant Cell Rep., 7:379-384 (1988).
Zhong et al., "A forward genetic screen to explore chloroplast protein import in vivo identifies Moco sulfurase, pivotal for ABA and IAA biosynthesis and purine turnover," The Plant Journal, 63:44-59 (2010).

* cited by examiner

Figure 1

ATGGCTCAAGCTACTACCATCAACAATGGTGTCCATACTGGTCAATTGCACCATACTTTACCCAAAA
CCCAGTTACCCAAATCTTCAAAAACTCTTAATTTTGGATCAAACTTGAGAATTTCTCCAAAGTTCAT
GTCTTTAACCAATAAAAGAGTTGGTGGGCAATCATCAATTGTTCCCAAGATTCAAGCTTCTGTTGCT
GCTGCAGCTGAGAAACCTTCATCTGTCCCAGAAATTGTGTTACAACCCATCAAAGAGATCTCTGGTA
CTGTTCAATTGCCTGGGTCAAAGTCTTTATCCAATCGAATCCTTCTTTTAGCTGCTTTGTCTGAGGG
CACAACAGTGGTCGACAACTTGCTGTATAGTGATGATATTCTTTATATGTTGGACGCTCTCAGAACT
CTTGGTTTAAAAGTGGAGGATGATAGTACAGCCAAAAGGGCAGTCGTAGAGGGTTGTGGTGGTCTGT
TTCCTGTTGGTAAAGATGGAAAGGAAGAGATTCAACTTTTCCTTGGTAATGCAGGAACAGCGATGCG
CCCATTGACAGCTGCGGTTGCCGTTGCTGGAGGAAATTCAAGTTATGTGCTTGATGGAGTACCAAGA
ATGAGGGAGCGCCCCATTGGGGATCTGGTAGCAGGTCTAAAGCAACTTGGTTCAGATGTAGATTGTT
TTCTTGGCACAAATTGCCCTCCTGTTCGGGTCAATGCTAAAGGAGGCCTTCCAGGGGGCAAGGTCAA
GCTCTCTGGATCGGTTAGTAGCCAATATTTAACTGCACTTCTCATGGCTACTCCTTTGGGTCTTGGA
GACGTGGAGATTGAGATAGTTGATAAATTGATTTCTGTACCGTATGTTGAAATGACAATAAAGTTGA
TGGAACGCTTTGGAGTATCCGTAGAACATAGTGATAGTTGGGACAGGTTCTACATTCGAGGTGGTCA
GAAATACAAATCTCCTGGAAAGGCATATGTTGAGGGTGATGCTTCAAGTGCTAGCTACTTCCTAGCC
GGAGCCGCCGTCACTGGTGGGACTGTCACTGTCAAGGGTTGTGGAACAAGCAGTTTACAGGGTGATG
TAAAATTTGCCGAAGTTCTTGAGAAGATGGGTTGCAAGGTCACCTGGACAGAGAATAGTGTAACTGT
TACTGGACCACCCAGGGATTCATCTGGAAAGAAACATCTGCGTGCTATCGACGTCAACATGAACAAA
ATGCCAGATGTTGCTATGACTCTTGCAGTTGTTGCCTTGTATGCAGATGGGCCCACCGCCATCAGAG
ATGTGGCTAGCTGGAGAGTGAAGGAAACCGAACGGATGATTGCCATTTGCACAGAACTGAGAAAGCT
TGGGGCAACAGTTGAGGAAGGATCTGATTACTGTGTGATCACTCCGCCTGAAAAGCTAAACCCCACC
GCCATTGAAACTTATGACGATCACCGAATGGCCATGGCATTCTCTCTTGCTGCCTGTGCAGATGTTC
CCGTCACTATCCTTGATCCGGGATGCACCCGTAAAACCTTCCCGGACTACTTTGATGTTTTAGAAAA
GTTCGCCAAGCATTGA

SEQ ID NO:1

Figure 2

GGCCCATAGGCCTTTTTCTAAAATAGGCCCATTTAAGCTATTAACAATCTTCAAAAGTACCACATCG
CTTAGGTAAAGAAAGCAGCTGAGTTTATATATGGTTAGAGACGAAGTAGTGATTGCGACGAGCGACG
TCTCGCCCTCATCGCAATCCACGCCATTGAGCTTGAGGCCATTGGCGACGGCCGAGAGGCGGTCGCT
TAAGATTAGCATGTCCTTGACGCGGAGTTCTTCCAGACCGTTCATCACGGTCGCCCCTTCCGCGAAG
GCGGCGGCGACAGCGAGAATCGGATATTCGTCGATCATCGAAGGCGCGCGGTCTTCCGGCACCGTGA
CGCATAAAcacggtgccggaagaccgcgcgccttcgatgatcgacgaatatccgattctcgctgtcg
ccgccgccttcgcggaaggggcgaccgtgatgaacggtctggaagaactccgcgtcaaggaaagcga
ccgcctctcggccgtcgccaatggcctcaagctcaatggcgtggattgcgatgagggcgagacgtcg
ctcgtcgTTTTTTTTGGCAAAAA

SEQ ID NO:3

```
ATGCCCCAAATCGGACTTGTATCTGCTGTTAATTTGAGAGTCCAAGGTAATTCAGCTTATCTTTGGA
GCTCGAGGTCTTCGTTGGGAACTGAAAGTCAAGATGTTTGCTTGCAAAGGAATTTGTTATGTTTTGG
TAGTAGCGACTCCATGGGGCATAAGTTAAGGATTCGTACTCCAAGTGCCACGACCCGAAGATTGACA
AAGGACTTTAATCCTTTAAAGGTAGTCTGCATTGATTATCCAAGACCAGAGCTAGACAATACAGTTA
ACTATTTGGAGGCGGCGTTATTATCATCATCGTTTCGTACTTCCTCACGCCCAACTAAACCATTGGA
GATTGTTATTGCTGGTGCAGGTTTGGGTGGTTTGTCTACAGCAAAATATCTGGCAGATGCTGGTCAC
AAACCGATATTGCTGGAGGCAAGAGATGTCCTAGGTGGGAAGGTAGCTGCATGGAAAGATGATGATG
GAGATTGGTACGAGACTGGGTTGCACATATTCTTTGGGGCTTACCCAAATATGCAGAACCTGTTTGG
AGAACTAGGGATTGATGATCGGTTGCAGTGGAAGGAACATTCAATGATATTTGCGATGCCTAACAAG
CCAGGGGAGTTCAGCCGCTTTGATTTTCCTGAAGCTCTTCCTGCGCCATTAAATGGAATTTTGGCCA
TACTAAAGAACAACGAAATGCTTACGTGGCCCGAGAAAGTCAAATTTGCTATTGGACTCTTGCCAGC
AATGCTTGGAGGGCAATCTTATGTTGAAGCTCAAGACGGTTTAAGTGTTAAGGACTGGATGAGAAAG
CAAGGTGTGCCTGATAGGGTGACAGATGAGGTGTTCATTGCCATGTCAAAGGCACTTAACTTCATAA
ACCCTGACGAGCTTTCGATGCAGTGCATTTTGATTGCTTTGAACAGATTTCTTCAGGAGAAACATGG
TTCAAAAATGGCCTTTTTAGATGGTAACCCTCCTGAGAGACTTTGCATGCCGATTGTGGAACATATT
GAGTCAAAAGGTGGCCAAGTCAGACTAAACTCACGAATAAAAAAGATCGAGCTGAATGAGGATGGAA
GTGTCAAATGTTTTATACTGAATAATGGCAGTACAATTAAAGGAGATGCTTTTGTGTTTGCCACTCC
AGTGGATATCTTGAAGCTTCTTTTGCCTGAAGACTGGAAAGAGATCCCATATTTCCAAAAGTTGGAG
AAGCTAGTGGGAGTTCCTGTGATAAATGTCCATATATGGTTTGACAGAAAACTGAAGAACACATCTG
ATAATCTGCTCTTCAGCAGAAGCCCGTTGCTCAGTGTGTACGCTGACATGTCTGTTACATGTAAGGA
ATATTACAACCCCAATCAGTCTATGTTGGAATTGGTATTTGCACCCGCAGAAGAGTGGATAAATCGT
AGTGACTCAGAAATTATTGATGCTACAATGAAGGAACTAGCGAAGCTTTTCCCTGATGAAATTTCGG
CAGATCAGAGCAAAGCAAAAATATTGAAGTATCATGTTGTCAAAACCCCAAGGTCTGTTTATAAAAC
TGTGCCAGGTTGTGAACCCTGTCGGCCCTTGCAAAGATCCCCTATAGAGGGTTTTTATTTAGCTGGT
GACTACACGAAACAGAAGTACTTGGCTTCAATGGAAGGTGCTGTCTTATCAGGAAAGCTTTGTGCAC
AAGCTATTGTACAGGATTACGAGTTACTTCTTGGCCGGAGCCAGAAGATGTTGGCAGAAGCAAGCGT
AGTTAGCATAGTGAACTAA
```

SEQ ID NO:2

Figure 10

```
>gi|93117609|gb|DQ469932.1| Nicotiana benthamiana
phytoene desaturase mRNA, complete cds
ATGCCCCAAATCGGACTTGTATCTGCTGTTAATTTGAGAGTCCAAGGTAATTCAGCTTATCTTTGGA
GCTCGAGGTCTTCGTTGGGAACTGAAAGTCAAGATGTTTGCTTGCAAAGGAATTTGTTATGTTTTGG
TAGTAGCGACTCCATGGGGCATAAGTTAAGGATTCGTACTCCAAGTGCCACGACCCGAAGATTGACA
AAGGACTTTAATCCTTTAAAGGTAGTCTGCATTGATTATCCAAGACCAGAGCTAGACAATACAGTTA
ACTATTTGGAGGCGGCGTTATTATCATCATCGTTTCGTACTTCCTCACGCCCAACTAAACCATTGGA
GATTGTTATTGCTGGTGCAGGTTTGGGTGGTTTGTCTACAGCAAAATATCTGGCAGATGCTGGTCAC
AAACCGATATTGCTGGAGGCAAGAGATGTCCTAGGTGGGAAGGTAGCTGCATGGAAAGATGATGATG
GAGATTGGTACGAGACTGGGTTGCACATATTCTTTGGGCTTACCCAAATATGCAGAACCTGTTTGG
AGAACTAGGGATTGATGATCGGTTGCAGTGGAAGGAACATTCAATGATATTTGCGATGCCTAACAAG
CCAGGGGAGTTCAGCCGCTTTGATTTTCCTGAAGCTCTTCCTGCGCCATTAAATGGAATTTTGGCCA
TACTAAAGAACAACGAAATGCTTACGTGGCCCGAGAAAGTCAAATTTGCTATTGGACTCTTGCCAGC
AATGCTTGGAGGGCAATCTTATGTTGAAGCTCAAGACGGTTTAAGTGTTAAGGACTGGATGAGAAAG
CAAGGTGTGCCTGATAGGGTGACAGATGAGGTGTTCATTGCCATGTCAAAGGCACTTAACTTCATAA
ACCCTGACGAGCTTTCGATGCAGTGCATTTTGATTGCTTTGAACAGATTTCTTCAGGAGAAACATGG
TTCAAAAATGGCCTTTTTAGATGGTAACCCTCCTGAGAGACTTTGCATGCCGATTGTGGAACATATT
GAGTCAAAAGGTGGCCAAGTCAGACTAAACTCACGAATAAAAAGATCGAGCTGAATGAGGATGGAA
GTGTCAAATGTTTTATACTGAATAATGGCAGTACAATTAAAGGAGATGCTTTTGTGTTTGCCACTCC
AGTGGATATCTTGAAGCTTCTTTTGCCTGAAGACTGGAAAGAGATCCCATATTTCCAAAAGTTGGAG
AAGCTAGTGGGAGTTCCTGTGATAAATGTCCATATATGGTTTGACAGAAAACTGAAGAACACATCTG
ATAATCTGCTCTTCAGCAGAAGCCCGTTGCTCAGTGTGTACGCTGACATGTCTGTTACATGTAAGGA
ATATTACAACCCCAATCAGTCTATGTTGGAATTGGTATTTGCACCCGCAGAAGAGTGGATAAATCGT
AGTGACTCAGAAATTATTGATGCTACAATGAAGGAACTAGCGAAGCTTTTCCCTGATGAAATTTCGG
CAGATCAGAGCAAAGCAAAAATATTGAAGTATCATGTTGTCAAAACCCCAAGGTCTGTTTATAAAAC
TGTGCCAGGTTGTGAACCCTGTCGGCCCTTGCAAAGATCCCTATAGAGGGTTTTTATTTAGCTGGT
GACTACACGAAACAGAAGTACTTGGCTTCAATGGAAGGTGCTGTCTTATCAGGAAAGCTTTGTGCAC
AAGCTATTGTACAGGATTACGAGTTACTTCTTGGCCGGAGCCAGAAGATGTTGGCAGAAGCAAGCGT
AGTTAGCATAGTGAACTAA
```

SEQ ID NO:2

Figure 12
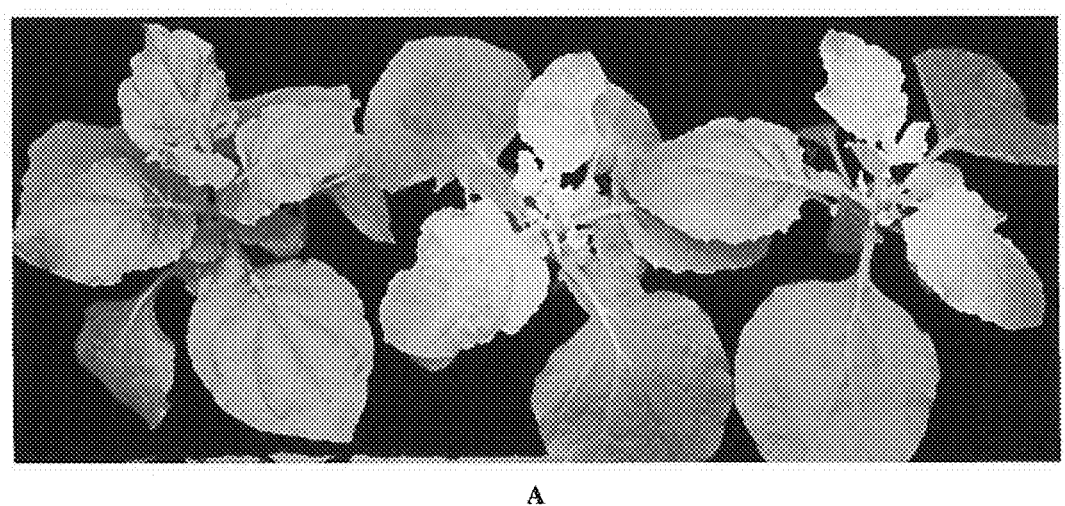
A
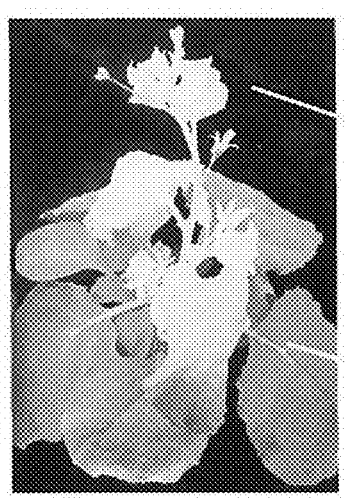
B

Figure 16

```
                       10                  20
Palmer        T-----CAA-------TTTCATCT-------ATTGGA-------AGTGAT  SEQ ID NO:37
              :::          ::  ::::        :::  ::      ::  :
Benthamiana   ATGCCCCAAATCGGACTTGTATCTGCTGTTAATTTGAGAGTCCAAGGTAA  SEQ ID NO:38
              10        20        30        40        50

30              40        50
Palmer        TT-----------TTTGG---------GTCATTCTGTGAGAAATTTCAGTG--
              ::           :::::         :::  :::  ::  :::  :   :::
Benthamiana   TTCAGCTTATCTTTGGAGCTCGAGGTC-TTCGTTGGGAACTGAAAGTCAA
                  60        70        80        90

60
Palmer        ----------------------TTAGTAAAGTTT----------------AT
                                    ::  ::  :  ::::                 ::
Benthamiana   GATGTTTGCTTGCAAAGGAATTTGTTATGTTTTGGTAGTAGCGACTCCAT
                100       110       120       130       140

70        80        90
Palmer        GGAGCA-AAGCAAAGAAATGGGC-----ACTGCC----------------
              ::  :::  :::    :::  :  :  :           :  ::::
Benthamiana   GGGGCATAAGTTAAGGATTCGTACTCCAAGTGCCACGACCCGAAGATTGA
                150       160       170       180       190

100       110       120       130
Palmer        ---------------CTTTAAAGGTTGTTTGTATAGATTATCCTAGGCCA
                             ::::::::  ::  ::  ::  :::::::  ::  :::
Benthamiana   CAAAGGACTTTAATCCTTTAAAGGTAGTCTGCATTGATTATCCAAGACCA
                200       210       220       230       240

140       150       160       170       180
Palmer        GAGCTTGAAAGTACATCCAATTTCTTGGAAGCCGCCTACTTATCTTCTAC
              ::::  ::  :  ::::    ::  :   :::::  ::  ::   :   :::::  ::  :
Benthamiana   GAGCTAGACAATACAGTTAACTATTTGGAGGCGGCGTTATTATCATCATC
                250       260       270       280       290

190       200       210       220       230
Palmer        TTTTCGGAATTCGCCTCGTCCTCAGAAGCCATTAGAAGTTGTAATTGCTG
              :::::  :  :::    :  ::  ::        ::  :::::  ::    ::::  :::::::
Benthamiana   GTTTCGTACTTCCTCACGCCCAACTAAACCATTGGAGATTGTTATTGCTG
                300       310       320       330       340

240       250       260       270       280
Palmer        GAGCAGGTTTGGCTGGTCTATCCACGGCAAAGTATTTAGCTGATGCAGGT
              :  :::::::::::  ::::  :  ::  ::  :::::  :::  :  ::  ::::::  :::
Benthamiana   GTGCAGGTTTGGGTGGTTTGTCTACAGCAAAATATCTGGCAGATGCTGGT
                350       360       370       380       390

290       300       310       320       330
Palmer        CACAAACCCATATTGTTGGAAGCACGAGATGTTTTAGGAGGAAAGGTTGC  SEQ ID NO:37
              ::::::::  ::::::  ::::  :::  :::::::  ::::  ::  :::::  ::
Benthamiana   CACAAACCGATATTGCTGGAGGCAAGAGATGTCCTAGGTGGGAAGGTAGC  SEQ ID NO:38
                400       410       420       430       440
```

Figure 16 (continued)

```
             340        350        360        370        380
Palmer       AGCGTGGAAGGATGAGGATGGTGACTGGTATGAGACTGGGCTACATATAT   SEQ ID NO:37
             ::  :::::  ::::   :::::  ::  :::::  :::::::::  :  ::  ::::
Benthamiana  TGCATGGAAAGATGATGATGGAGATTGGTACGAGACTGGGTTGCACATAT   SEQ ID NO:38
             450        460        470        480        490

390        400        410        420        430
Palmer       TCTTTGGGGCATATCCAAATGTCCAAAATCTATTTGGAGAACTTGGTATA
             :::::::::: ::  ::::::  :  ::  ::  :::::::::::  ::  ::
Benthamiana  TCTTTGGGGCTTACCCAAATATGCAGAACCTGTTTGGAGAACTAGGGATT
             500        510        520        530        540

440        450        460        470        480
Palmer       AATGACCGACTGCAATGGAAGGAGCACTCTATGATTTTTGCAATGCCCAG
             ::::  ::   ::::  ::::::::  ::  ::  :::::  :::::  ::::: :
Benthamiana  GATGATCGGTTGCAGTGGAAGGAACATTCAATGATATTTGCGATGCCTAA
             550        560        570        580        590

490        500        510        520        530
Palmer       CAAGCCCGGTGAATTCAGTCGCTTTGATTTTCCCGAAATCCTGCCTGCAC
             :::::::  ::  ::  :::::  ::::::::::::::  :::       ::  :::::  :
Benthamiana  CAAGCCAGGGGAGTTCAGCCGCTTTGATTTTCCTGAAGCTCTTCCTGCGC
             600        610        620        630        640

540        550        560        570        580
Palmer       CATTAAATGGCATATGGGCAATCCTAAGAAATAATGAAATGCTAACCTGG
             ::::::::::  ::  :  :::  ::  ::::   ::  ::  :::::::::  ::  :::
Benthamiana  CATTAAATGGAATTTTGGCCATACTAAAGAACAACGAAATGCTTACGTGG
             650        660        670        680        690

590        600        610        620        630
Palmer       CCAGAAAAAATCAAGTTTGCCATTGGCTTGTTGCCTGCTATGGCAGGCGG
             ::  ::   :::  ::::  :::::  :::::   :  :::::  :::::           ::  ::
Benthamiana  CCCGAGAAAGTCAAATTTGCTATTGGACTCTTGCCAGCAATGCTTGGAGG
             700        710        720        730        740

640        650        660        670        680
Palmer       ACAGTCATATGTTGAAGCACAAGATGGTTTGAGTGTCCAAGAGTGGATGA
             ::  ::  ::::::::::::  :::::  :::::  ::::::  :  ::  :::::::
Benthamiana  GCAATCTTATGTTGAAGCTCAAGACGGTTTAAGTGTTAAGGACTGGATGA
             750        760        770        780        790

690        700        710        720        730
Palmer       GAAAACAAGGAGTACCCGATCGTGTAACTGATGATGTGTTTATTGCCATG
             ::::  :::::  ::  ::  :::  :  ::  ::  :::::  :::::  :::::::::
Benthamiana  GAAAGCAAGGTGTGCCTGATAGGGTGACAGATGAGGTGTTCATTGCCATG
             800        810        820        830        840

740        750        760        770        780
Palmer       TCAAAGGCACTGAACTTCATAAATCCCGATGAACTTTCAATGCAGTGCAT   SEQ ID NO:37
             :::::::::::  :::::::::  ::  ::  ::  :::::  :::::::::::
Benthamiana  TCAAAGGCACTTAACTTCATAAACCCTGACGAGCTTTCGATGCAGTGCAT   SEQ ID NO:38
             850        860        870        880        890
```

Figure 16 (continued)

```
                790       800       810       820       830
Palmer      CTTGATTGCTCTGAACCGATTCCTGCAGGAGAAACATGGTTCTAAGATGG  SEQ ID NO:37
            ::::::::  :::: ::::  ::  ::::::::::::::::::  ::  ::::
Benthamiana TTTGATTGCTTTGAACAGATTTCTTCAGGAGAAACATGGTTCAAAAATGG  SEQ ID NO:38
                900       910       920       930       940

840       850       860       870       880
Palmer      CCTTCCTAGACGGAAACCCTCCAGAGAGGCTGTGCATGCCTATTGTTAAA
            ::::  ::::  ::  ::::::::  :::::  ::  :::::::::  :::::  ::
Benthamiana CCTTTTTAGATGGTAACCCTCCTGAGAGACTTTGCATGCCGATTGTGGAA
                950       960       970       980       990

890       900       910       920       930
Palmer      CACATCGAGTCACTAGGTGGTGAAGTTAAACTTAACTCTCGTATACAAAA
            ::  ::  ::::::  :::::::  ::::  :  :::  ::::::  ::  ::  ::::
Benthamiana CATATTGAGTCAAAAGGTGGCCAAGTCAGACTAAACTCACGAATAAAAAA
                1000      1010      1020      1030      1040

940       950       960       970       980
Palmer      GATTCAGTTGGACCAGAGTGGAAGCGTGAAGAGTTTTTTGCTAAATAACG
            :::  ::  ::  :   ::  ::::::  ::  ::  :::::  :  ::  :::::  :
Benthamiana GATCGAGCTGAATGAGGATGGAAGTGTCAAATGTTTATACTGAATAATG
                1050      1060      1070      1080      1090

990       1000      1010      1020      1030
Palmer      GGAGGGAAATACGAGGAGATGCCTATGTTTTTGCCACCCCAGTTGACATC
            :  ::   :::   :::::::::  :  :::  :::::::::  :::::  ::  :::
Benthamiana GCAGTACAATTAAAGGAGATGCTTTTGTGTTTGCCACTCCAGTGGATATC
                1100      1110      1120      1130      1140

1040      1050      1060      1070      1080
Palmer      TTGAAGCTGTTACTACCTGATACTTGGAAGGAAATCTCATACTTCAAAAA
            :::::::::  :  :  :::::    ::::  ::  :::  ::::  :::  ::::
Benthamiana TTGAAGCTTCTTTTGCCTGAAGACTGGAAAGAGATCCCATATTTCCAAAA
                1150      1160      1170      1180      1190

1090      1100      1110      1120      1130
Palmer      ACTTGAGAAATTAGTGGGCGTTCCTGTGATTAATGTTCACATATGGTTTG
            :  :::::  :::::::::  :::::::::::  :::::  ::  :::::::::
Benthamiana GTTGGAGAAGCTAGTGGGAGTTCCTGTGATAAATGTCCATATATGGTTTG
                1200      1210      1220      1230      1240

1140      1150      1160      1170      1180
Palmer      ACAGAAAATTAAAGAATACATATGACCATCTACTCTTCAGCAGGAGTCCT
            :::::::::  :  :::::  ::::  :::    ::::  :::::::::::  ::  ::
Benthamiana ACAGAAAACTGAAGAACACATCTGATAATCTGCTCTTCAGCAGAAGCCCG
                1250      1260      1270      1280      1290

1190      1200      1210      1220      1230
Palmer      CTTTTGAGTGTCTATGCTGATATGTCGGAGACATGCAAGGAATATAAGGA  SEQ ID NO:37
            :   :  :::::  ::  ::::::  :::::  :   :::::  :::::::::  :   :
Benthamiana TTGCTCAGTGTGTACGCTGACATGTCTGTTACATGTAAGGAATATTACAA  SEQ ID NO:38
                1300      1310      1320      1330      1340
```

Figure 16 (continued)

```
                 1240       1250       1260       1270       1280
Palmer      TCCAAATAGATCCATGCTGGAATTGGTTTTTGCACCCGCGGAGGAATGGA   SEQ ID NO:37
            : : :::   ::  :::  :::::::::: ::::::::::: :: :: ::::
Benthamiana CCCCAATCAGTCTATGTTGGAATTGGTATTTGCACCCGCAGAAGAGTGGA   SEQ ID NO:38
                 1350       1360       1370       1380       1390

1290       1300       1310       1320       1330
Palmer      TTTCACGAAGCGACACTGATATTATAGAGGCAACAATGAAAGAGCTTGCC
            :    :: :: ::: : :: ::::: :: :: :::::::: :: :: ::
Benthamiana TAAATCGTAGTGACTCAGAAATTATTGATGCTACAATGAAGGAACTAGCG
                 1400       1410       1420       1430       1440

1340       1350       1360       1370       1380
Palmer      AAGCTTTTCCCGGATGAAATCGCTGCCGATGGAAGCAAGGCCAAGATCCT
            :::::::::::: :::::::: : :: :::   ::::: :: :: :: :
Benthamiana AAGCTTTTCCCTGATGAAATTTCGGCAGATCAGAGCAAAGCAAAAATATT
                 1450       1460       1470       1480       1490

1390       1400       1410       1420       1430
Palmer      CAAATATCATGTCGTCAAAACTCCAAGGTCGGTTTATAAGACTGTACCGG
            :: :::::::: :::::::: :::::::: ::::::: ::::: :: :
Benthamiana GAAGTATCATGTTGTCAAAACCCCAAGGTCTGTTTATAAAACTGTGCCAG
                 1500       1510       1520       1530       1540

1440       1450       1460       1470       1480
Palmer      ATTGTGAACCTTGTCGGCCGCTGCAAAGATCACCAATAGAGGGTTTCTAT
            :::::::::  :::::::: ::::::::::: :: :::::::::::: :::
Benthamiana GTTGTGAACCCTGTCGGCCCTTGCAAAGATCCCCTATAGAGGGTTTTTAT
                 1550       1560       1570       1580       1590

1490       1500       1510       1520       1530
Palmer      TTAGCTGGTGATTACACAAAACAAAAATATTTGGCTTCTATGGAAGGTGC
            :::::::::::  :::: :::::: :: :: :::::::: ::::::::::::
Benthamiana TTAGCTGGTGACTACACGAAACAGAAGTACTTGGCTTCAATGGAAGGTGC
                 1600       1610       1620       1630       1640

1540       1550       1560       1570       1580
Palmer       TGTCTTATCTGGGAAGCTTTGTGCACAGGCTATCGTACAGGATTATGA--
            :::::::: :: :::::::::::::: ::::: ::::::::::: ::
Benthamiana TGTCTTATCAGGAAAGCTTTGTGCACAAGCTATTGTACAGGATTACGAGT
                 1650       1660       1670       1680       1690

1590       1600       1610
Palmer      ----TCT--GCTG--------AGTTCTCG--AGCACAAAGAAA-TTGGC
            :::  :: :       ::  :  :: :   :::  :  :: ::
Benthamiana TACTTCTTGGCCGGAGCCAGAAGATGTTGGCAGAAGCAAGCGTAGTTAGC
                 1700       1710       1720       1730       1740

Palmer      G----------   SEQ ID NO:37

Benthamiana ATAGTGAACTAA  SEQ ID NO:38
                 1750       1760
```

Figure 20

ATGGCTCAAGCTACTACCATCAACAATGGTGTCCATACTGGTCAATTGCACCATACTTTACCCAAAA
CCCAGTTACCCAAATCTTCAAAAACTCTTAATTTTGGATCAAACTTGAGAATTTCTCCAAAGTTCAT
GTCTTTAACCAATAAAAGAGTTGGTGGGCAATCATCAATTGTTCCCAAGATTCAAGCTTCTGTTGCT
GCTGCAGCTGAGAAACCTTCATCTGTCCCAGAAATTGTGTTACAACCCATCAAAGAGATCTCTGGTA
CTGTTCAATTGCCTGGGTCAAAGTCTTTATCCAATCGAATCCTTCTTTTAGCTGCTTTGTCTGAGGG
CACAACAGTGGTCGACAACTTGCTGTATAGTGATGATATTCTTTATATGTTGGACGCTCTCAGAACT
CTTGGTTTAAAAGTGGAGGATGATAGTACAGCCAAAAGGGCAGTCGTAGAGGGTTGTGGTGGTCTGT
TTCCTGTTGGTAAAGATGGAAAGGAAGAGATTCAACTTTTCCTTGGTAATGCAGGAACAGCGATGCG
CCCATTGACAGCTGCGGTTGCCGTTGCTGGAGGAAATTCAAGTTATGTGCTTGATGGAGTACCAAGA
ATGAGGGAGCGCCCCATTGGGGATCTGGTAGCAGGTCTAAAGCAACTTGGTTCAGATGTAGATTGTT
TTCTTGGCACAAATTGCCCTCCTGTTCGGGTCAATGCTAAAGGAGGCCTTCCAGGGGGCAAGGTCAA
GCTCTCTGGATCGGTTAGTAGCCAATATTTAACTGCACTTCTCATGGCTACTCCTTTGGGTCTTGGA
GACGTGGAGATTGAGATAGTTGATAAATTGATTTCTGTACCGTATGTTGAAATGACAATAAAGTTGA
TGGAACGCTTTGGAGTATCCGTAGAACATAGTGATAGTTGGGACAGGTTCTACATTCGAGGTGGTCA
GAAATACAAATCTCCTGGAAAGGCATATGTTGAGGGTGATGCTTCAAGTGCTAGCTACTTCCTAGCC
GGAGCCGCCGTCACTGGTGGGACTGTCACTGTCAAGGGTTGTGGAACAAGCAGTTTACAGGGTGATG
TAAAATTTGCCGAAGTTCTTGAGAAGATGGGTTGCAAGGTCACCTGGACAGAGAATAGTGTAACTGT
TACTGGACCACCCAGGGATTCATCTGGAAAGAAACATCTGCGTGCTATCGACGTCAACATGAACAAA
ATGCCAGATGTTGCTATGACTCTTGCAGTTGTTGCCTTGTATGCAGATGGGCCCACCGCCATCAGAG
ATGTGGCTAGCTGGAGAGTGAAGGAAACCGAACGGATGATTGCCATTTGCACAGAACTGAGAAAGCT
TGGGGCAACAGTTGAGGAAGGATCTGATTACTGTGTGATCACTCCGCCTGAAAAGCTAAACCCCACC
GCCATTGAAACTTATGACGATCACCGAATGGCCATGGCATTCTCTCTTGCTGCCTGTGCAGATGTTC
CCGTCACTATCCTTGATCCGGGATGCACCCGTAAAACCTTCCCGGACTACTTTGATGTTTTAGAAAA
GTTCGCCAAGCATTGA

SEQ ID NO:40

Figure 21
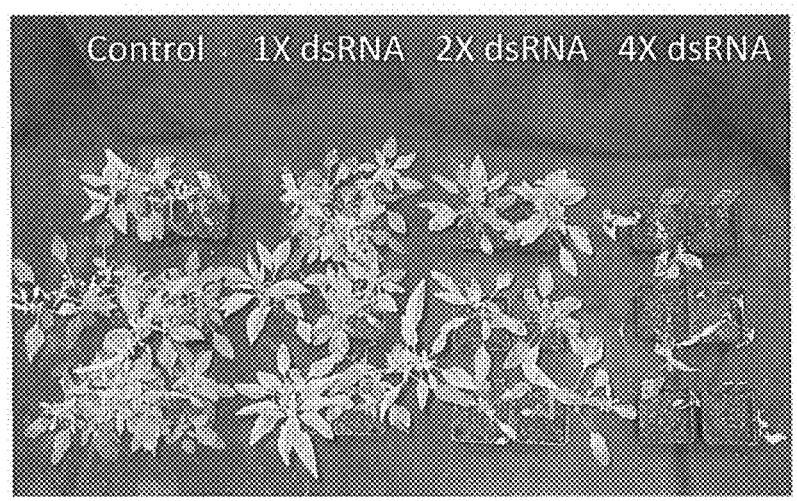
A
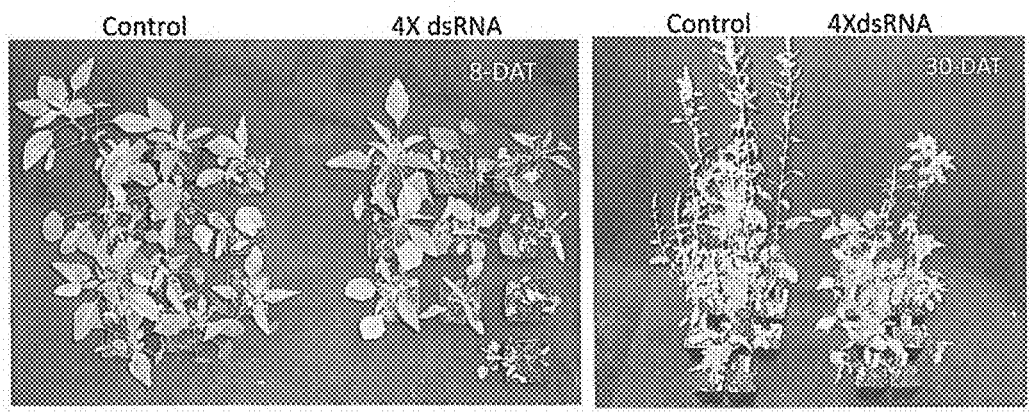
B

Figure 25
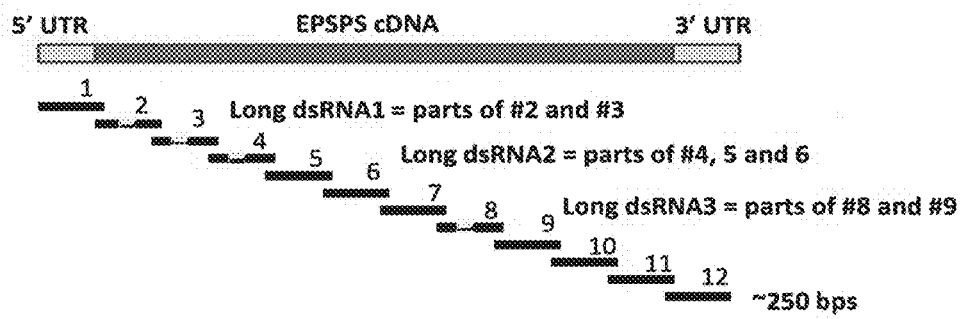
A
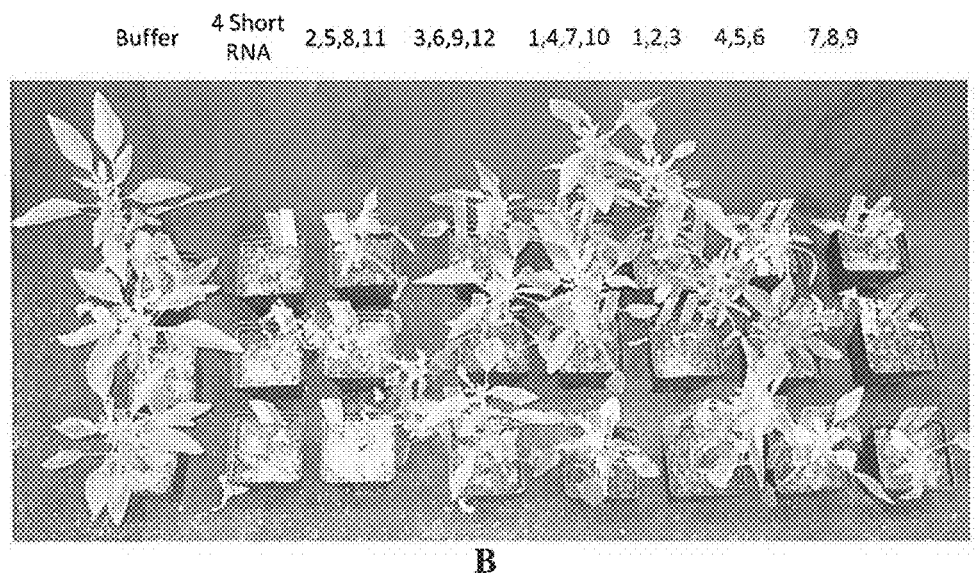
B
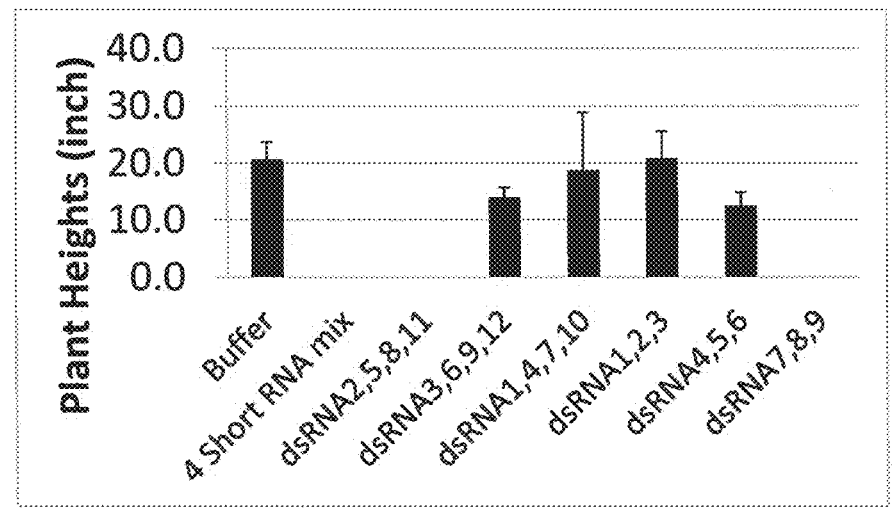
C

Figure 29
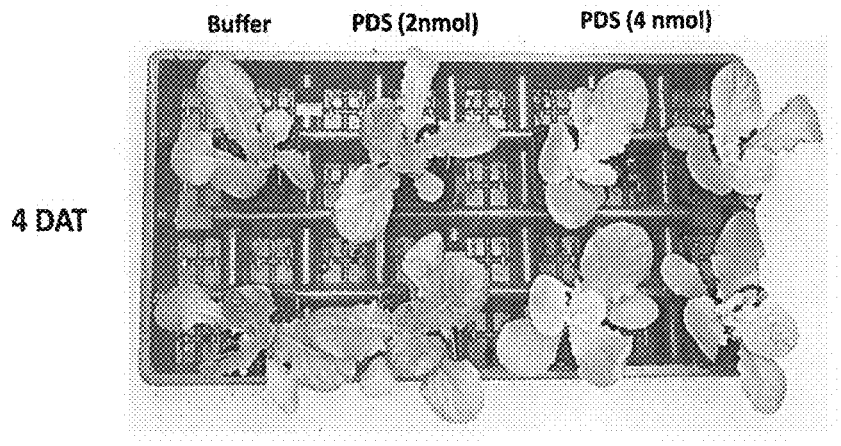
4 DAT
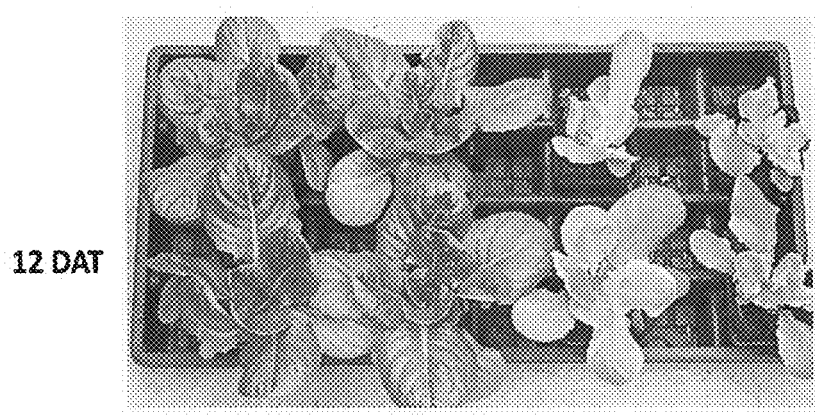
12 DAT
A
B

Figure 34

```
              810        820        830        840        850        860
PDS-2_ GTATGAACTTTCAGAATATTATACCGGATCAATATATTATGCT--GAAATATT--TTTCG
                            ||||  ||||   ||  ||  ||| |   ||||
PDS-1_ GCTGTATCATATCTTCTTCTTTAGAACACTAATAAATTAAACTTCGAGATAATGATTTCT
              330        340        350        360        370        380

870        880        890        900        910
PDS-2_ GAC-----TTTAAATAATTTCTT-TATTTAAATTTATTTTTATACAAAAATAACTAAATT
       |||     | ||||  ||  |  |  |||   |  ||||    || | ||||||    ||||
PDS-1_ GACAAGAGTATAAACAAGTGCATCTATGAAGATTTGAGGTTGTCCAAAAAAGTGACAATT
              390        400        410        420        430        440

920        930        940        950        960        970
PDS-2_ TCAATTACTTTTAAA----ATTATGATTATTTTTCAATTACCACT-TATACATCCTGC--
         |    |  |  ||||    |||     ||||||| || || | |  ||  ||   |
PDS-1_ TTGGGTTCCTATAAACTGTATTTACATTATTGTT-ATTGCAACTATAAAAATTTTAGAT
              450        460        470        480        490

980        990        1000       1010
PDS-2_ TATTTTGAAT--------TTCACCCGAAA-GAAC-TACTACTATACGTGGATC---CTC
       |||||  ||        |||| |   ||| |||  ||  |  |  |||    |    |||
PDS-1_ TATTTCCAAGCTCAGTTTCTTCAACTTAAATGAAGGTAGCACTTGAATTTCATCAGCCTC
              500        510        520        530        540        550

1020       1030       1040       1050       1060       1070
PDS-2_ AATGACCCAGTAACCCAAGTGGGAGATGTGTGCAAAGTGGTCAAATCTTAGAAGGAATGA
        ||||||||||||||||| |||||||||| | |||||||||||||| |||||||||||
PDS-1_ TATGACCCAGTAACCCATGTGGGAGATGGGAGCAAAGTGGTCAAACTTTAGAAGGAAT
              560        570        580        590        600        610
```

PDS-1 promoter sequence (SEQ ID NO:319)

and

PDS-2 promoter sequence (SEQ ID NO:320)

Comparison of spermine (SPM), spermidine (SPMD), ammonium sulfate (AMS)

POLYNUCLEOTIDE MOLECULES FOR GENE REGULATION IN PLANTS

CROSS-REFERENCE TO RELATED APPLICATIONS AND INCORPORATION OF SEQUENCE LISTING

This application is a Divisional of U.S. patent application Ser. No. 13/042,856 filed 8 Mar. 2011, issued as U.S. Pat. No. 9,121,022, which claims the benefit of priority of U.S. Provisional Patent Applications 61/311,762 filed 8 Mar. 2010, 61/349,807 filed 28 May 2010, and 61/381,556 filed 10 Sep. 2010, which are incorporated by reference in their entirety herein. The sequence listing that is contained in the file named "38-21_56855_D.txt", which is 133 kilobytes (measured in operating system MS-Windows) and was created on 7 Mar. 2011 and was filed in U.S. patent application Ser. No. 13/042,856 on 8 Mar. 2011 is incorporated herein by reference.

FIELD OF THE INVENTION

Disclosed herein are polynucleotide molecules for regulating genes in plants and methods of making and using such molecules.

BACKGROUND

The failure of herbicides to control resistant weeds is a problem especially when such weeds are growing in field of herbicide resistant crops that may have lower herbicide resistance than the weed. Herbicide-resistant weeds are identified with a variety of modes of action. Resistance resulting from selection for multiple copies of genes producing herbicide targeted proteins in pigweed is reported by Gaines et al. (2010) *Proc. Natl. Acad. Sci. USA,* 107(3): 1029-1034. Resistance resulting from mutations in genes producing herbicide targeted proteins in goosegrass, prickly lettuce, and ryegrass are reported by Baerson et al. (2002) *Plant Physiol.,* 129(3):1265-1275; Preston et al. (2006) *Pesticide Biochem. Physiol.,* 84(3):227-235; and Wakelin et al. (2006) *Weed Res.* (Oxford), 46(5):432-440. Vacuolar sequestration of glyphosate is an observed mechanism in glyphosate resistant horseweed; see Ge et al. (2010) *Pest Management Sci.,* 66:576-576. Resistance resulting from expression of enzymes that metabolize herbicides to an inactive chemical form in hairy crabgrass is reported by Hidayat et al. (1997) *Pesticide Biochem. Physiol.,* 57(2): 137-146. Reddy et al. (2008) *J. Agric. Food Chem.,* 56(6): 2125-2130 reported the accumulation of aminomethylphosphonic acid in plant species treated with glyphosate.

SUMMARY OF THE INVENTION

This invention provides polynucleotide molecules and methods for regulating genes in plants, e. g., by providing RNA for systemic regulation of genes. Various aspects of the invention provide polynucleotide molecules and methods for regulating endogenous genes and transgenes in a plant cell and polynucleotide molecules. The polynucleotides, compositions, and methods disclosed herein are useful for regulating endogenous genes of a plant pest or pathogen. In an aspect of the invention, the polynucleotide molecules are provided in compositions that can permeate or be absorbed into living plant tissue to initiate systemic gene silencing of endogenous genes or transgenes, or of their transcribed RNA. In some aspects of the invention polynucleotide molecules ultimately provide to a plant, or allow the production in cells in a plant, RNA that is capable of hybridizing under physiological conditions in a plant cell to RNA transcribed from a target endogenous gene or target transgene in the plant cell, thereby effecting regulation of the target gene, e. g., silencing or suppression of the target gene. In other aspects of the invention polynucleotide molecules disclosed herein are useful also for ultimately providing to a plant, or allowing the production in cells of a plant, RNA that is capable of hybridizing under physiological conditions to RNA transcribed from a target gene in a cell of an invertebrate pest or of a viral pathogen of the plant, thereby effecting regulation of the target gene, e. g., silencing or suppression of the target gene. In some aspects, the silencing or suppression of the target gene leads to the upregulation of another gene that is itself affected or regulated by the target gene's expression.

The compositions and methods of this invention are believed to operate through one or more of the several natural cellular pathways involved in RNA-mediated gene suppression as generally described in reviews by Brodersen and Voinnet (2006), *Trends Genetics,* 22:268-280; Tomari and Zamore (2005) *Genes & Dev.,* 19:517-529; Vaucheret (2006) *Genes Dev.,* 20:759-771; Meins et al. (2005) *Annu. Rev. Cell Dev. Biol.,* 21:297-318; and Jones-Rhoades et al. (2006) *Annu. Rev. Plant Biol.,* 57:19-53. RNA-mediated gene suppression generally involves a double-stranded RNA (dsRNA) intermediate that is formed intramolecularly within a single RNA molecule or intermolecularly between two RNA molecules. This longer dsRNA intermediate is processed by a ribonuclease of the RNase II family (Dicer or Dicer-like ribonuclease) to one or more shorter double-stranded RNAs, one strand of which is incorporated into the RNA-induced silencing complex ("RISC"). For example, the siRNA pathway involves the cleavage of a longer double-stranded RNA intermediate to small interfering RNAs ("siRNAs"). The size of siRNAs is believed to range from about 19 to about 25 base pairs, but the most common classes of siRNAs in plants include those containing 21 base pairs or 24 base pairs. See, Hamilton et al. (2002) *EMBO J.,* 21:4671-4679. As used herein, "oligonucleotide" means a polynucleotide molecule having a length of 18-25 nucleotides, similar to the size of processed small RNA molecules in gene silencing mechanisms. Various embodiments of this invention include compositions including oligonucleotides or polynucleotides or a mixture of both.

Aspects of the invention include compositions and methods for: providing single-stranded RNA molecules in a plant cell for systemic regulation of genes; herbicidal treatment with compositions including surfactant and a plant lethal agent which provides single-stranded RNA for suppression of an endogenous gene in a plant cell; topical coating onto a plant surface including a surfactant (e. g., an organosilicone surfactant) and an oligonucleotide or polynucleotide molecule for suppression of an endogenous gene in a plant cell; topically applied compositions for inducing systemic silencing of a target gene in a plant including (a) an agent for conditioning of a plant to permeation by polynucleotides and (b) polynucleotide molecules; and, herbicidal treatment with compositions including (a) an agent for conditioning of a plant to permeation by polynucleotide molecules, (b) polynucleotide molecules. Optionally these compositions can include a non-nucleotide herbicide.

In other aspects the invention provides methods for: controlling herbicide-resistant volunteer plants; investigating reverse genetics by modulating an endogenous gene in a plant by applying onto tissue of a growing plant a composition for providing single-stranded RNA molecules in a plant cell for systemic regulation of genes; inducing systemic silencing of a target gene including topical application of polynucleotides to a plant; inducing systemic silencing of a target gene in a plant by (a) conditioning of a plant to permeation by polynucleotides and (b) topically applying polynucleotides to the plant; investigating reverse genetics by modulating an endogenous gene in a plant by topically applying onto a living plant a topically applied composition including polynucleotide molecules and an agent for conditioning of a plant to permeation by such polynucleotide molecules.

In other aspects the invention provides a plant with exogenous DNA or RNA for suppressing an endogenous gene, where the exogenous DNA is not integrated into a chromosome of the plant, the exogenous RNA is not transcribed from DNA integrated into a chromosome of the plant, and the endogenous gene is suppressed by topical application of a polynucleotide to the plant. These and other aspects of the invention are described in greater detail in the following sections.

BRIEF DESCRIPTION OF THE DRAWINGS

FIG. 1 presents SEQ ID NO:1, a nucleotide sequence encoding Palmer amaranth EPSPS.

FIG. 2 presents SEQ ID NO:3 which is a nucleotide sequence of a synthesized Pol HI gene.

FIG. 3A depicts the plants 7 days after the glyphosate treatment. FIG. 3B depicts surfactant-treated plants that were treated with the long dsRNA solution followed by glyphosate treatment after 72 hours. FIG. 3C depicts surfactant-treated plants that were treated with the short dsRNA solution followed by glyphosate treatment after 72 hours.

FIG. 5 presents SEQ ID NO:2 which is a nucleotide sequence of a *Nicotiana benthamiana* phytoene desaturase.

FIG. 10 depicts the nucleotide sequence of a *Nicotiana benthamiana* phytoene desaturase (SEQ ID NO:2).

FIG. 12A illustrates apical leaf bleaching in *Nicotiana benthamiana* plants topically treated with buffer ("Control"), a 200-mer dsRNA polynucleotide with an RNA sequence corresponding to the segment consisting of nucleotides 914-1113 of SEQ ID NO:2 ("200 nt dsRNA"), and a combination of single-stranded DNA oligonucleotides and polynucleotides (SEQ ID NOs: 16, 17, 20, 21, 24, 25, and 26) ("ssDNA oligos") as described in Example 10.

FIG. 12B illustrates results of northern blot analysis of RNA isolated from *Nicotiana benthamiana* plants treated with buffer (control), the 200-mer dsRNA polynucleotide, and the ssDNA oligonucleotides. Also shown is RNA isolated from plants that had been stressed by being kept at 4 degrees Celsius and in the dark overnight prior to treatment with the 200-mer dsRNA polynucleotides.

FIG. 16 illustrates an alignment of the Palmer amaranth and *Nicotiana benthamiana* PDS DNA sequences showing about 71% identity (1252/1762) as described in Example 11.

FIG. 20 illustrates location of two small RNAs identified as abundant in EPSPS dsRNA-treated Palmer amaranth plants and which are shown as italicized underlined nucleotides at positions 564-588 and 743-767 of the full-length EPSPS (SEQ ID NO:40), as described in Example 14. The EPSPS sequence also shows the location of the four oligonucleotide-size "short" EPSPS dsRNA molecules (underlined, non-italicized text) and the three "long" double-stranded RNA polynucleotides (bolded text as described in Example 1.

FIG. 21A illustrates results of treating Palmer amaranth plants with surfactant followed by dsRNA at one of three application amounts, followed by herbicide, as described in Example 17. FIG. 21B illustrates results of assay 1 carried out on glyphosate-resistant Palmer amaranth grown from field-collected seeds as described in Example 17; plants are shown at 8 days and 30 days after treatment with herbicide.

FIG. 25A illustrates twelve dsRNA polynucleotides corresponding to DNA segments of approximately 250 bp each covering in a tiling manner the full coding sequence and part of the 5' and 3' untranslated regions of the Palmer EPSPS gene, as described in Example 21; the four oligonucleotide-size "short" EPSPS dsRNA molecules as described in Example 1 and FIG. 1 are located in the tiling segments 2, 3, 4, and 8 respectively, and are shown as light grey bars within those segments. FIG. 25B and FIG. 25C illustrates results of treating glyphosate-resistant Palmer amaranth plants with dsRNAs designed from these tiling segments or the four "short" dsRNA molecules or buffer.

FIG. 29A illustrates systemic silencing in lettuce plants evidenced by bleaching observed at 4 or 12 days after topical treatment with polynucleotides, as described in Example 24. FIG. 29B depicts the systemic silencing evidenced by bleaching observed at 4 after topical treatment with the four individual anti-sense ssDNAs ("HL287", SEQ ID NO:43; "HL288", SEQ ID NO:44; "HL289", SEQ ID NO:45; and "HL290", SEQ ID NO:46) or with a mixture of all four.

FIG. 30 also illustrates the stunting of the tomato plants treated with PDS polynucleotides (lower panel).

FIG. 34 illustrates an alignment of the *Nicotiana benthamiana* PDS locus 1 promoter (SEQ ID NO:319) and PDS locus 2 promoter (SEQ ID NO:320), as described in Example 30.

DETAILED DESCRIPTION OF THE INVENTION

Figure 3:
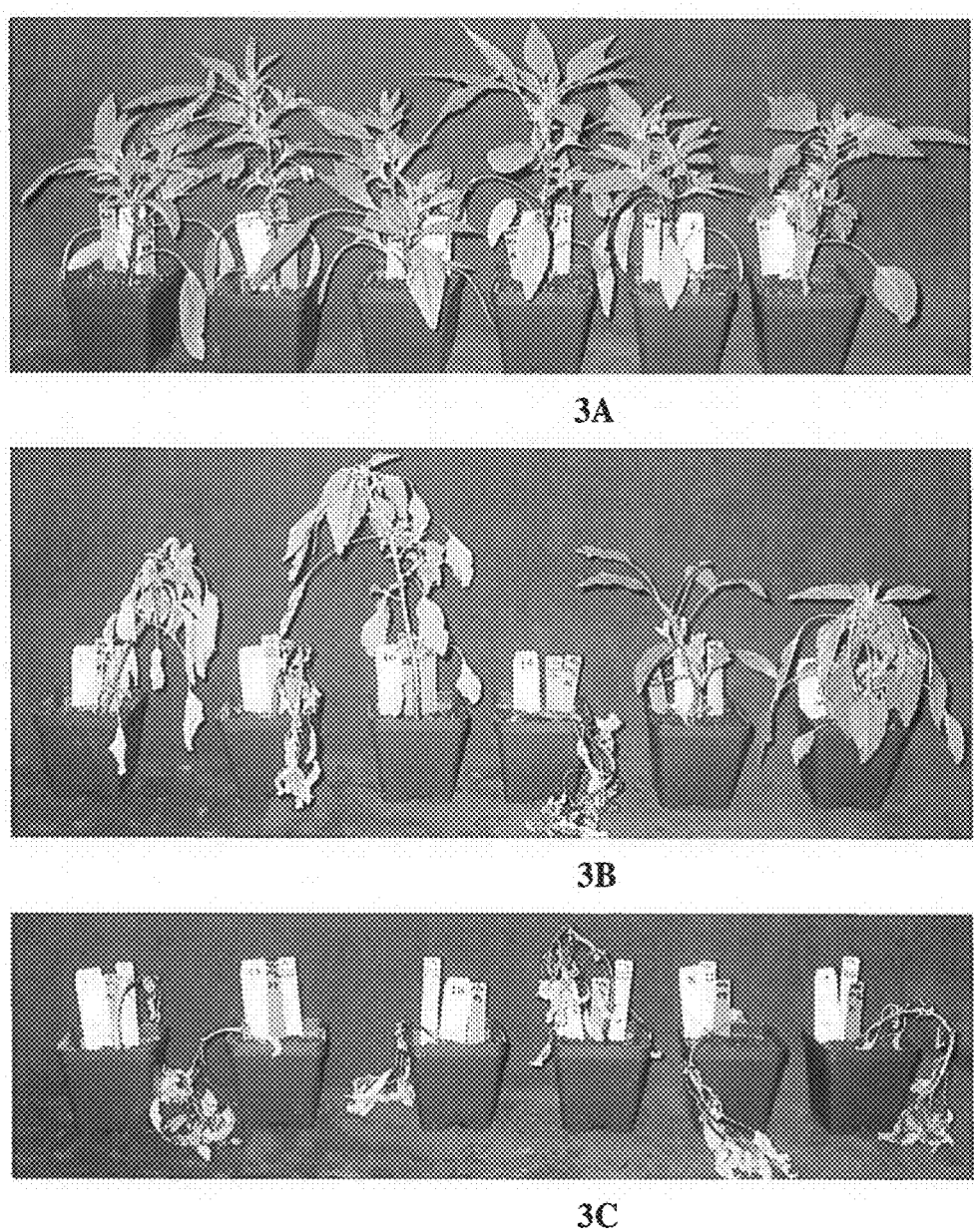
FIG. 3 illustrates the morbidity of Palmer amaranth plants treated with a dsRNA.

Unless otherwise stated, nucleic acid sequences in the text of this specification are given, when read from left to right, in the 5' to 3' direction. Nucleic acid sequences may be provided as DNA or as RNA, as specified; disclosure of one necessarily defines the other, as is known to one of ordinary skill in the art. Where a term is provided in the singular, the inventors also contemplate aspects of the invention described by the plural of that term. By "non-transcribable" polynucleotides is meant that the polynucleotides do not comprise a complete polymerase II transcription unit. As used here "solution" refers to homogeneous mixtures and non-homogeneous mixtures such as suspensions, colloids, micelles, and emulsions.

Polynudeotides

As used herein, "polynucleotide" refers to a nucleic acid molecule containing multiple nucleotides and generally refers both to "oligonucleotides" (a polynucleotide molecule of 18-25 nucleotides in length) and polynucleotides of 26 or more nucleotides. Embodiments of this invention include compositions including oligonucleotides having a length of 18-25 nucleotides (e. g., 18-mers, 19-mers, 20-mers, 21-mers, 22-mers, 23-mers, 24-mers, or 25-mers), or medium-length polynucleotides having a length of 26 or more nucleotides (e. g., polynucleotides of 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, about 65, about 70, about 75, about 80, about 85, about 90, about 95, about 100, about 110, about 120, about 130, about 140, about 150, about 160, about 170, about 180, about 190, about 200, about 210, about 220, about 230, about 240, about 250, about 260, about 270, about 280, about 290, or about 300 nucleotides), or long polynucleotides having a length greater than about 300 nucleotides (e. g., polynucleotides of between about 300 to about 400 nucleotides, between about 400 to about 500 nucleotides, between about 500 to about 600 nucleotides, between about 600 to about 700 nucleotides, between about 700 to about 800 nucleotides, between about 800 to about 900 nucleotides, between about 900 to about 1000 nucleotides, between about 300 to about 500 nucleotides, between about 300 to about 600 nucleotides, between about 300 to about 700 nucleotides, between about 300 to about 800 nucleotides, between about 300 to about 900 nucleotides, or about 1000 nucleotides in length, or even greater than about 1000 nucleotides in length, for example up to the entire length of a target gene including coding or non-coding or both coding and non-coding portions of the target gene). Where a polynucleotide is double-stranded, its length can be similarly described in terms of base pairs.

Polynucleotide compositions used in the various embodiments of this invention include compositions including oligonucleotides or polynucleotides or a mixture of both, including RNA or DNA or RNA/DNA hybrids or chemically modified oligonucleotides or polynucleotides or a mixture thereof. In some embodiments, the polynucleotide may be a combination of ribonucleotides and deoxyribonucleotides, e. g., synthetic polynucleotides consisting mainly of ribonucleotides but with one or more terminal deoxyribonucleotides or synthetic polynucleotides consisting mainly of deoxyribonucleotides but with one or more terminal dideoxyribonucleotides. In some embodiments, the polynucleotide includes non-canonical nucleotides such as inosine, thiouridine, or pseudouridine. In some embodiments, the polynucleotide includes chemically modified nucleotides. Examples of chemically modified oligonucleotides or polynucleotides are well known in the art; see, e. g., Verma and Eckstein (1998) *Annu. Rev. Biochem.*, 67:99-134. For example, the naturally occurring phosphodiester backbone of an oligonucleotide or polynucleotide can be partially or completely modified with phosphorothioate, phosphorodithioate, or methylphosphonate internucleotide linkage modifications, modified nucleoside bases or modified sugars can be used in oligonucleotide or polynucleotide synthesis, and oligonucleotides or polynucleotides can be labelled with a fluorescent moiety (e. g., fluorescein or rhodamine) or other label (e. g., biotin).

The polynucleotides can be single- or double-stranded RNA or single- or double-stranded DNA or double-stranded DNA/RNA hybrids or modified analogues thereof, and can be of oligonucleotide lengths or longer. In more specific embodiments of the invention the polynucleotides that provide single-stranded RNA in the plant cell are selected from the group consisting of (a) a single-stranded RNA molecule, (b) a single-stranded RNA molecule that self-hybridizes to form a double-stranded RNA molecule, (c) a double-stranded RNA molecule, (d) a single-stranded DNA molecule, (e) a single-stranded DNA molecule that self-hybridizes to form a double-stranded DNA molecule, and (f) a single-stranded DNA molecule including a modified Pol III gene that is transcribed to an RNA molecule, (g) a double-stranded DNA molecule, (h) a double-stranded DNA molecule including a modified Pol III gene that is transcribed to an RNA molecule, (i) a double-stranded, hybridized RNA/DNA molecule, or combinations thereof. In some embodiments these polynucleotides include chemically modified nucleotides or non-canonical nucleotides. In embodiments of the method the polynucleotides include double-stranded DNA formed by intramolecular hybridization, double-stranded DNA formed by intermolecular hybridization, double-stranded RNA formed by intramolecular hybridization, or double-stranded RNA formed by intermolecular hybridization. In one embodiment the polynucleotides include single-stranded DNA or single-stranded RNA that self-hybridizes to form a hairpin structure having an at least partially double-stranded structure including at least one segment that will hybridize under physiological conditions in the cell to RNA transcribed from the gene targeted for suppression. Not intending to be bound by any mechanism, it is believed that such polynucleotides are or will produce single-stranded RNA with at least one segment that will hybridize under physiological conditions in a cell to RNA transcribed from the gene targeted for suppression. In certain other embodiments the polynucleotides further includes a promoter, generally a promoter functional in a plant, e. g., a pol II promoter, a pol III promoter, a pol IV promoter, or a pol V promoter.

In some embodiments, the polynucleotide compositions are formulated with counter-ions or other molecules that are known to associate with nucleic acid molecules, e. g., tetraalkyl ammonium ions, trialkyl ammonium ions, sulfonium ions, lithium ions, and polyamines such as spermine, spermidine, or putrescine. In some embodiments, the polynucleotide compositions are formulated with a non-polynucleotide herbicide (e. g., the chemical herbicides disclosed herein in the section headed "Herbicide-Tolerance Proteins") or with a transferring agent or permeability-enhancing agent (see the section headed "Permeability-Enhancing Agents and Treatments").

The polynucleotides are designed to induce systemic regulation or suppression of an endogenous gene in a plant and are designed to have a sequence essentially identical or essentially complementary to the sequence (which can be coding sequence or non-coding sequence) of an endogenous gene of a plant or to the sequence of RNA transcribed from an endogenous gene of a plant. By "essentially identical" or "essentially complementary" is meant that the polynucleotides (or at least one strand of a double-stranded polynucleotide) are designed to hybridize under physiological conditions in cells of the plant to the endogenous gene or to RNA transcribed from the endogenous gene to effect regulation or suppression of the endogenous gene.

Embodiments of single-stranded polynucleotides functional in this invention have sequence complementarity that need not be 100% but is at least sufficient to permit hybridization to RNA transcribed from the target gene to form a duplex under physiological conditions in a plant cell to permit cleavage by a gene silencing mechanism. Thus, in embodiments the segment is designed to be essentially identical to, or essentially complementary to, a sequence of 18 or more contiguous nucleotides in either the target gene or messenger RNA transcribed from the target gene. By "essentially identical" is meant having 100% sequence identity or at least about 83, 84, 85, 86, 87, 88, 89, 90, 91, 92, 93, 94, 95, 96, 97, 98, or 99% sequence identity when compared to the sequence of 18 or more contiguous nucleotides in either the target gene or RNA transcribed from the target gene; by "essentially complementary" is meant having 100% sequence complementarity or at least about 83, 84, 85, 86, 87, 88, 89, 90, 91, 92, 93, 94, 95, 96, 97, 98, or 99% sequence complementarity when compared to the sequence of 18 or more contiguous nucleotides in either the target gene or RNA transcribed from the target gene. In some embodiments of this invention polynucleotide molecules are designed to have 100% sequence identity with or complementarity to one allele of a given target gene (e. g., coding or non-coding sequence of a gene for an herbicide-tolerance protein, an herbicide-deactivating protein, a stress-response gene, or an essential gene); in other embodiments the polynucleotide molecules are designed to have 100% sequence identity with or complementarity to multiple alleles of a given target gene.

In one aspect of the invention the polynucleotides are modified RNA polymerase III genes, e. g., genes that transcribe 7SL signal recognition particle RNA or U6 spliceosomal RNA (Pol III genes) or polynucleotides containing a functional Pol III promoter sequence. In one embodiment, the polynucleotides are modified Pol III genes containing sense and anti-sense DNA corresponding to RNA of the targeted gene identified for regulation replacing the DNA sequence originally transcribed by the Pol III gene.

The polynucleotides useful in this invention typically effect regulation or modulation (e. g., suppression) of gene expression during a period during the life of the treated plant of at least 1 week or longer and typically in systemic fashion. For instance, within days of treating a plant leaf with a polynucleotide composition of this invention, primary and transitive siRNAs can be detected in other leaves lateral to and above the treated leaf and in apical tissue.

Methods of making polynucleotides are well known in the art. Commercial preparation of oligonucleotides often provides 2 deoxyribonucleotides on the 3' end of the sense strand. Long polynucleotide molecules can be synthesized from commercially available kits, e. g., kits from Ambion have DNA ligated on the 5' end that encodes a bacterial T7 polymerase promoter that makes RNA strands that can be assembled into a dsRNA. Alternatively, dsRNA molecules can be produced from expression cassettes in bacterial cells that have regulated or deficient RNase II enzyme activity. Long polynucleotide molecules can also be assembled from multiple RNA or DNA fragments. In some embodiments design parameters such as Reynolds score and Tuschl rules are known in the art and are used in selecting polynucleotide sequences effective in gene silencing. In some embodiments random design or empirical selection of polynucleotide sequences is used in selecting polynucleotide sequences effective in gene silencing. In some embodiments the sequence of a polynucleotide is screened against the genomic DNA of the intended plant to minimize unintentional silencing of other genes.

The polynucleotide compositions of this invention are useful in compositions, such as solutions of polynucleotide molecules, at low concentrations, alone or in combination with other components (e. g., surfactants, salts, and non-polynucleotide herbicides) either in the same solution or in separately applied solutions. While there is no upper limit on the concentrations and dosages of polynucleotide molecules that can useful in the methods of this invention, lower effective concentrations and dosages will generally be sought for efficiency. The concentrations can be adjusted in consideration of the volume of spray applied to plant leaves. In one embodiment, a useful treatment for herbaceous plants using 25-mer oligonucleotide molecules is about 1 nanomole of oligonucleotide molecules per plant, e. g., from about 0.05 to 1 nanomole per plant. Other embodiments for herbaceous plants include useful ranges of about 0.05 to about 100 nanomoles, or about 0.1 to about 20 nanomoles, or about 1 nanomole to about 10 nanomoles of polynucleotides per plant. Very large plants, trees, or vines may require correspondingly larger amounts of polynucleotides. When using long dsRNA molecules that can be processed into multiple oligonucleotides, lower concentrations can be used. In the examples to below to illustrate embodiments of the invention the factor 1× when applied to oligonucleotide molecules is arbitrarily used to denote a treatment of 0.8 nanomoles of polynucleotide molecule per plant; 10×, 8 nanomoles of polynucleotide molecule per plant; and 100×, 80 nanomoles of polynucleotide molecule per plant, For example, in example 23 plants were treated with an aqueous solution comprising a 100× treatment of EPSPS dsRNA (264 micrograms or 80 nanomoles) per plant.

Single-Stranded RNA Molecules

This invention provides polynucleotide molecules for providing single-stranded RNA for systemic regulation of genes in a plant cell. More specifically, the invention also provides compositions and methods for inducing systemic regulation (e. g., systemic suppression or silencing) of a target gene in a plant by topical application to the plant of a polynucleotide molecule with a segment in a nucleotide sequence essentially identical to, or essentially complementary to, a sequence of 18 or more contiguous nucleotides in either the target gene or RNA transcribed from the target gene, whereby the composition permeates the interior of the plant and induces systemic regulation of the target gene by the action of single-stranded RNA that hybridizes to the transcribed RNA, e. g., messenger RNA. The polynucleotide molecule can be one or more polynucleotide molecules with a single such segment, multiples of such a segment, multiple different such segments, or combination thereof.

Transferring Agents, Permeability-Enhancing Agents and Treatments

The compositions and methods of this invention can comprise transferring agents or permeability-enhancing agents and treatments to condition the surface of plant tissue, e. g., leaves, stems, roots, flowers, or fruits, to permeation by the polynucleotide molecules into plant cells. The transfer of polynucleotides into plant cells can be facilitated by the prior or contemporaneous application of a polynucleotide-transferring agent to the plant tissue. In some embodiments the transferring agent is applied subsequent to the application of the polynucleotide composition. The polynucleotide transferring agent enables a pathway for polynucleotides through cuticle wax barriers, stomata and/or cell wall or membrane barriers and into plant cells. Suitable agents to facilitate transfer of the composition into a plant cell include agents that increase permeability of the exterior of the plant or that increase permeability of plant cells to oligonucleotides or polynucleotides. Such agents to facilitate transfer of the composition into a plant cell include a chemical agent, or a physical agent, or combinations thereof. Chemical agents for conditioning includes (a) surfactants, (b) an organic solvents or an aqueous solutions or aqueous mixtures of organic solvents, (c) oxidizing agents, (e) acids, (f) bases, (g) oils, (h) enzymes, or combinations thereof. Embodiments of the method can optionally include an incubation step, a neutralization step (e. g., to neutralize an acid, base, or oxidizing agent, or to inactivate an enzyme), a rinsing step, or combinations thereof. Embodiments of agents or treatments for conditioning of a plant to permeation by polynucleotides include emulsions, reverse emulsions, liposomes, and other micellar-like compositions. Embodiments of agents or treatments for conditioning of a plant to permeation by polynucleotides include counter-ions or other molecules that are known to associate with nucleic acid molecules, e. g., inorganic ammonium ions, alkyl ammonium ions, lithium ions, polyamines such as spermine, spermidine, or putrescine, and other cations. Organic solvents useful in conditioning a plant to permeation by polynucleotides include DMSO, DMF, pyridine, N-pyrrolidine, hexamethylphosphoramide, acetonitrile, dioxane, polypropylene glycol, other solvents miscible with water or that will dissolve phosphonucleotides in non-aqueous systems (such as is used in synthetic reactions). Naturally derived or synthetic oils with or without surfactants or emulsifiers can be used, e. g., plant-sourced oils, crop oils (such as those listed in the 9$^{th}$ Compendium of Herbicide Adjuvants, publicly available on line at www.herbicide.adjuvants.com) can be used, e. g., paraffinic oils, polyol fatty acid esters, or oils with short-chain molecules modified with amides or polyamines such as polyethyleneimine or N-pyrrolidine.

Such agents for conditioning of a plant to permeation by polynucleotides are applied to the plant by any convenient method, e.g., spraying or coating with a powder, emulsion, suspension, or solution; similarly, the polynucleotide molecules are applied to the plant by any convenient method, e. g., spraying or wiping a solution, emulsion, or suspension.

Examples of useful surfactants include sodium or lithium salts of fatty acids (such as tallow or tallowamines or phospholipids) and organosilicone surfactants. Other useful surfactants include organosilicone surfactants including nonionic organosilicone surfactants, e. g., trisiloxane ethoxylate surfactants or a silicone polyether copolymer such as a copolymer of polyalkylene oxide modified heptamethyl trisiloxane and allyloxypolypropylene glycol methylether (commercially available as SILWET® L-77 surfactant having CAS Number 27306-78-1 and EPA Number: CAL.REG.NO. 5905-50073-AA, currently available from Momentive Performance Materials, Albany, N.Y.). When SILWET L-77 surfactant is used as a pre-spray treatment of plant leaves or other surfaces, concentrations in the range of about 0.015 to about 2 percent by weight (wt %) (e. g., about 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.5 wt %) are efficacious in preparing a leaf or other plant surface for transfer of polynucleotide molecules into plant cells from a topical application on the surface.

Useful physical agents can include (a) abrasives such as carborundum, corundum, sand, calcite, pumice, garnet, and the like, (b) nanoparticles such as carbon nanotubes or (c) a physical force. Carbon nanotubes are disclosed by Kam et al. (2004) *J. Am. Chem. Soc.*, 126 (22):6850-6851, Liu et al. (2009) *Nano Lett.*, 9(3): 1007-1010, and Khodakovskaya et al. (2009) *ACS Nano*, 3(10):3221-3227. Physical force agents can include heating, chilling, the application of positive pressure, or ultrasound treatment. Embodiments of the method can optionally include an incubation step, a neutralization step (e. g., to neutralize an acid, base, or oxidizing agent, or to inactivate an enzyme), a rinsing step, or combinations thereof. The methods of the invention can further include the application of other agents which will have enhanced effect due to the silencing of certain genes. For example, when a polynucleotide is designed to regulate genes that provide herbicide resistance, the subsequent application of the herbicide can have a dramatic effect on herbicide efficacy.

Agents for laboratory conditioning of a plant to permeation by polynucleotides include, e. g., application of a chemical agent, enzymatic treatment, heating or chilling, treatment with positive or negative pressure, or ultrasound treatment. Agents for conditioning plants in a field include chemical agents such as surfactants and salts.

Target Genes and Essential Genes

Compositions and methods of the invention are useful for modulating the expression of an endogenous or transgenic target gene in a plant cell. In various embodiments, a target gene includes coding (protein-coding or translatable) sequence, non-coding (non-translatable) sequence, or both coding and non-coding sequence. Compositions of the invention can include polynucleotides and oligonucleotides designed to target multiple genes, or multiple segments of one or more genes. The target gene can include multiple consecutive segments of a target gene, multiple non-consecutive segments of a target gene, multiple alleles of a target gene, or multiple target genes from one or more species. Examples of target genes include endogenous plant genes and transgenes expressed in plant cells. Other examples of target genes include endogenous genes of plant viral pathogens or endogenous genes of invertebrate plant pests.

Target genes can include genes encoding herbicide-tolerance proteins, non-coding sequences including regulatory RNAs, and essential genes, which are genes necessary for sustaining cellular life or to support reproduction of an organism. Embodiments of essential genes include genes involved in DNA or RNA replication, gene transcription, RNA-mediated gene regulation, protein synthesis, energy production, and cell division. One example of a compendium of essential genes is described in Zhang et al. (2004) *Nucleic Acids Res.*, 32:D271-D272, and is available at tubic.tju. edu.cn/deg/; version DEG 5.4 lists 777 essential genes for *Arabidopsis thaliana*. Examples of essential genes include translation initiation factor (TIF) and ribulose-1,5-bisphosphate carboxylase oxygenase (RuBisCO). Target genes can include genes encoding transcription factors and genes encoding enzymes involved in the biosynthesis or catabolism of molecules in plants such as, but not limited to, amino acids, fatty acids and other lipids, sugars and other carbohydrates, biological polymers, and secondary metabolites including alkaloids, terpenoids, polyketides, non-ribosomal peptides, and secondary metabolites of mixed biosynthetic origin.

Compositions and Methods

Single-stranded RNA molecules of this invention can be provided directly to the plant cell as RNA or provided indirectly, e. g., where a polynucleotide molecule in the treatment composition causes in cells of a plant the production of the single-stranded RNA that is capable of hybridizing to the target gene's transcript. In many embodiments compositions of polynucleotide molecules further include one or more permeability enhancing agents to facilitate transfer of the polynucleotide molecules into a plant cell, such as agents for conditioning of a plant to permeation by polynucleotides. In aspects of the invention methods include one or more applications of the polynucleotide composition and one or more applications of a permeability-enhancing agent for conditioning of a plant to permeation by polynucleotides. When the agent for conditioning to permeation is an organosilicone surfactant, embodiments of the polynucleotide molecules are double-stranded RNA oligonucleotides, single-stranded RNA oligonucleotides, double-stranded RNA polynucleotides, single-stranded RNA polynucleotides, double-stranded DNA oligonucleotides, single-stranded DNA oligonucleotides, double-stranded DNA polynucleotides, single-stranded DNA polynucleotides, chemically modified RNA or DNA oligonucleotides or polynucleotides or mixtures thereof.

An aspect of the invention provides a method for inducing systemic silencing of a target gene in a plant including (a) conditioning of a plant to permeation by polynucleotides and (b) topical application of polynucleotide molecules to the plant, where the polynucleotide molecules include at least one segment of 18 or more contiguous nucleotides cloned from or otherwise identified from the target gene in either anti-sense or sense orientation, whereby the polynucleotide molecules permeate the interior of the plant and induce systemic silencing of the target gene. The conditioning and polynucleotide application can be performed separately or in a single step. When the conditioning and polynucleotide application are performed in separate steps, the conditioning can precede or can follow the polynucleotide application within minutes, hours, or days. In some embodiments more than one conditioning step or more than one polynucleotide molecule application can be performed on the same plant. In embodiments of the method, the segment can be cloned or identified from (a) coding (i. e., protein-encoding), (b) non-coding, or (c) both coding and non-coding parts of the target gene. Non-coding parts include DNA (or the RNA encoded by the DNA) encoding RNA regulatory sequences (e. g., promoters, introns, 5' or 3' untranslated regions, and microRNAs, trans-acting siRNAs, natural anti-sense siRNAs, and other small RNAs with regulatory function) or encoding RNAs having structural or enzymatic function (e. g., ribozymes, ribosomal RNAs, t-RNAs, aptamers, and riboswitches).

In various embodiments of the method for inducing systemic silencing of a target gene in a plant the target gene is (a) an endogenous gene of the plant, (b) an endogenous gene of a viral pathogen of the plant, (c) an endogenous gene of an invertebrate pest of the plant, (d) an endogenous gene of a symbiont of an invertebrate pest of the plant, or (e) an man-made gene inserted into a transgenic plant. In embodiments where the target gene is endogenous to a plant, the target gene (a) is an endogenous gene of the plant that is essential for maintaining the growth or life of the plant, (b) encodes a protein that provides herbicide resistance to the plant, or (c) transcribes to an RNA regulatory molecule. In embodiments of the method for inducing systemic silencing of a target gene in a plant, the conditioning includes application of a chemical agent, abrasion, wounding, enzymatic treatment, heating or chilling, treatment with positive or negative pressure, ultrasound treatment, or combinations thereof. In some embodiments, the conditioning includes application of a surfactant, such as organosilicone surfactants, e. g., a silicone polyether copolymer such as a copolymer of polyalkylene oxide modified heptamethyl trisiloxane and allyloxypolypropylene glycol methylether (commercially available as SILWET® L-77 surfactant). In embodiments of the method, the conditioning includes application of (a) a surfactant, (b) an organic solvent or an aqueous solution or aqueous mixture of an organic solvent, (c) a polypropylene glycol or an aqueous solution or aqueous mixture of polypropylene glycol, (d) nanoparticles, (e) an oxidizing agent, (f) an acid or a base, or (g) an oil, or of a combination thereof. Embodiments of the method can optionally include an incubation step, a neutralization step (e. g., to neutralize an acid, base, or oxidizing agent, or to inactivate an enzyme), a rinsing step, or combinations thereof.

The invention provides topical compositions for inducing systemic silencing of a target gene in a plant including (a) an agent for conditioning of a plant to permeation by polynucleotides and (b) polynucleotide molecules with at least one segment of 18 or more contiguous nucleotides essentially identical or complementary to the sequence of nucleotides of the target gene in either anti-sense or sense orientation. Such compositions can be used for the various methods disclosed herein including methods for investigating reverse genetics by modulating an endogenous gene in a plant, and as herbicidal compositions for the disclosed methods of weed control and volunteer plant control. Another aspect of the invention provides a plant including exogenous DNA or RNA for suppressing an endogenous gene, wherein the exogenous DNA is not integrated into a chromosome of the plant and the exogenous RNA is not transcribed from DNA integrated into a chromosome of the plant, and wherein the endogenous gene is suppressed by topical application of a polynucleotide to the plant. Alternatively, the exogenous DNA or RNA can be designed for suppressing an endogenous plant gene involved in responding to a pest or pathogen to provide control of plant pests or diseases. Such plant can be grown from seed or produced by a cutting, cloning, or grafting process (i. e., a plant not grown from a seed). Such plant is a row crop plant, a fruit, a vegetable, a tree, or an ornamental plant. For example, in embodiments of the inventions disclosed herein the plant is a row crop plant (e. g., corn, soybean, cotton, canola, sugar beet, alfalfa, sugarcane, rice, and wheat), or is a vegetable (e. g., tomato, sweet pepper, hot pepper, melon, watermelon, cucumber, eggplant, cauliflower, broccoli, lettuce, spinach, onion, peas, carrots, sweet corn, Chinese cabbage, leek, fennel, pumpkin, squash or gourd, radish, Brussels sprouts, tomatillo, garden beans, dry beans, or okra), or is an culinary plant (e. g., basil, parsley, coffee, or tea,), or is a fruit (e. g., apple, pear, cherry, peach, plum, apricot, banana, plantain, table grape, wine grape, citrus, avocado, mango, or berry), or is a tree grown for ornamental or commercial use (e. g., a fruit or nut tree, or is an ornamental plant (e. g., an ornamental flowering plant or shrub or turf grass). Embodiments of a plant produced by a cutting, cloning, or grafting process (i. e., a plant not grown from a seed) include fruit trees and plants including citrus, apples, avocados, tomatoes, eggplant, cucumber, melons, watermelons, and grapes as well as various ornamental plants.

Methods for Investigating Reverse Genetics

In yet another aspect, the invention provides a method for investigating reverse genetics by regulating or modulating an endogenous target gene in a plant; such method includes applying onto tissue of a growing plant a composition for providing (directly or indirectly) single-stranded RNA of this invention for systemic regulation of genes in a plant cell. In embodiments of such a method, messenger RNA encoding a protein or regulatory RNA gene is targeted by a polynucleotide of the invention, effecting modulation of the gene during a period of at least 1 week during the life of the plant, e. g., to identify traits that can be imparted by topical application of polynucleotides. The method can further include additional steps, e. g., exposing the plant to an array of compounds to identify herbicide interactions or exposing the plant to abiotic stress (e. g., water deficit stress, nutrient deficit stress, heat stress, cold stress, salinity stress) or to biotic treatments (e. g., challenge with an insect or nematode pest or with a viral, fungal, or bacterial pathogen or exposure to a chemical compound or biological treatment) to identify responses by the plant to the stress or treatment. In another aspect of the invention libraries of plants with a variety of transiently silenced genes are screened against libraries of compounds (e. g., herbicides, phytohormones, endogenous or exogenous defense elicitors such as salicylic acid or harpins, deficiencies of molecules providing a plant nutrient such as nitrogen, phosphorous, potassium, sulfur, calcium, magnesium, iron, and zinc) to identify interactions with such compounds. Examples of plants useful in such screens include *Amaranthus palmeri* and *Nicotiana benthamiana*.

Methods for Transgene Silencing

In still yet another aspect of the invention, this method can be used to silence a transgene being expressed in a plant, thus providing a negative control that is an event-independent measurement of a transgene's contribution to plant performance or effect on a trait. Imparting a negative control effect may require multiple successive treatments with the polynucleotide molecules of this invention during the life cycle of a plant.

Specific Applications

In a related aspect the compositions and methods of the invention are also useful for transiently silencing one or more genes in a growing plant cell or whole plant to effect a desired phenotype in response to culture conditions, environmental or abiotic or biotic stress, or change in market demand during the growing season or in the post-harvest environment. For example, compositions and methods of the invention are useful for transiently suppressing a biosynthetic or catabolic gene in order to produce a plant or plant product with a desired phenotype, such as a desired nutritional composition of a crop plant product, e. g., suppressing a FAD2 gene to effect a desired fatty acid profile in soybean or canola or other oilseed or suppressing a lignin biosynthetic genes such as COMT and CCOMT to provide more easily digestible forage plants. Similarly, compositions and methods of the invention are useful for transiently suppressing an RNA regulatory molecule such as a microRNA (miRNA) or an endogenous miRNA decoy such as an endogenous miRNA, miRNA precursor, or miRNA decoy as disclosed in US Patent Application Publication 2009/0070898 which is incorporated herein by reference. Embodiments of the invention are useful for suppressing an endogenous plant gene involved in responding to a pest or pathogen, thus providing control of plant pests or diseases. The polynucleotides, compositions, and delivery methods disclosed herein are further useful in suppressing an endogenous target gene of an invertebrate pest of a plant, e. g., lepidopteran or coleopteran pests which can ingest RNA from the plant, thus providing control of plant pests or pest-induced diseases, e. g., by use of a topical spray for crop plants, vegetables, or fruit trees with DNA or RNA molecules targeting an invertebrate essential gene or a gene of a symbiont of the invertebrate pest. The polynucleotides, compositions, and delivery methods disclosed herein are further useful in providing control of a viral pathogen, e. g., by use of a topical anti-viral spray for crop plants, vegetables, or fruit trees with DNA or RNA molecules targeting a viral gene.

Herbicidal Compositions and Methods

An aspect of the invention provides a liquid herbicidal composition comprising polynucleotide molecules as a plant lethal agent which provides at least one species of single-stranded RNA which can hybridize under physiological conditions in a plant cell to RNA transcribed from endogenous gene(s) in the plant cell. In some embodiments, the target gene encodes a protein that provides tolerance to an herbicide or encodes a gene essential for maintaining the growth or life of the plant. The liquid herbicidal composition can further include permeability-enhancing agents, non-nucleotide herbicides, or combinations thereof and can be used in a multi-step treatment with the non-nucleotide herbicide and/or the permeability-enhancing agents applied separately. An embodiment of the liquid herbicidal composition is a liquid including an organosilicone surfactant as permeability-enhancing agent and oligonucleotides or polynucleotides as plant lethal agent which provide to cells of the plant single-stranded RNA capable of hybridizing under physiological conditions in the plant cells to RNA transcribed from a target gene in the plant cell to effect silencing of the target gene. In one embodiment a liquid herbicidal composition effective against glyphosate-resistant plants includes an organosilicone surfactant such as SILWET® L-77 surfactant and polynucleotide molecules for providing single-stranded RNA capable of hybridizing under physiological conditions in the plant cells to the RNA transcript of an endogenous or transgenic EPSPS gene encoding an EPSPS protein that provides tolerance to glyphosate When the polynucleotide molecule is designed to hybridize under physiological conditions in a plant cell to mRNA encoding an endogenous, protein or non-protein coding RNA that essential for maintaining plant growth or life and to effect gene silencing and reduction of the essential protein, the polynucleotide molecule can function as a plant lethal agent, i.e., a nucleotide herbicide. These herbicidal compositions including polynucleotide molecules can be adapted for topical coating onto leaves of a growing plant or for application onto roots or cut stems, e. g., of hydroponically grown or pot-grown plants.

An aspect of the invention provides a composition adapted for topical coating onto leaves or other surfaces of a living plant including a permeability-enhancing agent, e.g., a surfactant such as an organosilicone surfactant, and oligonucleotides or polynucleotides that provide (directly or indirectly) single-stranded RNA that can hybridize under physiological conditions in a plant cell to RNA transcribed from an endogenous plant gene in the cell. In one embodiment the endogenous plant gene is an endogenous plant gene encoding a protein that provides herbicide tolerance to herbicides such as glyphosate, dicamba, or sulfonylurea. Examples of such proteins that provide herbicide tolerance are disclosed below in the section "Herbicide-Tolerance Proteins".

Another aspect of the invention provides a method for controlling herbicide-resistant volunteer plants growing in a field of herbicide-resistant crop plants including applying onto the leaves or other surface of the volunteer plants a composition that provides to, or allows the production in, cells of the volunteer plants a single-stranded RNA molecule that is capable of hybridizing under physiological conditions in cells of the volunteer plants to RNA that is transcribed from an endogenous gene in the cells, wherein the endogenous gene (i) is an essential gene for maintaining the growth or life of the volunteer plant, (ii) encodes a protein that provides herbicide resistance to the volunteer plant, or (iii) transcribes to an RNA regulatory agent (e. g., promoters, also miRNA precursors, miRNAs, trans-acting siRNAs, and other non-coding RNAs having a regulatory function such as aptamers and riboswitches). The composition that provides to, or allows the production in, cells of the volunteer plants a single-stranded RNA molecule that is capable of hybridizing under physiological conditions in cells of the volunteer plants to RNA that is transcribed from an endogenous gene in the cells includes at least one polynucleotide molecule selected from the group consisting of (a) a single-stranded RNA molecule, (b) a single-stranded RNA molecule that self-hybridizes to form a double-stranded RNA molecule, (c) a double-stranded RNA molecule, (d) a single-stranded DNA molecule, (e) a single-stranded DNA molecule that self-hybridizes to form a double-stranded DNA molecule, and (f) a single-stranded DNA molecule including a modified Pol III gene that is transcribed to an RNA molecule, (g) a double-stranded DNA molecule, (h) a double-stranded DNA molecule including a modified Pol III gene that is transcribed to an RNA molecule, and (i) a double-stranded, hybridized RNA/DNA molecule; In embodiments for silencing or suppression of an endogenous gene of a volunteer plant that encodes a protein that provides herbicide resistance to the volunteer plant, the method can include applying onto the volunteer plant a quantity of the herbicide for which the protein provides resistance. Compositions and methods of the invention are useful in controlling herbicide-tolerant (resistant) weeds or volunteer herbicide-tolerant (resistant) transgenic plants that may be growing in crop fields, e. g., a field of herbicide-resistant crop plants such as corn, soybean, cotton, canola, sugar beet, alfalfa, sugarcane, rice, wheat, as well as fruit and vegetable crops. In some such embodiments the weed or the volunteer plant is pigweed (e. g., Palmer amaranth) and other amaranth species, mare's tail (horseweed), waterhemp, giant ragweed, common ragweed, johnsongrass, goosegrass, ryegrass, hairy crabgrass, prickly lettuce, velvetleaf, alfalfa, corn, soybean, canola, cotton, sugar beet, sugarcane, rice, or wheat. In some such embodiments the endogenous gene encodes a protein that provides herbicide tolerance; examples of such proteins are disclosed herein in the section "Herbicide-Tolerance Proteins". In other such embodiments single-stranded RNA selectively suppresses a gene in a specific plant species but not in others, to permit selective control of that plant species. In still other such embodiments a non-selective, single-stranded RNA molecule suppresses a common gene in multiple plant species, permitting broader control across a group or taxon of plants. In more specific embodiments the method further includes applying onto the weed or volunteer plant a quantity of non-nucleotide herbicide (e. g., glyphosate, dicamba, glufosinate or sulfonylurea) for which the protein targeted by an RNA molecule provides resistance allowing dual modes of action through reducing production of the target protein by action of the RNA molecule and inhibiting the function of protein that is produced by action of the non-nucleotide herbicide; the herbicide can be applied in a separate (earlier or later) step from, or together with, the nucleotide composition. Applying a polynucleotide composition concurrently with, or followed by, application of a conventional non-nucleotide herbicide in some cases provides weed or volunteer plant control with synergistic effect (i. e., where the combined effect is greater than the sum of effects of the treatments made separately).

Herbicide-Tolerance Proteins

Natural (non-transgenic) and transgenic plants exhibiting herbicide tolerance (resistance) often have a gene that encodes a protein that is responsible for the herbicide tolerance, e. g., a transgene that provides the tolerance, a mutated endogenous gene that provides the tolerance or multiple copies of an endogenous gene that is normally targeted by an herbicide. A strategy for control of such plants is to apply an agent that suppresses, or at least reduces the expression of, the gene encoding the protein that imparts herbicide tolerance. Examples of a protein that provides tolerance to an herbicide include e. g., a 5-enolpyruvylshikimate-3-phosphate synthase (EPSPS), a glyphosate oxidoreductase (GOX), a glyphosate decarboxylase, a glyphosate-N-acetyl transferase (GAT), a dicamba monooxygenase, a phosphinothricin acetyltransferase, a 2,2-dichloropropionic acid dehalogenase, an acetohydroxyacid synthase, an acetolactate synthase, a haloarylnitrilase, an acetyl-coenzyme A carboxylase, a dihydropteroate synthase, a phytoene desaturase, a protoporphyrin IX oxygenase, a hydroxyphenylpyruvate dioxygenase, a para-aminobenzoate synthase, a glutamine synthase, a cellulose synthase, a beta-tubulin, and a serine hydroxymethyltransferase.

Examples of nucleic acids encoding proteins conferring tolerance to herbicides include 5-enolpyruvylshikimate-3-phosphate synthases (EPSPS; see, e. g., U.S. Pat. Nos. 5,627,061, 5,633,435 RE39247, 6,040,497, and 5,094,945, and PCT International Application Publications WO04074443 and WO04009761), glyphosate oxidoreductase (GOX; U.S. Pat. No. 5,463,175), glyphosate decarboxylase (PCT International Application Publication WO05003362, U.S. Pat. No. 7,405,347, and U. S. Patent Application Publication 2004/0177399), glyphosate-N-acetyl transferase (GAT; U.S. Pat. No. 7,714,188) conferring tolerance to glyphosate; dicamba monooxygenase conferring tolerance to auxin-like herbicides such as dicamba (U.S. Pat. No. 7,105,724); phosphinothricin acetyltransferase (pat or bar) conferring tolerance to phosphinothricin or glufosinate (U.S. Pat. No. 5,646,024); 2,2-dichloropropionic acid dehalogenase conferring tolerance to 2,2-dichloropropionic acid (Dalapon) (PCT International Application Publication WO9927116); acetohydroxyacid synthase or acetolactate synthase conferring tolerance to acetolactate synthase inhibitors such as sulfonylurea, imidazolinone, triazolopyrimidine, pyrimidyloxybenzoates and phthalide (U.S. Pat. No. 6,225,105); haloarylnitrilase (Bxn) for conferring tolerance to bromoxynil (U.S. Pat. No. 4,810,648); modified acetyl-coenzyme A carboxylase for conferring tolerance to cyclohexanedione (sethoxydim) and aryloxyphenoxypropionate (haloxyfop) (U.S. Pat. No. 6,414,222); dihydropteroate synthase (sul I) for conferring tolerance to sulfonamide herbicides (U.S. Pat. No. 5,719,046); 32 kDa photosystem II polypeptide (psbA) for conferring tolerance to triazine herbicides (Hirschberg et al., 1983, *Science*, 222:1346-1349); anthranilate synthase for conferring tolerance to 5-methyltryptophan (U.S. Pat. No. 4,581,847); dihydrodipicolinic acid synthase (dap A) for conferring to tolerance to aminoethyl cysteine (PCT International Application Publication WO8911789); phytoene desaturase (crtI) for conferring tolerance to pyridazinone herbicides such as norflurazon (Japan Patent JP06343473); hydroxyphenylpyruvate dioxygenase, a 4-hydroxyphenylacetic acid oxidase and a 4-hydroxyphenylacetic 1-hydrolase (U.S. Pat. No. 7,304,209) for conferring tolerance to cyclopropylisoxazole herbicides such as isoxaflutole (U.S. Pat. No. 6,268, 549); modified protoporphyrinogen oxidase I (protox) for conferring tolerance to protoporphyrinogen oxidase inhibitors (U.S. Pat. No. 5,939,602); aryloxyalkanoate dioxygenase (AAD-1) for conferring tolerance to an herbicide containing an aryloxyalkanoate moiety (WO05107437); a serine hydroxymethyltransferase (US Patent Application Publication 2008/0155716), a glufosinate-tolerant glutamine synthase (US Patent Application Publication 2009/0018016). Examples of such herbicides include phenoxy auxins (such as 2,4-D and dichlorprop), pyridyloxy auxins (such as fluroxypyr and triclopyr), aryloxyphenoxypropionates (AOPP) acetyl-coenzyme A carboxylase (ACCase) inhibitors (such as haloxyfop, quizalofop, and diclofop), and 5-substituted phenoxyacetate protoporphyrinogen oxidase IX inhibitors (such as pyraflufen and flumiclorac). The nucleotide sequences of the nucleic acids encoding herbicide-tolerance proteins and the sequences of the herbicide-tolerance proteins, as disclosed in the U. S. patent and patent application publications cited in this paragraph are incorporated herein by reference.

Aspects of this invention provide polynucleotides and methods that directly or indirectly provide to a plant cell RNAs that hybridize to RNA encoding such herbicide-tolerance proteins at a level to be lethal to the plant or at least at a level to reduce herbicide tolerance. Due to the sequence degeneracy of the DNA encoding herbicide-tolerance proteins it is possible to design a polynucleotide for use in this invention that is specifically effective in a particular plant. Due to conservation of domains of DNA among a multitude of plants it is possible to design a polynucleotide for use in this invention that is effective across a variety of plants.

In an embodiment the polynucleotide is admixed with the corresponding herbicide to potentiate the activity of the herbicide by providing improved herbicidal activity. In an embodiment the polynucleotide is utilized separately from the herbicide but in combination with an application of the herbicide as a pre- or post-treatment. In embodiments the organosilicone surfactant is advantageously combined with the herbicide and the polynucleotide or is combined with one or the other when the compositions are applied in a sequential manner. Plants in a greenhouse setting can be treated using a track sprayer or laboratory sprayer with a 11001XR spray nozzle to deliver the sample solution at a determined rate (e. g., 140 L/ha) at 0.25 MPa pressure. In the field the treatment solution can be applied with a $CO_2$ pressurized backpack sprayer calibrated to deliver the appropriate rate of the composition with a 11015 flat fan spray nozzle with a customized single nozzle assembly (to minimize waste) at a spray pressure of 0.25 MPa; the single nozzle sprayer provides an effective spray swath of 60 cm above the canopy of 3 to 12 inch tall growing plants.

Example 1

This example illustrates the utility of the polynucleotide molecules of this invention in controlling herbicide resistant weeds. Genotypes of glyphosate-resistant Palmer amaranth were identified as having multiple copies, e. g., from 4 to more than 100 copies, of the gene encoding 5-enolpyruvyl-shikimate-3-phosphate synthase (EPSPS) which is targeted by the glyphosate compounds in herbicide treatments.

With reference to SEQ ID NO:1 as shown in FIG. 1, four oligonucleotide-size "short" dsRNA molecules were designed with an anti-sense strand that is capable of hybridizing to the mRNA transcribed from the Palmer amaranth EPSPS gene at positions 14-38 (short dsRNA-1), positions 153-177 (short dsRNA-2), 345-369 (short dsRNA-3), and 1105-1129 (short dsRNA-4), as indicated by underlined nucleotides in FIG. 1. The four designed short dsRNAs were purchased from Integrated DNA Technologies (IDT); the dsRNAs had a two nucleotide overhang at the 3' end of the anti-sense strand, and had two deoxynucleotides as the terminal nucleotides at the 3' end of the sense strand.

With reference to SEQ ID NO:1 and FIG. 1, three "long" double-stranded RNA polynucleotides were designed with one strand that is capable of hybridizing to the mRNA transcribed from the Palmer amaranth EPSPS gene at positions 16-170 (long dsRNA-1), 451-722 (long dsRNA-2), and 1109-1328 (long dsRNA-3) as indicted by the bolded nucleotides in FIG. 1. The three designed long dsRNAs were made using an Ambion MEGAscript® RNAi Kit, Cat. No. 1626.

Vegetative clones of glyphosate-resistant Palmer amaranth with 16 copies of the endogenous gene encoding EPSPS (Gaines, et al. (2010) *Proceedings of the National Academy of Sciences* 107(3): 1029-1034) were grown in 3.5 inch square pots with SunGro® Redi-earth seedling mix containing 3.5 kg/cubic meter Osmocote® 14-14-14 fertilizer in a greenhouse with 14-hour photoperiod and a daytime temperature of 30 degrees centigrade and night temperature of 20 degrees centigrade; the plants were watered with deionized water as necessary.

A pretreatment surfactant solution for leaf dip was prepared by diluting SILWET L-77 brand organosilicone surfactant with distilled water to 0.1% (v/v). A pretreatment 5% (w/v) carborundum solution was prepared by mixing 2 g carborundum (400 grit) in 40 ml distilled water. A treatment buffer solution was prepared with 10 mM sodium phosphate and 0.01% (v/v) SILWET L-77 organosilicone surfactant in DEPC water (Omega Bio-Tek) and adjusted to pH 6.8. A short dsRNA solution was prepared with equimolar amounts of each of the four short dsRNAs (identified above) in treatment buffer solution at a concentration of 0.005 nanomoles of each short dsRNA per microliter. A long dsRNA solution was prepared with equimolar amounts of each of the three long dsRNAs in treatment buffer at a concentration of 0.0006 nanomoles of each of long dsRNA per microliter. A mixed (short/long) dsRNA solution was prepared with 0.005 nanomoles of each of the four short dsRNAs and 0.0006 nanomoles of each of the three long dsRNAs per microliter.

Vegetative clones of glyphosate-resistant Palmer amaranth with 16 copies of the endogenous gene encoding EPSPS were pre-treated with carborundum solution or surfactant solution to condition the leaves to transfer or permeation of dsRNA. For carborundum solution pre-treatment leaf abrasion was effected by gently rubbing 0.5 ml of the carborundum solution on the upper surface of a leaf, rinsing with water and blotting dry. For surfactant solution pre-treatment four, fully-expanded, mature source leaves were dipped in the surfactant solution and allowed to dry. After leaf pre-treatment by carborundum solution or surfactant solution, the conditioned leaves were treated with either buffer solution (as a control) or 40 microliters of a dsRNA solution (applying 10 microliters of dsRNA solution on each of 4 leaves per plant). Treatment with the short dsRNA solution applied about 0.8 nanomoles of short dsRNA molecules (0.2 nanomoles of each short dsRNA) to each treated plant. Treatment with the long dsRNA solution applied about 0.072 nanomoles of long dsRNA molecules (0.024 nanomoles of each long dsRNA) to each treated plant. Treatment with the mixed (short/long) dsRNA solution applied about 0.8 nanomoles of the short dsRNA molecules and about 0.072 nanomoles of the long dsRNA molecules to each treated plant. Except for controls, all plants were sprayed with a glyphosate herbicide solution (1682 g acid equivalent per hectare of Roundup® WeatherMAX® brand herbicide) immediately, 48, or 72 hours after dsRNA treatment and evaluated at least after 7 days post-glyphosate treatment.

Results:

Six surfactant-treated, control plants (no dsRNA molecule treatment) survived glyphosate treatment. See FIG. 3A for a picture of the plants 7 days after the glyphosate treatment.

Two of four carborundum abrasive-treated, control plants (no dsRNA molecule treatment) were killed by glyphosate treatment.

Six surfactant-treated plants that were treated with glyphosate immediately after application of the mixed (short/long) dsRNA solution survived but were stunted.

Six surfactant-treated plants that were treated only with the mixed (short/long) dsRNA solution and no glyphosate survived. Five of six surfactant-treated plants that were treated with the mixed (short/long) dsRNA solutions followed by glyphosate treatment were killed.

Five of six surfactant-treated plants that were treated with glyphosate 48 hours after application of the mixed (short/long) dsRNA solution were killed.

Three of four carborundum-treated plants that were treated with glyphosate 48 hours after application of the mixed (short/long) dsRNA solution were killed.

Five of six surfactant-treated plants, that were treated with the long dsRNA solution, followed by glyphosate treatment after 72 hours, were killed; see FIG. 3B. Six of six surfactant-treated plants, that were treated with the short dsRNA solution, followed by glyphosate treatment after 72 hours, were killed; see FIG. 3C.

Example 2

This example illustrates the utility of the polynucleotide molecules of this invention for improving the control of glyphosate herbicide-sensitive weeds. The mixed (short/long) dsRNA solutions prepared in Example 1 were applied to glyphosate-sensitive velvetleaf plants (a total of 40 microliters applied to two leaves) that had been pre-treated with the surfactant solution used in Example 1. Control plants were treated with buffer only following pre-treatment with the surfactant solution. 48 hours after dsRNA treatment the plants were treated with glyphosate herbicide solution (53 g acid equivalent per hectare of Roundup® WeatherMAX® brand glyphosate herbicide). A two-fold increase in glyphosate activity as estimated by observing plant growth (measured as plant height) was observed in the plants treated with the polynucleotide composition and herbicide as compared to control plants treated with buffer and herbicide. The plants treated with the polynucleotide composition and herbicide survived with severe stunting; the control plants treated with buffer and herbicide survived and fully recovered. Similar results were obtained with other glyphosate herbicide-sensitive weeds, i. e., glyphosate herbicide-sensitive waterhemp, redroot pigweed, giant ragweed, prickly lettuce, tobacco, and dandelion.

Example 3

This example illustrates the utility of the polynucleotide molecules of this invention for controlling weeds in transgenic glyphosate-resistant crops. Transgenic alfalfa, canola, corn, cotton, rice, soybean, sugarcane, sugar beet, and wheat plants having recombinant DNA for expressing a bacterial EPSPS (see U.S. Pat. RE39,247 for a description of glyphosate-resistant "class II" EPSPS genes) are treated with (a) the surfactant solution used in Example 1, (b) the mixed (short/long) dsRNA solution prepared in Example 1, and (c) glyphosate herbicide solution (1682 g acid equivalence per hectare Roundup® WeatherMAX®) 48 hours after dsRNA treatment. After 30 days all transgenic glyphosate-resistant crop plants survive and exhibit no stunting.

Example 4

Figure 4:
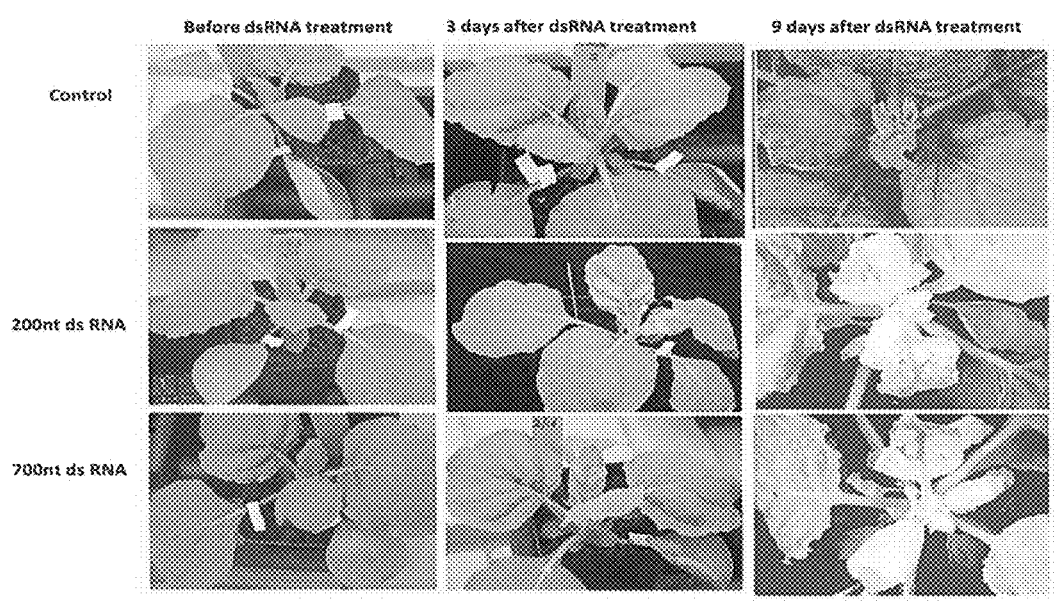
FIG. 4 illustrates the bleaching in *Nicotiana benthamiana* plants treated with a dsRNA composition.

This example illustrates the utility of the polynucleotide molecules of the invention as herbicidal agents. Two dsRNA polynucleotide molecules were designed to target overlapping segments of mRNA encoding phytoene desaturase in tobacco (*Nicotiana benthamiana*). With reference to SEQ ID NO:2 and FIG. 5, a dsRNA targeting a 192 nt length (shown in bold in FIG. 5) and a 685 nt length (shown in underline in FIG. 5) of the mRNA were made using an Ambion® MEGAscript® kit. Separate dsRNA solutions were prepared. Tobacco plant leaves were pretreated with surfactant solution prepared as in Example 1 and then treated with either one of the dsRNA solutions applying about 0.6 micromoles of dsRNA per plant. On day 9 after dsRNA treatment phytoene desaturase silencing was apparent from visible leaf bleaching on apical leaves; see FIG. 4. At 15 days after treatment with dsRNA one half of the treated plants appeared to be dead and the other half of the plants had most of the above ground tissues bleached. Northern blot analysis indicates the presence of siRNAs corresponding to the dsRNAs used in treatment.

Example 5

This example further illustrates the utility of polynucleotide molecules of the invention as herbicidal agents. dsRNA oligonucleotide molecules are designed to target RNA encoding EPSPS for each of the following plants: ragweed (*Ambrosia artemisiifolia*), giant ragweed (*Ambrosia trifida*), Johnsongrass (*Sorghum halepense*), hairy fleabane (*Conzya bonariensis*), sourgrass (*Digitaria insularis*), liverseedgrass (*Urochloa panicoides*), euphorbia (*Euphorbia heterophylla*), junglerice (*Echinochloa colona*), lambsquarters (*Chenopodium album*), green foxtail (*Setaria viridis*), foxtail millet (*Setaria italic*), barnyard grass (*Echinochloa crus-galli*), crabgrass (*Digitaria sanguinalis*), cocklebur (*Xanthium strumarium*), blackgrass (*Alopecurus myosuroides*), wild oat (*Avenafatua*), sicklepod (*Senna obtusifolia*), morning glories (*Ipomoea* sp.), field bindweed (*Convolvulus arvensis*), shattercane (*Sorghum bicolor*), dayflower (*Commelina*), Spiderwort (*Tradescantia* sp.), ryegrass (*Lolium* sp.), goosegrass (*Eleusine indica*), horseweed (Conzya canadensis), buckhorn plantain (*Plantago lanceolata*), pigweed (*Amaranthus palmeri*), rough-fruit amaranth (*Amaranthus tuberculatus*), tumble pigweed (*Amaranthus albus*), smooth pigweed (*Amaranthus hybridus*), redroot pigweed (*Amaranthus retroflexus*), waterhemp (*Amaranthus rudis/tuberculatus*), slender amaranth (*Amaranthus viridis*), Thunberg's amaranth (*Amaranthus thumbergii*), spiny amaranth (*Amaranthus spinosis*), (*Amaranthus rubra*), (*Amaranthus lividus*), Mediterranean amaranth (*Amaranthus graecizans*), rough amaranth (*Amaranthus chlorostachys*), Powell amaranth (*Amaranthus powellii*), Mat amaranth (*Amaranthus blitoides*), Kochia (*Kochia sco-*

*paria*), Yellow starthistle (*Centaurea solstitialis*), and Velvetleaf (*Abutilon theophrasti*). Plant leaves are pretreated with surfactant solution prepared as in Example 1 and treated with dsRNA solutions at a treatment of about 1 nanomole per plant. After 15 days treated plants are dead, dying, or stunted.

Example 6

This example further illustrates the utility of polynucleotide molecules of the invention as herbicidal agents. dsRNA oligonucleotide molecules are designed to target RNA encoding acetolactate synthase and phytoene desaturase for each of the plants listed in Example 5. Plant leaves are pretreated with surfactant solution prepared as in Example 1 and treated with dsRNA solutions at a treatment of about 1 nanomole per plant. After 15 days treated plants are dead, dying, or stunted.

Example 7

This example further illustrates the utility of the polynucleotide molecules of the invention as herbicidal agents. The method of Example 4 is repeated to provide short dsRNA oligonucleotides that are designed to target RNA encoding each of the following proteins in Palmer amaranth: a 5-enolpyruvylshikimate-3-phosphate synthase (EPSPS), an acetyl-coenzyme A carboxylase, a dihydropteroate synthase, a protoporphyrin IX oxygenase, a hydroxyphenylpyruvate dioxygenase, a glutamine synthase, D1 protein, a translation initiation factor (TIF), a ribulose-1,5-bisphosphate carboxylase oxygenase (RuBisCO), and a DNA-dependent ATPase (ddATPase). Leaves of separate glyphosate-resistant Palmer amaranth plants are treated with the surfactant solution prepared as in Example 1 and separately each of the dsRNA oligonucleotide molecules in the manner of Example 1 at a treatment of 1 nanomole of dsRNA per plant. After 30 days the treated plants are dead, dying, or stunted.

Example 8

This example illustrates the utility of employing a synthetic Pol m gene in compositions and methods of this invention. With reference to SEQ ID NO:3 and FIG. 2, a synthetic Pol m gene is created using elements from an *Arabidopsis thaliana* U6 snRNA gene to provide a dsDNA molecule with two copies of RGCCCR elements (bold and underlined), an upstream sequence element (USE) having the sequence "TCCCACATCG" (SEQ ID NO:4, bold and underlined), a TATA box (bold and underlined), a "G" nucleotide (bold and underlined), anti-sense DNA (italics) corresponding to a bacterial DNA encoding an EPSPS protein (see U.S. Pat. RE39,247) that imparts resistance to glyphosate herbicide when expressed in transgenic corn plants, an "AAGATTAGCACGG" element (SEQ ID NO:5, bold and underlined) embedded in the anti-sense DNA, an "ACGCATAAAAT" element (SEQ ID NO:6, bold and underlined) followed by sense DNA (lower case) and a "TTTTTT" terminator element (SEQ ID NO:7, bold and underlined). A solution of 0.1 wt % SILWET L-77 brand organosilicone surfactant and a solution of multiple copies of the dsDNA molecule are sprayed onto leaves of volunteer glyphosate-resistant corn plants growing in a field of glyphosate-resistant soybean plants, followed 7 days later by treatment with Roundup WeatherMAX® brand glyphosate herbicide. 15 days later the corn plants are dead and the soybean plants are thriving; control glyphosate-resistant corn plants treated only with surfactant and glyphosate herbicide are thriving.

Example 9

This example illustrates an aspect of the invention. In this example, polynucleotide molecules were applied to and permeated into plant tissue thereby inducing systemic regulation, i. e., silencing, of a target gene (an endogenous EPSPS). More specifically, a composition including single-stranded DNA (ssDNA) oligonucleotides suppressed the expression of an endogenous EPSPS in glyphosate-tolerant Palmer amaranth (*Amaranthus palmeri*).

The anti-sense ssDNA oligonucleotides were designed using IDT SciTools software (available at idtdna.com/Scitools/Applications/Anti-sense/Anti-sense.aspx). The oligonucleotides included four ssDNA oligonucleotides anti-sense to *Amaranthus palmeri* EPSPS (SEQ ID NOs:8, 9, 10, and 11), two chemically modified (phosphorothioate modified) ssDNA oligonucleotides anti-sense to *Amaranthus palmeri* EPSPS (SEQ ID NOs:12 and 13), a control ssDNA oligonucleotide anti-sense to a control gene, barley (*Hordeum vulgare*) seed protein, GenBank ID X97636 (SEQ ID NO:14), and a chemically modified (5'-labelled with Alexa Fluor 488 from Invitrogen) ssDNA oligonucleotide anti-sense to *Amaranthus palmeri* EPSPS (SEQ ID NO:15), as indicated in Table 1.

TABLE 1

Anti-sense ssDNA oligonucleotides

| Name | SEQ ID NO: | Sequence (5' to 3') | Note |
|---|---|---|---|
| Anti-sense_PO1 | 8 | ACCCTCCACGACTGCCCTTT | |
| Anti-sense_PO2 | 9 | GTTTCCTTCACTCTCCAGC | |
| Anti-sense_PO3 | 10 | GTAGCTTGAGCCATTATTGT | |
| Anti-sense_PO4 | 11 | GTTGATGGTAGTAGCTTGAG | |
| Anti-sense_PS1 | 12 | ACCCTCCACGACTGCCCTTT | phosphorothioate modification of the three 5'-terminal and three 3'-terminal nucleotides |

TABLE 1-continued

Anti-sense ssDNA oligonucleotides

| Name | SEQ ID NO: | Sequence (5' to 3') | Note |
|---|---|---|---|
| Anti-sense_PS2 | 13 | GTTTCCTTCACTCTCCAGC | phosphorothioate modification of the three 5'-terminal and three 3'-terminal nucleotides |
| Anti-sense_ck | 14 | AAGCGGTTGAGCACTGAA | Control sequence, barley seed protein, GenBank ID X97636 |
| Anti-sense_PO1_488 | 15 | ACCCTCCACGACTGCCCTTT | 5'-labelled with Alexa Fluor 488 |

Figure 6:
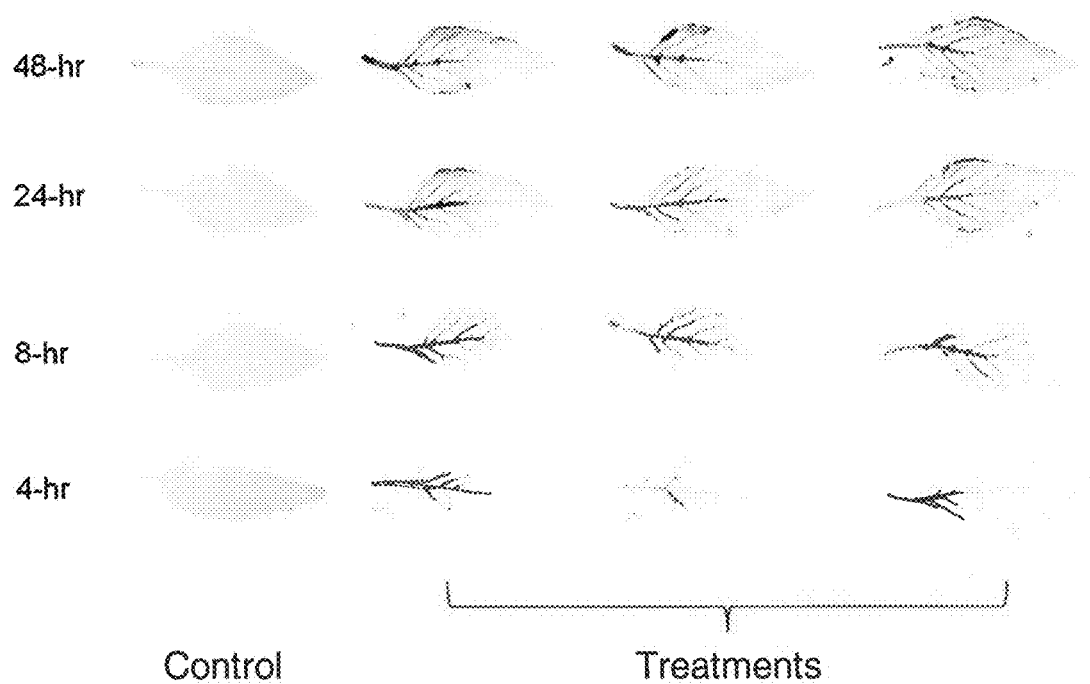
FIG. 6 illustrates 5'-Alexa Fluor 488-labelled anti-sense ssDNA oligonucleotides (SEQ ID NO:15) permeating glyphosate-resistant Palmer amaranth leaves as described in Example 9.

Oligonucleotide uptake was demonstrated with the fluorescently labelled ssDNA oligonucleotides (SEQ ID NO:15) confirming that ssDNA oligonucleotides permeated the leaf tissue. Petioles of detached leaves of glyphosate-resistant Palmer amaranth were placed in 200 mM sucrose solution with fluorescently labelled ssDNA oligonucleotides (SEQ ID NO:15). Leaf images were taken by Bio-Rad PharosFX imager equipped with a 488 nm laser from 4 h up to 48 h after uptake through petiole. Leaves incubated with 200 mM sucrose alone served as control. A slightly time-dependent vascular uptake of the fluorescently labelled ssDNA oligonucleotides was observed (see FIG. 6). Fluorescently labelled ssDNA oligonucleotides were released from vascular tissue into cells as early as 8 h after treatment and were observed to accumulate at the leaf edge at 24 h and 48 h, suggesting a transpiration effect.

EPSPS suppression was demonstrated with detached leaves of glyphosate-resistant Palmer amaranth using the petiole uptake technique. Petioles of detached leaves of glyphosate-resistant Palmer amaranth were placed in 200 mM sucrose solution with oligonucleotides according to the treatments listed in Table 2. Control leaves were permeated with the anti-sense control (SEQ ID NO:14), and additionally treated with or without 50 micrograms/mL glyphosate. EPSPS mRNA, EPSPS protein, and shikimate levels were measured after 48 h incubation. To assess the effects of anti-sense ssDNA oligonucleotides on EPSPS mRNA, total leaf RNA was isolated and quantitative real-time RT-PCR was performed to compare EPSPS mRNA levels. To assess the effects of anti-sense ssDNA oligonucleotides on EPSPS protein, total leaf soluble protein was isolated, separated by SDS-PAGE, and EPSPS protein levels measured by Western blot using antibodies against maize EPSPS_TIPA. Effects of anti-sense ssDNA oligonucleotides on shikimate accumulation as an indication of suppression of EPSPS were assessed in two experiments: in experiment 1, the oligonucleotide-treated leaves were incubated with 50 microgram/mL glyphosate for an additional 48 h either by petiole uptake (control leaves were permeated with the anti-sense control (SEQ ID NO:14), and additionally treated with or without 50 micrograms/mL glyphosate); in experiment 2, leaf disc assays were performed on the oligonucleotide-treated leaves, and shikimate levels measured by HPLC (controls in this case were leaves that had not been treated with oligonucleotides but incubated with 50 microgram/mL glyphosate).

TABLE 2

List of treatments using anti-sense ssDNA oligonucleotides

| Treatment | Anti-sense ssDNAs | Final concentration |
|---|---|---|
| #1 | Anti-sense_PO1 (SEQ ID NO: 8) | 5 microM |
| #2 | Anti-sense_PO2 (SEQ ID NO: 9) | 5 microM |
| #3 | Anti-sense_PS1 (SEQ ID NO: 12) | 5 microM |
| #4 | Anti-sense_PS2 (SEQ ID NO: 13) | 5 microM |
| #5 | Anti-sense_PS1, PS2 (SEQ ID NOs: 12, 13) | 10 microM each (20 microM total) |
| #6 | Anti-sense_PO1, PO2, PO3, PO4 (SEQ ID NOs: 8, 9, 10, 11) | 5 microM each (20 microM total) |
| Control | Anti-sense_ck (SEQ ID NO: 14) | 5 microM or 20 microM |

Figure 7:
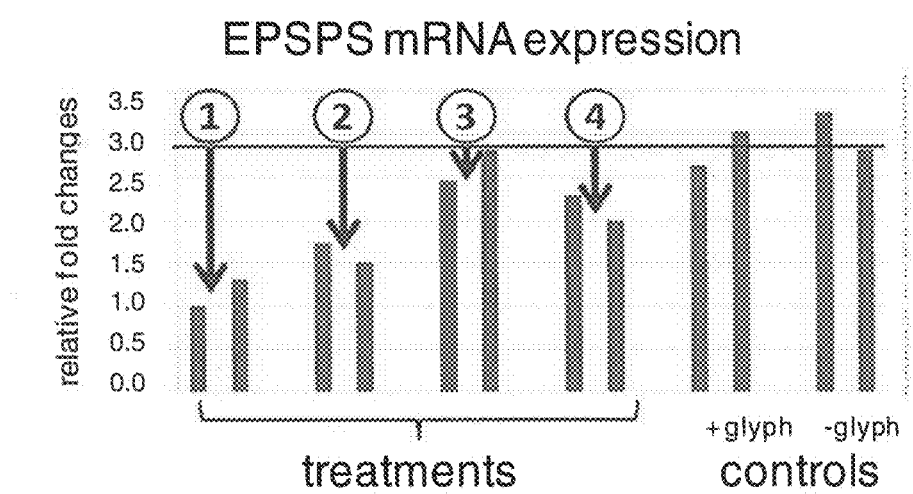
FIG. 7 depicts results of EPSPS mRNA measured in glyphosate-resistant Palmer amaranth leaves treated with anti-sense ssDNA oligonucleotides for EPSPS as described in Example 9. Bars represent replicate experiments for each of treatments #1-#4 (indicated by the numbers enclosed in circles and referring to Table 2) and for controls (leaves permeated with anti-sense ssDNA oligonucleotides for a barley seed protein, SEQ ID NO:14, treated with or without glyphosate).
Figure 8:
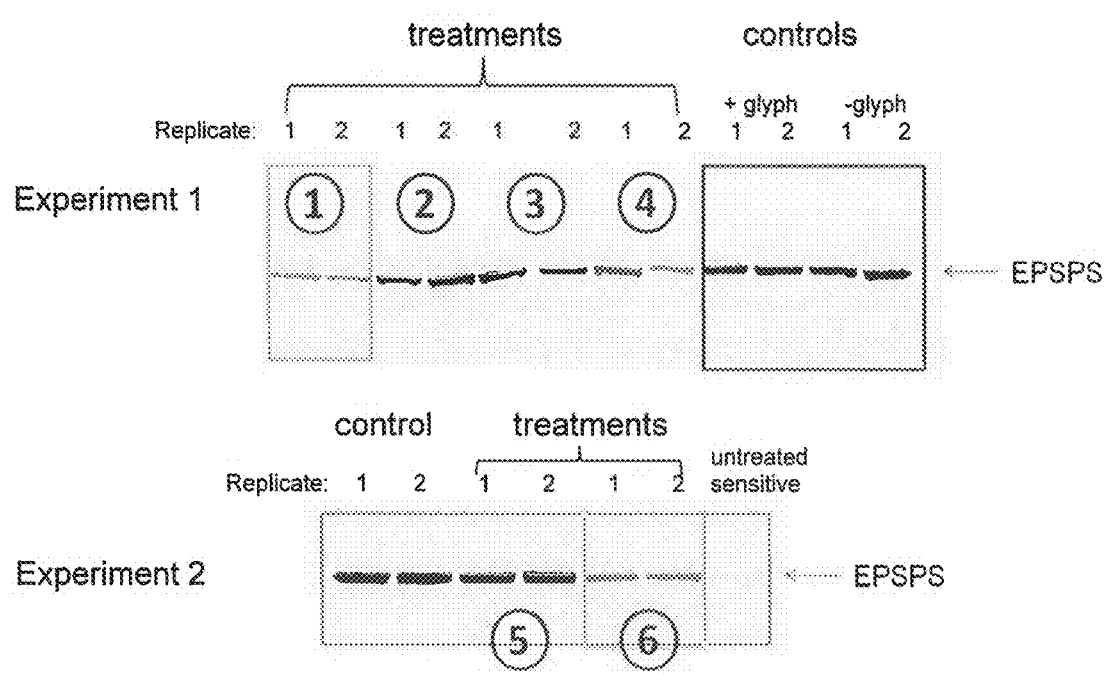
FIG. 8 depicts results of EPSPS protein measured in glyphosate-resistant Palmer amaranth leaves topically treated with anti-sense ssDNA oligonucleotides for EPSPS as described in Example 9; treatments are indicated by the numbers enclosed in circles and refer to Table 2.
Figure 9:
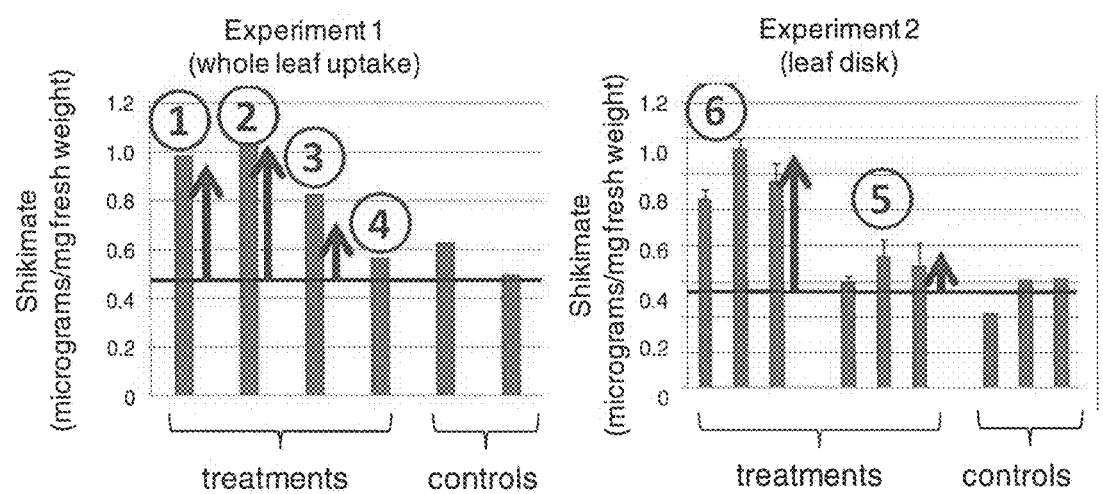
FIG. 9 depicts results of shikimate accumulation measured in glyphosate-resistant Palmer amaranth leaves treated with anti-sense ssDNA oligonucleotides for EPSPS in two experiments as described in Example 9; treatments are indicated by the numbers enclosed in circles and refer to Table 2.

Results for EPSPS mRNA expression, EPSPS protein levels, and shikimate levels are shown in FIGS. 7, 8, and 9, respectively. These results demonstrate that treatment with the anti-sense ssDNA oligonucleotides systematically regulated or suppressed the target gene by decreasing levels of the target gene transcript (EPSPS mRNA) or of the protein (EPSPS) encoded by the target gene in the plant tissue. In this particular experiment, treatments #1 and #6 appeared to be more efficacious in suppressing levels of EPSPS mRNA and protein and in increasing glyphosate efficacy as evidenced by the increased accumulation of shikimate. These results also indicate that glyphosate efficacy is improved by suppressing EPSPS mRNA and protein in glyphosate-resistant Palmer amaranth.

Example 10

This example illustrates an aspect of the invention. In this example, growing plants were treated with a topically applied composition for inducing systemic silencing of a target gene in a plant including (a) an agent for conditioning of a plant to permeation by polynucleotides and (b) polynucleotides including at least one polynucleotide strand including at least one segment of 18 or more contiguous nucleotides of the target gene in either anti-sense or sense orientation. More specifically, tobacco (Nicotiana benthamiana) plants were treated with (a) a topically applied surfactant solution for conditioning of the plant to permeation by polynucleotides and (b) a composition including topically applied DNA oligonucleotides or polynucleotides having at least one strand including at least one segment of 18 or more contiguous nucleotides of the target gene in either anti-sense or sense orientation, whereby systemic regulation or suppression of the target gene (a phytoene desaturase, "PDS") was achieved.

Figure 11:
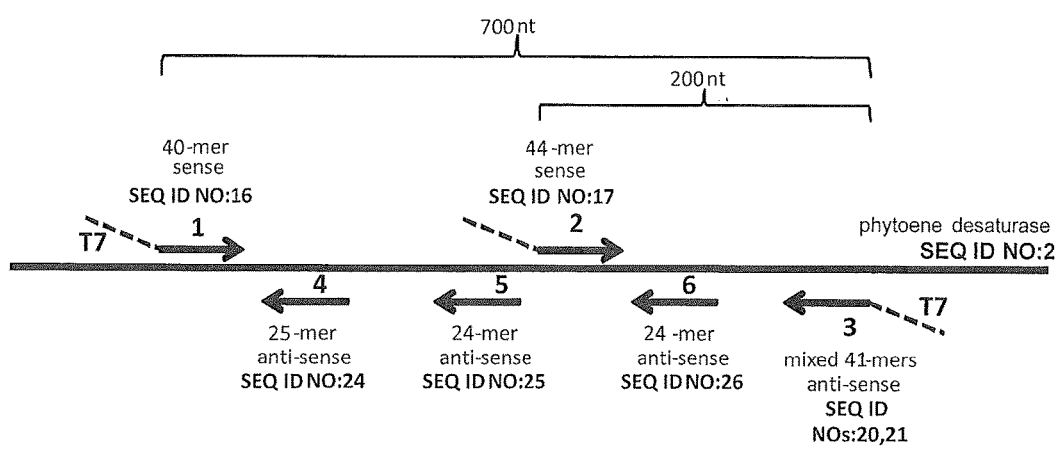
FIG. 11 schematically depicts the location of the sequences of assayed oligonucleotides and polynucleotides (see Table 3) in relation to the phytoene synthase sequence (SEQ ID NO:16) as described in Example 10.

The target gene used was a *Nicotiana benthamiana* phytoene desaturase (SEQ ID NO:2), shown in FIG. 10; the segment consisting of nucleotides 421-1120 of SEQ ID NO:2 (underlined text in FIG. 10) was used to design a 700-mer dsRNA polynucleotide ("PDS 700-mer") and the segment consisting of nucleotides 914-1113 of SEQ ID NO:2 (bolded underlined text in FIG. 10) was used to design a 200-mer dsRNA polynucleotide ("PDS 200-mer"). Sequences of other polynucleotides or oligonucleotides used in the treatments are listed in Table 3. FIG. 11 schematically depicts the location of the sequences of these oligonucleotides and polynucleotides in relation to the phytoene synthase (SEQ ID NO:2) sequence. Non-plant sequences obtained from corn rootworm ("CRW"), SEQ ID NOs:27, 28, 29, and 30 were used as non-homologous controls. Some of the polynucleotides included a T7 promoter sequence (indicated by lower-case text in Table 3) that is a promoter recognized by a bacteriophage T7 RNA polymerase.

solution was applied to the top surface of each of the two pre-treated leaves to provide a total of 40 microliters (1 nmol oligonucleotide or polynucleotide) for each plant. Leaf bleaching was observed 3 days post treatment.

FIG. 12A illustrates results of an assay where a 200-mer dsRNA polynucleotide with an RNA sequence corresponding to the "PDS 200-mer" segment (nucleotides 914-1113 of SEQ ID NO:2) and a combination of single-stranded DNA oligonucleotides and polynucleotides (SEQ ID NOs:16, 17, 20, 21, 24, 25, and 26) were separately applied to tobacco plants. The 200-mer dsRNA polynucleotide was applied at a concentration of 0.6 microM. Bleaching of apical leaves was observed after topical treatment with the polynucleotides and oligonucleotides, indicating systemic regulation or suppression of the target phytoene desaturase gene.

FIG. 12B illustrates results of northern blot analysis of RNA isolated from *Nicotiana benthamiana* plants treated with buffer (control), the 200-mer dsRNA polynucleotide,

TABLE 3

| Description | sense/anti-sense | sequence | Number of nucleotides | SEQ ID NO: |
|---|---|---|---|---|
| oligo 1 with T7 promoter | S | taatacgactcactataggGCAAGAGATGTCCTAGGTGGG | 40 | 16 |
| oligo 2 with T7 promoter | S | taatacgactcactataggACAGATTTCTTCAGGAGAAACATGG | 44 | 17 |
| oligo 1 w/o T7 promoter | S | GCAAGAGATGTCCTAGGTGGG | 21 | 18 |
| oligo 2 w/o T7 promoter | S | ACAGATTTCTTCAGGAGAAACATGG | 25 | 19 |
| oligo 3 mix with T7 promoter | AS | taatacgactcactataggCATCTCCTTTAATTGTACTGCC (SEQ ID NO: 20) and taatacgactcactataggTTTAATTGTACTGCCATTATTC (SEQ ID NO: 21) | 41 (SEQ ID NO: 20), 41 (SEQ ID NO: 21) | 20, 21 |
| oligo 3 mix w/o T7 promoter | AS | CATCTCCTTTAATTGTACTGCC (SEQ ID NO: 22) and TTTAATTGTACTGCCATTATTC (SEQ ID NO: 23) | 22 (SEQ ID NO: 22), 22 (SEQ ID NO: 23) | 22, 23 |
| oligo 4 w/o T7 promoter | AS | CACTTCCATCCTCATTCAGCTCGAT | 25 | 24 |
| oligo 5 w/o T7 promoter | AS | ACACCTCATCTGTCACCCTATCAG | 24 | 25 |
| oligo 6 w/o T7 promoter | AS | CAGTCTCGTACCAATCTCCATCAT | 24 | 26 |
| CRW oligo mixture with T7 promoter | S and AS | taatacgactcactatagggATCCATGATATCGTGAACATC (SEQ ID NO: 27) and taatacgactcactatagggGCAAAGAAAAATGCGTCG (SEQ ID NO: 28) | 41 (SEQ ID NO: 27), 38 (SEQ ID NO: 28) | 27, 28 |
| CRW oligo mixture w/o T7 promoter | S and AS | ATCCATGATATCGTGAACATC (SEQ ID NO: 29) and GCAAAGAAAAATGCGTCG (SEQ ID NO: 29) | 21 (SEQ ID NO: 29), 18 (SEQ ID NO: 30) | 29, 30 |

The following procedure was used for all assays described in this example. Four-week old *Nicotiana benthamiana* plants were used in all assays. Plants were treated with 0.1% SILWET L-77 solution freshly made with ddH2O. Two fully expanded leaves per plant (one cotyledon, one true leaf) were dipped into the SILWET L-77 solution for a few seconds, and allowed to dry for 15-30 minutes before application of the polynucleotide composition. Final concentration for each oligonucleotide or polynucleotide was 25 microM (in 0.01% SILWET L-77, 5 mM sodium phosphate buffer, pH 6.8) unless otherwise stated. 20 microliters of the and the ssDNA oligonucleotides. Also shown is RNA isolated from plants that had been stressed by being kept at 4 degrees Celsius and in the dark overnight prior to treatment with the 200-mer dsRNA polynucleotides.

Figure 13:
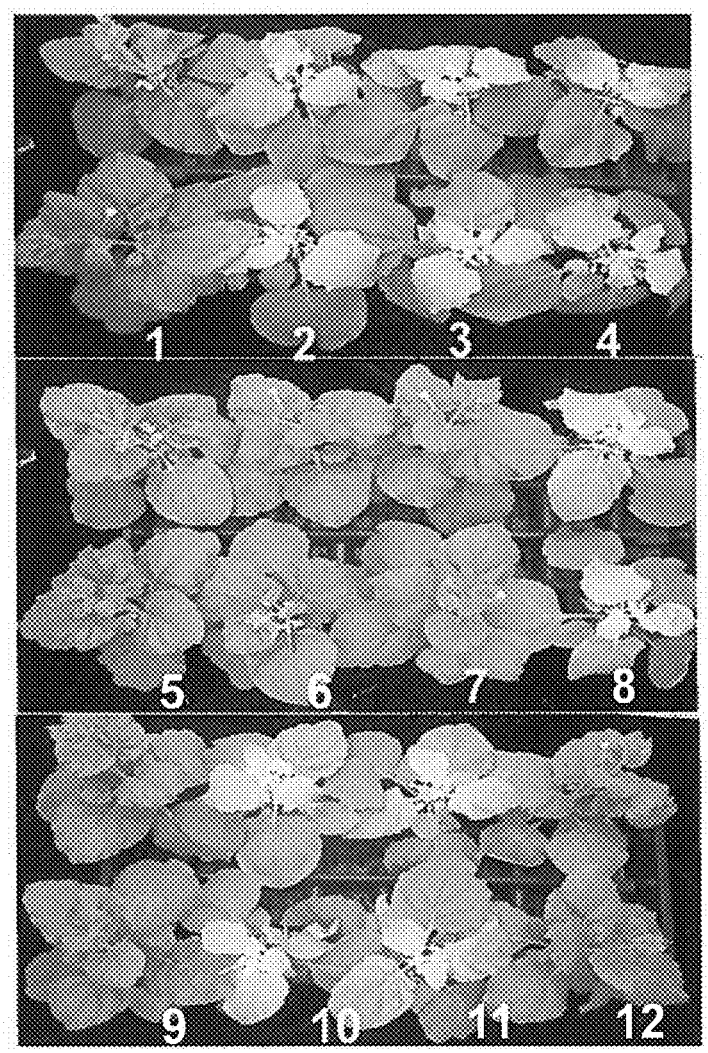
FIG. 13 illustrates apical leaf bleaching in *Nicotiana benthamiana* plants topically treated in duplicate with various combinations of polynucleotides or oligonucleotides (numbers refer to the treatments listed in Table 4) as described in Example 10. The control (Treatment 13 in Table 4) plants are not shown.

FIG. 13 illustrates phenotypes observed at day 12 after treatment in another assay of the effect from twelve combinations of polynucleotides or oligonucleotides (see Table 4). Table 4 also lists observations of visible bleaching of the plants at day 5 after treatment and the results of chlorophyll measurements taken at days 7 and 12 after treatment. Chlorophyll measurements are an indication of suppression of the target gene phytoene desaturase, and measurements were taken at 6 spots on the apical area, focussing on visibly bleached leaves or (in plants without visible bleaching) on leaves in equivalent locations on the plants; lower chlorophyll measurement values indicate suppression of phytoene desaturase. These results show that the combinations of oligonucleotides and polynucleotides in treatments 2, 3, 4, 8, and 11 were effective in systematically regulating (suppressing) the target gene in the treated plants; treatment 1 also effected systematic regulation (suppression) of the target gene to a lesser extent. The 200-mer dsRNA polynucleotide was also effective in systematically regulating (suppressing) the target gene in the treated plants. Oligonucleotides from a non-homologous (corn rootworm) gene (treatments 5 and 6) did not suppress the target phytoene desaturase gene. These results demonstrate that both sense and anti-sense single-stranded DNA oligonucleotides and polynucleotides were effective in systematically regulating (suppressing) the target gene in the treated plants. In this particular example, sense oligonucleotides with the T7 promoter (treatment 1) effected a weak systematic suppression of the phytoene desaturase gene, whereas sense oligonucleotides without the T7 promoter (treatment 7) did not suppress the phytoene desaturase gene. In this particular example, anti-sense oligonucleotides with the T7 promoter (treatment 2) as well as anti-sense oligonucleotides without the T7 promoter (treatment 8) both provided strong bleaching, indicating strong systemic regulation of the target phytoene desaturase gene.

TABLE 4

| Treatment | Description | SEQ ID NO: | Comment | Bleaching (day 5) | Chlorophyll (day 7) | Chlorophyll (day 12) |
|---|---|---|---|---|---|---|
| 1 | Oligos 1 and 2 | 16, 17 | Sense oligos with T7 promoter | weak | 18.6 | 17.5 |
| 2 | Oligo 3 | 20, 21 | Anti-sense oligos with T7 promoter | strong | 12.7 | 1.6 |
| 3 | Oligos 1, 2, and 3 | 16, 17, 20, 21 | Sense and anti-sense oligos with T7 promoter | strong | 11.5 | 2.6 |
| 4 | Oligos 1, 2, 3, 4, 5 and 6 | 16, 17, 20, 21, 24, 25, 26 | Sense and anti-sense oligos with T7 promoter, plus anti-sense oligos without T7 promoter | strong | 15.1 | 2.5 |
| 5 | CRW oligo mixture with T7 promoter | 27, 28 | Sense and anti-sense oligos with T7 promoter | not yet | 30.8 | 37.3 |
| 6 | CRW oligo mixture without T7 promoter | 29, 30 | Sense and anti-sense oligos without T7 promoter | not yet | 34.2 | 38.2 |
| 7 | Oligos 1 and 2 without T7 promoter | 18, 19 | Sense oligos without T7 promoter | not yet | 32.0 | 41.1 |
| 8 | Oligo 3 without T7 promoter | 22, 23 | Anti-sense oligos without T7 promoter | strong | 11.3 | 3.2 |
| 9 | Oligos 1, 2, and 3 w/o T7 promoter and oligos 4, 5, & 6 | 18, 19, 22, 23, 24, 25, 26 | Sense and anti-sense oligos without T7 promoter | not yet | 30.2 | 34.4 |
| 10 | 200-mer dsRNA polynucleotide | RNA sequence corresponding to the "PDS 200-mer" segment consisting of nucleotides 914-1113 of SEQ ID NO: 2 | Sense and anti-sense dsRNA polynucleotide | strong | 11.3 | 4.0 |
| 11 | 1/10th of Experiment 4 oligonucleotide mixture | 16, 17, 20, 21, 24, 25, 26 | Sense and anti-sense oligos with T7 promoter, plus anti-sense oligos without T7 promoter | strong | 11.4 | 4.5 |

TABLE 4-continued

| Treatment | Description | SEQ ID NO: | Comment | Bleaching (day 5) | Chlorophyll (day 7) | Chlorophyll (day 12) |
|---|---|---|---|---|---|---|
| 12 | 1/100th of Experiment 4 oligonucleotide mixture | 16, 17, 20, 21, 24, 25, 26 | Sense and anti-sense oligos with T7 promoter, plus anti-sense oligos without T7 promoter | not yet | 31.0 | 38.0 |
| 13 | Control | (none) | Buffer only | not yet | 31.2 | 38.4 |

Figure 14:
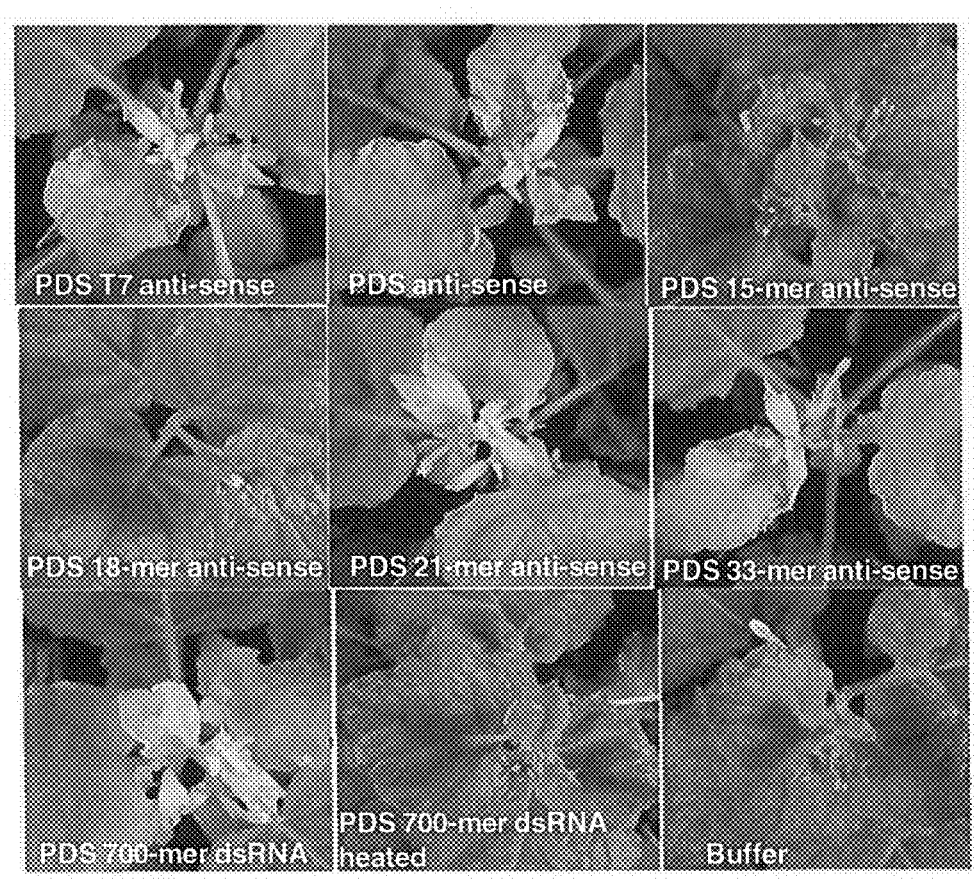
FIG. 14 illustrates apical leaf bleaching in *Nicotiana benthamiana* plants topically treated with the polynucleotides listed in Table 5 as described in Example 10.

Table 5 shows six polynucleotides: a 40-mer segment ("PDS 40-mer sense ssDNA", SEQ ID NO:31) consisting of the 5'-most 40 nucleotides of the "PDS 700-mer" (nucleotides 1081-1120 of SEQ ID NO:2), and four anti-sense single-stranded DNA polynucleotides and one sense single-stranded DNA polynucleotide synthesized based on the "PDS 40-mer sense ssDNA" sequence (SEQ ID NO:31). FIG. 14 illustrates results of topical treatment of tobacco plants with the polynucleotides and oligonucleotides. Strong bleaching of apical leaves indicating systemic regulation or suppression of the target gene phytoene desaturase was observed after topical treatment with the PDS 21-mer anti-sense ssDNA and PDS 33-mer anti-sense ssDNA, as well as after topical treatment with the PCR-amplified and column-purified 700-mer dsRNA polynucleotide ("PDS 700-mer dsRNA"), previously assayed PDS anti-sense 22-mer oligonucleotides with a T7 promoter (SEQ ID NOs:20 and 21) ("PDS T7 anti-sense"), or previously assayed PDS anti-sense 22-mer oligonucleotides without a T7 promoter (SEQ ID NOs:22 and 23) ("PDS anti-sense"). Little or no visible bleaching of apical leaves was observed after topical treatment with the buffer only ("Buffer"), or after topical treatment with heat-denatured (5 minutes at 95 degrees Celsius, then stored on ice) 700-mer dsRNA polynucleotide ("PDS 700-mer dsRNA heated"), the PDS15-mer anti-sense ssDNA, or the PDS 18-mer anti-sense ssDNA.

TABLE 5

| Description | Sequence | SEQ ID NO: |
|---|---|---|
| PDS 40-mer sense ssDNA | TGTTTTATACTGAATAATGGCAGTACAATTAAAGGAGATG | 31 |
| PDS 15-mer anti-sense ssDNA | CATCTCCTTTAATTG | 32 |
| PDS 18-mer anti-sense ssDNA | CATCTCCTTTAATTGTAC | 33 |
| PDS 21-mer anti-sense ssDNA | CATCTCCTTTAATTGTACTGC | 34 |
| PDS 33-mer anti-sense ssDNA | CATCTCCTTTAATTGTACTGCCATTATTCAGTA | 35 |
| PDS 21-mer sense ssDNA | GCAGTACAATTAAAGGAGATG | 36 |

Figure 15:
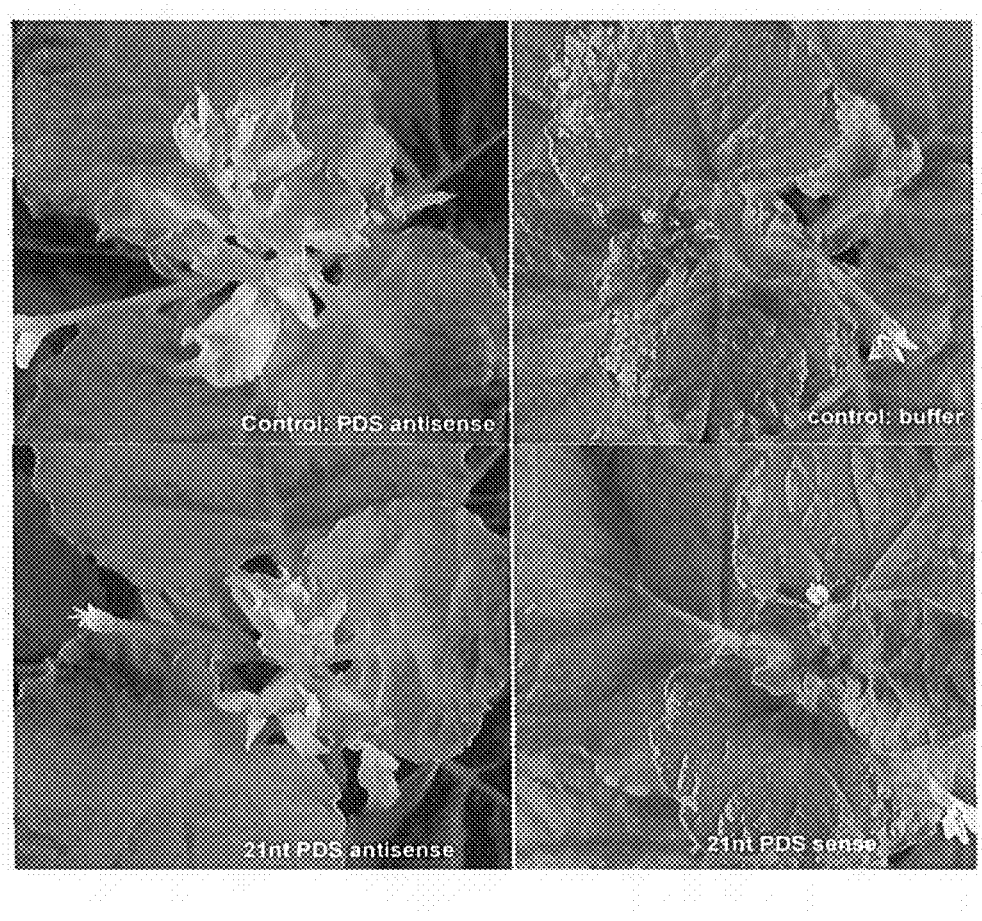
FIG. 15 illustrates apical leaf bleaching observed in *Nicotiana benthamiana* plants after topical treatment with the PDS 21-mer anti-sense ssDNA (SEQ ID NO:34, "21nt PDS anti-sense") or with previously assayed PDS anti-sense 22-mer oligonucleotides without a T7 promoter (SEQ ID NOs:22 and 23) ("PDS anti-sense"). Little or no visible bleaching of apical leaves was observed after topical treatment with the buffer only or after topical treatment with PDS 21-mer sense ssDNA (SEQ ID NO:36, "21nt PDS sense") as described in Example 10.
Figure 17:
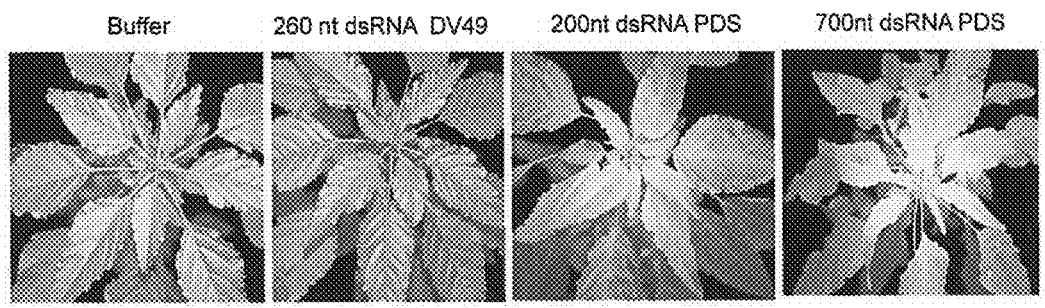
FIG. 17 illustrates apical leaf bleaching observed in Palmer amaranth plants topically treated with 678 bp or 198 bp Palmer PDS dsRNA but not in Palmer amaranth plants topically treated with a 260 base pair dsRNA of corn root worm gene as described in Example 11.

Results of another assay are shown in FIG. 15, strong bleaching of apical leaves indicating systemic regulation or suppression of the target gene phytoene desaturase was observed after topical treatment with the PDS 21-mer anti-sense ssDNA (SEQ ID NO:34, "21nt PDS anti-sense") or with previously assayed PDS anti-sense 22-mer oligonucleotides without a T7 promoter (SEQ ID NOs:22 and 23) ("PDS anti-sense"). Little or no visible bleaching of apical leaves was observed after topical treatment with the buffer only ("control: buffer"), or after topical treatment with PDS 21-mer sense ssDNA (SEQ ID NO:36, "21nt PDS sense").

Example 11

This example illustrates treatment of growing plants with a topically applied composition for inducing systemic silencing of a target gene in a plant including (a) an agent for conditioning of a plant to permeation by polynucleotides and (b) polynucleotides including at least one polynucleotide strand including at least one segment of 18 or more contiguous nucleotides of the target gene in either anti-sense or sense orientation. More specifically, this example demonstrates the target specificity (sequence specificity) of the polynucleotides.

Palmer amaranth phytoene desaturase (PDS) has the sequence TCAATTTCATCTATGGAAGT-GATTTTTGGGTCATTCTGTGAGAAATTTCAGTG-TAGTAAAGTTTATG GAG-CAAAGCAAAGAAATGGGCACTGCCCTTAAAGGTT-GTTTGTATAGATTATCCTAGGCCAGAGCTT GAAAG-TACATCCAATTTCTTGGAAGCCGCCTACTTATCTTC-TACTTTCGGAATTCGCCTCGTCCTCAG AAGC-CATTAGAAGTTGTAATTGCTGGAGCAGGTTTGGC-TGGTCTATCCACGGCAAAGTATTTAGCTGA TGCAG-GTCACAAACCCATATGTTGGAAGCACGAGAT-GTTTTAGGAGGAAAGGTTG-CAGCGTGGAAGATGAGGATGGTGACTGGTATGA-GACTGGGCTACATATATCTTTGGGGCATATCCAAA-TGTCCAAAATCTATTTGGAGAACTTGGTATAAAT-GACCGACTGCAATGGAAGGAGCACTCTATGATT-TFGCAATGCCCAGCAAGCCCGGTGAATTCAGTCG-CTTTGATTTTCCCGAAATCCTGCCTGCACCATTAA-ATGGCATATGGGCAATCCTAAGAAATAATGAAA-TGCTAACCTGGCCAGAAAAAATCAAGTTTGCCA-TTGGCTGTTGCCTGCTATGGCAGGCGGACAGTCA-TATGTTGAAGCACAAGATGGTTTGAGTGTCCAA-GAGTGGATGAGAAAACAAGGAGTACCCGATCGT-GTAACTGATGATGTGTTTATTGCCATGTCAAAGG-CACTGAACTTCATAAATCCCGATGAACTTTCAAT-GCAGTGCATCTGATTGCTCTGAACCGATTCCTGC-AGGAGAAACATGGTTCTAAGATGGCCTTCCTAG-ACGGAAACCCTCCAGAGAGGCGTGCATGCCATT-GTTAAACACATCGAGTCACTAGGTGGTGAAGTT-AAACFTAACTCTCGTATACAAAAGATTCAGTTG-GACCAGAGTGGAAGCGTGAAGAGTTTTTTGCTA-AATAACGGGAGGGAAATACGAGGAGATGCCTAT-GTTTGCCACCCCAGTTGACATCTTGAA GCTGTTAC-TACCTGATACTTGGAAGGAAATCTCATACT-TCAAAAAACTTGAGAAATTAGTGGGCGTTC CTGT- GATTAATGTTCACATATGGTJTTGACAGAAAATTA-AAGAATACATATGACCATCTACTCTTCAGCA-GGAGTCCTTTTGAGTGTCTATGCTGATATGTCGGA-GACATGCAAGGAATATAAGGATCCAAATA-GATCCATGCTGGAATTGGTTTTGCACCCGCGGAG-GAATGGATTCACGAAGCGACACTGATATATAGA-GGCAACAATGAAAGAGCTGCCAAGCTTTTCCCG-GATGAAATCGCTGCCGATGGAAGCAAGGCCAAG ATCCTCAAATATCATGTCGTCAAAACTC-CAAGGTCGGTTATAAGACTGTACCGGATTGTGAAC-CTTGT CGGCCGCTGCAAAGATCACCAATA-GAGGGTCTATTAGCTGGTGATACACAAAACAAAA-ATATTT GGCTTCTATGGAAGGTGCTGTCT-TATCTGGGAAGCTTGTGCACAGGCTATCGTACAG-GATTATGATCT GCTGAGTTCTCGAGCACAAAGA-GAATTGGCG (SEQ ID NO:37). A 678 base pair dsRNA polynucleotide with an anti-sense strand capable of hybridizing to the RNA encoded by the nucleotides at positions 317-994 (shown as underlined text) in SEQ ID NO:37 and a 198 base pair dsRNA polynucleotide with an anti-sense strand capable of hybridizing to the RNA encoded by the nucleotides at positions 797-994 (shown as italicized and underlined text) in SEQ ID NO:37 were synthesized.

*Nicotiana benthamiana* phytoene desaturase has the sequence TCGAGGTCTTCGTTGGGAACTGAAAGT-CAAGATGTGCTTGCAAAGGAATTTGTTATGTTTTG-GTAGT AGCGACTCCATGGCATAAGTTAAGGATTCG- TACTCCAAGTGCCACGACCCGAAGATTGACAAAGG ACTTTAATCCTTAAAGGTAGTCTGCATTGATATC- CAAGACCAGAGCTAGACAATACAGTTAACTATT TGGAGGCGGCGTTATTATCATCATCGTTTCGTACT- TCCTCACGCCCAACTAAACCATTGGAGATTGTTA TTGCTGGTGCAGGTTGGTGGTJTGTCTACAG- CAAAATATCGGCAGATGCTGTCACAAACCGATA TTGCTGGAGGCAAGAGATGTCCTAGGTGGGAAGG- TAGCTGCATGGAAAGATGATGATGGAGATTGGT- ACGAGACTGGGTTGCACATATTCTTTGGGGCTTA- CCCAAATATGCAGAACCTGTTTGGAGAACTAGG- GATTGATGATCGGTTGCAGTGGAAGGAACATTC- AATGATATTTGCGATGCCTAACAAGCCAGGGGA- GTTCAGCCGCTTTGATTTTCCTGAAGCTCTTCCTG- CGCCATTAAATGGAATTTTGGCCATACTAAAGA- ACAACGAAATGCTTACGTGGCCCGAGAAAGTCA- AATTTGCTATTGGACTCTTGCCAGCAATGCTTGG- AGGGCAATCTTATGTTGAAGCTCAAGACGGTTTA- AGTGTTAAGGACTGGATGAGAAAGCAAGGTGTG- CCTGATAGGGTGACAGATGAGGTGTTCATTGCC ATGTCAAAGGCACTTAACTTCATAAACCCTGACG- AGCTTTCGATGCAGTGCATTTTGATTGCTTTGAA- CAGATTTCTTCAGGAGAAACATGGTTCAAAAAT- GGCCTTTTTAGATGGTAACCCTCCTGAGAGACTT- TGCATGCCGATTGTGGAACATATTGAGTCAAAA- GGTGGCCAAGTCAGACTAAACTCACGAATAAA- AAAGATCGAGCTGAATGAGGATGGAAGTGTCAA- ATGTTTTATACTGAATAATGGCAGTACA ATTAAAGGAGATGCTTTTGTGTTTGCCACTCCA- GTGGATATCTTGAAGCTTCTTTTGCCTGAAGACTGG AAAGAGATCCCATATTTCCAAAAGTTGGA- GAAGCTAGTGGGAGTTCCTGTGATAAATGTC- CATATATG GTTTGACAGAAAACTGAAGAACA- CATCTGATAATCTGCTCTTCAGCAGAAGCCCGTTG- CTCAGTGTGT ACGCTGACATGTCTGTACATG- TAAGGAATATACAACCCCAATCAGTCTATGTTG- GAATTGGTATTTG CACCCGCAGAAGAGTGGA- TAAATCGTAGTGACTCAGAAATTATTGATGCTACA- ATGAAGGAACTAGC GAAGC-TTTCCCTGAT- GAAATTTCGGCAGATCAGAGCAAAGCAAAAATAT- GAAGTATCATGTGTCA AAACCCCAAGGTCTGTT- TATAAAACTGTGCCAGGTTGTGAACCCTGTCGGC- CCTTGCAAAGATCCCCT ATAGAGGGGTTTATT- TAGCTGGTGACTACACGAAACAGAAGTACTTGGCT- CAATGGAAGGTGCTGT CTTATCAGGAAAGCTTTGT- GCACAAGCTATTGTACAGGATTACGAGTTACTTC- TTGGCCGGAGCCAGA AGATGTTGGCA- GAAGCAAGCGTAGTTAGCATAGTGAACTAA (SEQ ID NO:38). A 685 base pair dsRNA polynucleotide with an anti-sense strand capable of hybridizing to the RNA encoded by the nucleotides at positions 421-1105 (shown as underlined text) in SEQ ID NO:38 and a 192 base pair dsRNA polynucleotide with an anti-sense strand capable of hybridizing to the RNA encoded by the nucleotides at positions 914-1105 (shown as italicized and underlined text) in SEQ ID NO:38 were synthesized.

An alignment of the Palmer amaranth and *Nicotiana benthamiana* PDS DNA sequences was performed using a global pairwise alignment (stretcher) and is illustrated in FIG. 16; with this method the two sequences showed about 71% identity (1252/1762).

Palmer amaranth plants having 16 copies of EPSPS and 5-8 inches high were treated with 0.1% SILWET L-77 solution freshly made with ddH2O. Four fully expanded leaves per plant were dipped into the SILWET L-77 solution for a few seconds, and allowed to dry for 30 minutes to 1 hour before application of the polynucleotide composition. Individual polynucleotide solutions were made for each of the 678 bp Palmer PDS dsRNA, 198 bp Palmer PDS dsRNA, the 685 bp *Nicotiana benthamiana* PDS dsRNA, and the 192 bp *Nicotiana benthamiana* PDS dsRNA (0.6 micromolar polynucleotide in 0.01% SILWET L-77, 5 mM sodium phosphate buffer, pH 6.8). 10 microliters of polynucleotide solution (or buffer as a control) was applied to the top surface of each of the four pre-treated leaves per plant to provide a total of 40 microliters for each plant. Plants were kept in a growth chamber, and leaf bleaching was observed 3 days post treatment Plants topically treated with either 678 bp Palmer PDS dsRNA or 198 bp Palmer PDS dsRNA, showed bleaching of leaves (indicating silencing of the endogenous phytoene desaturase) but Palmer amaranth plants topically treated with either 685 bp *Nicotiana benthamiana* PDS dsRNA or 192 bp *Nicotiana benthamiana* PDS dsRNA did not show bleaching of leaves. This sequence specificity demonstrates that the polynucleotide compositions and methods of the invention are useful in selective control of a given species or taxon having a specific target gene sequence, e. g., in controlling herbicide-resistant volunteer plants growing in a field of crop plants resistant to the same herbicide.

In a separate assay, Palmer amaranth plants topically treated with 678 bp Palmer PDS dsRNA (labelled "700 nt dsRNA PDS") or 198 bp Palmer PDS dsRNA (labelled "200 nt dsRNA PDS") showed bleaching of leaves (indicating silencing of the endogenous phytoene desaturase) but Palmer amaranth plants topically treated with a 260 base pair dsRNA of an invertebrate gene (labelled "260 nt dsRNA DV49", from corn root worm *Diabrotica virgifera*) did not result in a bleaching phenotype, indicating no silencing of the endogenous phytoene desaturase (FIG. 17). This sequence specificity demonstrates that the polynucleotide compositions and methods of the invention are useful in selective control of a given species or taxon.

Example 12

This example describes use of a topically applied composition including at least one polynucleotide strand including at least one segment of 18 or more contiguous nucleotides of a target gene in either anti-sense or sense orientation to induce systemic silencing of a target gene in a plant. More specifically this example demonstrates using a single treatment with a phytoene desaturase (PDS) oligonucleotide to induce systemic silencing in different plant organs including leaves, stems, and flowers.

Figure 18:
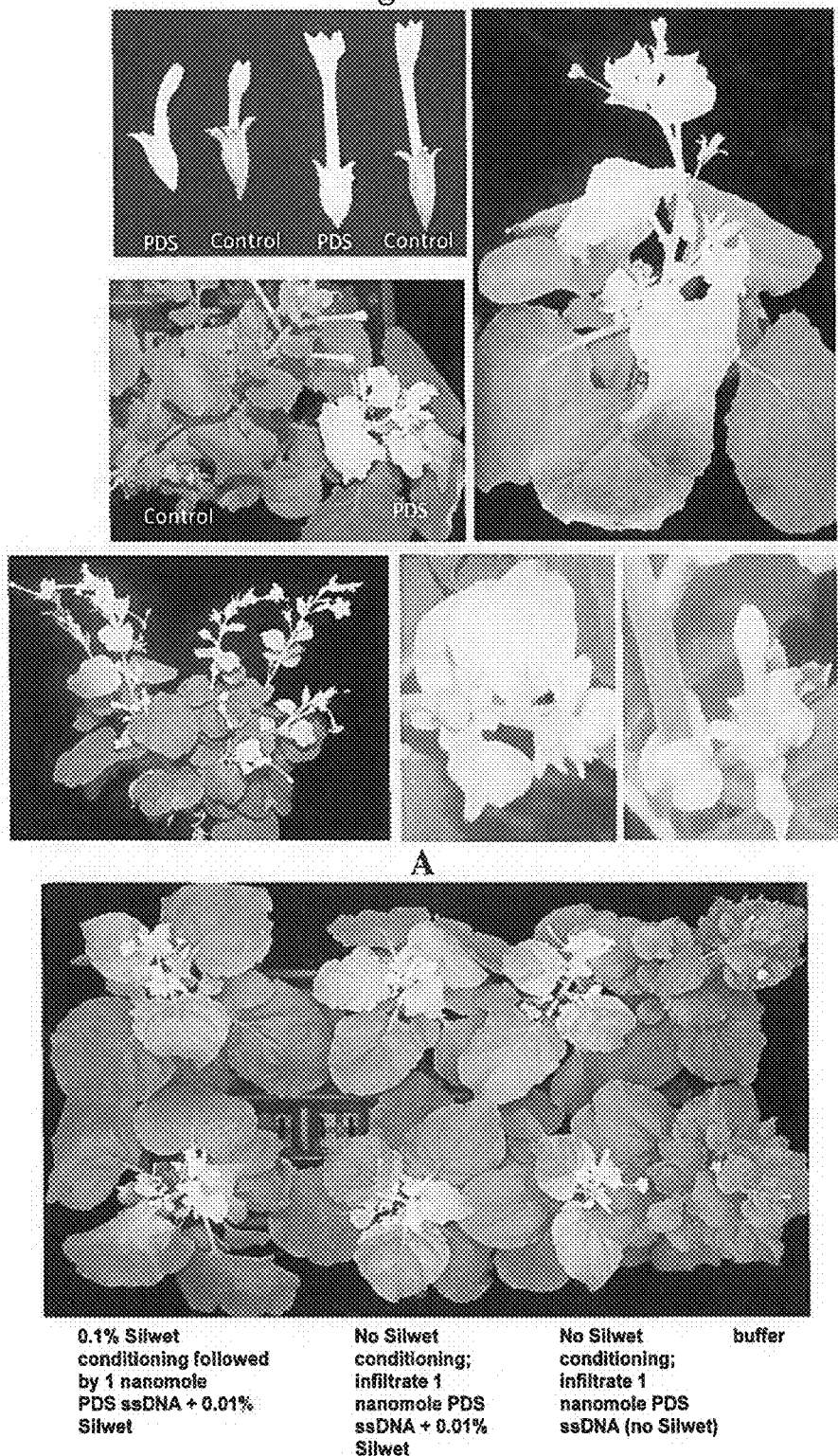
FIG. 18A illustrates bleaching of apical leaves, stems, and flowers of *Nicotiana benthamiana* plants topically treated first with a surfactant solution and then with an ssDNA PDS oligonucleotide to induce systemic silencing of phytoene desaturase as described in Example 12.
FIG. 18B illustrates bleaching of apical leaves, stems, and flowers of *Nicotiana benthamiana* plants topically treated with an ssDNA PDS oligonucleotide to induce systemic silencing of phytoene desaturase, with or without conditioning with a surfactant solution, as described in Example 12.

Four-week old tobacco (Nicotiana benthamiana) plants were used in all treatments. Two fully expanded leaves (one cotyledon, one true leaf) were conditioned by dipping into freshly made surfactant solution (0.1% SILWET L-77 in double-distilled water) for a few seconds and allowed to dry for 15-30 minutes. Twenty microliters of a single-stranded DNA (ssDNA) 22-mer oligonucleotide with the sequence GGCAGTACAATTAAAGGAGATG (SEQ ID NO:39), corresponding to the nucleotides at positions 1099-1120 of Nicotiana benthamiana phytoene desaturase (SEQ ID NO:2) was applied as a 25 micromolar solution in 0.01% SILWET L-77 in 5 millimolar sodium phosphate buffer, pH 6.8 to the top surface of each conditioned leaf for a total of 40 microliters (1 nanomole oligonucleotide) per plant. Control plants were treated with the SILWET solution without the DNA oligonucleotide. Plants were observed for bleaching 3 days post-treatment. Apical leaves, stems, and flowers of plants treated with the ssDNA oligonucleotide all displayed bleaching indicating systemic silencing of PDS (FIG. 18A).

Flowers of both control and ssDNA-treated plants were allowed to set seed. Seeds were collected from mature fruits, weighed, and allowed to germinate. Seed weights were identical (about 11 mg per 100 seeds) and seed morphology appeared similar between the ssDNA-treated and the control plants. A reduced amount of seed produced per fruit and a reduction in germination rate (4 out of 100 seeds germinated) was observed in seeds from the ssDNA-treated plants, compared to the amount of seed per fruit and germination rate (95 out of 100 seeds germinated) of seeds from control plants.

In a separate assay using a similar procedure, tobacco plants were conditioned by dipping in 0.1% SILWET L-77 in double-distilled water, allowed to dry for 15-30 minutes, and treated with the PDS ssDNA 22-mer (SEQ ID NO:39) applied as a 25 micromolar solution in 0.01% SILWET L-77 in 5 millimolar sodium phosphate buffer, pH 6.8 to the top surface of each conditioned leaf for a total of 40 microliters (1 nanomole oligonucleotide) per plant. Other plants were not conditioned with a surfactant treatment, but were treated only with 1 nanomole of the PDS ssDNA 22-mer (SEQ ID NO:39) applied either by infiltration with a needleless syringe (shown in FIG. 18B) or by hand application of drops to the leaf surface (not shown in FIG. 18B), and either as a 25 micromolar solution in 0.01% SILWET L-77 in 5 millimolar sodium phosphate buffer, pH 6.8 or as a 25 micromolar solution in 5 millimolar sodium phosphate buffer, pH 6.8 (without surfactant). Negative control plants were treated with the SILWET buffer solution without the DNA oligonucleotide. Results are depicted in FIG. 18B. All plants treated only with direct application of the PDS ssDNA (without conditioning by SILWET L-77 surfactant treatment), whether applied by infiltration or by hand application of drops, displayed bleaching of apical leaves, stems, and flowers, indicating systemic silencing of PDS.

Example 13

This example illustrates methods and topically applied compositions for inducing systemic silencing including the use of agents for conditioning of a plant to permeation by polynucleotides. More specifically, this example describes use of polynucleotides of the invention to control herbicide-resistant Palmer amaranth.

Palmer amaranth plants having lower (fewer than 30) copy numbers of 5-enolpyruvylshikimate-3-phosphate synthase (EPSPS) are susceptible to treatment with dsRNA designed to silence EPSPS followed by treatment with glyphosate (see details in Example 1). However, Palmer amaranth plants having high copy numbers of EPSPS (i. e., 30 or more copies of EPSPS) are resistant to glyphosate treatment and are a challenge for weed resistance management. For example, in one assay (results not shown) on glyphosate resistant high-copy Palmer amaranth using treatments similar to those described in Example 1 but where either dose of dsRNA was increased up to ten-fold (i. e., 8 nanomoles of short dsRNAs described in Example 1 per plant) or where a proprietary glyphosate formulation ("Roundup® WeatherMAX® brand herbicide") combined with a tallowamine surfactant was used, glyphosate activity was improved (estimated by observing plant growth measured as plant height) but the resistant plants were not killed.

Figure 19:
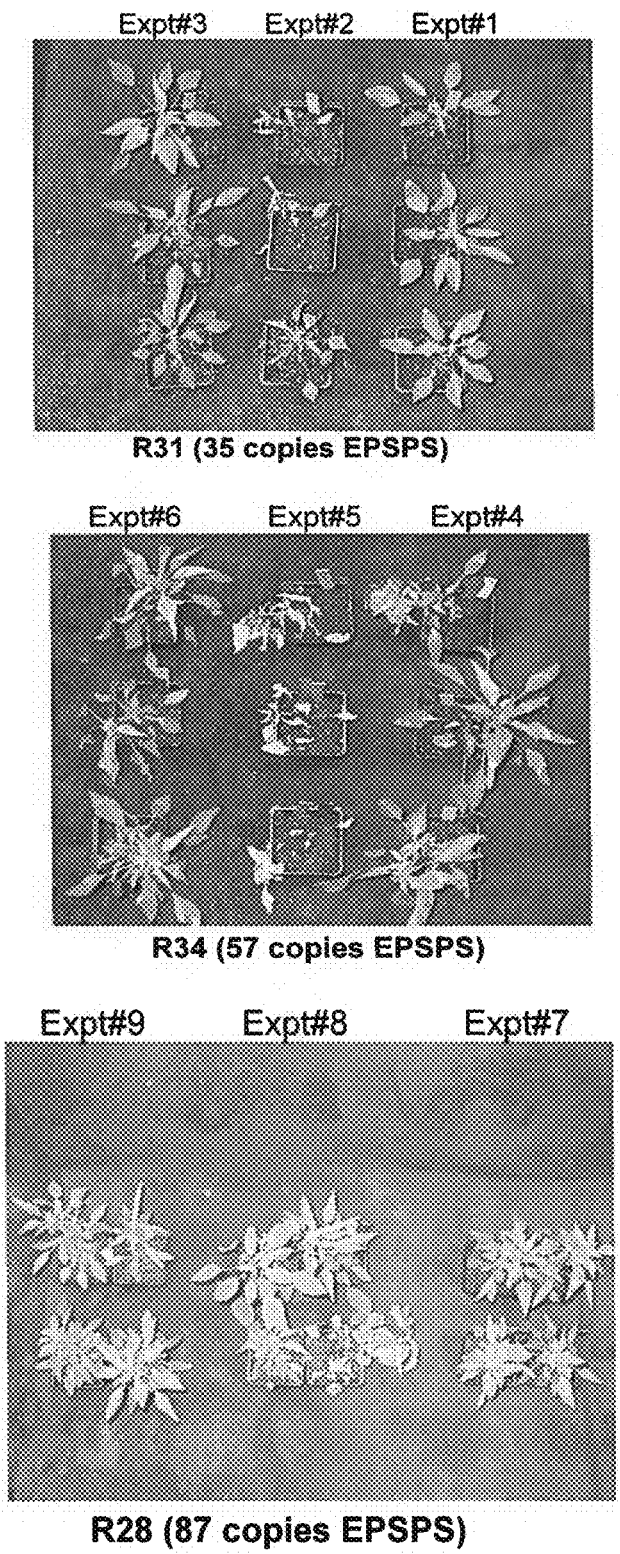
FIG. 19 illustrates results of assays on different glyphosate-resistant Palmer amaranth lines (3 plants per replicate) treated with the conditions listed in Table 6, as described in Example 13. Photographs were taken at 7 days after glyphosate treatment (experiments 1-6) or at 9 days after glyphosate treatment (experiments 7-9).

Three different glyphosate resistant high-copy Palmer amaranth lines (3 plants per replicate) were treated with dsRNA using the treatment conditions listed in Table 6, where the dsRNA delivery vehicle, permeabilization or conditioning agent, and order of steps were varied. Results are depicted in FIG. 19. Treatment with "4×" glyphosate (i. e., treatment with 3360 g acid equivalent per hectare of Roundup® WeatherMAX® brand herbicide which is four-fold the standard rate of application of 840 g acid equivalent per hectare) alone did not kill 35-copy (experiment 3) or 57-copy (experiment 6) Palmer amaranth.

In one set of experiments (1-3, Table 6), including 2% ammonium sulfate in an aqueous dsRNA delivery vehicle comprising 0.1% tallowamine surfactant and 10% glycerol (experiment 2) improved the efficacy of a 10-fold dose of dsRNA followed by a 4× glyphosate application. Improved efficacy of a 10-fold dose of dsRNA followed by glyphosate application was also observed when ammonium sulfate was included in a dsRNA delivery vehicle without a tallowamine surfactant (experiment 8).

In another set of experiments (4-6, Table 6), applying the SILWET L-77 surfactant prior to applying the dsRNA in a delivery vehicle containing ammonium sulfate was effective, whereas combining the SILWET L-77 surfactant with the dsRNA in the dsRNA delivery vehicle containing ammonium sulfate was not effective. Applying glyphosate ("Roundup® WeatherMAX® brand herbicide") at 72 hours (experiment 7) was less effective than applying glyphosate at 48 hours (experiment 2) after treatment with dsRNA.

TABLE 6

| Palmer amaranth line | EPSPS Copy number | Experiment number | Step 1 EPSPS dsRNA relative concentration | dsRNA delivery vehicle | Step 2 | Step 3* |
|---|---|---|---|---|---|---|
| R31 | 35 | 1 | 10X | 0.1% tallowamine surfactant + 10% glycerol | 1% Silwet L-77 | 4x WeatherMAX (48 h) |
| | | 2 | 10X | 2% ammonium sulfate + 0.1% tallowamine surfactant + 10% glycerol | 1% Silwet L-77 | 4x WeatherMAX (48 h) |
| | | 3 | Buffer only (control) | 2% ammonium sulfate + 0.1% tallowamine surfactant + 10% glycerol | 1% Silwet L-77 | 4x WeatherMAX (48 h) |

| Palmer amaranth line | EPSPS Copy number | Experiment number | Step 1 | Step 2 EPSPS dsRNA relative concentration | dsRNA delivery vehicle | Step 3* |
|---|---|---|---|---|---|---|
| R34 | 57 | 4 | — | 10X | 1% Silwet L-77 + 2% ammonium sulfate | 4x WeatherMAX (48 h) |
| | | 5 | 1% Silwet L-77 | 10X | 2% ammonium sulfate | 4x WeatherMAX (48 h) |
| | | 6 | 1% Silwet L-77 | Buffer only (control) | 2% ammonium sulfate | 4x WeatherMAX (48 h) |

| Palmer amaranth line | EPSPS Copy number | Experiment number | Step 1 EPSPS dsRNA relative concentration | dsRNA delivery vehicle | Step 2 | Step 3* |
|---|---|---|---|---|---|---|
| R28 | 87 | 7 | 10X | 2% ammonium sulfate + 0.1% tallowamine surfactant + 10% glycerol | 1% Silwet L-77 | 4x WeatherMAX (72 h) |

| Palmer amaranth line | EPSPS Copy number | Experiment number | Step 1 | Step 2 EPSPS dsRNA relative concentration | dsRNA delivery vehicle | Step 3* |
|---|---|---|---|---|---|---|
| R28 | 87 | 8 | 1% Silwet L-77 | 10X | 2% ammonium sulfate | 4x WeatherMAX (72 h) |
| | | 9 | 1% Silwet L-77 | Buffer only (control) | 2% ammonium sulfate | 4x WeatherMAX (72 h) |

*glyphosate (as the commercial formulation "Roundup ® WeatherMAX ® brand herbicide", which contains 660 g/L glyphosate K+ salt in a carrier including the MON56151 tallowamine surfactant blend of tallowamine (16-18C) and cocoamine (12-14C) in the ratio of 55:45) is listed at the amount used (where 1X = 840 g acid equivalent per hectare of Roundup ® WeatherMAX ® brand herbicide, 4X = 3360 g acid equivalent per hectare of Roundup ® WeatherMAX ® brand herbicide) and hours after application of dsRNA Example 14

This example illustrates methods and topically applied compositions for inducing systemic silencing including the use of agents for conditioning of a plant to permeation by polynucleotides.

Two small RNAs identified through small RNA sequencing were found to be abundant in and unique to Palmer amaranth plants that had been treated with four oligonucleotide-size "short" EPSPS dsRNA molecules as described in Example 1. These two small RNAs were respectively mapped to nucleotide positions 743-764 and 566-585 of the full-length EPSPS having the sequence shown in FIG. 20 (SEQ ID NO:40). Two 25 nucleotide long oligonucleotide-size "short" dsRNA molecules were designed with an antisense strand that is capable of hybridizing to the mRNA transcribed from the Palmer amaranth EPSPS gene at nucleotide positions 743-767 ("short dsRNA-5") and 564-588 ("short dsRNA-6"), as indicated by the italicized underlined nucleotides in SEQ ID NO:40 shown in FIG. 20, which also shows the four oligonucleotide-size "short" EPSPS dsRNA molecules (underlined, non-italicized text) and the three "long" double-stranded RNA polynucleotides (bolded text as described in Example 1.

Application of a mixture of the four oligonucleotide-size "short" EPSPS dsRNA molecules (described in Example 1)

followed by application of glyphosate replicating the treatment procedure described in Example 1 resulted in 4 out of 4 Palmer amaranth plants with 16 copies of EPSPS being killed. Using the same treatment procedure but applying short dsRNA-5 and short dsRNA-6 together resulted in 0 out of 4 Palmer amaranth plants being killed. Adding either or both short dsRNA-5 and short dsRNA-6 to the mixture of the four oligonucleotide-size "short" EPSPS dsRNA molecules (described in Example 1) resulted in 4 out of 4 Palmer amaranth plants being killed, i. e., no antagonistic effect of short dsRNA-5 and short dsRNA-6 was observed.

Example 15

This example illustrates methods and topically applied compositions for inducing systemic silencing including the use of agents for conditioning of a plant to permeation by polynucleotides. More specifically, this example describes use of salicylic acid and polynucleotides.

Salicylic acid (SA) induces virus resistance in tobacco; see, e. g., Chivasa et al. (1997) *Plant Cell,* 19:547-557. Glyphosate-resistant Palmer amaranth plants having 49 or 63 copies EPSPS were pretreated with 15 millimolar SA. A solution of the four oligonucleotide-size "short" EPSPS dsRNA molecules (described in Example 1) was applied by hand at 1, 5, or 24 hours after treatment with SA, followed 72 hours later by spraying with glyphosate (1682 g acid equivalent per hectare of Roundup® WeatherMAX® brand herbicide). No improvement of the effects of the dsRNAs and glyphosate activity (estimated by observing plant growth measured as plant height) was observed for any of the SA treatments at 7 days after glyphosate treatment.

Example 16

This example illustrates methods and topically applied compositions for inducing systemic silencing including the use of agents for conditioning of a plant to permeation by polynucleotides. More specifically, this example describes variations in the order and timing of application of polynucleotides and surfactant solution.

These assays were conducted on Palmer amaranth plants with high copy numbers (56, 63, or 100 copies) of EPSPS, using a protocol including the following steps: (1) application of dsRNA (a solution of the four oligonucleotide-size "short" EPSPS dsRNA molecules described in Example 1) in a solution containing tallowamine surfactant and glycerol; (2) application of 1% SILWET L-77 silicone surfactant; and (3) application of glyphosate (1682 g acid equivalent per hectare of Roundup® WeatherMAX® brand herbicide). Spacing of the timing of the application of the polynucleotides and application of SILWET was assessed, with the SILWET spray applied at 30 minutes, 1 hour, or 2 hours after application of the dsRNA solution. In this set of assays, the three different times of the SILWET solution application all produced similar results, i. e., stunting of growth of most of the high copy plants that were treated with the dsRNA solution, as compared to control high copy plants which were treated with a control solution containing only tallowamine surfactant and glycerol.

Example 17

This example illustrates methods and topically applied compositions for inducing systemic silencing including the use of agents for conditioning of a plant to permeation by polynucleotides. More specifically, this example describes application of polynucleotides of the invention by low-volume spray and the use of a silicone surfactant and ammonium sulfate.

A solution of dsRNA (a solution of the four oligonucleotide-size "short" EPSPS dsRNA molecules described in Example 1) in a solution containing 2% ammonium sulfate was applied by low-volume spray to Palmer amaranth having 16 copies of EPSPS, followed by spraying with glyphosate (1682 g acid equivalent per hectare of Roundup® WeatherMAX® brand herbicide), resulting in the Palmer amaranth plants being killed.

Six Palmer amaranth plants per treatment were treated with a three-step procedure using low-volume spray: (1) spraying 1% SILWET L-77; (2) spraying 2 milliliters of a dsRNA solution containing equal amounts of the four oligonucleotide-size "short" EPSPS dsRNA molecules described in Example 1 at one of 3 doses (1X or 0.8 nanomoles per plant, 2× or 1.6 nanomoles per plant, or 4× or 3.2 nanomoles per plant); and (3) spraying glyphosate (1682 g acid equivalent per hectare of Roundup® WeatherMAX® brand herbicide) at a rate of 159 liters/acre. Nine days after the glyphosate spray, all six plants sprayed with 4× (3.2 nanomoles per plant) dsRNA were killed, and the plants sprayed with 2× (1.6 nanomoles per plant) dsRNA or 1× (0.8 nanomoles per plant) dsRNA were stunted (FIG. 21A).

Several assays were carried out on glyphosate-resistant Palmer amaranth grown from field-collected seeds. Plants were treated with various protocols described below, with some plants being treated topically with a dsRNA solution and control plants being treated with the buffer (dsRNA vehicle); application was by low-volume spray. Unless otherwise noted, the dsRNA solution contained equal amounts of the four oligonucleotide-size "short" EPSPS dsRNA molecules described in Example 1 in buffer at a "4×" dose (3.2 nanomoles per plant); the buffer consisted of 10 millimolar sodium phosphate and 0.01% (v/v) SILWET L-77 organosilicone surfactant in diethylpyrocarbonate (DEPC) water (Omega Bio-Tek) and adjusted to pH 6.8; and herbicide was a glyphosate herbicide applied at 840 g acid equivalent per hectare of Roundup® WeatherMAX® brand herbicide at a rate of 159 liters/acre. Results are provided in Table 7.

Assays 1 and 2: These assays were carried out on glyphosate-resistant Palmer amaranth grown from seeds obtained from a soil sample from a farm location with known glyphosate-resistant Palmer amaranth stands. For assay 1, ten plants per treatment were treated as follows: (1) spraying 1% SILWET L-77; (2) spraying 2 milliliters of the dsRNA solution; and (3) spraying glyphosate. For assay 2, eighteen plants per treatment were treated using the same procedure as in assay 1.

Assay 3: This assay compared treatments applied at different developmental stages and used seedlings grown from Palmer amaranth seeds from a Macon County, Ga. site and selected for glyphosate resistance. The buffer included 2% ammonium sulfate. Twelve small (3-leaf stage) or twelve large (5-leaf stage) seedlings per treatment were treated as follows: (1) spraying 1% SILWET L-77; (2) spraying 2 milliliters of the dsRNA solution; and (3) spraying glyphosate. This treatment provided better control (killed more plants) on small seedlings as compared to the larger seedlings. The dsRNA treatment killed or stunted more glyphosate-resistant plants than treatment with buffer and herbicide achieved, although at 16 days after treatment not all dsRNA-treated plants were killed.

Assays 4 and 5: These assays used Palmer amaranth plants grown from seeds in soil from a Pemiscot, Mo. farm. The buffer included 2% ammonium sulfate. Eleven small (3-leaf stage) seedlings per treatment were treated as follows: (1) spraying 1% SILWET L-77; (2) spraying 2 milliliters of the dsRNA solution; and (3) spraying glyphosate. For assay 5, twelve plants per treatment were treated using the same procedure as in assay 4.

Assay 6: This assay used Palmer amaranth plants grown from seeds in soil from the "Ivy2" farm. The buffer included 2% ammonium sulfate. Eighteen small (3-leaf stage) seedlings per treatment were treated as follows: (1) spraying 1% SILWET L-77; (2) applying 2 milliliters of the dsRNA solution, either by hand or by spraying; and (3) spraying glyphosate. In this assay the method of application (hand drop or spraying) provided similar results.

Assay 7: This assay used 3- to 4-leaf stage Palmer amaranth seedlings grown from F3 seeds selected for glyphosate resistance and more resistant to glyphosate than plants in assays 1-6. The buffer included 2% ammonium sulfate. Eighteen plants per treatment were treated as follows: (1) spraying 1% SILWET L-77; (2) spraying 2 milliliters of the dsRNA solution; and (3) spraying glyphosate.

TABLE 7

| | killed plants/total plants | | |
|---|---|---|---|
| Assay Number | dsRNA-treated | control | Comments |
| 1 | 2/10 | 0/10 | dsRNA-treated survivors stunted compared to controls (FIG. 21B) |
| 2 | 7/18 | 4/18 | dsRNA-treated survivors stunted at 8 and 30 days after treatment, compared to controls |
| 3 (large seedlings) | 5/12 | 3/12 | dsRNA/ammonium sulfate-treated survivors more stunted after treatment, compared to controls |
| 3 (small seedlings) | 9/12 | 6/12 | |
| 4 | 7/11 | 2/11 | dsRNA/ammonium sulfate-treated survivors more stunted after treatment, compared to controls |
| 5 | 8/12 | 3/12 | |
| 6 (hand drop) | 14/18 | — | |
| 6 (spray) | 13/18 | 9/18 | |
| 7 | 8/18 | 2/18 | |

Example 18

This example illustrates methods and topically applied compositions for inducing systemic silencing including the use of agents for conditioning of a plant to permeation by polynucleotides.

Figure 22:
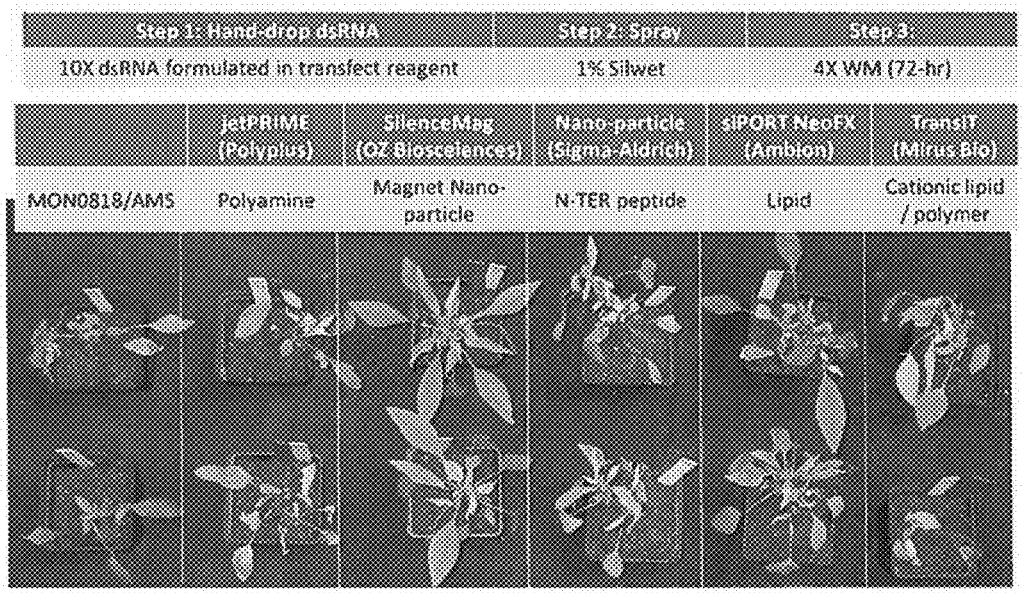
FIG. 22 illustrates results obtained from treating Palmer amaranth with tallowamine surfactant and ammonium sulfate or with transfection reagents, as described in Example 18.

In these assays, the dsRNA solution contained equal amounts of the four oligonucleotide-size "short" EPSPS dsRNA molecules described in Example 1 at a "10×" dose (8 nanomoles per plant) in a solution containing either 0.2% tallowamine surfactant and 2% ammonium sulfate (identified in FIG. 22 as "tallowamine/AMS"), or one of the following transfection reagents: (a) a polyamine (JetPRIME™, Polyplus-transfection SA, Illkirch, France), (b) a magnetic nanoparticle (SilenceMag, OZ Biosciences, Marseille, France), (c) a peptide (N-TER™ Nanoparticle, Sigma-Aldrich, St. Louis, Mo.), (d) a lipid (siPORT™ NeoFX™, Ambion, Foster City, Calif.), or (e) a cationic lipid/polymer (TransIT®, Mirus Bio, Madison, Wis.). Plants were treated as follows: (1) hand-applying dsRNA solution; (2) spraying 1% SILWET L-77; and (3) spraying with glyphosate applied at 840 g acid equivalent per hectare of Roundup® WeatherMAX® brand herbicide at a rate of 159 liters/acre. This protocol when used with dsRNA in the tallowamine surfactant/ammonium sulfate solution kills glyphosate-resistant Palmer amaranth having 35 copies EPSPS. Results are depicted in FIG. 22. Stunting or death of the plants was observed for plants treated with dsRNA in solutions containing polyamine (JetPRIME™), peptide (N-TER™ Nanoparticle), cationic lipid/polymer (TransIT®), or tallowamine surfactant/ammonium sulfate.

Example 19

This example illustrates methods using compositions including topically applied polynucleotides for inducing systemic silencing in a plant. More specifically, this example describes use of different types of polynucleotides for inducing systemic silencing.

Sense single-stranded DNAs (ssDNAs) and anti-sense single-stranded RNAs (ssRNAs) corresponding to the Palmer amaranth EPSPS gene at positions 14-38, positions 153-177, 345-369, and 1105-1129 (indicated by underlined nucleotides in FIG. 1) were purchased from Integrated DNA Technologies. The sense ssDNAs and anti-sense ssRNAs were annealed by heating equal moles of mixed ssDNAs and ssRNAs at 95 degrees Celsius for 5 minutes and slowly cooled over 1.5-2 hours to room temperature to yield the DNA/RNA hybrids.

16-copy glyphosate-resistant Palmer amaranth plants were used in the assays which used this procedure: (1) spraying 1% SILWET L-77; (2) hand-applying on four mature leaves of each plant a total of 0.8 nanomoles of either the Palmer EPSPS dsRNAs (as described in Example 1) or of the Palmer EPSPS DNA/RNA hybrids; and (3) spraying with glyphosate applied at 840 g acid equivalent per hectare of Roundup® WeatherMAX® brand herbicide at a rate of 159 liters/acre.

Figure 23:
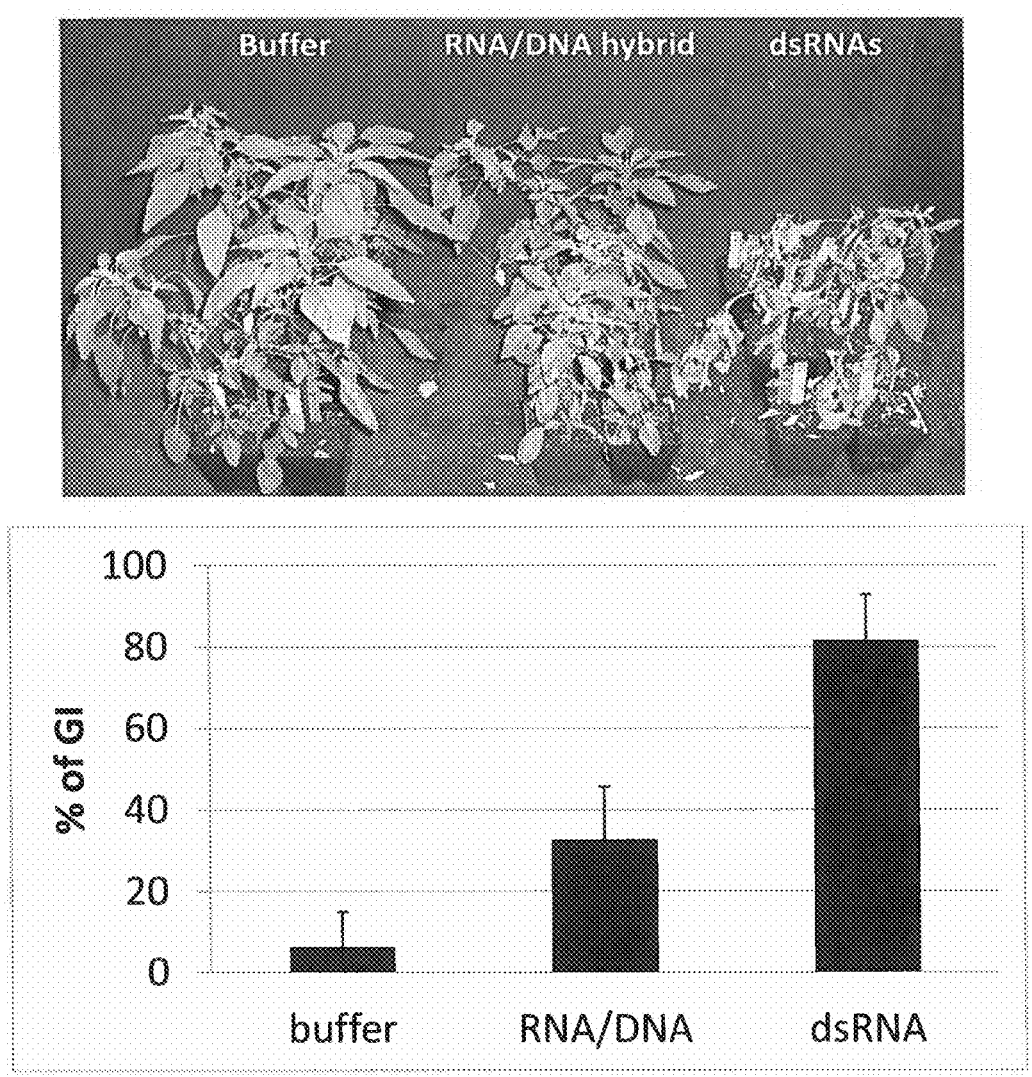
FIG. 23 illustrates results of treating glyphosate-resistant Palmer amaranth plants with either EPSPS dsRNAs or EPSPS DNA/RNA hybrids, as described in Example 19.

Results are depicted in FIG. 23. Seven days after the herbicide spraying, 4 out of 6 dsRNA-treated plants were dead and the remaining 2 were dying, whereas plants sprayed with the DNA/RNA hybrid were stunted in growth (glyphosate injury) compared to the control.

Example 20

This example illustrates methods using compositions including topically applied polynucleotides for inducing systemic silencing in a plant. More specifically, this example describes use of different types of polynucleotides for inducing systemic silencing.

Figure 24:
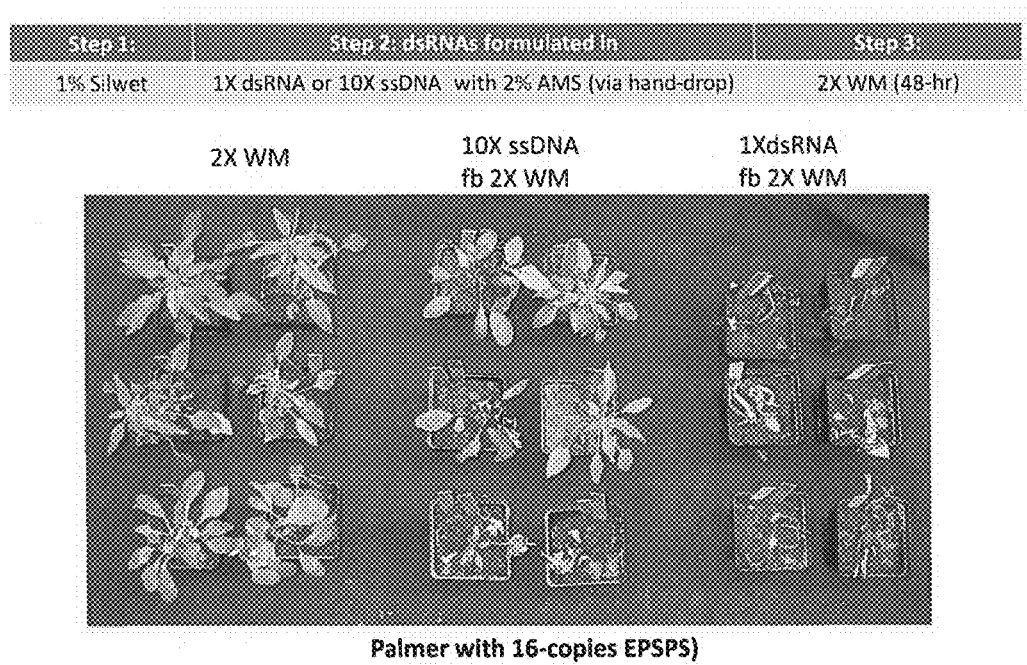
FIG. 24 illustrates results of treating glyphosate-resistant Palmer amaranth plants with either EPSPS dsRNA or EPSPS ssDNA polynucleotides, as described in Example 20. The upper photography was taken at 8 days after herbicide spray and the lower (bar) graph presents the results as a glyphosate injury (GI) scored 8 days after herbicide spray.

Six glyphosate-resistant Palmer amaranth plants having 16 copies of EPSPS were used per treatment in this assay. A 0.8 nanomoles ("1X") per plant treatment of dsRNA, a ten-fold greater amount (8 nanomoles per plant treatment, "10×") of ssDNA polynucleotides (described in Example 19) and buffer alone as a control, were applied to separate plants by hand in buffer containing 2% ammonium sulfate, followed 48 hours later by spraying with glyphosate applied at 840 g acid equivalent per hectare of Roundup® WeatherMAX® brand herbicide at a rate of 159 liters/acre. FIG. 24 depicts the results. Both polynucleotide treatments gave better control of the Palmer amaranth compared to plants treated only with buffer and herbicide. Of the plants treated with the 10× ssDNA treatment, two of six were killed, and the remaining four were stunted in growth by 30%. Of the plants treated with the 1×dsRNA treatment, all six plants were killed by 8 days after WM spray or 10-day after dsRNA treatment.

Example 21

This example illustrates methods using compositions including topically applied polynucleotides for inducing systemic silencing in a plant More specifically, this example describes selection of a polynucleotide sequence for inducing systemic silencing in a plant.

Twelve dsRNAs of approximately 250 bp each and having one strand of the dsRNA corresponding to the EPSPS tiled DNA sequences of SEQ ID NOS:41-52 (Table 8) were designed to cover in a tiling fashion the full coding sequence and part of the 5' and 3' untranslated regions of the Palmer amaranth EPSPS gene, as depicted in FIG. 25A.

TABLE 8

| Tiling segment number (see FIG. 25A) | Sequence | SEQ ID NO. |
|---|---|---|
| 1 | CGCCAGGGCTGCAGACGCGTTACGTANTCGGATCCAGAATTCGTGATTAAC GTCACAGCATGTCATGTAAAACACGCGAATCAGACCGGTCCACTCTTGTTT TAATTTGAGACAATTTTGATGTTGAGTCATCCCACACCAACCCCAAAAAAT TCAACAACAAACTCTTATAATGATTCCCTCTACTCTACTAGAGTCTACACC AACCCACTTTCTCTTTGCCCACCAAAACTTTGGTTTGGTAAGAACT | 41 |
| 2 | CACCAACCCACTTTCTCTTTGCCCACCAAAACTTTGGTTTGGTAAGAACTA AGCCCTCTTCTTTCCCTTCTCTCTCTTAAAAGCCTAAAATCCACCTAACTTT TTCAGCCAACAAACAACGCCAAATTCAGAGGAAGAATAATGATGGCTCAA GCTACTACCATCAACAATGGTGTCCATACTGGTCAATTGCACCATACTTTA CCCAAAACCCAGTTACCCAAATCTTCAAAAACTCTTAATT | 42 |
| 3 | CCATACTTTACCCAAAACCCAGTTACCCAAATCTTCAAAAACTCTTAATTTT GGATCAAACTTGAGAATTTCTCCAAAGTTCATGTCTTTAACCAATAAAAGA GTTGGTGGGCAATCATCAATTGTTCCCAAGATTCAAGCTTCTGTTGCTGCT GCAGCTGAGAAACCTTCATCTGTCCCAGAAATTGTGTTACAACCCATCAAA GAGATCTCTGGTACTGTTCAATTGCCTGGGTCAAAGTCTTTATCC | 43 |
| 4 | TCAAAGAGATCTCTGGTACTGTTCAATTGCCTGGGTCAAAGTCTTTATCCA ATCGAATCCTTCTTTTAGCTGCTTTGTCTGAGGGCACAACAGTGGTCGACA ACTTGCTGTATAGTGATGATATTCTTTATATGTTGGACGCTCTCAGAACTCT TGGTTTAAAAGTGGAGGATGATAGTACAGCCAAAAGGGCAGTCGTAGAGG GTTGTGGTGGTCTGTTTCCTGTTGGTAAAGATGGAAAGGAAGAGAT | 44 |
| 5 | GAGGGTTGTGGTGGTCTGTTTCCTGTTGGTAAAGATGGAAAGGAAGAGATT CAACTTTTCCTTGGTAATGCAGGAACAGCGATGCGCCCATTGACAGCTGCG GTTGCCGTTGCTGGAGGAAATTCAAGTTATGTGCTTGATGGAGTACCAAGA ATGAGGGAGCGCCCCATTGGGGATCTGGTAGCAGGTCTAAAGCAACTTGG TTCAGATGTAGATTGTTTTCTTGGCACAAATTGCCCTCCTGTTCGGG | 45 |
| 6 | TGGTTCAGATGTAGATTGTTTTCTTGGCACAAATTGCCCTCCTGTTCGGGTC AATGCTAAAGGAGGCCTTCCAGGGGGCAAGGTCAAGCTCTCTGGATCGGT TAGTAGCCAATATTTAACTGCACTTCTCATGGCTACTCCTTTGGGTCTTGGA GACGTGGAGATTGAGATAGTTGATAAATTGATTTCTGTACCGTATGTTGAA ATGACAATAAAGTTGATGGAACGCTTTGGAGTATCCGTAGAACAT | 46 |
| 7 | TTGAAATGACAATAAAGTTGATGGAACGCTTTGGAGTATCCGTAGAACAT AGTGATAGTTGGGACAGGTTCTACATTCGAGGTGGTCAGAAATACAAATCT CCTGGAAAGGCATATGTTGAGGGTGATGCTTCAAGTGCTAGCTACTTCCTA GCCGGAGCCGCCGTCACTGGTGGGACTGTCACTGTCAAGGGTTGTGGAAC AAGCAGTTTACAGGGTGATGTAAAATTTGCCGAAGTTCTTGAGAAGAT | 47 |
| 8 | ACAAGCAGTTTACAGGGTGATGTAAAATTTGCCGAAGTTCTTGAGAAGAT GGGTTGCAAGGTCACCTGGACAGAGAATAGTGTAACTGTTACTGGACCAC CCAGGGATTCATCTGGAAAGAAACATCTGCGTGCTATCGACGTCAACATG AACAAAATGCCAGATGTTGCTATGACTCTTGCAGTTGTTGCCTTGTATGCA GATGGGCCCACCGCCATCAGAGATGTGGCTAGCTGGAGAGTGAAGGAA | 48 |
| 9 | AGATGGGCCCACCGCCATCAGAGATGTGGCTAGCTGGAGAGTGAAGGAA CCGAACGGATGATTGCCATTTGCACAGAACTGAGAAAGCTTGGGGCAACA GTTGAGGAAGGATCTGATTACTGTGTGATCACTCCGCCTGAAAAGCTAAAC CCCACCGCCATTGAAACTTATGACGATCACCGAATGGCCATGGCATTCTCT CTTGCTGCCTGTGCAGATGTTCCCGTCACTATCCTTGATCCGGGATGC | 49 |
| 10 | CTCTTGCTGCCTGTGCAGATGTTCCCGTCACTATCCTTGATCCGGGATGCAC CCGTAAAACCTTCCCGGACTACTTTGATGTTTTAGAAAAGTTCGCCAAGCA TTGATGAGTAGCTATATACGAGATCCTTAAATTGTACGCCGAAGGTTTTGA TTTGAGTCTAATAGTAGATAAAAGGCTATAAATAAACTGGCTTTCTGCTTG AGTAATTATGAAATTCTTTGTATTATGTTTGTGAGATTTGAAGTAGCTTATA | 50 |

TABLE 8-continued

| Tiling segment number (see FIG. 25A) | Sequence | SEQ ID NO. |
|---|---|---|
| 11 | TAATTATGAAATTCTTTGTATTATGTTTGTGAGATTTGAAGTAGCTTATAAA<br>TTACAATGTACTAAAGTCTAGAAATAAGTTATGTATCTTTTAAATCAATGA<br>GAAATGCATACTTGAAAGGCTTGACCTTGTATTTGTGACCTAAAGAGTACT<br>AACTTTGGAGTTTCCAACTCATTTGTTTATCTCATTTTTTTTAATTTTTGAT<br>TTAAATTGTTTATTTTTATGAGTAATCATGTATCTTTCTTATTCTAACCAAA<br>TGTAATACTCCTTC | 51 |
| 12 | TATGAGTAATCATGTATCTTTCTTATTCTAACCAAATGTAATACTCCTTCCA<br>ACTCTCTTTAAACGTCCACACTCTGGGCACAGAGTGTAATAGTGTGGTGGT<br>TGGAGTCTTTTAAGTGATTATAATAATTGTAAATGTGGTAGTTAGAATATT<br>TTAAGTAATGTAGGTGGGGTATTATGGTCTTGTTGAACATAGGATATTTAG<br>GTAAAAAATCTATGCAAAAAAAGGAAAGTAAGCAAATAAAGCGAATTGA<br>CCTGAAAAGAAAAGTGGACATGTATAGTGAGTTGGAGGAAGTATTTT | 52 |

The four oligonucleotide-size "short" EPSPS dsRNA molecules as described in Example 1 and FIG. 1 are located in the tiling segments 2, 3, 4, and 8 respectively, and are shown as light grey bars within those segments. The polynucleotides were synthesized in vitro transcription using a pBR322 vector with the EPSPS polynucleotides inserted at EcoRI and BamHI cloning sites; plasmid DNA was isolated with Qiagen Maxi prep kits and digested with EcoRI and BamHI restriction enzymes. The digested DNA solution was used in the treatment of the plants without further purification.

Glyphosate-resistant Palmer amaranth plants having 16 copies of EPSPS were treated as follows: spraying with 1% SILWET L-77; (2) hand application of a dsRNA solution (containing polynucleotides selected from the twelve tiling segments or the four "short" dsRNA molecules described in Example 1 at the rate of 0.01 nanomole DNA/plant) or buffer as a control; and (3) 48 hours later spraying with glyphosate applied at 840 g acid equivalent per hectare of Roundup® WeatherMAX® brand herbicide at a rate of 159 liters/acre. Above-ground height of the treated plants was observed 11 days after herbicide treatment; plants that were dead or dying were assigned a height of zero. Results are depicted in FIGS. 25B and 25C. The dsRNA polynucleotides combinations showing the greatest efficacy in this assay included the four "short" dsRNA molecules described in Example 1, the combination of tiling segments 2, 5, 8, and 11, and the combination of tiling segments 7, 8, and 9.

Example 22

This example illustrates methods using compositions including topically applied polynucleotides for inducing systemic silencing in a plant. More specifically, this example describes topical application of polynucleotides following application of herbicide to a plant.

Figure 26:
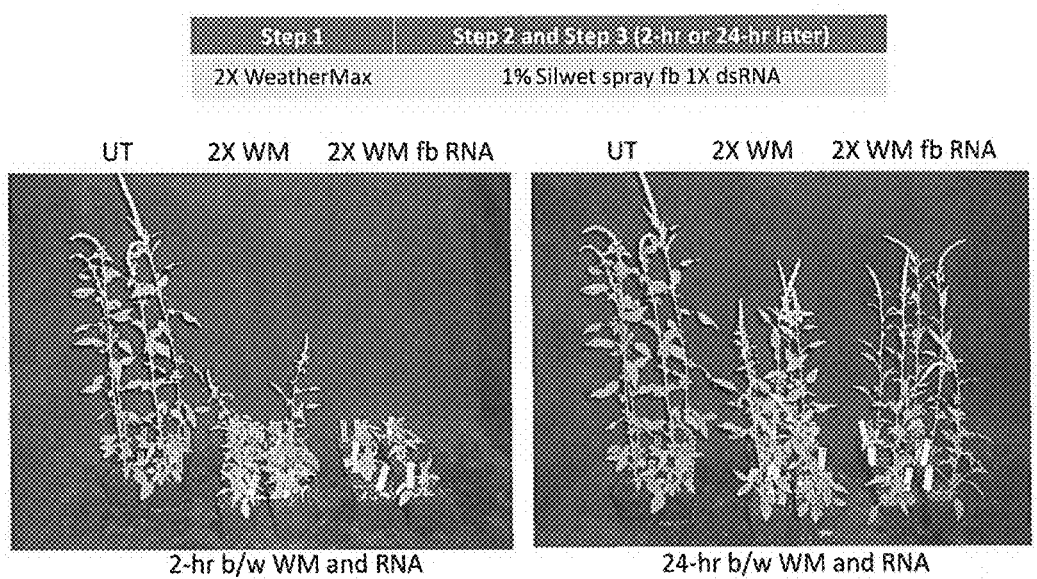
FIG. 26 illustrates results of treating glyphosate-resistant Palmer amaranth plants with glyphosate followed by spraying with 1% SILWET L-77 (Silicone Polyether Copolymer) followed by application of EPSPS dsRNA in buffer containing 2% ammonium sulfate, as described in Example 22. Untreated ("UT") control plants were treated only with the 1% SILWET L-77 spray but not with herbicide or dsRNA. Plants were photographed and rated at 16 days after treatment.

In one assay, glyphosate-resistant Palmer amaranth plants having 16 copies of EPSPS were sprayed with glyphosate applied at 840 g acid equivalent per hectare of Roundup® WeatherMAX® brand herbicide at a rate of 159 liters/acre. Two or 24 hours after herbicide application, the plants were treated by spraying with 1% SILWET L-77. Fifteen to 20 minutes after SILWET treatment, the plants were treated by hand application of either 0.8 nanomoles ("1×") per plant of the four oligonucleotide-size "short" EPSPS dsRNA molecules as described in Example 1 in buffer containing 2% ammonium sulfate or buffer containing 2% ammonium sulfate. In this assay, untreated ("UT") control plants were treated only with the 1% SILWET L-77 spray but not with herbicide or dsRNA. Results are depicted in FIG. 26. In this assay, application of 1% SILWET resulted in improved glyphosate activity by 60% when applied 2 hours after herbicide spraying and by 20% when applied 24 hours after herbicide spraying. In this assay, application of 1% SILWET followed by EPSPS dsRNA resulted in improved glyphosate activity by at least 80% when applied 2 hours after herbicide spraying and by 20% when applied 24 hours after herbicide spraying.

In another assay, Palmer amaranth plants grown from seeds in soil from a farm site in Macon, Ga. were sprayed with glyphosate applied at 840 g acid equivalent per hectare of Roundup® WeatherMAX® brand herbicide at a rate of 159 liters/acre. Three days after herbicide treatment, 9 of 40 plants were killed and 3 were severely stunted. Surviving plants were sprayed with 1% SILWET L-77, followed by topical application by hand of either 8 nanomoles ("10") per plant of the four oligonucleotide-size "short" EPSPS dsRNA molecules as described in Example 1 or buffer as a control. Three days later, 3 more plants in the dsRNA-treated group were dead and 2 more plants in the buffer-treated group were dead. At this point (6 days after the original herbicide treatment and 3 days after the SILWET/dsRNA or buffer treatment), half of the surviving plants in each group were sprayed with a second application of glyphosate (applied at the same dose as in the first application). Two weeks after this second herbicide treatment, the remaining dsRNA-treated plants showed 80% injury and the remaining buffer-treated plants showed 40% injury.

Example 23

This example illustrates methods using compositions including topically applied polynucleotides for inducing systemic silencing in a plant. More specifically, this example describes a single-step topical application of a single composition including polynucleotides, surfactant, and herbicide for controlling herbicide-resistant weeds.

This assay was carried out on a field population of glyphosate-resistant Palmer amaranth plants that were known to have very high copy numbers of EPSPS (plants from this study site have been reported to have from 5 to more than 160 copies of EPSPS by Gaines et al. (2010) *Proc. Natl. Acad. Sci. USA,* 107:1029-1034). The polynucleotides used in this assay were an equimolar mixture of the four oligonucleotide-size "short" EPSPS dsRNA molecules as described in Example 1.

Four to six inch tall plants in a treatment area of 1 foot by 5 feet were sprayed in a single treatment with either 264 micrograms ("100×") or 52.8 micrograms ("20×") of the EPSPS dsRNAs in a solution that also contained 1% SIL-WET L-77 surfactant, 2% ammonium sulfate, and glyphosate (applied at 1682 g acid equivalent per hectare of Roundup® WeatherMAX® brand herbicide at a rate of 159 liters/acre). For comparison, other plants in treatment areas of 1 foot by 5 feet were sprayed with glyphosate (in a solution that also contained 1% SILWET L-77 surfactant and 2% ammonium sulfate) applied at the same rate.

Figure 27:
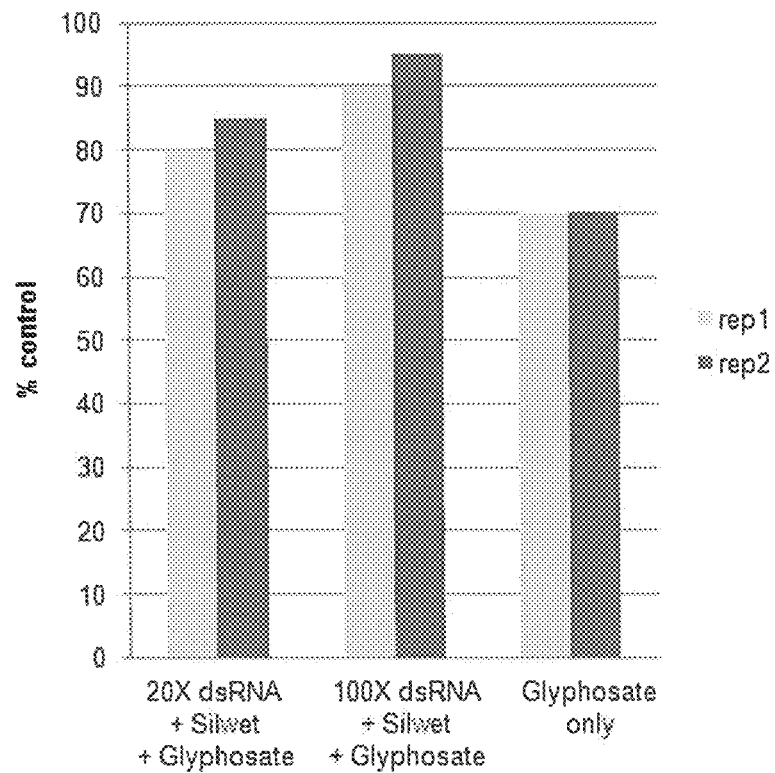
FIG. 27 illustrates results of treating a field population of high copy number glyphosate-resistant Palmer amaranth with a composition containing a 20× or 100× amount of EPSPS dsRNA polynucleotides, surfactant, ammonium sulfate, and herbicide or with a composition containing, surfactant, ammonium sulfate, and herbicide, as described in Example 23. For each treatment, two replicate 1 foot by 5 foot plots were treated.

Results are depicted in FIG. 27. Treating the plants with only glyphosate (applied at 1682 g acid equivalent per hectare of Roundup® WeatherMAX® brand herbicide at a rate of 159 liters/acre) in a solution that also contained SILWET L-77 and ammonium sulfate resulted in about 70% control (death of plants). The one-step treatment using a composition containing the 20×EPSPS dsRNA polynucleotides, surfactant, ammonium sulfate, and herbicide resulted in about 80-85% control of the glyphosate-resistant Palmer amaranth, which is the approximate control rate obtained by spraying with glyphosate applied at 6720 g acid equivalent per hectare of Roundup® WeatherMAX® brand herbicide at a rate of 159 liters/acre (i. e., at 8 times the standard application rate of about 840 g acid equivalent per hectare of Roundup® WeatherMAX® brand herbicide at a rate of 159 liters/acre). The one-step treatment using a composition containing the 100×EPSPS dsRNA polynucleotides, surfactant, ammonium sulfate, and herbicide resulted in about 90-95% control of the glyphosate-resistant Palmer amaranth, which is the approximate control rate obtained by spraying with glyphosate applied at 13440 g acid equivalent per hectare of Roundup® WeatherMAX® brand herbicide at a rate of 159 liters/acre (i. e., at 16 times the standard application rate of about 840 g acid equivalent per hectare of Roundup® WeatherMAX® brand herbicide at a rate of 159 liters/acre).

Example 24

This example illustrates a method for inducing systemic regulation of a target gene in a vegetable plant by topical application to the vegetable of a polynucleotide molecule including a segment with a nucleotide sequence essentially identical to, or essentially complementary to, a sequence of 18 or more contiguous nucleotides in either the target gene or RNA transcribed from the target gene, whereby the molecule permeates the interior of the vegetable plant and induces systemic regulation of the target gene. In this example, growing vegetable plants were treated with a topically applied composition for inducing systemic silencing of a target gene in a vegetable or fruit crop plant including (a) an agent for conditioning of a plant to permeation by polynucleotides and (b) polynucleotides including at least one polynucleotide strand including at least one segment of 18 or more contiguous nucleotides of the target gene in either anti-sense or sense orientation. More specifically, this example demonstrates the use of topically applied polynucleotides to induce systemic silencing of a phytoene desaturase (PDS) gene in a vegetable crop plant, i. e., lettuce (*Lactuca sativa*).

Lettuce PDS has the sequence ATGTCTCTGTTTG-GAAATGTTTCTGCCATTAACTCAAGTGGAAAGTG-TATAGTAATGAATCTTTCAAGC ACACAAATCACT-TCAAGAGATTGTTTCAAGATTACCTCAGGGCAAA-AAGATGTTTTGTCATTTGGATG CTGTGATGC-TATGGGTAACAGATTGCAATTCCCAAGTGCTCGT-TCTTTTACACCAAGATCAAAGAAGA ATGTCTC-CCCTCTAAAGGTAGTTTGTGTTGATTATCCAAGA-CCAGATCTTGATAACACATCTAATTTCT TGGAAGCT-GCTCACTTGTCTTCAACCTTCAGAACTTC-CCCACGCCCATCTAAGCCATTGAAGATTGTAA TTGCTGGTGCAGGTTTAGCTGGTTTATCAACT-GCTAAGTATTTAGCTGATGCAGGTCACAAGC-CAATTT TACTAGAAGCAAGAGATGTTCTTGGTG-GAAAGGTGGCAGCTTGGAAAGATGATGATGGAG-ATTGGTA TGAGACAGGTTTACACATATTCTTTG-GAGCTTACCCAAATGTACAAAATTTATTTGGA-GAGCTAGGAA TTAATGATAGATTACAGTG-GAAGGAGCATTCTATGATATTTGCAATGCCAAATA-AGCCTGGAGAATTT AGTAGGTTTGACTTCCCAGAT-GTTTTACCTGCACCATTGAATGGAATTTTTGCTAT-ATTGAGGAACAAT GAAATGCTGACGTGGCCT-GAGAAAGTGAAGTTTGCAATTGGGCTGTTGCCTG-CAATGTTAGGTGGACA GGCTTATGTTGAGGC-CCAAGATGGGCTTAGTGTTCAGGACTGGAT-GAGAAAGCAAGGTATACCTGATC GAGTTACTACT-GAAGTGTTTATTGCAATGTCAAAAGCATTAAACTT-TATAAATCCAGATGAACTTTCAA TGCAATGTATTCT-CATTGCTCTAAACCGTTTTCTTCAGGAAAAGCATG-GTTCCAAGATGGCATTTTTAG ATGGGAGCCCACCA-GAAAGACTTTGCAAGCCAATTGTTGACCACATCG-AGTCACTCGGTGGCCAAGTC AGAGTCAACTCAC-GAATACAAAAAATTGAGTTAAACAAAGACG-GAACTGTCCGGAACTTTCTATTGAG TGATGGGAAT-GTTCTAGAAGCTGATGCTTATGTTTCGCTACCC-CTGTTGACATTCTCAAGCTTCTTTTA CCCGAAGAATGGAAACCAATTCCAT-ATTTCAAAAAATTAGAGAAGTTAGTCGGTGTTCCT-GTTATAAA CGTTCATATATGGTTTGACAGAAAGCT-GAAAAACACATATGATCACTTACTTTTCAGTAGG-TCACCTCT GCTGAGTGTGTATGCTGACATGTCAGT-GACATGTAAGGAATATTATGATCCAATAAGTCAAT-GTTGG AGTTGGTTCTTGCTCCAGCTGAGGAATG-GATTTCAAGAAGTGACACTGATATTATTGATGCA-ACAATG AGTGAACTTTCAAGGCTTTTTCCTGAT-GAAATTGCAGCTGATCAAAGTAAAGCAAAAATCTT-GAAATA TAAAGTTGTTAAAACACCAAGGTCTGTT-TATAAAACTGTTCCAGATTGTGAACCATGTCGAC-CCCTACA AAGATCTCCAATTCAAGGATTTTATT-TATCTGGTGATTATACTAAACAAAAGTATTTGGCT-TCAATGGG GGGTGCTGTTTTATCTGGAAAAATTT-GTGCACAAGCTATTTTACAAGATTATGAGATGCTT-GCTACA (SEQ ID NO:53). Polynucleotide single-stranded DNAs of 21-45 nucleotides in length with the following sequences were synthesized: taatacgactcactatagggtttggagct-tacccaaATGtac ("HL286", sense orientation, SEQ ID NO:54), taatacgactcactatagggaggccacgtcagcatttcattgttc ("HL287", anti-sense orientation, SEQ ID NO:55), ccat-tcaATGgtgcaggtaaaac ("HL288", anti-sense orientation, SEQ ID NO:56), catagaATGctccttccactg ("HL289", anti-sense orientation, SEQ ID NO:57), and caaataaattttgta-camgggtaagctccaa ("HL290", anti-sense orientation, SEQ ID NO:58). An ssDNA solution was made with an equal mixture of all five polynucleotides in 0.01% SILWET L-77 in 5 millimolar sodium phosphate buffer, pH 6.8.

Figure 28:
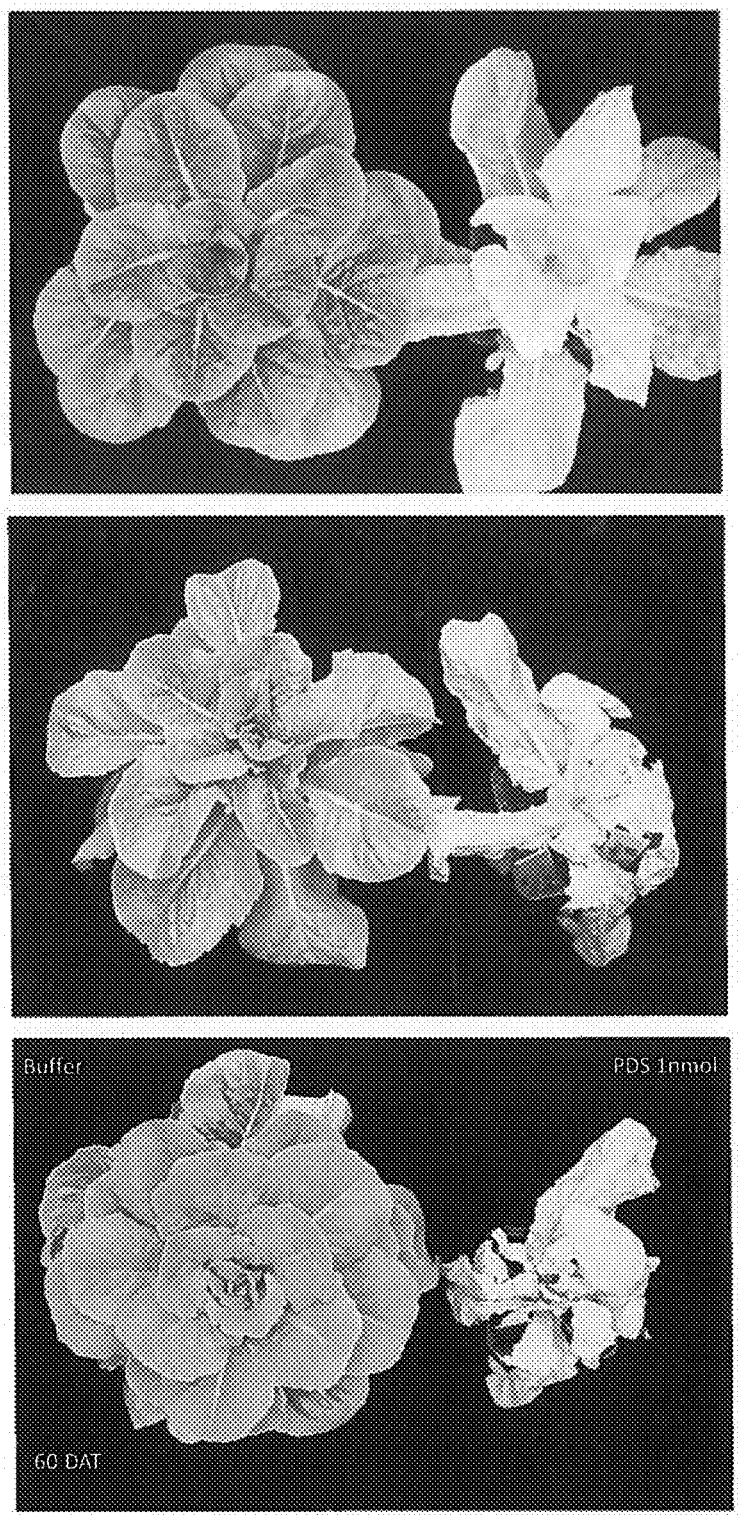
FIG. 28 depicts the progression of bleaching and death of the lettuce plants treated with 1 nanomole ssDNA per plant at (from top to bottom) 37, 46, and 60 days after treatment, as described in Example 24.

Lettuce variety LS49 "Green Tower" was used in the assays. Two fully expanded leaves of each plant were dipped into a freshly made 0.1% SILWET L-77 in double-distilled water solution for a few seconds. The leaves were allowed to dry for 15-30 minutes. Each plant was then treated by applying 20 microliters ssDNA solution to the top surface of two SILWET-treated leaves (total 40 microliters per plant). Table 9 lists the assay conditions used and the observed bleaching of plants topically treated with ssDNA polynucleotides. FIG. 28 depicts the progression of bleaching and death of the lettuce plants treated with 1 nanomole ssDNA per plant at (from top to bottom) 37, 46, and 60 days after treatment.

TABLE 9

| Developmental stage | Amount of each ssDNA applied (nanomoles/plant) | Earliest observation of bleaching |
| --- | --- | --- |
| 4 weeks post-germination, plants have 2 fully expanded leaves | 1 | 3 weeks post-treatment |
| 5 weeks post-germination, plants have 4 fully expanded leaves | 4 | 4 days post-treatment |

The assays were repeated with 2 or 4 nanomoles ssDNA applied per plant. FIG. 29A depicts the systemic silencing evidenced by bleaching observed at 4 or 12 days after topical treatment with the polynucleotides.

The assays were repeated using each individual anti-sense ssDNAs ("HL287", SEQ ID NO:55; "HL288", SEQ ID NO:56; "HL289", SEQ ID NO:57; and "HL290", SEQ ID NO:58) with 8 nanomoles polynucleotide applied per plant; positive control plants were treated with a mixture of the four individual anti-sense ssDNAs at 2 nanomoles each (for a total of 8 nanomoles polynucleotide applied per plant) and negative control plants were treated only with buffer. FIG. 29B depicts the systemic silencing evidenced by bleaching observed at 4 after topical treatment with the anti-sense ssDNAs.

Example 25

This example illustrates an aspect of the invention. In this example, growing plants were treated with a topically applied composition for inducing systemic silencing of a target gene in a plant including (a) an agent for conditioning of a plant to permeation by polynucleotides and (b) polynucleotides including at least one polynucleotide strand including at least one segment of 18 or more contiguous nucleotides of the target gene in either anti-sense or sense orientation. More specifically, this example demonstrates the use of topically applied polynucleotides to induce systemic silencing of a phytoene desaturase (PDS) gene in a vegetable crop, i. e., tomato (Solanum lycopersicum).

Tomato PDS has the sequence GGGTTTATCTCGCAAGTGTGGCTATGGTGGGACGTGTCAAATTTGGATTGTAGCCAAACATGAGATTT GATTTAAAGGGAATTGGCCAAATCACCGAAAGCAGGCATCTTCATCATAAATTAGTTTGTTTATTTATACAGAATTATACGCTTTTACTAGTTATAGCATTCGGTATCTTTTTCTGGGTAACTGCCAAACCACCACAAATTTCAAGTTTCCATTTAACTCTTCAACTTCAACCCAACCAAATTTATTTGCTTAATTGTGCAGAACCACTCCCTATATCTTCTAGGTGCTTTCATTCGTTCCGAGTAAAATGGCCTCAAATTGGACTTGTTTCTGCTGTTAACTTGAGAGTCCAAGGTAGTTCAGCTTATCTTTGGAGCTCGAGGTCGTCTTCTTTGGGAACTGAAAGTCGAGATGGTTGCTTGCAAAGGAATTCGTTATGTTTTGCTGGTAGCGAATCAATGGGTCATAAGTTAAA GATTCGTACTCCCCATGCCACGACCAGAAGATTGGTTAAGGACTTGGGGCCTTTAAAGGTCGTATGCA TTGATTATCCAAGACCAGAGCTGGACAATACAGTTAACTATTTGGAGGCTGCATTTTTATCATCAACGT TCCGTGCTTCTCCGCGCCCAAACTAAACCATTGGAGATTGTTATTGCTGGTGCAGGTTTGGGTGGTTTGT CTACAGCAAAATATTTGGCAGATGCTGGTCACAAACCGATACTGCTGGAGGCAAGGGATGTTCTAGGT GGAAAGGTAGCTGCATGGAAAGATGATGATGGAGATTGGTACGAGACTGGTTTGCATATATTCTTTGG GGCTTACCCAAATATTCAGAACCTGTTTGGAGAATTAGGGATTAACGATCGATTGCAATGGAAGGAAC ATTCAATGATATTTGCAATGCCAAGCAAGCCAGGAGAATTCAGCCGCTTTGATTTCTCCGAAGCTTTAC CCGCTCCTTTAAATGGAATTTTAGCCATCTTAAAGAATAACGAAATGCTTACATGGCCAGAGAAAGTC AAATTTGCAATTGGACTCTTGCCAGCAATGCTTGGAGGGCAATCTTATGTTGAAGCTCAAGATGGGAT AAGTGTTAAGGACTGGATGAGAAAGCAAGGTGTGCCGGACAGGGTGACAGATGAGGTGTTCATTGCT ATGTCAAAGGCACTCAACTTTATAAACCCTGACGAACTTTCAATGCAGTGCATTTTGATCGCATTGAAC AGGTTTCTTCAGGAGAAACATGGTTCAAAAATGGCCTTTTTAGATGGTAATCCTCCTGAGAGACTTTGC ATGCCGATTGTTGAACACATTGAGTCAAAAGGTGGCCAAGTCAGACTGAACTCACGAATAAAAAAGA TTGAGCTGAATGAGGATGGAAGTGTCAAGAGTTTTATACTGAGTGACGGTAGTGCAATCGAGGGAGAT GCTTTTGTGTTTGCCGCTCCAGTGGATATTTTCAAGCTTCTATTGCCTGAAGACTGGAAAGAGATTCCA TATTTCCAAAAGTTGGAGAAGTTAGTCGGAGTACCTGTGATAAATGTACATATATGGTTTGACAGAAA ACTGAAGAACACATATGATCATTTGCTCTTCAGCAGAAGCTCACTGCTCAGTGTGTATGCTGACATGTC TGTTACATGTAAGGAATATTACAACCCCAATCAGTCTATGTTGGAATTGGTTTTTGCACCTGCAGAAGA GTGGATATCTCGCAGCGACTCAGAAATTATTGATGCAACGATGAAGGAACTAGCAACGCTTTTTCCTG ATGAAATTTCAGCAGATCAAAGCAAAGCAAAAATATTGAAGTACCATGTTGTCAAAACTCCGAGGTCT GTTTATAAAACTGTGCCAGGTTGTGAACCCTGTCGGCCTTTACAAAGATCCCCAATAGAGGGGTTTTAT TTAGCCGGTGACTACACGAAACAGAAATACTTGGCTTCAATGGAAGGCGCTGTCTTATCAGGAAAGCT TTGTGCTCAAGCTATTGTACAGGATTATGAGTTACTTGTTGGACGTAGCCAAAAGAAGTTGTCGGAAG CAAGCGTAGTTAGCTTTGTGGTTATTATTTAGCTTCTGTACACTAAATTTATGATGCAAGAAGCGTTG TACACAACATATAGAAGAAGAGTGCGAGGTGAAGCAAGTAGGAGAAATGTTAGGAAAGCTCCTATAC AAAAGGATGGCATGTTGAAGATTAGCATCTTTTTAATCCCAAGTTTAAATATAAAGCATATTTTATGTA CCACTTTCTTTATCTGGGGTTTGTAATCCCTTTATATCTTTATGCAATCTTTACGTTAGTTAAAAAAAAA AAAAAAAAAAAAAACTCGA (SEQ ID NO:59).

A 201 nucleotide dsRNA polynucleotide with an anti-sense strand capable of hybridizing to the RNA encoded by the sequence TCGCAGCGACTCAGAAATTATTGATGCAACGATGAAGGAACTAGCAACGCTTTTTCCTGATGAAATTT CAGCAGATCAAAGCAAAGCAAAAATATTGAAGTACCATGTTGTCAAAACTCCGAGGTCTGTTTATAAA ACTGTGCCAGGTTGTGAACCCTGTCGGCCTTTACAAAGATCCCCAATAGAGGGGTTTTATTTAG (SEQ ID NO:60) which correspond to the nucleotides at positions 1724-1923 of the mRNA transcribed from the tomato PDS gene sequence (SEQ ID NO:59) was synthesized by RT PCR using oligonucleotide primers with the sequences TAATACGACTCACTATAGGGTCGCAGC-GACTCAGAAATTATTG (SEQ ID NO:61, sense primer) and TAATACGACTCACTATAGGGGTAAAGGC-CGACAGGGTTCACAACC (SEQ ID NO:62, anti-sense primer). A 2.5 micromolar dsRNA solution was made with the 201 nucleotide dsRNA polynucleotide (SEQ ID NO:60) in 0.01% SILWET L-77 in 5 millimolar sodium phosphate buffer, pH 6.8.

Figure 30:
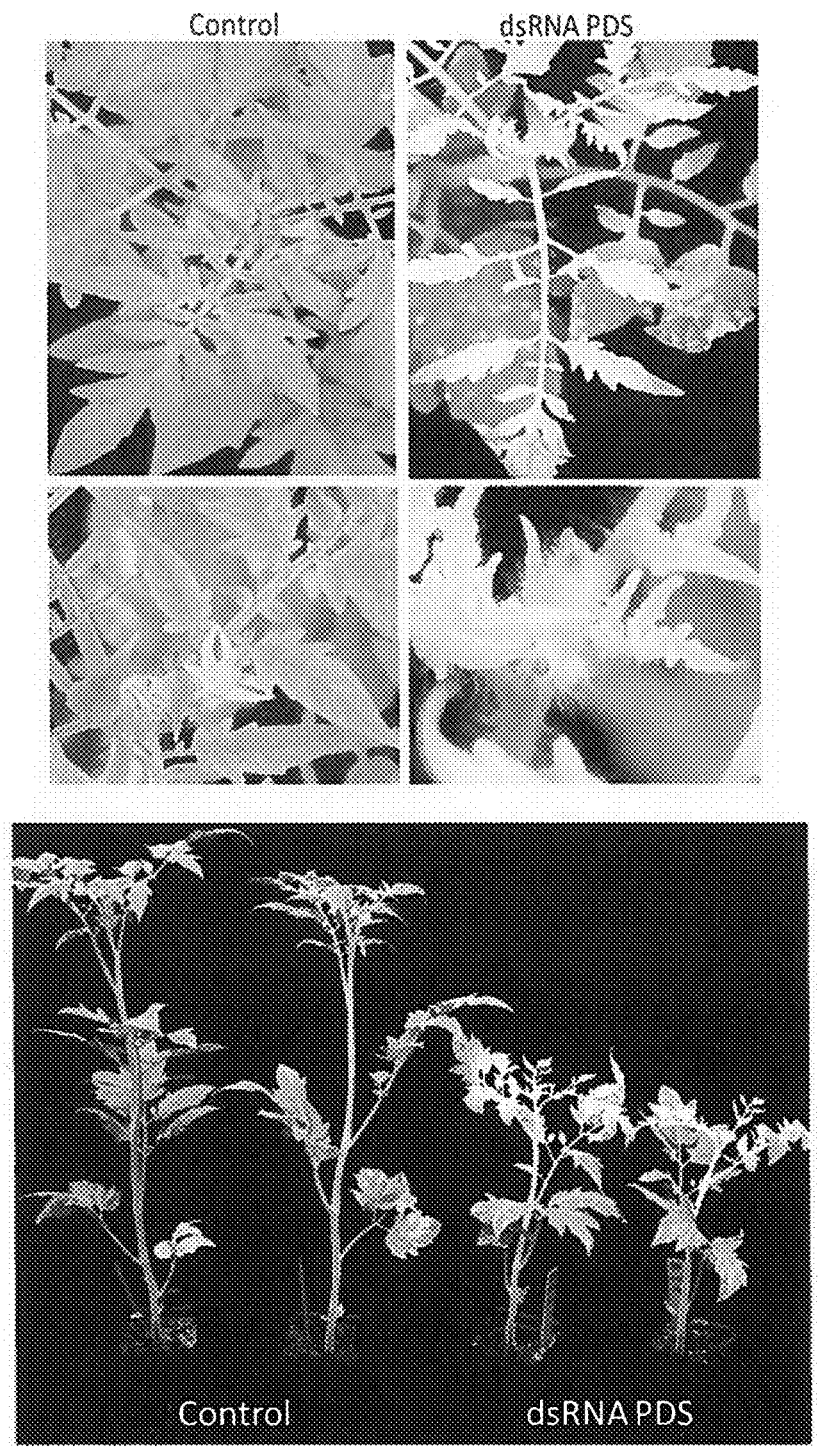
FIG. 30 illustrates bleaching of leaves (right top panel) and flowers (right middle panel) of tomato plants treated with tomato phytoene desaturase polynucleotides, as described in Example 25.

Three-week old tomato seedlings were treated as follows. Two fully expanded leaves were dipped into a freshly made 0.1% SILWET L-77 solution in double-distilled water for a few seconds. The leaves were allowed to dry for 30 minutes to 1 hour. Each plant was then treated by applying 20 microliters dsRNA solution to the top surface of two SIL-WET-treated leaves (total 40 microliters per plant). Control plants were treated with buffer. The plants were kept in a growth chamber for observation. FIG. 30 depicts the systemic silencing of the target gene PDS as evidenced by bleaching of the dsRNA-treated plants 30 days after topical treatment. The dsRNA-treated plants were severely stunted, compared to control plants.

Example 26

This example illustrates an improvement to herbicidal compositions adapted for topical coating onto the exterior surface of a growing plant where the plant lethal agent includes polynucleotides having a sequence essentially identical or complementary to sequences of one or more plant genes or sequence of transcribed DNA from the plant genes. The polynucleotides effect systemic suppression of the plant gene in plant organs or tissues other than those that received the topical polynucleotide application. More specifically this example illustrates an herbicidal composition adapted for topical coating onto the exterior surface of a growing plant comprising surfactant and at least one plant lethal agent including combinations of polynucleotides having sequence targeting the 5-enolpyruvylshikimate-3-phosphate synthase (EPSPS) gene, a transcription initiation factor (TIF), and DNA-dependent ATPase (ddATPase) in Palmer amaranth.

The herbicidal composition includes at least one of the following 21-base-pair double-stranded RNA polynucleotides:

```
(1) nDsRNA1:
                                        (SEQ ID NO: 63)
  sense strand CUACCAUCAACAAUGGUGUCC
  and
                                        (SEQ ID NO: 64)
  anti-sense strand GGACACCAUUGUUGAUGGUAG (2) nDsRNA3:
                                        (SEQ ID NO: 65)
  sense strand GUCGACAACUUGCUGUAUAGU
  and
                                        (SEQ ID NO: 66)
  anti-sense strand ACUAUACAGCAAGUUGUCGAC (3) nDsRNA4:
                                        (SEQ ID NO: 67)
  sense strand GGUCACCUGGACAGAGAAUAG
  and
                                        (SEQ ID NO: 68)
  anti-sense strand CUAUUCUCUGUCCAGGUGACC
```

```
-continued
(4) nDsNA5:
                                        (SEQ ID NO: 69)
  sense strand AAUGCCAGAUGUUGCUAUGAC
  and
                                        (SEQ ID NO: 70)
  anti-sense strand GUCAUAGCAACAUCUGGCAUU
```

A mixture of multiple polynucleotides is advantageous for preventing selection of resistance in the treated plants. In an embodiment, the herbicidal composition includes a mixture of all four of the above dsRNA polynucleotides having SEQ ID NOS: 63-70. In another embodiment, the herbicidal composition includes single-stranded DNA polynucleotides with deoxyribonucleotide sequences corresponding to one or more of the dsRNA sequences SEQ ID NOS: 63-70. In another embodiment, the herbicidal composition includes RNA/DNA hybrids with nucleotide sequences corresponding to one or more of the dsRNA sequences SEQ ID NOS: 63-70. In another embodiment, the herbicidal composition includes dsRNA polynucleotides where the 2' hydroxyls are methylated for stability.

The herbicidal composition includes a surfactant such as SILWET L-77 (or other effective surfactants such as those provided in Example 36). Optionally, the herbicidal composition can include one or more additives such as a salt, chelating agent, or a humectant (such as those provided in Example 35) to improve herbicidal performance, e. g., by enhancing transfer of the polynucleotide into the interior of the plant, enhancing efficacy of the polynucleotides, or potentiating the herbicidal activity of the non-polynucleotide herbicide.

Optionally the herbicidal composition includes polynucleotides designed to regulate multiple genes in the plant. In an embodiment, the herbicidal composition includes polynucleotides having sequence essentially identical or complementary to the sequence of a second gene or to the sequence of RNA transcribed from the second gene, wherein the regulation of the second gene provides a synergistic enhancement of the herbicidal activity of the composition.

In an embodiment, the herbicidal composition includes polynucleotides having sequence essentially identical or complementary to the sequence of the endogenous Palmer amaranth 5-enolpyruvylshikimate-3-phosphate synthase (EPSPS) gene or to the sequence of RNA transcribed from the endogenous EPSPS gene as well as polynucleotides having sequence essentially identical or complementary to the sequence of the endogenous Palmer translation initiation factor (TIF) gene or to the sequence of RNA transcribed from the endogenous TIF gene. Translation initiation factor (TIF) is a nuclear-encoded chloroplast protein that is essential for initiating protein synthesis and is expressed throughout a plant. *Arabidopsis thaliana* has an orthologue named AT1G17220.1 (described on the publicly available database The *Arabidopsis* Information Resource found online at www.arabidopsis.org/servlets/TairObject?type=locus&name=AT1G17220) and assigned GenBank accession number GI: 186478573, which has been identified as a chloroplast localized protein with similarity to bacterial translation initiation factor 2; see also Miura et al. (2007) *Plant Cell*, 19:1313-1328 for a description of this gene. TIF sequences were identified from Palmer amaranth (*Amaranthus palmeri*); one TIF gene was identified to have the sequence of SEQ ID NO:71. Examples of polynucleotides for suppression of this TIF gene in *Amaranthus palmeri* are listed in Table 10.

TABLE 10

| Poly-nucleotide | Position in TIF sequence | Sequence | SEQ ID NO. |
|---|---|---|---|
| Palmer amaranth TIF | Entire sequence of SEQ ID NO: 71 | ATGGCAACAATGGCTTCCCTAGTGAGTTTGGGAAGCTCTGGAG CAACTTGCTCAGGGCAATTGGAGGTTTCCTTTTCATTGGTTAAG AAAATTACATTGCCTAGAAGAAATTGTAGTTGCAATTTTAGGCA ATTAGGAGGGGGGAGGAGATGGCGTTACGTTTCGGTGTGTAGA CTTTCTGTCACTACTGATTATGTTTCTGAGCAAGGAAATGCTGT TTCTCTTGAAAATGCATATAGTGAGAGTAAAGAAGAGGGTCTC ATCTTGAAGCCTTCTCCTAAGCCGGTTTTGAAATCCGGGTCTGA TGGAAATCGGAAATTTGGGGAGAGTTCGGTGGCGTTTTCGAGT AATGGGAAATTGGATAATGTAGAGGAGAGGAAGAAGGTTATTG ATTCATTGGATGAGGTATTAGAAAAGGCCGAGAGATTAGAAAC GGCGAACTTACAAGCAGATAATAGAAAGGATAGCACAAATGTA AATAAACCGTCTCCGAGTGTAAGTAGTTCAACCAATGGTAAAC CTGTAAATAATTTGAACAAAGGGAAGCCTAAAGCTGCGAAGAG CGTTTGGAGAAAGGGAAATCCAGTTTCTACTGTGCAAAAAGTA GTGCAAGAATCTCCGAAGATTGAAAAGGTTGAGAGAGTGGAAG CTCGAACGACCAGCCAATCGTCTGAAACGATAAGACCCCCAGT GCCACTACAGAGGCCTGAGATTAAGTTGCAGGCAAAGCCTTCT ACTGCTCCTCCACCCATGCCTAAGAAGCCGGTTTTGAAGGATGT GGGGATGTCCTCCAGAGCTGATGGGAAGGACCAGTCTGTGAAA TCTAAAGAGAGGAAGCCTATTCTAGTGGACAAATTTGCCACCA AGAAGGCATCAGTTGATCCGTCGATTGCTCAAGCAGTAATTGC CCCACCAAAACCTGCTAAATTTCCTTCTGGAAAGTTTAAAGATG ATTATCGGAAGAAGGGTCTTGCAGCTGGTGGGCCGAAGAGGCG TATGGTCAATGATGATGATATTGAAATGCATGAAGACACTTCA GAGCTCGGTCTTTCTATTCCTGGTGCTGCTACGGCTCGGAAAGG CAGGAAATGGAGTAAGGCAAGTCGCAAGGCTGCCAGACGCCA AGCAGCTAGAGATGCCGCTCCTGTTAAAGTGGAAATCTTAGAG GTTGAAGAAAAGGGCATGTCGACCGAAGAATTAGCATACAACT TGGCTATTAGCGAAGGTGAAATTCTTGGGTACCTGTATTCTAAG GGGATAAAACCAGATGGTGTGCAAACTCTTGACAAGGCAATGG TAAAGATGATATGTGAAAGATATGACGTGGAGGTTTTGGACGC ACTTTCTGAACAAATGGAAGAAATGGCTCGAAAGAAGGAAATT TTCGACGAAGATGACCTTGACAAGCTTGAAGATAGGCCTCCTG TGCTTACTATAATGGGTCATGTAGATCATGGCAAGACGACCCTT CTGGATTATATACGGAAGAGCAAGGTTGCTGCTTCTGAAGCTG GTGGGATTACACAAGGTATTGGTGCTTATAAAGTGGAAGTACC GGTTGATGGCAAGTTGCTGCCTTGTGTCTTTCTTGACACTCCCG GACACGAGGCGTTCGGGGCAATGAGGGCTCGTGGAGCAAGAGT GACAGATATTGCTATTATAGTTGTAGCTGCTGACGATGGGATCC GTCCTCAAACAAATGAAGCCATAGCACATGCAAAAGCAGCTGG TGTACCTATTGTGGTTGCAATTAATAAGATTGACAAGGATGGG GCTAATCCGGACCGTGTGATGCAAGAGCTTTCATCAATTGGTCT AATGCCAGAGGATTGGGGTGGTGATACCCCAATGGTCAAGATA AGTGCTCTAAAAGGTGAAATGTGGACGAGTTACTCGAGACAG CCATGCTTGTCGCCGAGTTGCAAGAGTTAAAGGCTAATCCTCAG AGGAACGCTAAGGGCACTGTAATTGAGGCTGGTCTTCATAAAT CAAAAGGACCCATTGCCACTTTTATTGTGCAGAATGGTACCCTC AAACAAGGGGATACTGTAGTTTGTGGGGAAGCATTTGGGAAGG TTCGTGCCCTATTTGATCACGGAGGGAATCGCGTTGATGAAGCT GGTCCATCTATTCCCGTGCAGGTTATTGGATTGAATAATGTTCC TTTTGCCGGTGATGAGTTCGAGGTAGTGAGTTCCCTTGATATAG CTCGTGAAAAGGCAGAGGTCCGTCAGAGTCTTTACGAAATGA GCGTATAGCTGCTAAGGCCGGAGACGGAAAGGTTACGCTGTCA TCCTTGGCATCGGCTGTTTCTTCAGGGAAGATGGCTGGTTTGGA TTTGCACCAGTTAAATATCATTTTGAAGGTTGATGTTCAGGGAT CAATCGAGGCATTGAGGCAAGCTCTAGAAGTTCTTCCTCAAGA TAACGTCACTTTGAAGTTTCTCTTACAAGCGACCGGAGATGTTA CTACAAGTGATGTTGATCTTGCAGTTGCTAGTAAAGCTATTATC TTGGGGTTCAATGTGAAGGCACCAGGTTCTGTCGAAAAATTAG CAGATAACAAAGGTGTTGAAATTCGGCTTTATAAAGTCATTTAT GATCTAATTGACGACATGCGGAGTGCAATGGAAGGAATGCTAG ATCCCGTTGAGGAACAAGTTGCAATTGGTTCAGCCGAAGTGCG GGCTACATTCAGTAGTGGTAGTGGCCGTGTCGCTGGATGCATG GTGACCGAGGGAAAGATTACCAAAGGCTGTGGGATTCGAGTGA TACGGAAGGGAAAAACTGTCCACGTTGGAGTTCTTGATTCGTTG CGTCGAGTAA | 71 |
| 200 bp DNA | 341-541 | TTTCGAGTAATGGGAAATTGGATAATGTAGAGGAGAGGAAGAA GGTTATTGATTCATTGGATGAGGTATTAGAAAAGGCCGAGAGA TTAGAAACGGCGAACTTACAAGCAGATAATAGAAAGGATAGCA CAAATGTAAATAAACCGTCTCCGAGTGTAAGTAGTTCAACCAA TGGTAAACCTGTAAATAATTTGAACAAA | 72 |

TABLE 10-continued

| Poly-nucleotide | Position in TIF sequence | Sequence | SEQ ID NO. |
|---|---|---|---|
| 160 bp dsRNA | 342-501 | Sense: UUCGAGUAAUGGGAAAUUGGAUAAUGUAGAGGAGAGGAAGA AGGUUAUUGAUUCAUUGGAUGAGGUAUUAGAAAAGGCCGAG AGAUUAGAAACGGCGAACUUACAAGCAGAUAAUAGAAAGGA UAGCACAAAUGUAAAUAAACCGUCUCCGAGUGUAAGU | 73 |
| | | Anti-sense: ACUUACACUCGGAGACGGUUUAUUUACAUUUGUGCUAUCCUU UCUAUUAUCUGCUUGUAAGUUCGCCGUUUCUAAUCUCUCGGC CUUUUCUAAUACCUCAUCCAAUGAAUCAAUAACCUUCUUCCU CUCCUCUACAUUAUCCAAUUUCCCAUUACUCGAA | 74 |
| anti-sense DNA TIF_AS1 | 555-576 | ATTTCTCCAAACGCTCTTCGCA | 75 |
| anti-sense DNA TIF_AS2 | 342-363 | ATCCAATTTCCCATTACTCGAA | 76 |
| anti-sense DNA TIF_AS3 | 412-433 | GTTTCTAATCTCTCGGCCTTTT | 77 |
| anti-sense DNA TIF_AS4 | 488-509 | TTGAACTACTTACACTCGGAG | 78 |
| anti-sense DNA TIF_AS5 | 368-389 | TAACCTTCTTCCTCTCCTCTA | 79 |
| anti-sense DNA TIF_AS6 | 790-811 | GTCCTTCCCATCAGCTCTGGA | 80 |
| anti-sense DNA TIF_AS7 | 1052-1073 | CGTAGCAGCACCAGGAATAG | 81 |
| anti-sense DNA TIF_AS8 | 1655-1676 | CAGCAGCTACAACTATAATAG | 82 |

In an embodiment, the herbicidal composition includes a mixture of at least two of the above EPSPS dsRNA polynucleotides having SEQ ID NOS: 63-70 and also at least one polynucleotide having sequence essentially identical or complementary to the sequence of the endogenous Palmer translation initiation factor (TIF) gene or to the sequence of RNA transcribed from the endogenous TIF gene, such as those provided in Table 10. In a specific embodiment, the herbicidal composition includes a mixture of the four EPSPS dsRNA polynucleotides having SEQ ID NOS: 63-70 and a 160 base-pair TIF double-stranded RNA polynucleotide having the sense sequence of UUCGAGUAAUGGGAAAUUGGAUAAUGUAGAGGAGAGGAAGAAGGUUAUUGAUUCAUUGGAUGAGGUAUUAGAAAAGGCCGAGAGAUUAGAAACGGCGAACUUACAAGCAGAUAAUAGAAAGGAUAGCACAAAUGUAAAUAAACCGUCUCCGAGUGUAAGU (SEQ ID NO. 73) and the anti-sense sequence of ACUUACACUCGGAGACGGUUUAUUUACAUUUGUGCUAUCCUUUCUAUUAUCUGCUUGUAAGUUCGCCGUUUCUAAUCUCUCGGCCUUUUCUAAUACCUCAUCCAAUGAAUCAAUAACCUUCUUCCUCUCCUCUACAUUAUCCAAUUUCCCAUUACUCGAA (SEQ ID NO. 74).

In some embodiments, the polynucleotides are designed to regulate multiple target genes, resulting in a synergistic effect on herbicide activity. For example, a synergistic effect on herbicide activity was obtained by treatment of a plant with polynucleotides designed to suppress a translation initiation factor (TIF) and 5-enolpyruvylshikimate-3-phosphate synthase (EPSPS) followed by treatment with the non-polynucleotide herbicide glyphosate.

The polynucleotides listed in Table 11 were produced by synthesis or by in vitro transcription.

TABLE 11

| Name | Comments | Nucleotide sequences |
|---|---|---|
| IDT [1] | Palmer/EPSPS dsRNA with two 2-deoxyribonucleotides (in bold | Sense: CUACCAUCAACAAUGGUGUCCAUAC (SEQ ID NO. 83) |
| | | Anti-sense: GUAUGGACACCAUUGUUGAUGGUAGUA (SEQ ID NO. 84) |
| IDT [2] | | Sense: AGUUGGUGGGCAAUCAUCAAUUGTT (SEQ ID NO. 85) |
| | | Anti-sense: AACAAUUGAUGAUUGCCCACCAACUCU (SEQ ID NO. 86) |

TABLE 11-continued

| Name | Comments | Nucleotide sequences |
|---|---|---|
| IDT [3] <br> IDT [4] | underlined text) at 3' end of sense strand (25-mer) and a 2-nucleotide overhang at 3' end of anti-sense strand (27-mer); chemically synthesized by IDT | Sense: GGUCGACAACUUGCUGUAUAGUGAT (SEQ ID NO. 87) <br> Anti-sense: AUCACUAUACAGCAAGUUGUCGACCUC (SEQ ID NO. 88) <br> Sense: UGCAAGGUCACCUGGACAGAGAATA (SEQ ID NO. 89) <br> Anti-sense: UAUUCUCUGUCCAGGUGACCUUGCAAC (SEQ ID NO. 90) |
| IDT [5] | Palmer/EPSPS dsRNA (21-mer) with blunt ends; chemically synthesized by IDT | Sense: AACAUGAACAAAAUGCCAGAU (SEQ ID NO. 91) <br> Anti-sense: AUCUGGCAUUUUGUUCAUGUU (SEQ ID NO. 92) |
| IDT blunt[1] <br> IDT blunt [2] <br> IDT blunt [3] <br> IDT blunt [4] | Palmer/EPSPS dsRNA (27-mer) with blunt ends; synthesized via in vitro T7 transcription | 1S-Anti-sense GUAUGGACACCAUUGUUGAUGGUAGUA (SEQ ID NO. 93) <br> 1S-Sense UACUACCAUCAACAAUGGUGUCCAUAC (SEQ ID NO. 94) <br> 2S-Anti-sense AAUAAUUGAUGAUUGCCCACCAACUCU (SEQ ID NO. 95) <br> 2S-Sense AGAGUUGGUGGGCAAUCAUCAAUUAUU (SEQ ID NO. 96) <br> 3S-Anti-sense AUCACUAUACAGCAAGUUGUCGACCAC (SEQ ID NO. 97) <br> 3S-Sense GUGGUCGACAACUUGCUGUAUAGUGAU (SEQ ID NO. 98) <br> 4S-Anti-sense UAUUCUCUGUCCAGGUGACCUUGCAAC (SEQ ID NO. 99) <br> 4S-Sense GUUGCAAGGUCACCUGGACAGAGAAUA (SEQ ID NO. 100) |
| 3OH [1] <br> 3OH [2] <br> 3OH [3] <br> 3OH [4] | Palmer/EPSPS dsRNA (27-mer) with 3'-overhangs; synthesized via in vitro T7 transcription | 1S-Anti-sense gGUAUGGACACCAUUGUUGAUGGUAGUAC (SEQ ID NO. 101) <br> 1S-Sense GCUACCAUCAACAAUGGUGUCCAUACCAC (SEQ ID NO. 102) <br> 2S-Anti-sense gAAGAAUUGAUGAUUGCCCACCAACUCAC (SEQ ID NO. 103) <br> 2S-Sense GAGUUGGUGGGCAAUCAUCAAUUAUUCAC (SEQ ID NO. 104) <br> 3S-Anti-sense gAUCACUAUACAGCAAGUUGUCGACAC (SEQ ID NO. 105) <br> 3S-Sense GUCGACAACUUGCUGUAUAGUGAUCAC (SEQ ID NO. 106) <br> 4S-Anti-sense gUAUUCUCUGUCCAGGUGACCUUGCACAC (SEQ ID NO. 107) <br> 4S-Sense GUGCAAGGUCACCUGGACAGAGAAUACAC (SEQ ID NO. 108) |
| IDT HP [1] <br> IDT HP [2] <br> IDT HP [3] <br> IDT HP [4] | Palmer/EPSPS single strand of RNA designed to self-hybridize into a hairpin, containing anti-sense sequence on the 5' arm and anti-sense sequence on the 3' arm, with an intermediate GAAA tetranucleotide loop; chemically synthesized by IDT | 1S-GUAUGGACACCAUUGUUGAUGGUAGUAGAAAUACUACCAUCAACAAUGGUGUCCAUAC (SEQ ID NO. 109) <br> 2S-AAUAAUUGAUGAUUGCCCACCAACUCUGAAAAGAGUUGGUGGGCAAUCAUCAAUUAUU (SEQ ID NO. 110) <br> 3S-AUCACUAUACAGCAAGUUGUCGACCACGAAAGUGGUCGACAACUUGCUGUAUAGUGAU (SEQ ID NO. 111) <br> 4S-UAUUCUCUGUCCAGGUGACCUUGCAACGAAAGUUGCAAGGUCACCUGGACAGAGAAUA (SEQ ID NO. 112) |
| [TIF] | Palmer/translation initiation factor (TIF) dsRNA (160-mer) synthesized via in vitro T7 transcription | Sense: <br> UUCGAGUAAUGGGAAAUUGGAUAAUGUAGAGGAGAGGAAGAAGGUU <br> AUUGAUUCAUUGGAUGAGGUAUUAGAAAAGGCCGAGAGAUUAGAAA <br> CGGCGAACUUACAAGCAGAUAAUAGAAAGGAUAGCACAAAUGUAAAU <br> AAACCGUCUCCGAGUGUAAGU (SEQ ID NO. 73) <br> Anti-sense: <br> ACUUACACUCGGAGACGGUUUAUUUACAUUUGUGCUAUCCUUUCUAU <br> UAUCUGCUUGUAAGUUCGCCGUUUCUAAUCUCUCGGCCUUUUCUAAU <br> ACCUCAUCCAAUGAAUCAAUAACCUUCUUCCUCUCCUCUACAUUAUC <br> CAAUUUCCCAUUACUCGAA (SEQ ID NO. 74) |

TABLE 11-continued

| Name | Comments | Nucleotide sequences |
|---|---|---|
| [ddATPase] | Palmer/DNA-dependent ATPase (ddATPase) dsRNA (168-mer) synthesized via in vitro T7 transcription | Sense:<br>GAUCACAAAUUUGCCGGUUUAUGAUCAAAUACGGAACAUAAGACAGA<br>UACACUUGAACACCAUGAUUCGCAUUGGGGGUGUGGUUACUCGUCGU<br>UCUGGAGUAUUCCCUCAGUUGAUGCAGGUGAAGUAUGACUGCAAUAA<br>AUGUGGGGCUAUCCUGGGUCCCUUUUU (SEQ ID NO. 113)<br>Anti-sense:<br>AAAAAGGGACCCAGGAUAGCCCCACAUUUAUUGCAGUCAUACUUCAC<br>CUGCAUCAACUGAGGGAAUACUCCAGAACGACGAGUAACCACACCCC<br>CAAUGCGAAUCAUGGUGUUCAAGUGUAUCUGUCUUAUGUUCCGUAUU<br>UGAUCAUAAACCGGCAAAUUUGUGAUC (SEQ ID NO. 114) |

Solutions of the polynucleotides were prepared and applied to the leaves of Palmer amaranth using the protocols described in Table 12.

TABLE 12

| Protocol number (description) | Protocol |
|---|---|
| 1<br>(1-step hand) | 1. Apply mixture of polynucleotides in 1% Silwet L-77, 2% ammonium sulfate in 10 millimolar sodium phosphate buffer, pH 6.8 (or control buffer solution of 1% Silwet L-77, 2% ammonium sulfate in 10 millimolar sodium phosphate buffer, pH 6.8) by hand pipetting<br>2. 48 or 72 hours later, spray glyphosate ("2X Wmax" or 1682 g acid equivalent per hectare of Roundup ® WeatherMAX ® brand herbicide) by regular sprayer (10 gallons/acre) |
| 2<br>(1-step sprayer) | 1. Spray mixture of polynucleotides in 1% Silwet L-77, 2% ammonium sulfate in 10 millimolar sodium phosphate buffer, pH 6.8 (or control buffer solution of 1% Silwet L-77, 2% ammonium sulfate in 10 millimolar sodium phosphate buffer, pH 6.8) by Milli sprayer<br>2. 48 or 72 hours later, spray glyphosate ("2X Wmax" or 1682 g acid equivalent per hectare of Roundup ® WeatherMAX ® brand herbicide) by regular sprayer (10 gallons/acre) |
| 3<br>(2-step hand) | 1. Spray 1% Silwet as $1^{st}$ step by regular sprayer or Milli sprayer;<br>2. Apply mixture of polynucleotides in 1% Silwet L-77, 2% ammonium sulfate in 10 millimolar sodium phosphate buffer, pH 6.8 (or control buffer solution of 1% Silwet L-77, 2% ammonium sulfate in 10 millimolar sodium phosphate buffer, pH 6.8) by hand pipetting<br>3. 48 or 72 hours later, spray glyphosate ("2X Wmax" or 1682 g acid equivalent per hectare of Roundup ® WeatherMAX ® brand herbicide) by regular sprayer (10 gallons/acre) |
| 4<br>(2-step sprayer) | 1. Spray 1% Silwet as $1^{st}$ step by regular sprayer or Milli sprayer;<br>2. Spray mixture of polynucleotides in 1% Silwet L-77, 2% ammonium sulfate in 10 millimolar sodium phosphate buffer, pH 6.8 (or control buffer solution of 1% Silwet L-77, 2% ammonium sulfate in 10 millimolar sodium phosphate buffer, pH 6.8) by Milli sprayer<br>3. 48 or 72 hours later, spray glyphosate ("2X Wmax" or 1682 g acid equivalent per hectare of Roundup ® WeatherMAX ® brand herbicide) by regular sprayer (10 gallons/acre) |
| 5<br>(tank mix) | Spray mixture of polynucleotides in 1% Silwet L-77, 2% ammonium sulfate in 10 millimolar sodium phosphate buffer, pH 6.8 containing glyphosate at 1682 g acid equivalent per hectare of Roundup ® WeatherMAX ® brand herbicide (or control buffer solution of 1% Silwet L-77, 2% ammonium sulfate in 10 millimolar sodium phosphate buffer, pH 6.8 containing glyphosate at 1682 g acid equivalent per hectare of Roundup ® WeatherMAX ® brand herbicide) by Milli sprayer. |

Combinations of polynucleotides were tested as indicated in Table 13.

TABLE 13

| Polynucleotides applied in combination | SEQ ID NO. | Protocol | Amount applied of each polynucleotide (g/acre) | Total polynucleotide applied (g/acre) | EPSPS copy number* | Results** |
|---|---|---|---|---|---|---|
| IDT [1] | 83, 84, | 1 | 0.29 | 0.87 | 112 | 75% killed |
| IDT [3] | 87, 88 | | 0.29 | | | (27 DAT) |
| IDT [4] | 89, 90 | | 0.29 | | | |
| IDT [1] | 83, 84, | 1 | 0.29 | 1.4 | 112 | 100% killed |
| IDT [3] | 87, 88 | | 0.29 | | | (27 DAT) |
| IDT [4] | 89, 90 | | 0.29 | | | |
| [TIF] | 73, 74 | | 0.50 | | | |
| IDT [1] | 83, 84, | 1 | 0.29 | 1.37 | 112 | 11.2% |
| IDT [3] | 87, 88 | | 0.29 | | | stunted |
| IDT [4] | 89, 90 | | 0.29 | | | (27 DAT) |
| [ddATPase] | 113, 114 | | 0.50 | | | |
| IDT [1] | 83, 84, | 1 | 0.29 | 1.87 | 112 | 100% killed |

TABLE 13-continued

| Polynucleotides applied in combination | SEQ ID NO. | Protocol | Amount applied of each polynucleotide (g/acre) | Total polynucleotide applied (g/acre) | EPSPS copy number* | Results** |
|---|---|---|---|---|---|---|
| IDT [3] | 87, 88 | | 0.29 | | | (27 DAT) |
| IDT [4] | 89, 90 | | 0.29 | | | |
| [TIF] | 73, 74 | | 0.50 | | | |
| [ddATPase] | 114, 114 | | 0.50 | | | |
| IDT [1] | 83, 84, | 1 | 0.29 | 1.2 | 112, 36 | 0% control |
| IDT [2] | 85, 86 | | 0.29 | | | (11 DAT); |
| IDT [3] | 87, 88 | | 0.29 | | | 0% control |
| IDT [4] | 89, 90 | | 0.29 | | | (31 DAT) |
| IDT [1] | 83, 84, | 1 | 1.4 | 5.8 | 112, 36 | 0% control |
| IDT [2] | 85, 86 | | 1.4 | | | (11 DAT); |
| IDT [3] | 87, 88 | | 1.4 | | | 15% stunted |
| IDT [4] | 89, 90 | | 1.4 | | | (31 DAT) |
| IDT [1] | 83, 84, | 1 | 2.9 | 12 | 112, 36 | 0% control |
| IDT [2] | 85, 86 | | 2.9 | | | (11 DAT); |
| IDT [3] | 87, 88 | | 2.9 | | | 35% stunted |
| IDT [4] | 89, 90 | | 2.9 | | | (31 DAT) |
| IDT [1] | 83, 84, | 1 | 5.8 | 23 | 112, 36 | 51% stunted |
| IDT [2] | 85, 86 | | 5.8 | | | (11 DAT); |
| IDT [3] | 87, 88 | | 5.8 | | | 100% |
| IDT [4] | 89, 90 | | 5.8 | | | stunted (31 DAT) |
| IDT [1] | 83, 84, | 2 | 0.29 | 1.2 | 33, 54 | 9% stunted |
| IDT [2] | 85, 86 | | 0.29 | | | (6 DAT) |
| IDT [3] | 87, 88 | | 0.29 | | | |
| IDT [4] | 89, 90 | | 0.29 | | | |
| IDT [1] | 83, 84, | 2 | 5.8 | 23 | 33, 54 | 100% killed |
| IDT [2] | 85, 86 | | 5.8 | | | (6 DAT) |
| IDT [3] | 87, 88 | | 5.8 | | | |
| IDT [4] | 89, 90 | | 5.8 | | | |
| IDT [1] | 83, 84, | 2 | 0.29 | 0.87 | 33, 54 | 20% stunted |
| IDT [3] | 87, 88 | | 0.29 | | | (6 DAT) |
| IDT [4] | 89, 90 | | 0.29 | | | |
| IDT [1] | 83, 84, | 2 | 5.8 | 17 | 33, 54 | 100% killed |
| IDT [3] | 87, 88 | | 5.8 | | | (6 DAT) |
| IDT [4] | 89, 90 | | 5.8 | | | |
| IDT [5] | 91, 92 | 1 | 0.29 | 0.29 | 34, 36, 54 | 14.1% stunted (22 DAT) |
| IDT [5] | 91, 92 | 1 | 2.9 | 2.9 | 34, 36, 54 | 100% kill (22 DAT) |
| IDT [1] | 83, 84, | 1 | 2.9 | 12 | 34, 36, 54 | 100% killed |
| IDT [2] | 85, 86 | | 2.9 | | | (22 DAT) |
| IDT [3] | 87, 88 | | 2.9 | | | |
| IDT [4] | 89, 90 | | 2.9 | | | |
| IDT [1] | 83, 84, | 1 | 2.9 | 14 | 34, 36, 54 | 100% killed |
| IDT [2] | 85, 86 | | 2.9 | | | (22 DAT) |
| IDT [3] | 87, 88 | | 2.9 | | | |
| IDT [4] | 89, 90 | | 2.9 | | | |
| IDT [5] | 91, 92 | | 2.9 | | | |
| IDT [1] | 83, 84, | 1 | 2.9 | 8.7 | 34, 36, 54 | 100% killed |
| IDT [3] | 87, 88 | | 2.9 | | | (22 DAT) |
| IDT [4] | 89, 90 | | 2.9 | | | |
| IDT [1] | 83, 84, | 1 | 2.9 | 12 | 34, 36, 54 | 100% killed |
| IDT [3] | 87, 88 | | 2.9 | | | (22 DAT) |
| IDT [4] | 89, 90 | | 2.9 | | | |
| IDT [5] | 91, 92 | | 2.9 | | | |
| IDT [5] | 91, 92 | 1 | 0.29 | 0.29 | 33, 54, 55 | 71% stunted (18 DAT) |
| IDT [5] | 91, 92 | 1 | 2.9 | 2.9 | 33, 54, 55 | 100% killed (18 DAT) |
| IDT [1] | 83, 84, | 1 | 0.29 | 1.4 | 33, 54, 55 | 100% killed |
| IDT [2] | 85, 86 | | 0.29 | | | (18 DAT) |
| IDT [3] | 87, 88 | | 0.29 | | | |
| IDT [4] | 89, 90 | | 0.29 | | | |
| IDT [5] | 91, 92 | | 0.29 | | | |
| IDT [1] | 83, 84, | 1 | 0.29 | 1.2 | 33, 54, 55 | 100% killed |
| IDT [2] | 85, 86 | | 0.29 | | | (18 DAT) |
| IDT [3] | 87, 88 | | 0.29 | | | |
| IDT [4] | 89, 90 | | 0.29 | | | |
| IDT HP [1] | 109 | 3 | 0.29 | 1.2 | 16, 33 | 100% killed |
| IDT HP [2] | 110 | | 0.29 | | | (18 DAT) |
| IDT HP [3] | 111 | | 0.29 | | | |
| IDT HP [4] | 112 | | 0.29 | | | |

TABLE 13-continued

| Polynucleotides applied in combination | SEQ ID NO. | Protocol | Amount applied of each polynucleotide (g/acre) | Total polynucleotide applied (g/acre) | EPSPS copy number* | Results** |
|---|---|---|---|---|---|---|
| IDT [1] | 83, 84, | 3 | 0.29 | 1.2 | 16, 33 | 100% killed |
| IDT [2] | 85, 86 | | 0.29 | | | (18 DAT) |
| IDT [3] | 87, 88 | | 0.29 | | | |
| IDT [4] | 89, 90 | | 0.29 | | | |
| IDT [1] | 83, 84, | 3 | 0.29 | 0.87 | 16, 36 | 100% killed |
| IDT [3] | 87, 88 | | 0.29 | | | (18 DAT) |
| IDT [4] | 89, 90 | | 0.29 | | | |
| IDT [1] | 83, 84, | 3 | 5.8 | 17 | 16, 36 | 100% killed |
| IDT [3] | 87, 88 | | 5.8 | | | (18 DAT) |
| IDT [4] | 89, 90 | | 5.8 | | | |
| IDT [1] | 83, 84, | 3 | 29 | 87 | 16, 36 | 100% killed |
| IDT [3] | 87, 88 | | 29 | | | (18 DAT) |
| IDT [4] | 89, 90 | | 29 | | | |
| IDT [1] | 83, 84, | 3 | 0.29 | 1.1 | 16, 36 | 100% killed |
| IDT [2] | 85, 86 | | 0.29 | | | (18 DAT) |
| IDT [3] | 87, 88 | | 0.29 | | | |
| IDT [4] | 89, 90 | | 0.29 | | | |
| 3'-OH [1] | 101, 102 | 3 | Not applicable | 22-26 microliters (by volume) | 16 | 100% killed (10 DAT) |
| 3'-OH [2] | 103, 104 | | | | | |
| 3'-OH [3] | 105, 106 | | | | | |
| 3'-OH [4] | 107, 108 | | | | | |
| IDT Blunt [1] | 93, 94 | 3 | 0.29 | 1.1 | 16 | 75% killed |
| IDT Blunt [2] | 95, 96 | | 0.29 | | | (10 DAT) |
| IDT Blunt [3] | 97, 98 | | 0.29 | | | |
| IDT Blunt [4] | 99, 100 | | 0.29 | | | |
| IDT Blunt [1] | 93, 94 | 3 | 5.8 | 23 | 16 | 100% killed |
| IDT Blunt [2] | 95, 96 | | 5.8 | | | (10 DAT) |
| IDT Blunt [3] | 97, 98 | | 5.8 | | | |
| IDT Blunt [4] | 99, 100 | | 5.8 | | | |
| IDT [1] | 83, 84, | 3 | 29 | 87 | 16 | 34% stunted |
| IDT [2] | 85, 86 | | 29 | | | (14 DAT) |
| IDT [3] | 87, 88 | | 29 | | | |
| IDT [2] | 85, 86 | 3 | 29 | 87 | 16 | 48% stunted |
| IDT [3] | 87, 88 | | 29 | | | (14 DAT) |
| IDT [4] | 89, 90 | | 29 | | | |
| IDT [1] | 83, 84, | 3 | 29 | 87 | 16 | 25% stunted |
| IDT [2] | 85, 86 | | 29 | | | (14 DAT) |
| IDT [4] | 89, 90 | | 29 | | | |
| IDT [1] | 83, 84, | 3 | 29 | 58 | 16 | 44% stunted |
| IDT [4] | 89, 90 | | 29 | | | (14 DAT) |
| IDT [3] | 87, 88 | 3 | 29 | 58 | 16 | 41% stunted |
| IDT [4] | 89, 90 | | 29 | | | (14 DAT) |
| IDT [2] | 85, 86 | 3 | 29 | 58 | 16 | 40% stunted |
| IDT [4] | 89, 90 | | 29 | | | (14 DAT) |
| IDT [1] | 83, 84 | 3 | 29 | 29 | 16 | 51% stunted (13 DAT) |
| IDT [2] | 85, 86 | 3 | 29 | 29 | 16 | 0% control (13 DAT) |
| IDT [3] | 87, 88 | 3 | 29 | 29 | 16 | 51% stunted (13 DAT) |
| IDT [4] | 89, 90 | 3 | 29 | 29 | 16 | 51% stunted (13 DAT) |
| IDT [1] | 83, 84, | 3 | 29 | 116 | 16 | 75% killed |
| IDT [2] | 85, 86 | | 29 | | | (13 DAT) |
| IDT [3] | 87, 88 | | 29 | | | |
| IDT [4] | 89, 90 | | 29 | | | |

*where more than one copy number is listed, the treated plants were a mixture of copy numbers
**DAT = days after treatment; "0% control" means no difference between treated and control plants was observed; stunting % is calculated as [100 − (average height of the test plants/average height of control plants) * 100]

Double-stranded 25-mer RNA polynucleotide sequences for suppression of the TIF gene in *Amaranthus palmeri* were designed as listed in Table 14.

TABLE 14

| Name | Sequence | SEQ ID NO: |
|---|---|---|
| TIF_dsRNA1 | antisense: 5'-UUUUCUAAUACCUCAUCCAAUGAAU-3' | 115 |
| | sense: 5'-AUUCAUUGGAUGAGGUAUUAGAAAA-3' | 116 |
| TIF_dsRNA2 | antisense: 5'-UAUCUGCUUGUAAGUUCGCCGUUUC-3' | 117 |
| | sense: 5'-GAAACGGCGAACUUACAAGCAGAUA-3' | 118 |

TABLE 14-continued

| Name | Sequence | SEQ ID NO: |
|---|---|---|
| TIF_dsRNA3 | antisense:<br>5'-GGAGACGGUUUAUUUACAUUUGUGC-3'<br>sense:<br>5'-GCACAAAUGUAAAUAAACCGUCUCC-3' | 119<br><br>120 |
| TIF_dsRNA4 | antisense:<br>5'-UAUUUACAGGUUUACCAUUGGUUGA-3'<br>sense:<br>5'-UCAACCAAUGGUAAACCUGUAAAUA-3' | 121<br><br>122 |

The TIF 25-mer dsRNA polynucleotides were tested on both high (112) copy and low (16) copy EPSPS glyphosate-resistant Palmer amaranth.

High-copy plants were treated with a mixture of 4 short EPSPS dsRNAs (short dsRNA-1, short dsRNA-3, short dsRNA-4, as described in Example 1 and IDT [5] (SEQ ID NOS:91-92 as described in Table 11) at 11.5 grams/acre and one individual TIF dsRNA at 5.8 grams/acre, or with each individual TIF 25-mer dsRNA at 5.8 grams/acre; polynucleotide solutions were formulated in 10 millimolar sodium phosphate buffer (pH 6.8) containing 2% ammonium sulfate and 1% SILWET L-77. Thirty minutes after polynucleotide treatment, plants were either sprayed with glyphosate (1682 g acid equivalent per hectare of Roundup® WeatherMAX® brand herbicide) or not.

Low-copy plants were treated with a mixture of 4 short EPSPS dsRNAs (short dsRNA-1, short dsRNA-3, short dsRNA-4, as described in Example 1, and IDT [5] (SEQ ID NOS:91-92 as described in Table 11)) at 0.23 grams/acre and one individual TIF dsRNA at 5.8 grams/acre, or with each individual TIF 25-mer dsRNA at 5.8 grams/acre; polynucleotide solutions were formulated in 10 millimolar sodium phosphate buffer (pH 6.8) containing 2% ammonium sulfate and 1% SILWET L-77. Thirty minutes after polynucleotide treatment, plants were either sprayed with glyphosate (1682 g acid equivalent per hectare of Roundup@WeatherMAX® brand herbicide) or not.

Figure 31:
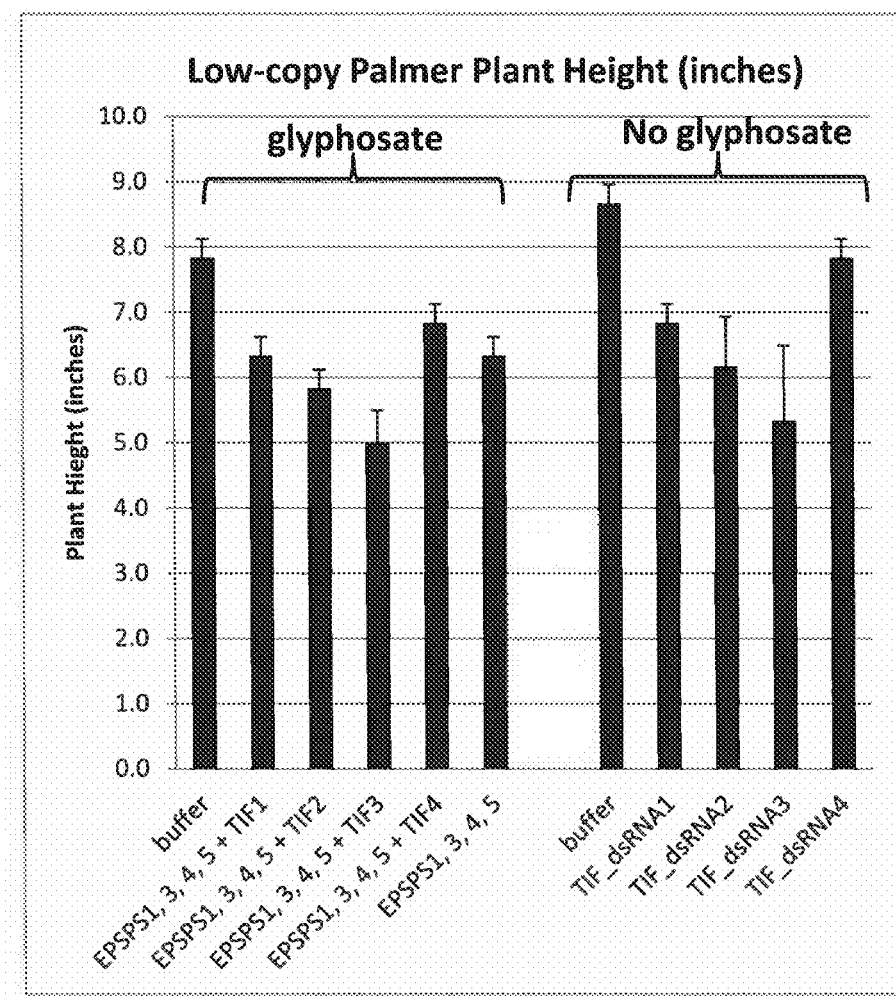
FIG. 31 illustrates enhancement of glyphosate herbicidal activity in low-copy number Palmer amaranth of the EPSPS polynucleotides by TIF polynucleotides and that the TIF polynucleotides have herbicidal activity on their own, as described in Example 26. EPSPS polynucleotides "1, 3, 4" refer to "short" dsRNAs having an anti-sense strand that is capable of hybridizing to the mRNA transcribed from the Palmer amaranth EPSPS gene (SEQ ID NO:1) at positions 14-38 (short dsRNA-1), 345-369 (short dsRNA-3), and 1105-1129 (short dsRNA-4), respectively as indicated by underlined nucleotides in FIG. 1 (see Example 1). EPSPS "5" refers to IDT [5] (SEQ ID NOS:91-92 as described in Table 11).
Figure 32:
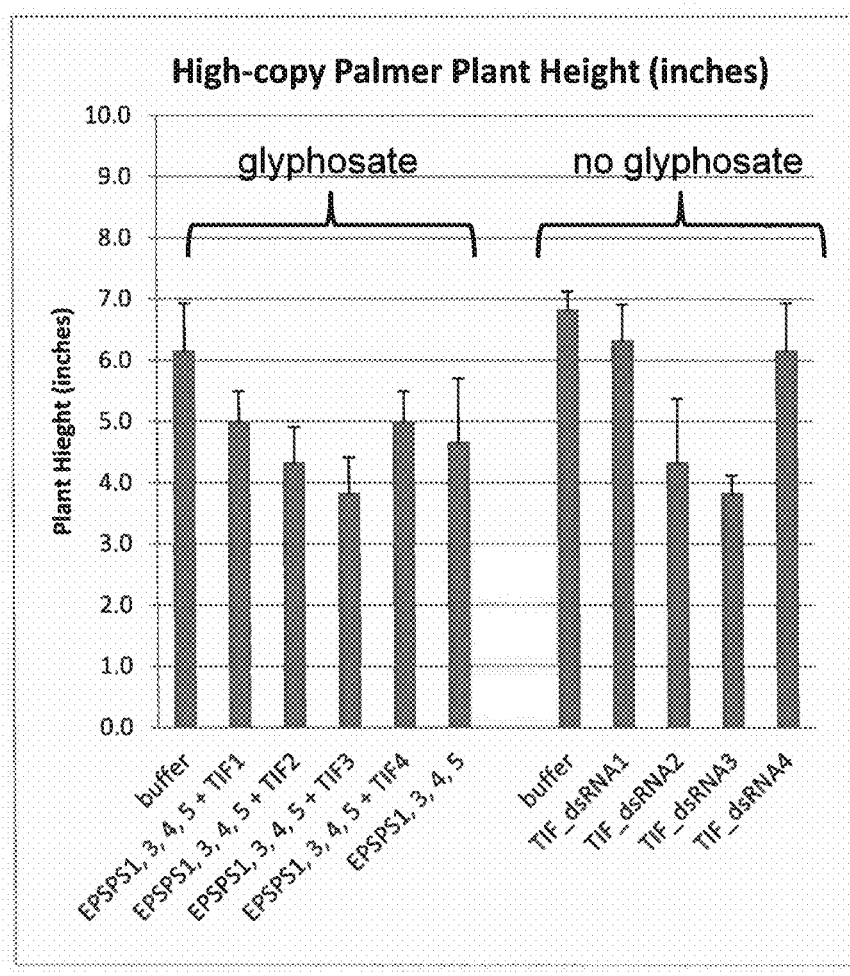
FIG. 32 illustrates enhancement of glyphosate herbicidal activity in high-copy number Palmer amaranth of the EPSPS polynucleotides by TIF polynucleotides and that the TIF polynucleotides have herbicidal activity on their own, as described in Example 26. EPSPS polynucleotides "1, 3, 4" refer to "short" dsRNAs having an anti-sense strand that is capable of hybridizing to the mRNA transcribed from the Palmer amaranth EPSPS gene (SEQ ID NO:1) at positions 14-38 (short dsRNA-1), 345-369 (short dsRNA-3), and 1105-1129 (short dsRNA-4), respectively as indicated by underlined nucleotides in FIG. 1 (see Example 1). EPSPS "5" refers to IDT [5] (SEQ ID NOS:91-92 as described in Table 11).

Results are depicted in FIGS. 31 and 32 and show that the TIF polynucleotides enhance the activity of the EPSPS polynucleotides and that the TIF polynucleotides have herbicidal activity on their own.

Example 27

Aspects of the invention include polynucleotide compositions and methods of use for potentiating the activity of a non-polynucleotide herbicide in a plant. For example, a polynucleotide composition designed to regulate an herbicide target gene, or an herbicide deactivation gene, or a stress response gene, or a combination of such target genes, is applied to a weed or to a volunteer plant, concurrently or followed or preceded by application of a non-polynucleotide herbicide (typically a conventional chemical herbicide), resulting in potentiation of the activity of the non-polynucleotide herbicide. The combination of a polynucleotide composition with a non-polynucleotide herbicide (e. g., a conventional chemical herbicide) provides a synergistic effect, i. e., the herbicidal effect of the combination is greater than the sum of the herbicidal effect of the polynucleotide composition and the herbicidal effect of the non-polynucleotide herbicide.

Examples of conventional chemical herbicides and their corresponding herbicide target genes are provided in Table 15.

TABLE 15

| Herbicide examples | Target gene (herbicide target gene) |
|---|---|
| glyphosate | 5-enolpyruvylshikimate-3-phosphate synthase (EPSPS) |
| Lactofen, flumioxazin, etc | protoporphyrinogen oxidase (PPO) |
| Mesotrione, isoxaflutole | 4-hydroxyphenyl-pyruvate-dioxygenase (HPPD) |
| Quizalofop, clethodim | acetyl coenzyme A carboxylase (ACCase) |
| Norflurazone, clomazone | phytoene desaturase (PDS) |
| glufosinate | glutamine synthase (GS) |
| Rimsulfuron, chlorsulfuron | acetolactate synthase (ALS) |
| Atrazine, diuron, bromoxynil, metribuzin | D1 protein of photosystem II (PSII) |
| Dinitroaniline, pendimethalin | tubulin |
| Dichlobenil, isoxaben | Cellulose synthase |

Examples of conventional chemical herbicides and their corresponding herbicide deactivation genes are provided in Table 16.

TABLE 16

| Herbicide examples | Target gene (herbicide deactivation gene) |
|---|---|
| Acetochlor, metolachlor | glutathione S-transferase (GST) |
| Many including SU herbicides | Mono-oxygenases including cytochromes P450 (see, e.g., a cytochrome P450 for conferring resistance to HPPD inhibitors, benzothiadiazinones, sulfonylureas, and other classes of herbicides, described in U.S. patent application publication 2009/0011936) |
| Thiazopyr | esterases (e.g., esterases involved in apoptosis or senescence) |
| 2,4-D, metribuzin, | glucosyl transferases; malonyl transferases |
| Glyphosate, paraquat | Cellular compartmentation and sequestration genes (e.g., ABC transporters) |

Example 28

This example illustrates a method for inducing systemic regulation of a target endogenous gene in a growing plant including topically coating onto leaves of the growing plant polynucleotides having sequence essentially identical to, or essentially complementary to, a sequence of 18 or more contiguous nucleotides in either the target endogenous gene or messenger RNA transcribed from the target endogenous gene, whereby the polynucleotides permeate the interior of the growing plant and induce systemic regulation of the target endogenous gene.

Double-stranded RNA or anti-sense ssDNA polynucleotides were designed for the herbicide targeted genes 5-enolpyruvylshikimate-3-phosphate synthase (EPSPS), phytoene desaturase (PDS), protoporphyrin IX oxygenase (PPO), phenylalanine ammonia lyase (PAL), hydroxyphenylpyruvate dioxygenase (HPPD), acetyl-coenzyme A carboxylase (ACCase), acetolactate synthase (ALS), and glutamine synthase (GS). For each herbicide targeted gene, a solution containing a mixture of 8 anti-sense ssDNA polynucleotides in 2% ammonium sulfate in 10 millimolar sodium phosphate buffer, pH 6.8, was applied at a rate of 2.32 g/acre following application of 0.5% SILWET L-77 spray (10 gallons/acre). The tested polynucleotides and resulting phenotype observations are listed in Table 17.

TABLE 17

| Gene | Name | Size (nt) | Sequence | SEQ ID NO: | Phenotype |
|---|---|---|---|---|---|
| EPSPS | | | (See sequences provided in working Examples 1, 9, 13, 14, 21, 26) | — | Topical dsRNA followed by glyphosate killed glyphosate-resistant Palmer (up to 60 copies of EPSPS) within 7-10 days |
| PDS | PDS sense | 185 | GACGGAAACCCUCCAGAGAGGCUGUGCAUGCCUAUUGUUAAACACAUCGAGUCACUAGGUGGUGAAGUUAAACUUAACUCUCGUAUACAAAAGAUUCAGUUGGACCAGAGUGGAAGCGUGAAGAGUUUUUUGCUAAAUAACGGGAGGGAAAUACGAGGAGAUGCCUAUGUUUUUGCCACCCCAGU | 123 | Topical dsRNA caused bleaching and stunting phenotype, and is systemic. |
| | PDS anti-sense | 185 | ACUGGGGUGGCAAAAACAUAGGCAUCUCCUCGUAUUUCCCUCCCGUUAUUUAGCAAAAAACUCUUCACGCUUCCACUCUGGUCCAACUGAAUCUUUUGUAUACGAGAGUUAAGUUUAACUUCACCACCUAGUGACUCGAUGUGUUUAACAAUAGGCAUGCACAGCCUCUCUGGAGGUUUCCGUC | 124 | |
| PPO | PPO_OLIGO1 | 21 | GTGATATTACCTCCAACACGAT | 125 | Topical anti-sense DNAs caused stunting of plant growth. |
| | PPO_OLIGO2 | 21 | ATAGTAAGCACAGGATCGGAG | 126 | |
| | PPO_OLIGO3 | 21 | CTTTCAATCCACTGTCAACCG | 127 | |
| | PPO_OLIGO4 | 21 | ATCAAGCGTTCGAAGACCTCAT | 128 | |
| | PPO_OLIGO5 | 21 | CAGCAATGGCGGTAGGTAACA | 129 | |
| | PPO_OLIGO6 | 21 | GCAATTGCCCGAATCCTTTTA | 130 | |
| | PPO_OLIGO7 | 21 | TAGCTCAATATCAAGGTCCTA | 131 | |
| | PPO_OLIGO8 | 21 | TCATAAGCACCCTCTATACAC | 132 | |
| PAL | PAL_OLIGO1 | 21 | TTCTTAACCTCGTCGAGATG | 133 | Topical anti-sense DNAs caused stunting of plant growth. |
| | PAL_OLIGO2 | 21 | ATACCCGAGTATCCTTGCAAA | 134 | |
| | PAL_OLIGO3 | 21 | TAGGGCCCACGGCCTTGGAGT | 135 | |
| | PAL_OLIGO4 | 21 | AGCGGATATAACCTCAGCTAG | 136 | |
| | PAL_OLIGO5 | 21 | CTTCGTGGCCCAACGAATGAC | 137 | |
| | PAL_OLIGO6 | 21 | CAAGCTCGGGTCCCTGCTTGC | 138 | |
| | PAL_OLIGO7 | 21 | GGAAGGTAGATGACATGAGTT | 139 | |
| | PAL_OLIGO8 | 21 | GATGGCATAGTTACCACTGTC | 140 | |
| HPPD | HPPD_OLIGO1 | 21 | TCCGTAGCTTACATACCGAAG | 141 | Topical anti-sense DNAs caused stunting of plant growth. |
| | HPPD_OLIGO2 | 21 | TCCAAGTGAATAGGAGAAACA | 142 | |
| | HPPD_OLIGO3 | 21 | AGCAGCTTCTGCGTCTTCTAC | 143 | |
| | HPPD_OLIGO4 | 21 | ACAGCACGCACGCCAAGACCG | 144 | |
| | HPPD_OLIGO5 | 21 | CGATGTAAGGAATTTGGTAAA | 145 | |
| | HPPD_OLIGO6 | 21 | CGAGGGGATTGCAGCAGAAGA | 146 | |
| | HPPD_OLIGO7 | 21 | GTAGGAGAATACGGTGAAGTA | 147 | |
| | HPPD_OLIGO8 | 21 | GACCCCAAGAAAATCGTCTGC | 148 | |
| ACCase | ACCA_OLIGO1 | 20 | GTCTTACAAGGGTTCTCAA | 149 | Topical anti-sense DNA caused stunting of plant growth. |
| | ACCA_OLIGO2 | 21 | ATCTATGTTCACCTCCCTGTG | 150 | |
| | ACCA_OLIGO3 | 21 | ATAAACCATTAGCTTTCCCGG | 151 | |
| | ACCA_OLIGO4 | 21 | TTTATTGGAACAAGCGGAGTT | 152 | |
| | ACCA_OLIGO5 | 21 | TATACACCCACTTCCCGATAG | 153 | |
| | ACCA_OLIGO6 | 21 | GCACCACGAGGATCACAAGAA | 154 | |
| | ACCA_OLIGO7 | 21 | CCACCCGAGAAACCTCTCCAA | 155 | |
| | ACCA_OLIGO8 | 21 | CAGTCTTGACGAGTGATTCCT | 156 | |
| ALS | ALS-OLIGO1 | 22 | GTTCTTCAGGGCTAAATCGGGA | 157 | No significant phenotype |
| | ALS-OLIGO2 | 22 | GTTCAAGAGCTTCAACGAGAAC | 158 | |
| | ALS-OLIGO3 | 22 | ATACAAACTCCAACGCGTCCAG | 159 | |
| | ALS-OLIGO4 | 22 | CTCTTGGAAAGCATCAGTACCA | 160 | |
| | ALS-OLIGO5 | 22 | CTAGAAAGATACCCACCCAATT | 161 | |
| | ALS-OLIGO6 | 22 | ACTAGAATTCAAACACCCACCC | 162 | |
| | ALS-OLIGO7 | 22 | TTTCTGCTCATTCAACTCCTCC | 163 | |
| | ALS-OLIGO8 | 22 | TATGTATGTGCCCGGTTAGCTT | 164 | |
| GS (glutamine synthase) | GS_OLIGO1 | 21 | TCATATCCAAGCCAGATCCTC | 165 | No significant phenotype |
| | GS_OLIGO2 | 21 | TGCATCACACATCACCAAGAT | 166 | |
| | GS_OLIGO3 | 21 | GTACTCCTGTTCAATGCCATA | 167 | |
| | GS_OLIGO4 | 21 | ATTGATACCAGCATAGAGACA | 168 | |
| | GS_OLIGO5 | 21 | AGCAATTCTCTCTAGAATGTA | 169 | |

TABLE 17-continued

| Gene | Name | Size (nt) | Sequence | SEQ ID NO: | Phenotype |
|------|------|-----------|----------|------------|-----------|
|      | GS_OLIGO6 | 21 | CATCATTCCTCATCGACTTAG | 170 | |
|      | GS_OLIGO7 | 21 | CTCTCGTTGCCCTCTCCATAA | 171 | |
|      | GS_OLIGO8 | 21 | CAACGCCCCAGGAGAAAGTTC | 172 | |

The herbicidal activity of ssDNA polynucleotides that target the enzymes 4-hydroxyphenylpyruvate (HPPD) and protoporphyrinogen oxidase (PPO), and a transcription initiation factor (TIF), and their effect on the herbicide activity when used in combination with the herbicides mesotrione, fomesafen, and atrazine in Palmer amaranth was investigated. The polynucleotides used in this experiment were 8 HPPD anti-sense ssDNA oligonucleotides (SEQ ID NOS: 141-148), 8 PPO anti-sense oligonucleotides (SEQ ID NOS: 125-132), and 8 TIF anti-sense ssDNA oligonucleotides (SEQ ID NOS:75-82, see Example 26).

Glyphosate-sensitive Palmer amaranth (*Amaranthus palmeri*) plants were grown in 4-inch square pots with Sun Gro® Redi-Earth seedling mix containing 3.5 kg/cubic meter Osmocote® 14-14-14 fertilizer in a greenhouse with 14 h photoperiod and a daytime temperature of 30 degrees Celsius and night temperature of 20 degrees Celsius. The plants were sub-irrigated as necessary.

Plants at 10 to 15 cm height were pre-treated manually with 40 microliters (4 fully expanded mature leaves were treated with 10 microliters of solution per leaf on each plant) of a buffer-surfactant solution (as a control; 0.5% SILWET L-77 and 2% ammonium sulfate), or a buffer-surfactant-ssDNA polynucleotide mixture of the anti-sense oligonucleotides targeting HPPD, PPO, or TIF. Some plants were left untreated and were used as controls. Twenty-four hours later, untreated plants, buffer-surfactant treated plants, and buffer-surfactant-ssDNA treated plants were treated using a track-sprayer equipped with a 9501E nozzle and calibrated to deliver 93 liters of solution per hectare with a HPPD inhibitor, mesotrione (4 pounds active ingredient per gallon;), or with a PPO inhibitor, fomesafen (2 pounds active ingredient per gallon), or with a Photosystem II inhibitor, atrazine (90% active ingredient) as indicated in Table 18. Crop oil concentrate (COC) at 1% was added to all herbicide treatments. A low rate of each herbicide (mesotrione: 13 g per acre, equivalent to ⅛× of the recommended field rate; fomesafen: 16 g per acre, equivalent to 1/22× of the recommended field rate; and atrazine: 170 g per acre, equivalent to ⅛× of the recommended field rate,) was used to be able to detect any improvement of herbicide activity by the oligonucleotide mixture.

TABLE 18

| Treatment number | Pre-treatment | Active Ingredient | Rate (grams per hectare of active ingredient) |
|---|---|---|---|
| 0 | Buffer-surfactant | — | |
| 1 | Untreated | Mesotrione | 13 |
| 2 | Buffer-surfactant | Mesotrione | 13 |
| 3 | Buffer-surfactant-ssDNA-HPPD | | |
| 4 | Buffer-surfactant-ssDNA-HPPD | Mesotrione | 13 |
| 5 | Untreated | Fomesafen | 16 |
| 6 | Buffer-surfactant | Fomesafen | 16 |
| 7 | Buffer-surfactant-ssDNA-PPO | | |
| 8 | Buffer-surfactant-ssDNA-PPO | Fomesafen | 16 |
| 9 | Untreated | Atrazine | 170 |
| 10 | Buffer-surfactant-ssDNA-TIF | | |
| 11 | Buffer-surfactant-ssDNA-TIF | Atrazine | 170 |

Figure 33:
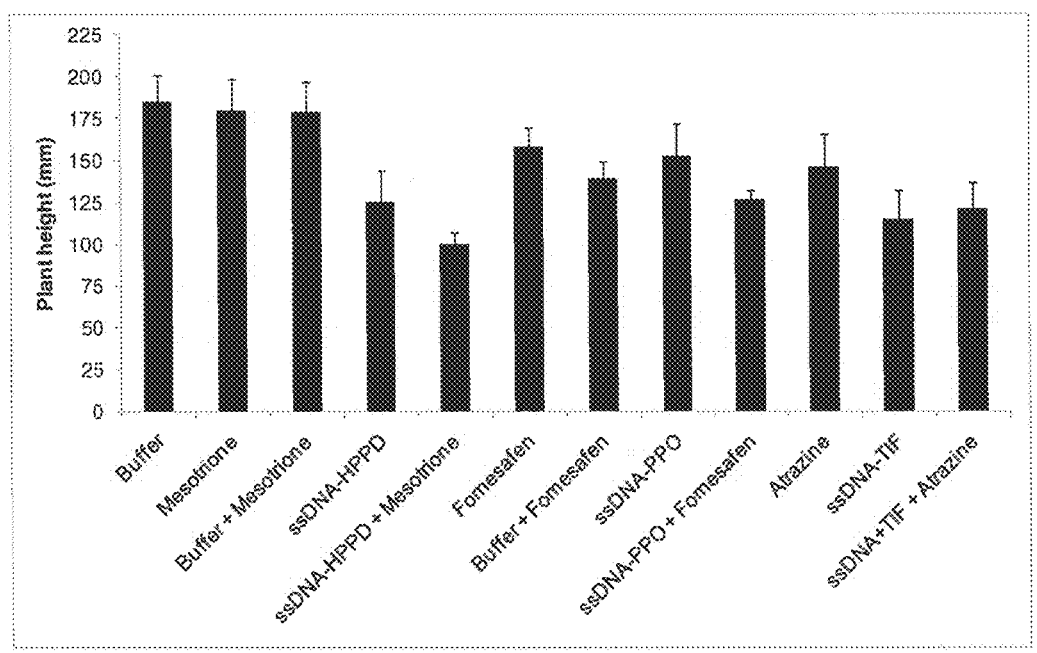
FIG. 33 illustrates the herbicidal effect on Palmer amaranth after treatment with the indicated combinations of non-polynucleotide herbicides and polynucleotides, as described in Example 28.

Plant height was determined at four days after herbicide treatment. Data were collected from one experiment with four replications per treatment. Results (expressed as Palmer amaranth plant height as affected by the buffer-surfactant solution, ssDNA, and herbicide treatment combinations) are presented in Table 19 and FIG. 33. Plants treated with HPPD anti-sense ssDNA oligonucleotides, PPO anti-sense ssDNA oligonucleotides, and TIF anti-sense ssDNA oligonucleotides showed growth stunting, measuring 125, 153, and 115 mm, respectively, while the plants treated with buffer-surfactant (control) measured 185 mm (FIG. 33). Treatment with HPPD anti-sense ssDNA oligonucleotides, PPO anti-sense ssDNA oligonucleotides, and TIF anti-sense ssDNA oligonucleotides respectively caused a 32%, 18%, and 38% growth reduction relative to the buffer-surfactant control.

No major differences in plant height were observed between plants treated with buffer-surfactant followed by herbicide, and plants treated with herbicide only. The plants treated with HPPD anti-sense ssDNA oligonucleotides followed by mesotrione showed the greatest reduction in plant growth, measuring 100 mm, a 46% reduction compared to the buffer-surfactant treated plants. The plants treated with PPO anti-sense ssDNA oligonucleotides followed by fomesafen measured 126 mm, a 32% reduction compared to the buffer-surfactant treated plants. The plants treated with TIF anti-sense ssDNA oligonucleotides followed by atrazine measured 121 mm, a 34% reduction compared to the buffer-surfactant treated plants.

TABLE 19

| Treatment number | Pre-treatment | Active Ingredient | Rate (grams per hectare of active ingredient) | Plant height (mm) | Standard Error |
|---|---|---|---|---|---|
| 0 | Buffer | — | — | 185 | 15 |
| 1 | Untreated | Mesotrione | 13 | 180 | 18 |
| 2 | Buffer | Mesotrione | 13 | 179 | 18 |
| 3 | ssDNA-HPPD | | | 125 | 19 |
| 4 | ssDNA-HPPD | Mesotrione | 13 | 100 | 7 |
| 5 | Untreated | Fomesafen | 23 | 158 | 12 |
| 6 | Buffer | Fomesafen | 23 | 139 | 10 |
| 7 | ssDNA-PPO | | | 153 | 20 |
| 8 | ssDNA-PPO | Fomesafen | 23 | 126 | 6 |
| 9 | Untreated | Atrazine | 170 | 146 | 19 |

TABLE 19-continued

| Treatment number | Pre-treatment | Active Ingredient | Rate (grams per hectare of active ingredient) | Plant height (mm) | Standard Error |
|---|---|---|---|---|---|
| 10 | ssDNA-TIF | | | 115 | 17 |
| 11 | ssDNA-TIF | Atrazine | 170 | 121 | 16 |

Example 29

This example illustrates tested sequences of double-stranded RNA polynucleotides designed for different essential genes to ascertain the effect of the tested sequence on observable phenotype. For each essential gene, a solution containing the dsRNA polynucleotide in 2% ammonium sulfate in 10 millimolar sodium phosphate buffer, pH 6.8, was applied to Palmer amaranth at a rate of 240 picomole per plant following application of 0.5% SILWET L-77 spray (10 gallons/acre). The tested polynucleotides and resulting phenotype observations are listed in Table 20.

TABLE 20

| Gene | Name | Size (nt) | Sequence | SEQ ID NO: | Phenotype |
|---|---|---|---|---|---|
| Translation initiation factor (TIF) | sense | 160 | UUCGAGUAAUGGGAAAUUGGAUAAUGUAGAGGAGAGGAAGAAGGUUAUUGAUUCAUUGGAUGAGGUAUUAGAAAAGGCCGAGAGAUUAGAAACGGCGAACUUACAAGCAGAUAAUAGAAAGGAUAGCACAAAUGUAAAUAAACCGUCUCCGAGUGUAAGU | 73 | Topical dsRNA caused stunting of plant growth. |
| | anti-sense | 160 | ACUUACACUCGGAGACGGUUUAUUUACAUUUGUGCUAUCCUUUCUAUUAUCUGCUUGUAAGUUCGCCGUUUCUAAUCUCUCGGCCUUUUCUAAUACCUCAUCCAAUGAAUCAAUAACCUUCUUCCUCUCCUCUACAUUAUCCAAUUUCCCAUUACUCGAA | 74 | |
| DNA-dependent ATPase (ddATPase) | sense | 168 | GAUCACAAAUUUGCCGGUUUAUGAUCAAAUACGGAACAUAAGACAGAUACACUUGAACACCAUGAUUCGCAUUGGGGUGUGGUUACUCGUCGUUCUGGAGUAUUCCCUCAGUUGAUGCAGGUGAAGUAUGACUGCAAUAAAUGUGGGGCUAUCCUGGGUCCCUUUUU | 113 | Topical dsRNA caused stunting of plant growth. |
| | anti-sense | 168 | AAAAAGGGACCCAGGAUAGCCCCACAUUUAUUGCAGUCAUACUUCACCUGCAUCAACUGAGGGAAUACUCCAGAACGACGAGUAACCACCCCCAAUGCGAAUCAUGGUGUUCAAGUGUAUCUGUCUUAUGUUCCGUAUUUGAUCAUAAACCGGCAAAUUUGUGAUC | 114 | |
| Hydroxy-3-Methylbut-2-enyl diphophate synthase (HMEDS) | sense | 200 | CUGAAGCUGGUGAAGGUGAAGAUGGACGAAUGAAAUCUGCGAUUGGAAUUGGGACCCUUCUUCAGGAUGGCUUGGGAGAUACGAUCAGGGUGUCUCUAACAGAACCACCAGAAGAGGAGAUAGACCCUUGCAGAAGGUUGGCAAAUCUUGGAACAAAAGCAGCUGAAAUUCAGCAAGGAGUGGCACCAUUUGAAG | 173 | No significant phenotype. |
| | anti-sense | 200 | CUUCAAAUGGUGCCACUCCUUGCUGAAUUUCAGCUGCUUUUGUUCCAAGAUUUGCCAACCUUCUGCAAGGGUCUAUCUCCUCUUCUGGUGGUUCUGUUAGAGACACCCUGAUCGUAUCUCCCAAGCCAUCCUGAAGAAGGGUCCAAUUCCAAUCGCAGAUUUCAUUCGUCCAUCUUCACCUUCACCAGCUUCAG | 174 | |
| Fertilization independent endosperm/ TF (FIE) | sense | 183 | UCCCAUCAAAGUUCCCUACAAAAUAUGUGCAGUUUCCUAUCUUCCUUGCCGCCAUUCAUACAAACUAUGUUGAUUGUACAAGGUGGCUUGGUGAUUUUGUUCUUUCUAAGAGUGUUGACAAUGAGAUUGUACUGUGGGAGCCAAUUAUGAAGGAGCAAUCUCCUGGAGAGGGUUCAGUUGACA | 175 | No significant phenotype. |
| | anti-sense | 183 | UGUCAACUGAACCCUCUCCAGGAGAUUGCUCCUUCAUAAUUGGCUCCCACAGUACAAUCUCAUUGUCAACACUCUUAGAAAGAACAAAAUCACCAAGCCACCUUGUACAAUCAACAUAGUUUGUAUGAAUGGCGGCAAGGAAGAUAGGAAACUGCACAUAUUUUGUAGGGAACUUUGAUGGGA | 176 | |
| 26S proteasome ATPase subunit | sense | 143 | UUGUGCUUAAAACAUCGACCAGACAGACAAUAUUUCUUCCUGUUGUUGGACUAGUUGAUCCUGAUACGCUGAAACCUGGUGAUUUAGUUGGUGUCAACAAAGAUAGUUAUCU | 177 | No significant phenotype. |

TABLE 20-continued

| Gene | Name | Size (nt) | Sequence | SEQ ID NO: | Phenotype |
|---|---|---|---|---|---|
| RPT5B (RPTB) | | | UAUCCUGGACACUCUGCCGUCGGAAUAUGAU | | |
| | anti-sense | 143 | AUCAUAUUCCGACGGCAGAGUGUCCAGGAUAAGAUAACUAUCUUUGUUGACACCAACUAAAUCACCAGGUUUCAGCGUAUCAGGAUCAACUAGUCCAACAACAGGAAGAAAUAUUGUCUGUCUGGUCGAUGUUUUAAGCACAA | 178 | |
| ligase 1 (LIG1) | sense | 159 | CGCUGCAGUUGGUGAAGUAGAUCCCGGCAAGGGGAUUUCACUCCGGUUUCCACGUCUGGUUCGUAUCCGAGAGGAUAAAUCUCCAGAGGACGCCACAUCAUCUGAGCAGGUGGCGGAUAUGUACAGAUCUCAAGCAAACAAUCCACACCGCAAAAAGAG | 179 | No significant phenotype. |
| | anti-sense | 159 | CUCUUUUUGCGGUGUGGAUUGUUUGCUUGAGAUCUGUACAUAUCCGCCACCUGCUCAGAUGAUGUGGCGUCCUCUGGAGAUUUAUCCUCUCGGAUACGAACCAGACGUGGAAACCGGAGUGAAAUCCCCUUGCCGGGAUCUACUUCACCAACUGCAGCG | 180 | |
| tRNA synthetase (tS) | sense | 159 | UAAAGAUGGCGGAAAAAUCGACUAUGAUAAAUUGAUUGACAAAUUCGGCUGUCAGCGACUUGAUUUAUCGCUCAUUCAGAGAAUUGAGCGCAUCACUGCUCGUCCUGCUCAUGUAUUUCUUCGCCGCAACGUUUUCUUCGCUCACCGUGAUUUGAAUGA | 181 | No significant phenotype. |
| | anti-sense | 159 | UCAUUCAAAUCACGGUGAGCGAAGAAAACGUUGCGGCGAAGAAAUACAUGAGCAGGACGAGCAGUGAUGCGCUCAAUUCUCUGAAUGAGCGAUAAAUCAAGUCGCUGACAGCCGAAUUUGUCAAUCAAUUUAUCAUAGUCGAUUUUUCCGCCAUCUUUA | 182 | |
| Ubiquitin specific protease 14 (UBP) | sense | 150 | UGAAGCUGAUGCUGAAGGAAAGGAUAUUGAUGCUAGUGAAGUAGUUCGCCCAAGGGUGCCAUUAGAAGCUUGCCUAGCUAGCUACUCAGCUCCGGAGGAGGUGAUGGACUUCUACAGCACUGCAUUGAAGGCAAAGGCAACUGCUACAAA | 183 | No significant phenotype. |
| | anti-sense | 150 | UUUGUAGCAGUUGCCUUUGCCUUCAAUGCAGUGCUGUAGAAGUCCAUCACCUCCUCCGGAGCUGAGUAGCUAGCUAGGCAAGCUUCUAAUGGCACCCUUGGGCGAACUACUUCACUAGCAUCAAUAUCCUUUCCUUCAGCAUCAGCUUCA | 184 | |
| Serine hydroxymethly transferase 2 (SHMT) | sense | 155 | ACACCUGCCCUAACAUCUCGGGGUUUUCUCGAAGAAGAUUUUGUUAAAGUGGCCGAGUAUUUUGAUGCUGCUGUUAAGCUGGCUCUAAAAAUCAAGGCUGACACAAAAGGAACAAAGUUGAAGGACUUCGUUGCCACCUUGCAGUCUGGUGUUUU | 185 | No significant phenotype. |
| | anti-sense | 155 | AAAACACCAGACUGCAAGGUGGCAACGAAGUCCUUCAACUUUGUUCCUUUUGUGUCAGCCUUGAUUUUUAGAGCCAGCUUAACAGCAGCAUCAAAAUACUCGGCCACUUUAACAAAAUCUUCUUCGAGAAAACCCCGAGAUGUUAGGGCAGGUGU | 186 | |
| Methionine-tRNA ligase/synthase (MtS) | sense | 159 | UGAACUACGAAGCAGGCAAAUUCUCCAAAAGUAAAGGCAUUGGAGUUUUUGGGAAUGACGCCAAGAAUUCUAAUAUACCUGUAGAAGUGUGGAGAUACUAUCUGCUAACAAACAGGCCUGAGGUAUCAGACACAUUGUUCACUUGGGCGGAUCUUCAAG | 187 | No significant phenotype. |
| | anti-sense | 159 | CUUGAAGAUCCGCCCAAGUGAACAAUGUGUCUGAUACCUCAGGCCUGUUUGUUAGCAGAUAGUAUCUCCACACUUCUACAGGUAUAUUAGAAUUCUUGGCGUCAUUCCCAAAAACUCCAAUGCCUUUACUUUUGGAGAAUUGCCUGCUUCGUAGUUCA | 188 | |

Example 30

This example illustrates polynucleotides which are designed to target a particular low sequence homology region and are useful e. g., for selecting a specific allele of a target gene or a gene of a specific species. Polynucleotides designed to target non-coding sequence are useful in regulating non-coding RNAs that are involved in gene regulations, e. g., regulating non-coding RNAs that are processed to siRNAs in an RNAi-regulated pathway. FIG. 34 depicts an alignment of the *Nicotiana benthamiana* PDS locus 1 promoter (SEQ ID NO:319) and PDS locus 2 promoter (SEQ ID NO:320); in the case of locus 1 which contains multiple transcription start sites, the promoter sequence used in this alignment is the one with the most 5' transcription start site. The *Nicotiana benthamiana* PDS1 and PDS2 genes were found to have low sequence homology in the promoter region but high sequence homology in the coding region.

Polynucleotides designed to target different parts of the PDS1 and PDS2 promoters are listed in Table 21.

TABLE 21

| Poly-Mix | nucleotide | promoter target | Sequence | SEQ ID NO | position/dir |
|---|---|---|---|---|---|
| 2 | HL419 | PDS promoter 1 motif target | TCCCATCTCCCACATGGGTTACTG | 189 | 590-567 |
| 2 | HL420 | PDS promoter 1 motif target | CAGTAACCCATGTGGGAGATGGGA | 190 | 567-590 |
| 2 | HL421 | PDS promoter 1 motif target | GGCTGATGAAATTCAAGTGCTA | 191 | 557-536 |
| 2 | HL422 | PDS promoter 1 motif target | AAACTGAGCTTGGAAATAATC | 192 | 517-497 |
| 2 | HL423 | PDS promoter 1 motif target | GAACCCAAAATTGTCACTTTTT | 193 | 448-427 |
| 3 | HL424 | PDS promoter 1 motif target | ATGCACTTGTTTATACTCTTGTCA | 194 | 403-438 |
| 3 | HL425 | PDS promoter 1 motif target | ATTTATTAGTGTTCTAAAGAA | 195 | 357-337 |
| 3 | HL426 | PDS promoter 1 motif target | TGTAGTAGCTTATAAGATTAGCTT | 196 | 287-264 |
| 3 | HL427 | PDS promoter 1 motif target | GTTGTCCCTTTTATGGGTCTTT | 197 | 240-183 |
| 3 | HL428 | PDS promoter 1 motif target | CCCGTGCAATTTCTGGGAAGC | 198 | 86-66 |
| 5 | HL429 | PDS promoter 2motif target | ATTAGTTTTTTATACACGAAAGAT | 199 | 1313-1336 |
| 5 | HL430 | PDS promoter 2motif target | ATCTTTCGTGTATAAAAAACTAAT | 200 | 1336-1313 |
| 5 | HL431 | PDS promoter 2motif target | TTGGTGGTTTGGCCACTTCCGT | 201 | 1291-1270 |
| 5 | HL432 | PDS promoter 2motif target | TTTGTTTGCTATTTAGCTGGA | 202 | 1256-1236 |
| 5 | HL433 | PDS promoter 2motif target | CAATTTGCAGCAACTCGCACTGGA | 203 | 1205-1182 |
| 6 | HL434 | PDS promoter 2motif target | TCCCACCATTGGCTATTCCGAC | 204 | 1156-1135 |
| 6 | HL435 | PDS promoter 2motif target | CTGTCTCTCTTTTTAATTTCT | 205 | 1105-1085 |
| 6 | HL436 | PDS promoter 2motif target | CCACTTTGCACACATCTCCCACTT | 206 | 1056-1033 |
| 6 | HL437 | PDS promoter 2motif target | GAGGATCCACGTATAGTAGTAG | 207 | 1016-995 |
| 6 | HL438 | PDS promoter 2motif target | TTTAAATAAAGAAATTATTTA | 208 | 889-869 |
| 1 | HL439 | PDS promoter1 | TAATACGACTCACTATAGGGCTTGAGTTTATAACGAAGCT | 209 | |

TABLE 21-continued

| Poly-Mixnucleotide | promoter target | Sequence | SEQ ID NO | position/dir |
|---|---|---|---|---|
| 1 HL440 | PDS promoter1 | TAATACGACTCACTATAGGGCTTCTAATTTTCAAGGACG | 210 | |
| 1 HL441 | PDS promoter1 | AGCTTCTAATTTTCAAGGACGATA | 211 | Anti-sense |
| 1 HL442 | PDS promoter1 | GTCATGTGACTCCACTTTGATTTTG | 212 | Anti-sense |
| 1 HL443 | PDS promoter1 | CTCAATTCCGATAAATTTAAGAAAT | 213 | Anti-sense |
| 1 HL444 | PDS promoter1 | CGAAGCTATTGGACCGACCTAATTTC | 214 | Sense |
| 1 HL445 | PDS promoter1 | GGAATTGAGGGCTTCCCAGAAATTGC | 215 | Sense |
| 1 HL446 | PDS promoter1 | ATGACTTTTTGATTGGTGAAACTAA | 216 | Sense |
| 4 HL447 | PDS promoter2 | TAATACGACTCACTATAGGTGGAACTCCAACACACAAAAATTTC | 217 | Sense |
| 4 HL448 | PDS promoter2 | TAATACGACTCACTATAGGTTGAAAAATAATCATAATTTTA | 218 | Anti-sense |
| 4 HL449 | PDS promoter2 | GCATAATATATTGATCCGGTAT | 219 | Anti-sense |
| 4 HL450 | PDS promoter2 | CTGAAAGTTCATACATAGGTACTC | 220 | Anti-sense |
| 4 HL451 | PDS promoter2 | GGTACTCCAATTTTCAGTATAT | 221 | Anti-sense |
| 4 HL452 | PDS promoter2 | CTGAAAATTGGAGTACCTATGTAT | 222 | Sense |
| 4 HL453 | PDS promoter2 | ATGTATGAACTTTCAGAATATTATACC | 223 | Sense |
| 4 HL454 | PDS promoter2 | TACCGGATCAATATATTATGCT | 224 | Sense |

Figure 35:
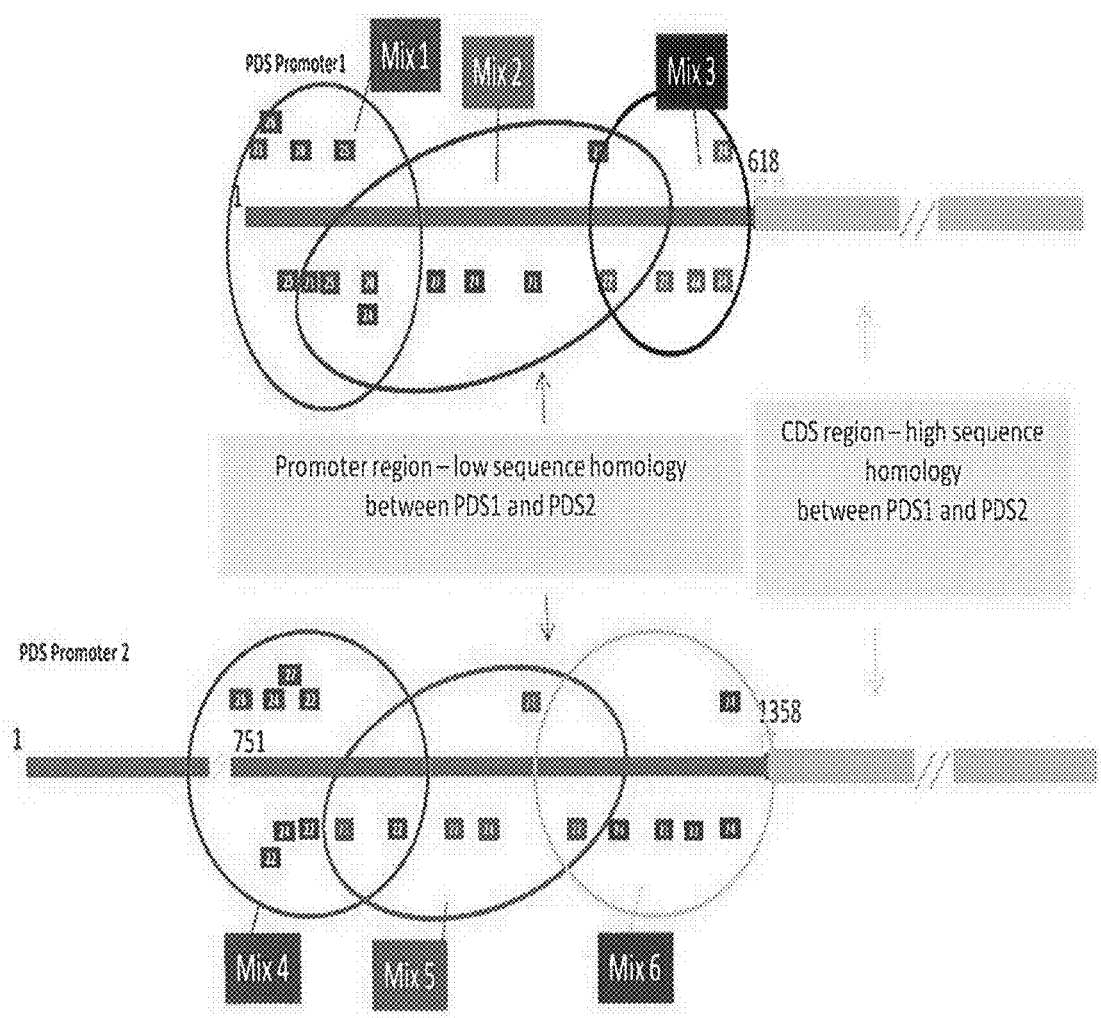
FIG. 35 schematically illustrates the *Nicotiana benthamiana* PDS locus 1 and locus 2 promoters and the regions targeted by mixtures of polynucleotides, as described in Example 30.

Six different combinations of polynucleotides (1 nanomole/plant of each applied polynucleotide) as listed in Table 21 and illustrated in FIG. 35 were tested on 4-week-old Nicotiana benthamiana plants using a procedure similar to that described in Example 12. Polynucleotide solutions were prepared in 0.01% (v/v) SILWET L-77 and 2% (w/v) ammonium sulfate in 5 millimolar sodium phosphate, pH 6.8. Two fully expanded leaves per plant were dipped into 0.1% SILWET L-77 solution freshly made with ddH2O for a few seconds, and allowed to dry. About 30 minutes later, 20 microliters of polynucleotide solution was applied to each of the two pre-treated leaves. Positive control plants were similarly treated with a DNA oligonucleotide targeting a conserved segment of the coding region of PDS1 and PDS2; negative control plants were similarly treated with a DNA oligonucleotide designed to silence green fluorescent protein (GFP). All six combinations of polynucleotides designed to target the PDS1 or PDS2 promoter regions induced systemic silencing in the treated plants as evidenced by bleaching. Treatment with either dsRNA or dsDNA polynucleotides of approximately 200 bp and targeting the PDS1 or PDS2 promoter regions also induced systemic silencing in the treated plants as evidenced by bleaching.

The following additional genomic sequences (including promoter and transcribed intron and exon sequence) listed in Table 22 were identified for Amaranthus palmeri genes for use in designing polynucleotides for topical application:

TABLE 22

| Gene Name | Sequence | SEQ ID NO. |
|---|---|---|
| ACC1 | TTCAAAATGAATTTAAAATTATATAAAAATCAATATGGACACAAGACCGGAT<br>ATCAATCCGACCCGAAATAGTTGACTTGAAATCAACCTGATGACCCGAATGA<br>ACACCTCTAGTTATCACTAACAAGGGTCAGATTGCGTACATCAAACCCCTCA<br>AATCCTGCTTAGGTGGGAGCTTGTCAATGGCTTAGGGGTAACGGGAATGTGT<br>GTGCTATGTACATTGTGCATCTATTCTTATGCTTATTTATGTTGAGTTAGTTTT<br>TTTTTTGGATCAAATATAAAGAGCTTAACTTTTGTATTTTCTTGATGTGGTGT<br>AGTGGTGATGAAGATCAGGCTGAGAGAATCTAAATTGGCCAAAATTCTGAG<br>AGAACAAGAAGTGAGTTCAGCCCTTCGTGCTGCTGGTGTTGGTGTGATTAGT<br>TGCATCATACAGAGAGATGAAGGGCGAACTCCGATGAGGCATTCATTCTATT<br>GGTCAGCAGAAAAACAATATTATAGTGAGGAGCCTTTACTACGTCATTTGGA | 225 |

TABLE 22-continued

| Gene Name | Sequence | SEQ ID NO. |
|---|---|---|
| | ACCCCCTCTATCTATGTATCTCGAGCTGGTACTAGTCTCTGAACCGATTGCCT<br>TTCTTCTGCTTTGTTATTTTGTGTGATATTTCGACTTAAGTCTAATTTACATCG<br>TTTTGTACATTTGTTATC | |
| ACC3 | TTTTGCTTTTTTACTATTATTTCCTTCTTTTCAAGGATTTGAGTTGTTTATTGCT<br>GACTGCTTCCTATGTATTACCCATATGTCTCTGTATAGGCATTACGGGAGCTG<br>TACCTACATCTAACTCCTATACAACGTGTGAATATTGCCCGGCATCCTAATCG<br>CCCCACTTTTCTTGACCACGTATTCAGCATCACAGAAAAGGTTTCTGATTTAT<br>TATAATTTTTGTCATTTGTATTCACTCTTCAATAAAGTACATCCATTATCAAT<br>CTTTACGGAGGTTGTTCACACAACTTCTTGTTTCATTTTGCATAATTAGTTTGT<br>GGAACTACATGGAGATCGTGCTGGTTATGATGACCCTGCTATAGTTACTGGC<br>CTTGGTACGATAGATGGTAGGCGTTATATGTTCATTGGTCATCAAAAGGGAA<br>GAAATACGAAGGAAAATATTGCACGGAATTTCGGGATGCCTACTCCTCATGG<br>GTAAATGCTTTACTATAATGTTTTACTTTAATTTAATTACCTATGTTATTTAGG<br>ATGAAAATGAATACTTTTCTTATTACTATTACTTAGGTTCCTAATGCACAAAA<br>ACCGTAATTATTAATGTACCCTAATGGAATTAACACATGGTAATTAAGCTCT<br>CCGCTTTGTGTAATTAATCCAATTTTTTAGAGAGTCAAATATTGTTCAGGTTAAA<br>CTAGAGCTTTTCATACCCAAATAATAAAACCAAGGGTAAATTTCCAAAA | 226 |
| ACC4 | ATGTGATCAATTAAAGAAAAAGTCTAATTATATGAGCCCGTCTCACAGTGAC<br>GGAGCTATCATAGAGCCCATGGGGTCACGTGCCCTTCGGGGTTTTAGAAAA<br>AATTCAAAGTATACTTTTCTATTAATAAGAGTAAAAATGTAAAATTAATATT<br>AAACTCTTTTGATAATAAATACTCTCACTTTAGTAATTTTGTCTTATTTATT<br>TATTTTATCTCATGTGTTTAATAAGGTCAGTTGACTTATTTTGTTCCATTTTCT<br>TTTATGGTATGCCGTATTTAAAATTTTAGCAAGTAAAGATAAAATAGTTGTT<br>AATCTTACAAATAAAACTCTATCGAAATTTCATCCATTAGTTAATGTCCCCAA<br>AAAGTCCGAACTACAAATCGACCACTGTCATCACATGGTGAGATAGTCTCAT<br>ATAAAACGAGTTCAGTTATTAAAGGAAAATAGGAAACACGAAACAGTTAAT<br>TTAGGCGGGGCCTATGTATTATCCAAATGTGATACTCCAGTCCACATTACTC<br>AGTCCTTCCAATTGAACAGTTGGCTTAATCTACCAAGCGCGTGGCCATAAAT<br>GCCTCTAACACTTTTCAATCTCTCAGATAACTCTCACACCACTTATCATCACA<br>ATTCACAATTACTCTAATTCTTTTTATTCCTTTCCATGTCGCTAATTTTCTACT<br>GATTCAGGTTTTATTCTCAGCTTTTATCAATTTTATTTCATGCTTTTTATGTCA<br>ATTTCTTGTTTCGCATTTTGTCTTCCACTTGCTGTCTGTTTTATTAATCAATTTT<br>GTATGATTGTTGGAATAATTGTATGTATTTTTCATGATTTTCCTCTTATGGAG<br>GTTCATAATGTATTGCTAGATTTGTTTACTTTCAC | 227 |
| ACC5 | AATTTGAGCGGGAAAATTTTAATATCATTAAAATAGTCTTTGCTTTAGTATATA<br>GAATAGTTAAAATTAATAGTCAAACTTATTGTAATAGCATGCACTAATCTAT<br>AATAATCTTATCCTGAAAGCTATAATAAAATTATAAAAAAATATATGTGAAA<br>AACTAATTTGAGCGGGAAAATTTTAACCAAGGGCTAACACGTATCATTAAAT<br>AGTCTTTACTTTAGTATATAGAATGATAATTAACGATCATAAAACAAAATTG<br>TCACTTTCAGTAGCAAACTTACAAAATGAGCAGAGTACCTCATATCATAAAA<br>TTGCTTCTTTCTCATTTGTTGTGTTGCTCTCATTTTAGGAGTTCATCGTTTATA<br>TCGTCGTCTTACCACTCAATCACTTTTAGATTTATTAGTAGCACTTCCTCAAT<br>CTACAGCAGCAATTTCTACAGTTCAACAACCTC | 228 |
| ACC6 | GGAAAATTTACCTAGAATAATCCAATTTATTCGTGATTTTTCTACAAATTCCA<br>ACTTCAAGGGGTATTTGCCTAAAGTAATTAAACTTGGATACCCCGATGACCT<br>GCTATAGTAGATAATTTACCAGAAAATTAAAAATGAAAATTAATTTAAAATT<br>AGAGAAAAATTTTGAAATTTCATATAAAAAATTTTAAATAATAAAAAAATA<br>TAAATTTTTTTGAACATTTTATTTTAATCTATCTTTTTTGAAAAAATAAAACTT<br>AGTTATAGCAAGTGATCTGGTCACCGGGTTTACTCTAGGAAAATATCCCTCA<br>AAGTTGAGATTATTCATGGTTAATAAATAGGTGAGATTATTATAGAAAAATT<br>ACGAATAAATTGGATTATTGTTGGTAATTTTTTTTTCAAAACTATCCCTAGGA<br>AGGACCTATTAGTGATTCTCCCTCTACTTTGGAGGAGTATATTGTGGACTTC<br>CCATCTTCCTTAATTGTATTGTAACTTTTAACTATTGATTCTTTAAAAAAAG<br>AACTTATAAAATTGTAGGGTTAATAAAATCTAAGATTTTATCTAATTTCACTT<br>TGATTATTCCGATTTTGTATTCACATTATTTTAAATGACATTCGTCAAATAAA<br>AAAAAATAGTTTCATTGCATTCCAATTTTGTTGACTAGGGGGATTAAAGAAA<br>GAATAGTATCAATAATCGTAATGTAGCAAGTAGTACAAAAGAAGTATATTTC<br>AATATGTCAAACTTTGATCTCGTTGTAACTTGTAATTTGTACGATGCGGTGTG<br>AATGACATACTTCACCTTTTCATTATTTTATACTGGTAGTGACATGGGATTA<br>TTATTGCGATATTTGCAGTAATGAAAATTTTTTGGTTGTTGCTTTTACAAAC<br>AAAAATTCTACCGAATTTTTATTAATTTAATTCAACACGTTGGTGTTACCCA<br>TGATTTATAGGTCTGGGTCCGCCACTGCTAGCTAACATTAAACAATTTAACA<br>AACTCAATACACCAACCTAAAAATAAAATTTTTTGGCCATAATTTTTAGAA<br>TTTTAGTTTTTAAACATTATATTTGGGAATTTTTTTCCTTTTATATATATAAA<br>ATAAAAAAAATCCAAAAAGGGGACACACATTAATACACACTTGAAAGCA<br>TCGATGATATCGAAGAAAAACCAGATGGGGTGCCCAATTATCTTCGTCTCCT<br>TCGATATATCGAATTCATTAACAACATTATATCAAAAACCAACCAAATTAC<br>CAACTTTCGAAACCAATATTCGCCGTATTTTCTCTATTCAACAATCCCTACA<br>ATGGCGGCATTGCCAGCTTCTTCTTCTCCTGCAATTTCGGAATCACCCACTTG<br>CAATTTTCTTCCTATTCAAAAAATCACTACCACTCGCTTTCTAAGGTTTCATT<br>CGGTTTTACTCCCAAGCCTAAATTTGGCCTTTTCTCCAAGGTTTATTTTCTATC<br>TCTTTTTTAATTGGTTAATCAATTGGATTGTTGAATTTTTCAGGGTTTAACGG | 229 |

TABLE 22-continued

| Gene Name | Sequence | SEQ ID NO. |
|---|---|---|
| | TATAATATTTGTGGGTTTTTTCGAGTACATTCTGGGTTTGTAGTATTGGATTT<br>GGCATTGCTTTTAATTTTTGAGATTGGGTTTTTTGGGTTTTATTTGGTTCTTGT<br>GATTCAAGGTTATTGATTTGCTGCATTAAACTGTATTTATGGAATGATGTCAA<br>TTAACTGTTACATTACATTGCTTTATGGTTTTCATCATGCTGATTAGTGATTA<br>CTGTGTTTGAATCTCTTGCTTCTCTATGTACTATTTAATCTGATACAACAAGT<br>ACAACCTAGAAAACAGGTTAAAGGGAAATCTATAAGCTTAGTAAATTAACA<br>CTTGAAAGAAGCTAATGACGGAGAGAGGGGTCTTTTTGGAGAAGGCAGTTTT<br>CATATTATTGCTCAGTTCTCTAGTGCAGCTTTACTTCACTTAGACACTCTTAA<br>GTAGAGGTCATAGGTGTTCAGAATAGATCCAAAGACCCGATATTTACCGGAC<br>TTTGTAAACAACTTAACCCGACTTCAAAATGAATTTACAATCATATAAAGC<br>AATATGGACTTAAACCGATTTTGAACCGACCTTGACCGGTTGATCCGAATGA<br>ATGCCTCTACTCTTAAGCATGTCAACTGTAATATGAAATAGAATTATAATAT<br>AAACTAAGTTCATGTTTTCTTCAACTACAAATGAAATTTTATGACCCAAATA<br>ATGTGTGAATACCCCCAGCAATAGGTTGAATGGCATTTAGTTCAGTTGATTTT<br>AGCAGACCACATCTGCCCTCATATTCCATTGTTCAGTTTAGTTGTTAGTAGCT<br>GTACATAATAGACTAATTAAGTTGTCATTTGATCCATGTTATGGTTGTCTGG<br>GATAAACGGATTGGAATTGTATAATAAAAGTTTGGGTTAGTTTATTTTGCTCT<br>AGGAGGGGTTATGTCATATGTGCACTCTGTTGGCAACCCGACAATGCAAAAC<br>ATTTTCATACTTGGTACGTTGTTGCGTGTTTTGTGCCCTTCGTATTTTGTAACT<br>GTTGATGAATGTGTAAAAATATACTACATGATCATATGCTAGTAGGTCTTCTT<br>CACCTAGTAAAGAAATTTTTCTAACACGAGAAGTTCAAAACATATTCCCATT<br>ACCATTATCCAACATCAGTACCCGAGTCCAAGTAACATAGGGTGTCCCTTTA<br>TGATAGTATAAGAATTGGTGCATGAAAAACGCGTGATTGTAGCGAGGATAG<br>TAGGCGGGAGAGGTACAGGATTTGAAAATTTTGAATTGCTAAAACGCTATCA<br>GGATCTTGTTTTTCTTACTTTGATGTTGCTTTTTTGAAATTTGATCCAAATTGT<br>TAAATTATTGAGACTAATTCCTGTTGATCCTGTCGTGAACTTTGTAGAATCTT<br>TCAGGCCGCATTCTCACAGTGAAGGCTCAATTAAACAAGGTGAGTCTTTTTT<br>TGTCTTAACTCTTATGCAGTTCATTATCTCTTCTACTGATGAGAAACCACTA<br>TTTGGCCTAATTCTAATTTCCTTCTAGGTTGCTTTGGATGGTTCAAATCATGC<br>TCCATCACCTTCGCACGAAAAATCTGGGCTACCAGCCCAAGAAAAGAAGAA<br>CGATGAGCCGTCTAGTGAATCTTCTCCTGCAGCATCAGTGTCTGAAGAACGA<br>GTCTCCGAATTCTTGAGCCAAGTTGCCGGTCTTGTCAAGTATGTAACATTCTT<br>TATTTTCATTCTTCCACACACTCGCAATTTGGATAACGAGATGTCTTTAGAGA<br>CGTCTGGGGAACAAGGGAGAAATGAGTCTAGAGGTTGCTAGAGAGAACGAG<br>ATAAATACTAATATATATGAATATTTCATAATCCACATTAAAAAAATACAAT<br>TGAATTTGCATTATGGTGAACTACCAAAGAATCGAATATTTTTAATACTCCA<br>TGTTTTGTGGTCTAGACTTGTGGATTCTAGAGACATTGTAGAGTTGCAATTAA<br>AACAACTGGACTGTGAGATATTGATCCGCAAGCAGGAAGCTATTCCTCAACC<br>ACAAATTCCTAATCCTACACATGTCGTTGCAATGCAACCACCACCACCTGCT<br>GTAGCGTCTGCCCCAGCTCCCGTCTCTTCACCAGCCACTCCTCGTCCTGCGTT<br>ACCTGCCCCAGCGCCTGCTGCCACGTCAGCTAAGCCATCACTTCCACCTCTC<br>AAGAGCCCTATGTCAGGCACATTCTACCGTAGTCCAGCTCCTGGCGAGCCGC<br>CTTTCGTGAAGGTAAGTGTATACCCCTTTTTTAGTGTTGTATTTCTGTGTTATA<br>TCAATTTTTGCATTTTGTGAAGCTGAAAATAAATCTTTCATTTTCCATAGGTT<br>GGAGATAAAGTTAAGAAAGGACAAGTCATATGCATTATCGAGGCTATGAAG<br>TTGATGAATGAAATCGAGGTACGTATGTTATTGCTTTAAACTTCATGCCTTAG<br>GCCGTGAAGTT | |
| ALS1 | ACAAAAAGCACAAATTCAATAATATACTCTTTAAGTTTGTTTATCTTCTAATT<br>AGTTCGGTTAAAACGGTTCCCCACTTTCTTCTCCGACTCTCACAATTATCTTC<br>CCCTATTCATTTTTCTTCCACCCTCTCTAATGGCGGCTGTTTCCTTCAATATCA<br>ATGGTGGAAAGATTGGAACTTTATGTTCAAGACACGAATTCGTTTGTGGGTT<br>TGTAAGAAAATTTCATTTTAGAACTCATACTTCTATATTTGAAAAACATATGC<br>CAAAAACTTCAAGGTTTAAAGCAATGGAAGTTTCTGCAAATGCAACAGTAA<br>ATATAGTTCCTGTTTCAGCTCATTCTAGGTAATTTTATTTCTCGAAAATTTCC<br>GATTTACAATTAAATTAATCTTGTTTTGTAGGTAATGAATTGCAGAAGAAAT<br>AGATGGATTCTTATTTGTTTATTGGTATTTGTTTATAAATTTTTGTTTATATTA<br>GTTTCTGAATTGTGATTATTCTGATTGTATGTCAAGGTTTAGGTTGTTATTAA<br>TAAATGTAAATTGGATTGATTGAAGTTGCAATAAGGTGATGGCGTGATGCTG<br>ATTGTTGTAAATTTT | 230 |
| ALS2 | CAACAATGAGAATTTAGAATCCATATCAATCTTGATATTCAAGGGTATTTAA<br>GTAATTAAAGAACAACCATTGTTAAGCGCCTCCACTATCTTCTTCCTTCTCAT<br>TCTCCATTCTCGCTTAGCTTTCCTCTCGCACTAATTACCTCCATTTGCAACCTT<br>TCAAGCTTTCAACAATGGCGTCCACTTCTTCAAACCCACCATTTTCCTCTTTT<br>ACTAAACCTAACAAAATCCCTAATCTGCAATCATCCATTTACGCTATCCCTTT<br>GTCCAATTCTCTTAAACCCACTTCTTCTTCTTCAATCCTCCGCCGCCCCCTTCA<br>AATCTCATCATCTTCTTCTCAATCACCTAAACCTAAACCTCCTTCCGCTACTA<br>TAACTCAATCACCTTCATCTCTCACCGATGATAAACCCTCTTCTTTTGTTTCCC<br>GATTTAGCCCTGAAGAACCCAGAAAAGGTTGCGATGTTCTCGTTGAAGCTCT<br>TGAACGTGAAGGTGTTACCGATGTTTTTGCTTACCCTGGTGGAGCATCCATG<br>GAAATCCATCAAGCTCTTACTCGTTCTAATATCATTAGAAATGTTCTTCCTCG<br>ACATGAACAAGGTGGGGTTTTCGCTGCTGAAGGCTACGCTCGTGCTACTGGA<br>CGCGTTGGAGTTTGTATTGCCACTTCTGGTCC | 231 |

TABLE 22-continued

| Gene Name | Sequence | SEQ ID NO. |
|---|---|---|
| EPSPS1 | ATTTGGATAACTTTTTCCTTTGATTCGAATCGGATTATTTTTAATACAGTATT<br>ATGAACTGATTTAATGAAAGTGGAGGAAGTTTCAATTTTTAAAGTTGTAGGT<br>GTAATGTTTTCTCATTTTGGATATGAAAGTGGAGGAAGTTTCAATTTCGAATC<br>ATGTTTGCCAGTTGATTCAATGAATGCTCTTGGAAATGACCAAGAGTTCAAG<br>GCTTCTTGTTATAAAACATTTCAATTTTGATCTAAGAATGAACTATTTAGAAC<br>TTAAAGTAATTAAATTATTAGTTATAACTTATAAAAAAATTCAATTTTAACCT<br>TAAATTTATAAATTATGACCTTAAAAAGATCAAGTATTGAACGCATATTTAG<br>AAAAATTATAATTCGGCTTATCAGTCTCATATTGAGACGGTCTCGTCCAAGA<br>CAAGTTGTATCATTTATATAATCAAATATAATTATGAGTGTATTCATGTAGGT<br>TTCAACTTTAAAGCCTAGGTGAAAGATATGTTGTAGCATCTTTGTGAAAGTC<br>AGCCTATAACTTGGTTCTAAAATTTTGAAGCATAACCATATAGTCCCTCGAA<br>TTCATTCAAGTTGTCCAATTTACTTTTTTATACTTGCCAGACAACATTTAAA<br>CCCTTAATATTTCTAATTAATCTTAATTAAAAATTATGAAAATTTGATATTAA<br>TAATCTTTGTATTGAAACGAATTTAACAAGATCTCACATGACTATGTTTTAAC<br>TTATAGATTAAAAAAAAATACAAATTAAGAGTGATAAGTGAATAGTGCCCC<br>AAAACAAATGGGACAACTTAGATGAATTGGAGGTAATATTAGGTAGCAAGT<br>GATCACTTTAACATCAAAATTGATCACTTATAGGTTCAAATTGAAACTTTTAC<br>TTTAATTGATATGTTTAAATACTACTTTAAATTGAAATTGATATTTTTAAGGT<br>CAAAATTGAAACCTTTAAGATTATAATTGAAAATTGGCAGAAGAAAAACAA<br>AGAGAAAGAATATAAGACACGCAAATTGTACCGATCTACTCTTATTTCAATT<br>TGAGACGGTCTCGCCCAAGACTAGATGTTCGGTCATCCTACACCAACCCCAA<br>AAAATTCAACAACAAAGTCTTATAATGATTCCCTCTAATCTACTACAGTCTA<br>CACCAACCCACTTTCTCTTTGCCCACCAAAACTTTGGTTTGGTAAGAACTAAG<br>CCCTCTTCTTTCCCTTCTCTCTCTTAAAAGCCTGAAAAATCCACCTAACTTT<br>TTTTTAAGCCAACAAACAACGCCAAATTCAGAGAAAGAATAATGGCTCAAG<br>CTACTACCATCAACAATGGTGTCCAAACTGGTCAATTGCACCATACTTTACC<br>CAAATCCCAGTTACCCAAATCTTCAAAAACTCTTAATTTTGGATCAAACTTG<br>AGAATTTCTCCAAAGTTCATGTCTTTAACCAATAAAAAGAGTTGGTGGGCA<br>ATCATTCAATTGTTCCCAAGATTCAAGCTTCTGTTGCTGCTGCAGCTGAGAAA<br>CCTTCATCTGTCCCAGAAATTGTGTTACAACCCATCAAAGAGATCTCTGGTA<br>CTGTTCAATTGCCTGGGTCAAAGTCTTTATCCAATCGAATCCTTCTTTTAGCT<br>GCTTTGTCTGAGGTATTTATTTCTCAACTGCGAAAACAATCTCTATTTGATAT<br>TGGAATTTATATTACATACTCCATCTTGTTGTAATTGCATTAGTAGATACTTA<br>TGTTTTGACCTTTGTTCATTTGTTTGTTGAATTGGTAGTGTTGAGAATTTGAAT<br>GTAATTATTTGTTTTCCATGTGAATTTAATCTGATTAAATCCACTTCTTATTT<br>ATGTTAAGTTGCAATGATGTTTGCCAAATGGTTATCATTGAAGGATAAGTTT<br>GCCTACTTTTGACCCTCCCAACTTCGCGGTGGTAGAGCCATTTTATGTTATTG<br>GGGGAAATTAGAAAGATTTATTTGTTTTGCCTTTCGAAATAGTAGCGTTCGT<br>GATTCTGATTTGGGTGTCTTTATAGATATGATATATGGGTTATTCATGTAATG<br>TGTAGGTTTATGCATTATGTTGGATGCATGTCTGGTGTTATTGCTGTAAATGG<br>ATGAATGTTGTTATTTGGAGACATTTTTTCATTCATTTTTTCCCTTTTTAATTG<br>GAACTGGAAGAGGGAAAGTTATTGGGAGTAATTAAAAGGTTGTGAGTTCGA<br>TACACTGCATCAAAGACGAAGAACTTGACATAGATGTTGAAGGCTAATCCTT<br>ATCACTGCTTGAATTCAATATGTATCTGAAAATTTTACCCCTCTATATGCATC<br>TGTTTTTGCTAATAAAGTGTTTTTGGACTATCATGTTTTGTGATGCTTAAGAG<br>GGTGATATTACTGAGATAAATGGAAATATCAAAATAACATCTATTGTGAAGT | 232 |
| EPSPS2 | CAAGCTTCAATTATCGTTTTCAAAATAAGTATTTCAAAGTCTATAAAGATATT<br>GTATAAGTTTTAGTTCAAATTTAATAAGTTTTTTTTTTTTTTTTTTTTTTTT<br>TGAAAATCCAAATTGAATAAGTTAATARTTAAATTATGACATATAATTATGA<br>CATATAATTTGACCATGATATTTTACAATCTAACTTAATTTTGAACTTATTAT<br>TTCTAATATTCAATTATCGTTCTAAAAATAAGTATTTAAATTGTATAGATATA<br>TTGTATAACATTTAGTTCAAATTTAATTATTGATAGTTTTATTGACTATTTATT<br>TGGKGTTTGAAATTCATCCATAGAATGATAGAATAACACCATTTTTTATATA<br>ACTTCGTTCTAAAATTTTGAAGCATAACCATATACTCCCTCCAATTCATCCAA<br>GTTGTCCAATTTACTTTTTCATACTTGCCGAGGCAACATTTAAACCCTTAATA<br>TTTCTAATTAATGTTAATTAAAAATTATGAAAATTTGATATTAATAATCCTTG<br>TATTGAAACAAATCTAACAAGATCCCACATGACTATGTTTTAACTTATAGAT<br>TAAGAATAAAATACAAATTAAGAGTAATAAGTGAATAGTGTCCCAAAACAA<br>ATAGGACAACTTGGATGAATTGGAGGTAGTATTAGGTAGCAAGTGATCACTT<br>TAACATCAAAATTGATCAGTTACAGGTTCAAATTGAAACTTTTACTTTAATTG<br>ATATGTTTAAATACTACTTTAAATTGAAATTGATATTCTTAAGGTCAAATTG<br>AAAACTTTAAGATTATAATTGAAAAATGCCCGAAGATGAAAAAACAGAGA<br>GAAAGCATGTAAGACACGCAAATTGAACCAGTCTACTCTTGTTTCAATTTGA<br>GACGGTCTCGCCCAAGACCAGATGTTCAGTCATCCTACACCAACCCCAAAA<br>ATTCAACAACAAACTCTTATAATGATTCCCTCTAATCTACTAGAGTCTACACC<br>AACCCACTTTCTCTTTGCCCACCAAAACTTTGGTTGGTGAGAACTAAGCCCT<br>CTTCTTTCCCTTCTCTCTCTTAAAAGCCTAAAACCCACCAACTTTTTCAGCCA<br>AGAACAACGCGAAATTCAGAGGAAGAATAATGGCTCAAGCTACTACCATC<br>AACAATGGTGTCCATACTGGTCAATTGCACCATACTTTACCCAAAACCCAGT<br>TACCCAAATCTTCAAAAACTCTTAATTTTGGATCAAACTTGAGAATTTCTCCA<br>AAGTTCATGTCTTTAACCAATAAAAGAGTTGGTGGGCAATCATCAATTGTTC<br>CCAAGATTCAAGCTTCTGTTGCTGCTGCAGCTGAGAAACCTTCATCTGTCCCA<br>GAAATTGTGTTACAACCCATCAAAGAGATCTCTGGTACTGTTCAATTGCCTG<br>GGTCAAAGTCTTTATCCAATCGAATCCTTCTTTTAGCTGCTTTGTCTGAGGGC<br>ACAACAGTGGTCGACAACTTGCTGTATAGTGATGATATTCTTTATATGTTGG | 233 |

TABLE 22-continued

| Gene Name | Sequence | SEQ ID NO. |
|---|---|---|
| | ACGCTCTCAGAACTCTTGGTTTAAAAGTGGAGGATGATAGTACAGCCAAAAG<br>GGCAGTCGTAGAGGGTTGTGGTGGTCTGTTTCCTGTTGGTAAAGATGGAAAG<br>GAAGAGATTCAACTTTTCCTTGGTAATGCAGGAACAGCGATGCGCCCATTGA<br>CAGCTGCGGTTGCCGTTGCTGGAGGAAATTCAAGTTATGTGCTTGATGGAGT<br>ACCAAGAATGAGGGAGCGCCCCATTGGGGATCTGGTAGCAGGTCTAAAGCA<br>ACTTGGTTCAGATGTAGATTGTTTTCTTGGCACAAATTGCCCTCCTGTTCGGG<br>TCAATGCTAAAGGAGGCCTTCCAGGGGGCAAGGTCAAGCTCTCTGGATCGGT<br>TAGTAGCCAATATTTAACTGCACTTCTCATGGCTACTCCTTTGGGTCTTGGAG<br>ACGTGGAGATTGAGATAGTTGATAAATTGATTTCTGTACCGTATGTTGAAAT<br>GACAATAAAGTTGATGGAACGCTTTGGAGTATCCGTAGAACATAGTGATAGT<br>TGGGACAGGTTCTACATTCGAGGTGGTCAGAAATACAAATCTCCTGGAAAGG<br>CATATGTTGAGGGTGATGCTTCAAGTGCTAGCTACTTCCTAGCCGGAGCCGC<br>CGTCACTGGTGGGACTGTCACTGTCAAGGGTTGTGGAACAGCAGTTTACAG<br>GTATAATGTTAACCCTTACCCTTCACATTGTTCTGCTAAATTCTAGAGGACCC<br>TTTCAATTCTGGGTGGGATAAGCACGGCAATTTGACCGCAAAAAAATTGCAA<br>AATTATTCTGCTGATAGAACATCTCGAGATGAGATCATATTGAGTTTTGGCG<br>TCAACATAAACCTAATCAAATAATGAAAAATACAAACATCATATGGTTTCTT<br>TTGTCTTTATGACTAGACACTCTCTATTATTCCTTGATTGGGATCTTATTTGAA<br>ATTGCTGTGTAGCCTACACCTCATGTTCAGATTTTGTTCGTATACCAGACTTT<br>TCTTGATTGGGATCTTATTTGTCCCTGGATTTTGCATAGGGTGATGTAAAAT<br>TTGCCGAAGTTCTTGAGAAGATGGGTTGCAAGGTCACCTGGACAGAGAATA<br>GTGTAACTGTTACTGGACCACCCAGGGATTCATCTGGAAAGAAACATCTGCG<br>TGCTATCGACGTCAACATGAACAAAATGCCAGATGTTGCTATGACTCTTGCA<br>GTTGTTGCCTTGTATGCAGATGGGCCCACCGCCATCAGAGATGTGGCTAGCT<br>GGAGAGTGAAGGAAACCGAACGGATGATTGCCATTTGCACAGAACTGAAGA<br>AGCTTGGGGCAACAGTTGAGGAAGGATCTGATTACTGTGTGATCACTCCGCC<br>TGAAAAGCTAAACCCCACCGCCATTGAAACTTATGACGATCACCGAATGGCC<br>ATGGCATTCTCTCTTGCTGCCTGTGCAGATGTTCCCGTCACTATCCTTGATCC<br>GGGATGCACCCGTAAAACCTTCCCGGACTACTTTGATGTTTTAGAAAAGTTC<br>GCCAAGCATTGA | |
| GS3 | TCTTAATTTGTATTTTATTATTAATCTATAAGTTAAAACATAGTCAAGTGAGA<br>TCTTGTTTGATTCGTCTCTATGCAAGGATTTTCATATCAACTTTTTCATAATTTT<br>TGATTATACACAATTACAAATATTAACGAACGAATAAGTGCATTAAAAAGA<br>GTGCAAAAAGCAAATGGGACACTTGTGTTGAATAGGAGGGAGTATACATTA<br>AGATGAATCTAACGAGATCTCACATGGATATAATTTGTCTTCTATATATGTCT<br>AAAAAATCTTGATCAAATTTCTCTTTCCAAAATAGAATATTCTAAATGGGAA<br>GAACATTAAGAAACGGAGGGAGTACTTATAAGTTAAGATAGTTGGGGTAT<br>TTAGGTAAAAAAATCTATGCCAAAAGTAGAAAGTGGACAATTAGAGTGACT<br>TTACTAAATAAGGAAAGTGGACATTTAAAATGAATCGGAGGGAGCATATTA<br>ACTTTATTTTCAAAGTGTGAAACATAATCATATTTAGGTAAAAAAATTATCA<br>ATTTAACGTCAAAATTGATCACAAATAGGTTAAAATTGAAATTTTTTATGTTA<br>ATTGATCTATTGTTCACTTTAAATTGAAATTGATATCCTTTAAGGTTAAAATT<br>AATACCTCTAAAATTAAAATTATTAAAGGCCCAGAAAATAAAAAAAAAGA<br>AGACAGGCTATTAGTAAAATTATTAAGTATGTAAGGTTGATACACGCGCGAA<br>TTGAGCCGGCCCACTTTTAGTTTCAATTTGAAACAGTCTCAATCAAGACCAA<br>TTATTTATTATTTTATTATTTTATTGTTTTAAGCTCAATGGGTTGGACTTGATA<br>AATTATATTTTGAGGAGACGGGCTATTAGTAAAATTAATAGTTGGAATCTTT<br>TTTGATATACTATAAAAGAGGTATCTGGTGGAGCCTTAAATCTGCGCAATT<br>GAAGTCCTCAATACACATCTCGCTCTTCTTATTCTCTTTCATCTATTTCCTCCT<br>TTGATCAAACTACGCCATGTCTCTCTTAAATGATCTCGTTAACCTTAATCTCT<br>CTGAAACTACCGATAAGATTATCGCTGAATACATATGGTAATACAACAATCC<br>TTCCTCTTTTTCATTT | 234 |
| GS5 | AAAAAACCGTCTTATTTGTAGAAAATAAAAAACTAAAAGTAGTATCAACTT<br>TTAGACTAGTCATAAGTGAGTGGCATCAAACTTGTTCTATAAAAAGGGAAGA<br>GTTCCTCAACTTGAGATTCATATTTTTTGTGATTTCTAAATAGAAGAACATAC<br>TCATCTTCCACTTCTCTTATTCATCAAATTTTATTTGTTCCCCAAAAAAACAT<br>GTCTCTTCTTACAGATCTCCATCAATCTTAATCTTTCTGACTCCACTGAGAAGA<br>TCATTGCTGAATACATATGGTCAGTTTTCATCCCTTTTTTTACCTTTAATCCC<br>ACTTTTTTGTTTTTACCCACCATTTTTTTCATCTATTTTCTCTTAAAGATTTTAA<br>CTTTTTACTTTTTTGTGTATATAACATTCATTTTTTCAATTGGGTAGGTTAGAA<br>AATTTCTATAAATAAATAAATAAATNNNNNNNNNTACCTTAATCCCACTTTT<br>TGTTTCTACCCACCATTTTTTTCATCAATTTTTTCTTAAAGATTTTAACTTTTTTT<br>AACTTTTTCTTGGTTTTTGTGTATATACCAATCATTTATTTTCACTAGTGTAGG<br>TTAAAAAATATCTAAAAATAAATAAAATAGAATAAAAATGTAATCACTAGA<br>TTAACCCATGAATTATTTCCCTTGTTTTTACTCAAACTTTTTACCCTTGTTAAA<br>AAAATAATGATATAAATAAATTTTTGAGGGTTTGTTAAACCCATATGTAATC<br>TATATCGAAAAAATTAGATAGCGGGTTTTGTTGTGGACAAACTAAATAACAA<br>ATTTAGGAATAAACTTTTGAGGGTTTATTGAAAAAATAACCCATATTTAATC<br>TATATCGAAAAAATGATAGCGAGCTTTGTATAGAT | 235 |
| HPPD | CGTCGAAGTAGAAGACGCGGAAGCTGCTTTTAACATCAGCGTTTCGCATGGG<br>GCTATTCCCTGTGTTTCTCCTATTCAATTGGAAAACGGTGTCGTTTTATCTGA<br>GGTTCATTATATGGGGATGTTGTGCTTCGGTATGTAAGCTACGGAAATGAA<br>TGTGGGGATGTGTTTTTTCTTCCTGGGTTTGAGGAAATGCCGGAGGAATCAT | 236 |

TABLE 22-continued

| Gene Name | Sequence | SEQ ID NO. |
|---|---|---|
| | CGTTTAGAGGACTTGATTTTGGCATTCGAAGGTTGGATCATGCTGTAGGGAA TGTCCCTGAGTTGGCTCCTGCAATTGCTTATTTGAAGAAGTTTACTGGGTTTC ATGAGTTTGCTGAGTTTACAGCTGAAGATGTTGGGACGAGTGAAAGTGGATT GAATTCAGCCGTATTGGCAAACAATGATGAAATGGTGTTGTTTCCGATGAAT GAACCTGTGTATGGGACAAAAAGGAAGAGCCAAATTCAAACTTATTTGGAG CATAATGAAGGGCTGGTGTACAGCATTTGGCTTTGATGAGTGAAGACATAT TTTGGACTTTAAGGGAGATGAGGAAGAGAAGTGTTCTTGGTGGGTTTGAGTT TATGCCGTCGCCGCCTCCGACTTATTACCGGAATTTGAGGAACAGAGCTGCT GATGTATTGAGTGAGGAGCAGATGAAGGAGTGTGAAGAGTTGGGGATTTTG GTGGATAAAGATGATCAGGGCACTTTGCTTCAAATCTTCACCAAACCTATTG GAGACAGGTAAATTTTAATCTTGCTTTCAATTGCTTTTGCTTGATGGATTGAC TAGCAAATTTGATCGCATTTTGTTGCTTATATGACTTGATGATACTTCCTCTG TTTCGAAATACTCGCTACATTCGCTACATTTTGTTTTGTGCACTATTCATCGTT CAAGCTTATTTTACATATTGCGACTAATGTGTAACTAAAAATATAGTCAAGT GGGATCTTGTTTGAATCGTCTAATGGCATACTTTCATCATATTAAATTTTTAT AATTTTTAGATTAGTGTAGTTTAAGATATTAATGCTCAAAATTGTGCATTGGA TTGCGTAAAAAAGTGAAATGTAGCAAGTATTATGAAA | |
| PDS | AAAACCAAAGGAAATAAGTTATAGGTAGGAAAAATTGTTATTGAAGTTAAT GTAGTAAACTAGTAACTTAAACTGTGATACCCCGGATTTAGCTTAAAAAGAG ATTGATAGACTACTCATATCAACAAGGTGCATCTTCTTTTCTAGGGAGCCCAT TTGCTAAGAACTCTACAGTTAAGCGTGCTTGGTGGGGAGCAATCTTAGGATG GGTGACCTCCTGGGAAGTTTTCCTGGGTGCGCACGGGTGAGGCCAAAGTGCG TTAAAAAGACTTGTGTTGGTCTGTGGGGCTTGTCTACAGTCTCCATGAGTAGT CACCGGCGGTACGAGAGGCCGGGGTGTTACATAAACAGACTCAAAGGCGCT AAGCCAAGTAGCCAATAGCAACATGTGTGGCCTGCGGACAGTCACAAAAAC ACACAATTTCTTATTTTTACTCTCTTTTATCTCTTTTAGGCTTTAGCCATCAAC AATAAAACAACATGATAAAGCAATTCATTTACTGCTAAATTCCAACAATTTG GTCCCTTTTTCCTGTTCTTTCAGTTTCACATACCCTCTTATCAATCTATATCCA AAACTATTTCATTTTCCAAACTCTTTTAAACCCAAAAATCAAACTTTTGATT GAAGAACAAACTTTGGGGGTTTTGGAAAATGAGTCATTTTGGATATGCTTGT GCTACTCAATCCACATCAAGATATGTTCTTTTAGGAAATTCAAATAACCCCA CTTCAATTTCATCTATTGGAAGTGATTTTTTGGGTCATTCTGTGAGAAATTTC AGT | 237 |
| PPOX | TGGTACCTACCCTGTTTACATTTTCAATTTCCCCCTTTTTTCTCTACTACTCCT ACTTTATTGATTCTTATCCATGTGTGTTCTATGGGAATTGACATTAATTGTTC AGGTGTGTATGCTGGTGATCCTTCTAAGTTGAGTATGAAAGCTGCATTTGGA AAGGTCTGGACCTTAGAGCAAAAGGGTGGTAGTATCATTGCCGGTACACTCA AAACTATTCAGGAAAGGAAGAATAATCCTCCACCGCCTCGAGACCCGTCCGT AATCACCATTACTCATTGCTTTCCTTCACCTTGTATCTTACCTTAATATACATG TATTTAATTGATAATGTCACATTGCCTCATTTGCAGCCGCTTCCTAAACCTA AGGGCCAGACTGTTGGATCCTTTAGGAAAGGGCTCATTATGTTACCTACCGC CATTGCTGCTAGGTATCTTTTGACTCTCAAATCTTAAATATTTCTCATCTTCTC CTTCTGCTAATACTAGTATGTTTACCATCTTTTTATTTTTTTAGGCTTGGCAGT AAAGTCAAACTATCGTGGACACTTTCTAATATTGATAAGTCGCTCAATGGTG AATACAATCTCACTTATCAAACACCCGATGGACCGGTTTCTGTTAGGACCAA AGCGGTTGTCATGACTGTCCCTTCATACATTGCAAGTAGCCTGCTTCGTCCGC TCTCAGTGAGTATCATTCTTTCCTTCATTTCTTTTCGTTTATTGTTGTCCAATG TCTTGTTAAACACCAGTTTGGCCTTGTGCTCGTGAATTATGGCTACAATGTTA ACTGATTCAGGCACTGTGGGAGATGCCTAAGTTTCTAAAACCTCTGCGCATA ATGTTTGTTTGGATGTTAGGAATTGCATTGAAAAATTGCTTTTGTGATGTTGA TGTTAATACCAATTACAAGTGTGTTCTTCAACTTCTGCAATACCTTGTTCGAG TGAGCTTGAGGGGGTTTAGATTAGTGTCCAATGTGAAACTAGCAAATGAACT CCAAGCGCTGGGATAGGTCCTTGGGATGGAGCCCCTGATACCCAAGACAGT ATTCAAACCCTCTAAGTAGAGTGAGAGATCAAGGAAAGAAACTGGGTGGTT CCTCAAATCGTAAAAAATGAATACAGTGTCATGATTGCTAATCTTATCACAA ATCGTAAAAAATGAATTATGGTCGATTTTGGACTATTTTTGGGTCATTTTGAG TGAATCTCGAACTTAAAAAGCGAGTCTTCTAGCAGTTCTTGTTACAGCGGGG CATACATAGGTAGGAATTTGGTTTTTTACTATTTGAGCCTTTTGACTGTTGTG GCCGGTAATATGGAATAGTCTAGCACTTCTGCGTGTGTACAACTAGTATTTA TTGTAATTATGTGATCGCACTTAACTCTCAGATAAAACCTTAAGCACTAACA TTTTGTTTTGGTTGAAGGAATCAGGAGGAAAGAAAATTGAGGGATTTGTTGG TATATAGATTCCTTTGTTTGGATAACAAAATTGGAGTGGAGAGATTTGGAAG GAAGAATTTTATAGGGATTAGTTCCCATTACACTTATGTTGATTACAAAATTT CTCCAAAAGTGGAAAGATTTTGAGTGAAAATGTTTTTTATTTCTCTTCCTCTC CCTTTCTTTCCCTCTTAAACAAACAAGGAAAGTTAATCTTATCATTCCGTACC TTCCCCTTCTGTTCTTTTTTTCTCTCCAAAATTCTTATCCTAACGTAGTGTTA TTGTCACTGTCTTATGAACGAGAATTCTTTTCTTCCTAATACTGCTTGTGTTGC ACAGTCAATGATTTAGCTAGATCATCTTTGTTAGCTACTCAAAATATTTACA TAAAATACTTGTAGAAATAAATACCAATAGGTCTTGTCAAGAAGTAGTTTCA ATGCTATAAGTTTTAACCAATCCTCAAAATTTACACCATGGAGATATCTGCG GATAAGAACTAGTAACTGTAGCAGCTGTAACTGTTGCAATCAGTTTTATGGT TTGCCTTGCAAATCAAACTTTGGATGTTGTTTGCCTTACAATTTGTTACTATT ACGTGAAGTTTAGTGTTCGCCCTTCACATTGTACTTGGTTTTTGTTTTCCTTG CAATTTGCTCTTTGAAGTATAAAGTGCTGAGTGCTGAGTGCTGAGTGCTGAC | 238 |

TABLE 22-continued

| Gene Name | Sequence | SEQ ID NO. |
|---|---|---|
| | CTTTCCTGCTCAGGATGTTGCTGCAGATTCTCTTTCTCAATTTTACTATCCACC AGTCGCAGCAGTGTCCCTTTCTTATCCCAAAGAAGCAATTAGACCAGAATGC TTGATCGATGGAGAACTAAAAGGATTCGGGCAATTGCATCCTCGCAGCCAGG GTGTGGAAACCTTGGGTATATGCTCCCATTCAACTATATCTCAATTTTTATGA GTATTTTTCTTTCTCTGAATTATTCAATTTGGTGACGTTAAATTTTGATTGTAC TCGACAGGAACAATTTATAGTTCATCTCTTTTCCCTGGTCGAGCACCACCTGG TAGGACCTTGATCTTGAGCTACATTGGAGGTGCTACAAATGTTGGCATATTA CAAAAGGCAAGTCATTTATACAATTATATCTGTTGTATCCTCAAATAAGTGG GTATCAATCCTGACGACATGCTTGCTTGTATCGATGCAGAGTGAAGATGA | |

Example 31

This example illustrates a polynucleotide sequence that regulates gene expression in more than one plant species. Two highly conserved regions in EPSPS sequences from different weed species were identified and shown as the "Region 1" and "Region 2" sequences in Table 23.

TABLE 23

| Species/gene or consensus sequence | Region 1 | SEQ ID NO: | Region 2 | SEQ ID NO: |
|---|---|---|---|---|
| Euphorbia_heterophylla_1 Contig1 | AGTTTACAGGGAGATG TAAAGTT | 239 | TCGATGTGAACATGAACAAAA TGCCAGATGTCGCTATGACATT GGCTGTGGTTG | 251 |
| Euphorbia_heterophylla_2 Contig1 | AGTTTGCAGGGAGATG TGAAATT | 240 | TCGATGTGAATATGAACAAAAT GCCAGATGTTGCTATGACATTA GCTGTGGTTGC | 252 |
| Ambrosia_trifida_1Contig1 | AGTTTACAGGGGGATG TAAAGTT | 241 | TCGATGTTAACATGAACAAAAT GCCAGATGTTGCCATGACGCTT GCAGTCGTTGC | 253 |
| velvetleaf_1Contig1 | AGTTTGCAGGGTGATG TAAAATT | 242 | TTGATGTCAACATGAACAAAAT GCCAGATGTTGCCATGACTCTC GCTGTTGTTGC | 254 |
| Xanthium_strumarium_2 Contig1 | AGTTTGCAGGGTGATG TGAAATT | 243 | TTGATGTCAACATGAACAAAAT GCCTGATGTCGCAATGACTCTT GCTGTGGTTGC | 255 |
| Ipomoea_hederacea_1 Contig1 | AGTTTACAGGGGGATG TTAAGTT | 244 | TTGATGTCAACATGAACAAAAT GCCAGATGTTGCCATGACTCTT GCTGTAGTTGC | 256 |
| Chenopodium_album_1 Contig 1 | AGTTTACAGGGTGATG TAAAATT | 245 | TTGATGTCAACATGAACAAAAT GCCAGATGTCGCAATGACTCTT GCTGTTGTTGC | 257 |
| Digitaria_sanguinalis_1 Contig 1 | AGTTTGCAGGGTGATG TGAAATT | 246 | TTGACGTCAACATGAACAAAAT GCCTGATGTCGCAATGACTCTT GCTGTGGTTGC | 258 |
| Senna_obtusifolia_1Contig3 | AGTTTACAGGGAGATG TAAAATT | 247 | TTGATGTCAACATGAACAAGAT GCCAGATGTTGCCATGACGCTT GCTGTAGTTGC | 259 |
| Waterhemp_EPSPS | AGTTTACAGGGTGATG TAAAATT | 248 | TCGACGTCAACATGAATAAAAT GCCAGATGTTGCTATGACTCTT GCAGTTGTTGC | 260 |
| Palmer_EPSPS | AGTTTACAGGGTGATG TAAAATT | 249 | TCGACGTCAACATGAACAAAA TGCCAGATGTTGCTATGACTCT TGCAGTTGTTGC | 261 |
| palmer_1Contig1 | AGTTTACAGGGTGATG TAAAATT | 250 | TCGACGTCAACATGAACAAAA TGCCAGATGTTGCTATGACTCT TGCAGTTGTTGC | 262 |

Table 24 lists 21-, 22-, 24-, 35-, 45-, and 55-mer dsRNA polynucleotide sequences designed based on the EPSPS consensus sequence for region 2, (SEQ ID NO: 263)
TNGANGTcAAcATGAAcAAaATGCCaGATGTNGCNATGACNcTtGCNGT
NGTTGC.

TABLE 24

| Name | Sequence | SEQ ID NO: |
|---|---|---|
| Consensus_21mer dsRNA | Sense: AACAUGAACAAAAUGCCAGAU<br>Anti-sense: AUCUGGCAUUUUGUU CAUGUU | 264<br>265 |
| Consensus_22mer dsRNA | Sense: AACAUGAACAAAAUGCCAGAUG<br>Anti-sense: CAUCUGGCAUUUUGUU CAUGUU | 266<br>267 |
| Consensus_24mer dsRNA | Sense: CAACAUGAACAAAAUGCCAGAUGU<br>Anti-sense: ACAUCUGGCAUUUUGUUCA UGUUG | 268<br>269 |
| Consensus_35mer dsRNA | Sense: UCGACGUCAACAUGAACAAAAU GCCAGAUGUUGCU<br>Anti-sense: AGCAACAUCUGGCAUUUUG UUCAUGUUGACGUCGA | 270<br>271 |
| Consensus_45mer dsRNA | Sense: UCGACGUCAACAUGAACAAAAUGCCAGAUGU UGCUAUGACUCUUG<br>Anti-sense: CAAGAGUCAUAGCAACAUCUGGCAUUUUGU UCAUGUUGACGUCGA | 272<br>273 |
| Consensus_55mer dsRNA | Sense: UCGACGUCAACAUGAACAAAAUGCCAG AUGUUGCUAUGACUCUUGCAGUUGUUGC<br>Anti-sense: GCAACAACUGCAAGAGUCAUAGCAACAUCU GGCAUUUUGUUCAUGUUGACGUCGA | 274<br>275 |

The EPSPS consensus dsRNA polynucleotides were synthesized by in vitro transcription and topically applied as crude RNA preparations. Glyphosate-resistant weeds (16-copy Palmer amaranth and horseweed) were treated with the six individual (21-, 22-, 24-, 35-, 45-, 55-mer) consensus dsRNAs; non-glyphosate-resistant weeds (waterhemp, sicklepod, crabgrass, morning glory, lambsquarter, *Euphorbia*) were treated with the three individual shorter (21-, 22-, 24-mer) consensus dsRNAs. Following polynucleotide treatment glyphosate-resistant plants were treated with glyphosate (1682 g acid equivalent per hectare of Roundup® WeatherMAX® brand herbicide) and non-glyphosate-resistant plants were treated with glyphosate (105 g acid equivalent per hectare of Roundup® WeatherMAX® brand herbicide). At 7 days after treatment all six EPSPS region 2 consensus dsRNA polynucleotides were found to give 100% control (killed plants) of glyphosate-resistant Palmer amaranth; control Palmer amaranth plants treated with glyphosate alone were not killed. At 7 days after treatment, the three shorter (21-, 22-, 24-mer) EPSPS region 2 consensus dsRNA polynucleotides tested individually were found to give 95%, 80% and 65% control (combining killed and injured plants), respectively, of waterhemp; waterhemp plants treated with glyphosate alone gave about 40% control (combining killed and injured plants); and a mixture of all three shorter (21-, 22-, 24-mer) consensus dsRNA polynucleotides gave about the same control as glyphosate alone.

The EPSPS region 2 consensus dsRNA polynucleotides did not cause an observable effect on the other weed species (horseweed, sicklepod, crabgrass, morning glory, lambsquarter, *euphorbia*) tested.

Example 32

This example illustrates use of a topical polynucleotide treatment for transiently silencing a gene in a plant to effect a desired phenotype. Silencing polyphenol oxidase in plant tissues inhibits browning of cut or damaged plant tissues, a valuable trait for fruits and vegetables where resistance to browning is a desirable trait.

Anti-sense DNA oligonucleotides with the sequences shown in Table 25 were designed to target three polyphenol oxidase genes (PPO1, PPO2, and PPO3) from lettuce; the underlined text indicates T7 sequence that was included in the anti-sense polynucleotides.

TABLE 25

| Anti-sense oligo-nucleotide | Sequence (5'-3') | SEQ ID NO. | Length |
|---|---|---|---|
| HH07 | TAATACGACTCACTATAGGGCTTTATTGA ATTTAGCTATGTAATC | 276 | 45 |
| HH09 | TAATACGACTCACTATAGGGTTTATCAAC CAAATGTGCAGC | 277 | 41 |
| HH11 | TAATACGACTCACTATAGGGTTGTCTGTA CATAATTGTGAGATTTGTGG | 278 | 49 |

Three-week old lettuce plants (variety SVR3603 LA) were treated as follows. Two source leaves (leaves that are older and are ~60% of their mature size) on each plant were pre-treated with 0.1% (v/v) SILWET-L-77 and allowed to dry (~15 minutes). To each leaf 20 microliters of a mixture of the polyphenol oxidase anti-sense polynucleotides in a solution of 0.01% (v/v) SILWET L-77 and 2% (w/v) ammonium sulfate in 5 millimolar sodium phosphate, pH 6.8, were applied as small droplets; each plant was treated with 6.7 nanomoles of each of the three polynucleotides HH07, HH09, and HH11 (for a total of 20 nanomoles per plant). Control plants were treated either with an unrelated polynucleotide HH02-05 (anti-sense to phytoene desaturase) or with buffer (0.01% (v/v) SILWET L-77 and 2% (w/v) ammonium sulfate in 5 millimolar sodium phosphate, pH 6.8) alone.

Approximately 3 weeks after the topical polynucleotide treatment, "untreated" lettuce leaves (i.e., not those treated with the topical polynucleotides) were cut from the lettuce head under water and incubated in a cup with 1.33 millimolar methyl jasmonate in 5% ethanol. Leaves were inspected for central rib browning and photographed every 24 hours. Samples were taken from the remaining plants and frozen for small RNA and mRNA analysis Plants treated with the polyphenol oxidase anti-sense polynucleotides HH07, HH09, and HH11 showed significant reduction in central rib browning after treatment with methyl jasmonate. Plants treated with HH02-05 (anti-sense to phytoene desaturase) as a control showed a small reduction in central rib browning compared to the buffer-treated control.

Example 33

This example illustrates an herbicidal composition adapted for topical coating onto the exterior surface of a growing plant comprising surfactant and at least one plant lethal agent, the improvement wherein the plant lethal agent includes polynucleotides having a sequence essentially identical or complementary to sequence of a plant gene or sequence of the plant gene's transcribed RNA, the polynucleotides effecting systemic suppression of the plant gene. More specifically this example illustrates an herbicidal composition adapted for topical coating onto the exterior surface of a growing plant comprising surfactant and at least one plant lethal agent, the improvement wherein the plant lethal agent includes polynucleotides effecting suppression of the endogenous phytoene desaturase (PDS), 5-enolpyruvylshikimate-3-phosphate synthase (EPSPS), or ribulose-1,5-bisphosphate carboxylase oxygenase (RuBisCO) genes from Nicotiana benthamiana. This example also illustrates the use of topically applied polynucleotides to suppress a very highly expressed gene (ribulose-1,5-bisphosphate carboxylase oxygenase) in a plant.

An anti-sense polynucleotide with the sequence CATCTCCTTTAATTTGTACTGC (SEQ ID NO:34) was designed for the endogenous Nicotiana benthamiana phytoene desaturase (PDS) gene, which has the cDNA sequence fragments ATGCCCCAAATCGGACTTGTATCTGCTGTTAATTTGAGAGTCCAAGGTAATTCAGCTTATCTTTGGAGC TCGAGGTCTTCGTTGGGAACTGAAAGTCAAGATGTTTGCTTGCAAAGGAATTTGTTATGTTTTGGTAGT AGCGACTCCATGGGGCATAAGTTAAGGATTCGTACTCCAAGTGCCACGACCCGAAGATTGACAAAGG ACTTTAATCCTTTAAAGGTAGTCTGCATTGATTATCCAAGACCAGAGCTAGACAATACAGTTAACTATT TGGAGGCGGCGTTATTATCATCATCGTTTCGTACTTCCTCACGCCCAACTAAACCATTGGAGATTGTTA TTGCTGGTGCAGGTTTGGGTGGTTTGTCTACAGCAAAATATCTGGCAGATGCTGGTCACAAACCGATA TTGCTGGAGGCAAGAGATGTCCTAGGTGGGAAGGTAGCTGCATGGAAAGATGATGATGGAGATTGGT ACGAGACTGGGTTGCACATATTCTTTGGGGCTTACCCAAATATGCAGAACCTGTTTGGAGAACTAGGG ATTGATGATCGGTTGCAGTGGAAGGAACATTCAATGATATTTGCGATGCCTAACAAGCCAGGGGAGTT CAGCCGCTTTGATTTTCCTGAAGCTCTTCCTGCGCCATTAAATGGAATTTTGGCCATACTAAAGAACAA CGAAATGCTTACGTGGCCCGAGAAAGTCAAATTTGCTATTGGACTCTTGCCAGCAATGCTTGGAGGGC AATCTTATGTTGAAGCTCAAGACGGTTTAAGTGTTAAGGACTGGATGAGAAAGCAAGGTGTGCCTGAT AGGGTGACAGATGAGGTGTTCATTGCCATGTCAAAGGCACTTAACTTCATAAACCCTGACGAGCTTTC GATGCAGTGCATTTTGATTGCTTTGAACAGATTTCTTCAGGAGAAACATGGTTCAAAAATGGCCTTTTT AGATGGTAACCCTCCTGAGAGACTTTGCATGCCGATTGTGGAACATATTGAGTCAAAAGGTGGCCAAG TCAGACTAAACTCACGAATAAAAAAGATCGAGCTGAATGAGGATGGAAGTGTCAAATGTTTATACTG AATAATGGCAGTACAATTAAAGGAGATGCTTTTGTGTTTGCCACTCCAGTGGATATCTTGAAGCTTCTT TTGCCTGAAGACTGGAAAGAGATCCCATATTTCCAAAAGTTGGAGAAGCTAGTGGGAGTTCCTGTGAT AAATGTCCATATATGGTTTGACAGAAAACTGAAGAACACATCTGATAATCTGCTCTTCAGCAGAAGCC CGTTGCTCAGTGTGTACGCTGACATGTCTGTTACATGTAAGGAATATTACAACCCCAATCAGTCTATGT TGGAATTGGTATTTGCACCCGCAGAAGAGTGGATAAATCGTAGTGACTCAGAAATTATTGATGCTACA ATGAAGGAACTAGCGAAGCTTTTCCCTGATGAAATTTCGGCAGATCAGAGCAAAGCAAAAATATTGA AGTATCATGTTGTCAAAACCCCAAGGTCTGTTTATAAAACTGTGCCAGGTTGTGAACCCTGTCGGC- CCT TGCAAAGATCCCCTATAGAGGGTTTTTATTTAGCTGGTGACTACACGAAACAGAAGTACTTGGCTTCA ATGGAAGGTGCTGTCTTATCAGGAAAGCTTTGTGCACAAGCTATTGTACAGGATTACGAGTTACTTCTT GGCCGGAGCCAGAAGATGTTGGCAGAAGCAAGCGTAGTTAGCATAGTGAACTAA (SEQ ID NO:38). Anti-sense polynucleotides with the sequences CTGTGATCATCATATGTATCA (SEQ ID NO:279), CCITAACTCTCCAGCTAGCAA (SEQ ID NO:280), CAGCCCGCAAATGTCATTC (SEQ ID NO:281), GCCGTCAATGGCCGCATTGCT (SEQ ID NO:282), TCCTCCCTCAGAAAGGGCAG (SEQ ID NO:283), and TTGCCTCATGCTGCTAATCTG (SEQ ID NO:284) were designed for the endogenous Nicotiana benthamiana 5-enolpyruvylshikimate-3-phosphate synthase (EPSPS) gene, based on the Nicotiana benthamiana EPSPS cDNA sequence CTTATATGTGCTTAAGCCTAACGTGCACCCGGCCCCTTAACCCCAGCAGTTTTCAATCTACCTACCGTC TCTACCATTTTCTTCTAGTTGGTGAAAATTTCTAACTTTGAGAAAACAAGCCAAAGTTTTTGTTTCTAA GAACGCAAAATGAGTGAAATTTTTTGCAGCAATGGCACAGATTAGCAGCATGAGGCAAGGGATACAG ACCCCTAATCTTAATTCCTATTTTCCTAAAACCCAAAAGGTTCCTCTTTTTTCGCATTCTATCTTCTTTG GATCAAAGAAAATAACCCAAAATTCAGCAAAATCTTTGTGGGTGTGTAAGAAAGATTCAGTTTTGAGG GTGGCAAAGTCACCTTTTAGGATTTGTGCATCAGTGGCCACTGCACAGAAGCCAACGAGATTGTGCT GCAACCCATCAAAGATATATCAGGCACTGTTAAATTGCCTGGTTCTAAATCCCTTTCCAACCGTATTCT CCTTCTTGCTGCCCTTTCTGAGGGAAGGACTGTTGTTGACAATTTACTGAGTAGTGATGACATTCATTA CATGCTTGGTGCATTGAAAACACTTGGACTTCATGTAGAAGATGACAATGAAAACCAACGAGCAATTG TGGAAGGTTGTGGTGGGCAGTTTCCTGTCGGCGAGAAGTCTGAGGAAGAAATCCAACTATTCCTTGGA AATGCAGGAACAGCAATGCGGCCATTGACGGCAGCAGTTACTGTAGCTGGAGGACATTCAAGATATG TACTTGATGGAGTTCCTAGGATGAGAGAGAGACCGAT (SEQ ID NO:285), CACTGACGTTGGATTAGAGGTAGGCTCCTTATATGTGCTTAAGCCTAACGTGCAGCCGGCCCCCAACC CCAGCAGTTTTCAATCTACCTACCGTCTCTACCATTTTCTTATAGTAGTTGAAAATTTCTAACTTTGAGA AAACAAGCCAAAGTTTTGTTTCTAAGAACACAAAGGGAGTGAAATTTTTTGCAGCAATGGCACAGATT AGCAGCATGAGGCAAGGGATACAGACCCCTAATCTTAATTCCTATTTTCCTAAAACCCAAAAGGTTCC TCTTTTTTCGCATTCTATCTTCATTGGATCAAAGAAAATAACCCAAAATTCAGCAAAATCTTTGTGGGT GTGTAAGAAAGATTCAGTTTTGAGGGTGGCAAAGTCACCTTTTAGGATTTGTGCATCAGTGGCCACTG CACAGAAGCCTAACGAGATTGTGCTGCAACCTATCAAAGATATATCAGGCACTGTTAAATTACCTGGT TCTAAATCCCTTTCCAATCGTATTCTCCTTCTTGCTGCCCTTTCTGAGGGAAGGACTGTTGTTGACAATT TACTGAGTAGTGATGACATTCATTACATGCTTGGTGCATTGAAAACACTTGGACTTCATGTAGAAGAT GACAAT GAAAACCAACGAGCAATCGTAGAAGGTTGTGTGGGCAGTTTCCTGTCGGCAAGAAGTCTG AGGAAGAAATCCAACTATTCCTTGGAAATGCAGGAACAGCAATGCGGCCATTGACGGCAGCAGTTAC TGTAGCTGGTGGACATTCTAGATATGTACTTGATGGAGTTCCTAGGAT (SEQ ID NO:286), and AAATTCTTGGTTCGAGGAGGTCAGAAGTACAAGTCTCCTGGAAAAGCATATGTTGAAGGAGATGCCTC AAGTGCTAGCTACTTTTTGGCGGGTGCAGCTGTCACAGGTGGACTGTCACTGTTGAAGGTTGTGGAA CAAGCAGTTTACAGGGGGATGTTAAGTTTGCTGAG- GTCCTCGAAAAGATGGGGGCAGAAGTTACATG GACAGAGAACAGTGTCACGGTTAAAGGACCTC- CAAGGAACTCTTCTGGAATGAAACATTT- GCGGGCTG TTGACGTTAACATGAACAAAATGCCA- GATGTTGCCATGACTCTTGCTGTAGTTGCACTTTT- TGCTGATA GTCCTACTGCCATAAGAGATGTT- GCTAGCTGGAGAGTTAAGGAAACTGAGCGGAT- GATTGCCATATGC ACAGAACTTAGGAAGTTGGGTG- CAACAGTTGTAGAAGGGCCAGACTACTGCATAAT- CACTCCACCTGA AAAGTTAAAAGTAGCGGAAATT- GATACATATGATGATCACAGAATGGCCATG- GCTTTCTCTCTTGCGG CTTGTGCTGATGTTCCAGT- CACCATTAAGGACCCCGGTTGTACTCGCAAAACC- TTCCCCAACTACTTTG ACGTTCTCCAGCAGTATTC- CAAGCATTAAACCACTTTCCATTAAGAATTTT- GAAAAAGAGAGACTTTG ACAACAATGGTGTCAT- ACCGGAAGAGAAAAGCTTTGATCCAAGCTTTCA- ACTCCTTTTCATTTGTCATG TGATGATCATTGTATTT- GTTGAAGTTGAGCTGCTTTTCTTTTGTCCAGAAGA- CATGTATGGATACTATTA CTATATAGTTAAGGT- GAACTCAGCA (SEQ ID NO:287). Anti-sense polynucleotides with the sequences CCACATGGTCCAG- TATCTGCC (AK195, RBCS_1-2-3-4, SEQ ID NO:288), CAAGCAAGGAACCCATCCATT (AK196, RBCS_1-2-3-4, SEQ ID NO:289), GGCCACACCTGCATGCATTGC (AK197, RBCS_1-2-3-4, SEQ ID NO:290), GTGTTCACG- GTAGACAAATCC (AK198, RBCS_1-2, SEQ ID NO:291), TGCACTGCACTTGACGCACGT (AK199, RBCS_1-2, SEQ ID NO:292), AACTGATGCATTGCACTTGAC (AK200, RBCS_3-4, SEQ ID NO:293), CAAATCAG- GAAGGTATGAGAG (AK201, RBCS_3-4, SEQ ID NO:294), and TGTCAAGGTTTGTCCTGG (AK202, RBCS_3-4, SEQ ID NO:295) were designed for the endog- enous *Nicotiana benthamiana* ribulose-1,5-bisphosphate carboxylase oxygenase (RuBisCO) gene, based on the *Nico- tiana benthamiana* chloroplastic RuBisCO small chain 2A cDNA sequence fragments GCAATGGCTTCCTCAGT- TCTTTCCTCAGCAGCAGTTGCCACCCGCAGCAAT- GTTGCTCAAGCTAACATG GTTGCACCTTTCACAG- GTCTTAAGTCTGCTGCCTCATTCCCTGTTTCAAG- AAAGCAAAACCTTGACATC ACTTCCATTGCCAG- CAACGGCGGAAGAGTGCAATGCATGCAGGTGTG- GCCACCAATTAACATGAAGA AGTATGAGACTCTCT- CATACCTTCCCGATTTGAGCCAGGAGCAATTGCT- CTCCGAAATTGAGTACCTTT TGAAGAATG- GATGGGTTCCTTGCTTGGAATTCGAGACT- GAGAAAGGATTTGTCTACCGTGAACACCAC AAGT- CACCAGGATACTATGATGGCAGATACTGGACCAT- GTGGAAGCTACCTATGTTCGGATGCACTGA TGC- CACCCAAGTGTTGGCTGAGGTGGGAGAGGC- GAAGAAGGAATACCCACAGGCCTGGGTCCGTATC ATTGGATTTGACAACGTGCGTCAAGTGCAGTG- CATCAGTTTCATTGCCTCCAAGCCTGACGGCTAC (SEQ ID NO:296), ACAATGGCTTCCTCAGTTCTTTC- CTCAGCAGCAGTTGCCACCCGCAGCAATGTTGCT- CAAGCTAACATG GTTGCACCTTTCACTGGTCT- TAAGTCAGCTGCCTTTTTCCCTGTTTCAAGGAAG- CAAAACCTTGACATC ACTTCCATTGCCAGCAACG- GCGGAAGAGTGCAATGCATGCAGGTGTGGCCAC- CAATTAACAAGAAGA AGTACGAGACTCTCTCATAC- CTTCCTGATCTGAGCGTGGAGCAATTGCTTAGCGA- AATTGAGTACCTCT TGAAAAATGGATGGGTTCCTT- GCTTGGAATTCGAGACTGAGCGCGGATTTGTCTAC- CGTGAACACCAC AAGTCACCGGGATACTATGACG- GCAGATACTGGACCATGTGGAAGTTGCCTATGTT- CGGATGCACTGA TGCCACCCAAGTGTTGGCCGAG- GTGGAAGAGGCGAAGAAGGCATACCCACAGGC- CTGGATCCGTATT ATTGGATTCGACAACGTGCGT- CAAGTGCATGCATCAGTTTCATTGCCTACAAGC- CAGAAGGCTAC (SEQ ID NO:297), CAAGC- CAACATGGTTGCACCCTTCACTGGCCTCAAGTC- CGCCTCCTCCTTCCCTGTTACCAGGAAACAA AAC- CTTGACATTACCTCCATTGCTAGCAATGGTGGAA- GAGTTCAATGCATGCAGGTGTGGCCACCAAT TAACATGAAGAAGTACGAGACACTCTCATACCTTC- CTGATTTGAGCCAGGAGCAATTGCTTAGTGAAG TTGAGTACCTTTTGAAAAATGGATGGGTTCCTT- GCTTGGAATTCGAGACTGAGCGTGGATTCGTC- TACC GTGAACACCACAACTCACCAGGATACTAC- GATGGCAGATACTGGACCATGTGGAAGTTGCCC- ATGTTC GGGTGCACTGATGCCACTCAGGTGTTG- GCTGAGGTCGAGGAGGCAAAGAAGGCTTACCCA- CAAGCCT GGGTTAGAATCATTGGATTCGA- CAACGTCCGTCAAGTGCAATGCATCAGTTTTATCG- CCTCCAAGCCA GAAGGCTAC (SEQ ID NO:298), and GGCTCAGTTATGTCCTCAGCTGCCGCTGTTTCCAC- CGGCGCCAATGCTGTTCAAGCCAGCATGGTCGCA CCCTTCACTGGCCTCAAGGCCGCCTCCTCCTTC- CCGGTTTCCAGGAAACAAAACCTTGACATTACT- TCC ATTGCTAGAAATGGTGGAAGAGTCCAATGCAT- GCAGGTGTGGCCGCCAATTAACAAGAAGAAGTACG AGACACTCTCATACCTTCCTGATTTGAGCGTGGAG- CAATTGCTTAGCGAAATTGAGTACCTTTTGAAAA ATGGATGGGTTCCTTGCTTGGAATTCGAGACTGAG- CATGGATTCGTCTACCGTGAACACCACCACTCA CCAGGATACTACGATGGCAGATACTGGACGATGTG- GAAGTTGCCCATGTTCGGGTGCACCGATGCCAC TCAGGTCTTGGCTGAGGTAGAGGAGGC- CAAGAAGGCTTACCCACAAGCCTGGGTCAGAAT- CATTGGAT TCGACAACGTCCGTCAAGTGCAATG- CATCAGTTTCATCGCCTACAAGCCCGAAGGCTAT (SEQ ID NO:299).

Figure 36:
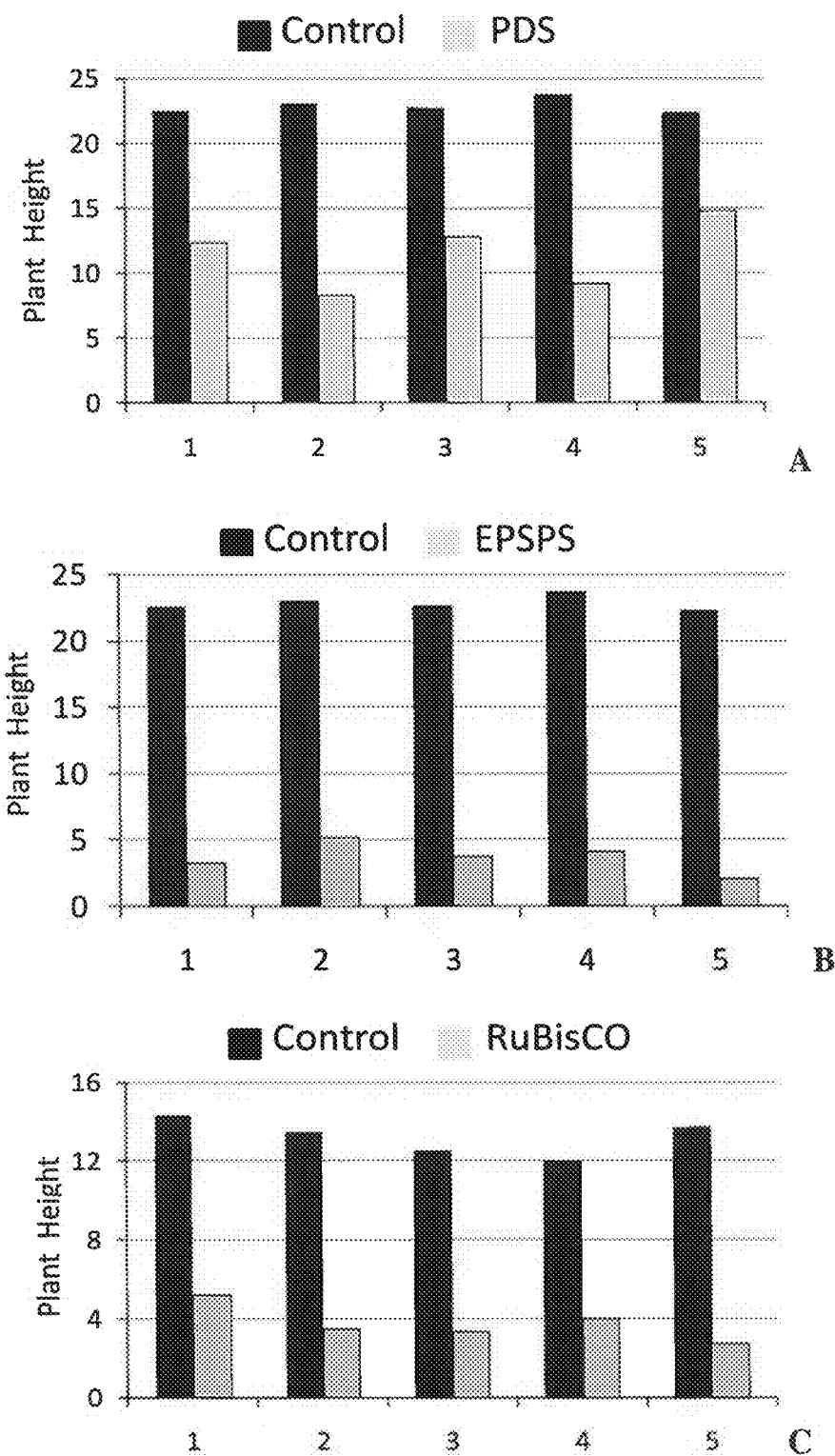
FIG. 36 illustrates the effect on plant height in *Nicotiana benthamiana* in plants treated with a PDS anti-sense polynucleotide (FIG. 36A), EPSPS anti-sense polynucleotides (FIG. 36B), or RuBisCO anti-sense polynucleotides (FIG. 36C), as described in Example 33.

*Nicotiana benthamiana* plants were treated using a pro- cedure similar to that described in Example 12. Polynucle- otide solution (or mixed polynucleotides in the case of EPSPS and RuBisCO) were prepared in 0.01% (v/v) SIL- WET L-77 and 2% (w/v) ammonium sulfate in 5 millimolar sodium phosphate, pH 6.8. Two fully expanded leaves per plant were dipped into 0.1% SILWET L-77 solution freshly made with ddH2O for a few seconds, and allowed to dry. About 30 minutes later, 20 microliters of polynucleotide solution, was applied to each of the two pre-treated leaves. For PDS, each of 5 plants received 25 nanomoles of the PDS anti-sense polynucleotide (SEQ ID NO:34); for EPSPS, each of 5 plants received 50 nanomoles of each EPSPS anti-sense polynucleotide (SEQ ID NOS:279-284); and for RuBisCO, each of 5 plants received 50 nanomoles of each RuBisCO anti-sense polynucleotide (SEQ ID NOS:288-295). Paired control plants were treated with buffer (0.01% (v/v) SILWET L-77 and 2% (w/v) ammonium sulfate in 5 millimolar sodium phosphate, pH 6.8). The results measured as plant height at 12 days (PDS and EPSPS) or 10 days (RuBisCO) after treatment, are shown in FIGS. 36A-36B. Plants treated with the PDS anti-sense polynucleotide dis- played severe stunting (FIG. 36A) and bleaching. Plants treated with the EPSPS anti-sense polynucleotides displayed severe stunting (FIG. 36B) and severe damage to the meri- stem and stem tissues. Plants treated with the RuBisCO anti-sense polynucleotides displayed severe stunting (FIG. 36C) and malformed apical tissues.

A second set of experiments was designed to investigate the effects of silencing a component of the endogenous RNAi silencing pathway in a plant. Argonaute (AGO) proteins are components of the RNA-induced silencing complex (RISC) which binds small RNAs in the RNAi silencing process. Suppression of Argonaute would be expected to reduce the observed phenotypic effect caused by an RNAi silencing process. AGO1 anti-sense polynucle- otides with the sequences GGAGGCAAAATACGAGC- CTCA (HL510, SEQ ID NO:300), CACTAATCTTAATAC- CAAACT (HL511, SEQ ID NO:301), TATGGGTCATTAGCATAGGCATTAT (HL512, SEQ ID NO:302), TCTCAAGAATATCACGCTCCC (HL513, SEQ ID NO:303), CCCTTGGGGACGCTGGCAGGTCAC (HL514, SEQ ID NO:304), TAATACGACTCAC-TATAGGGAGAGAGCTAGATCTTTG (HL515, SEQ ID NO:305), TAATACGACTCACTATAGGCACAGTATCT-TCCTCCAACC (HL516, SEQ ID NO:306), TTGCT-CATCTTAAATACATGT (HL517, SEQ ID NO:307), TCATCTTAAATACATGTTTTGTCA (HL518, SEQ ID NO:308), TTATCTTCAGGGATACATTAGC (HL519, SEQ ID NO:309), AATACTGCTTGCTCATCTTAAATA (HL520, SEQ ID NO:310), GACAATTCCAAGTTCAGTC (HL521, SEQ ID NO:311), CCGTTTTAGATCAC-CATAAAGAGA (HL522, SEQ ID NO:312), T1TGTCTGGTAATATCACAATC (HL523, SEQ ID NO:313) were designed for the endogenous Nicotiana benthamiana Argonaute-1 (AGO 1) gene, based on two Nicotiana benthamiana AGO1-2 partial cDNA sequences, ATG-GTGAGGAAGAGGAGAACTGAGTTACCTGGTTCT-GGTGAGAGCTCTGGGTCTCAAGAAACTGGCG GACAGGGTCGTGGCCAGCATCCACAGCAGCTG-CACCAAGCTACCTCCCAGACTCCATATCAAACT-GCA ATGACTACTCAGCCAATACCTTATGCAAGAC-CAACTGAAACATCTCCGAAGCTGGTTCCTCATC-TCA GCCACCTGAGCAGGCAGCTCTACAAGTGACA-CAACAGTTCCAGCAACTTGCTTTG-CAACAAGAAGCGG CTACAACGCAAGCAGTTC-CACCTGCATCAAGCAAATTACTAAGGTTTCCCCT-GCGTCCAGGGAAGGGG AGCAATGGTATGAGATG-CATAGTCAAAGCCAATCACTTCTTCGCAGAGCTGC-CTGACAAAGACTTGCA CCAGTATGATGTCA-CAATTTCTCCAGAGGTGTCATCACGTGGCGTCAA-CCGTGCTGTCATGGCGCAACT GGTGAAGCTGTAC-CAAGAATCTCATCTTGGGAAGAGACTTCCAG-CATATGATGGAAGGAAAAGTCTAT ACACTGCA-GGGCCCCTTCCATTTGTTCAAAAAGACTTCAAAA-TAACTCTTATTGATGATGAGGATGGG CCTGGTGGT-GCTAGAAGGGAAAGGGAATTTAAAGTTGTGAT-CAAATTGGCTGCCCGTGCTGATCTTCA TCACT-TGGGAATGTTTTTAGAAGGGAAACAGGCTGATG-CACCTCAAGAGGCGCTTCAAGTTCTGGATA TTGT-TCTGCGTGAGTTGCCAACATCTAGGTTTTGTCCT-GTGGGTCGTTCTTTCTATTCCCGTGATTTAGG GCGAAAGCAACCATTGGGTGAAGGTTTAGAAAGT-TGGCGTGGGTTCTATCAAAGCATTCGCCCCACAC AAATGGGCTTATCACTGAACATCGATATGTCTTC-CACTGCATTCATTGAGCCACTGCCAGTCATTGATT TTGTGACACAGCTTCTGAACCGAGATGTGC-CATCTAGACCACTGTCTGATGCTGGCCGTG-TAAAGATA AAAAAAGCTCTGAGAGGTGT-GAAGGTGGAGGTTACTCATCGTGGAAATATGCGG-AGGAAGTACCGCA TTTCGGGTTTAACATCT-CAAGCAACAAGAGAGTTGACCTTCCCTGTTGAT-GAAAATGGTACAGTGAAA TCTGTAATTGAGT-ATTTTCGAGAAACATATGGGTTTGTAATTCAGCAT-ACTCAGTGGCCTTGTCTACAA GTTGGAAATCA-GCAGAGACCTAATTACTTGCCAATGGAAGTCTG-CAAGATTGTGGAGGGACAAAGGT ACT-CAAAGCGCTTGAATGAGAGACAGATTACTGCACT-TCTGAAAGTGACCTGCCAGCGTCCCCAAGGG AGGGAGCGTGATATTCTTGAGACCGTACATCATAAT-GCCTATGCTAATGACCCATATGCCAAGGAGTT TGG-TATTAAGATTAGTGACAAGTTGGCACAAGTTGAG-GCTCGTATTTTGCCTCCACCTCGGCTTAAATA TCATGATAACGGTCGAGAAAAGGACTGCCTGCCA-CAAGTTGGCCAATGGAATATGATGAATAAGAAA ATGGTAAATGGAGGGACGGTGAACAATTGGATCT-GCATAAACTTCTCTCGCAATGTGCAAGATAGTGT TGCTCATGGGTTTTGCTCTGAGCTTGCACAAATGT-GCCAGATATCTGGCATGAATTTCAATCCAAATCC TGTTCTGCCACCTTCGAGTGCACGCCCTGATCAG-GTCGAAAGAGTATTGAAAACTCGATTTCATGATGC TATGACTAAGTTGCAGCTGCATGGGAGAGAGCTT-GATTTGCTAGTTGTCATCTTGCCAGACAATAATG GATCTCTTTATGGTGATCTGAAGCGCATTTGT-GAGACTGAACTAGGAGTCGTCTCACAGTGCT-GTTTGA CAAAACATGTATTTAAGATGAGCAAACAG-TATCTAGCCAATGTAGCGCTGAAAATCAATGTGA-AGGTG GGAGGGAGAAACACTGTGCTTGTTGATG-CAATATCGAGGCGAATTCCTCTTGTCAGCGACCG-GCCTAC CATCATTTTGGTGCAGATGTCACCCAC-CCTCACCCTGGGGAGGACTCTAGCCCATCCATT-GCCGCGGT GGTTGCTTCTCAAGATTGGCCTGAGAT-TACAAAGTATGCTGGTCTAGTTTCTGCTCAAGC-CCATAGGCA AGAGCTTATTCAGGATCTGTACAC-GACTAGGCAAGATCCTGTTAAGGGGACAGTTGC-TGGTGGAATGA TTAAGGACTTACTTATATCCTTC-CGAAGAGCTACTGGACAAAAGCCCCAGA-GAATAATTTTCTATAGG GATGGTGTTAGTGAAGGA-CAATTTTATCAAGTGCTTCTGTTCGAACTTGATG-CGATCCGCAAAGCATGT GCGTCTTTGGAGCCAAAT-TATCAGCCCCCAGTCACATTTGTTGTGGTTCA-GAAACGACATCACACAAG GCTTTTTGCCAATAAC-CACCGTGACAGAAATGCAGTTGACAGGAGCGG-GAACATTATACCTGGTACTG TTGTAGATTCAAAGA-TATGCCACCCGACAGAGTTTGATTTCTATCTTTG-TAGCCATGCCGGCATACAGG GTACGAGCCGTCCA-GCTCACTACCATGTTCTATGGGACGAGAACAAAT-TCACAGCCGATGCGCTGCAG TCTTTGAC-CAACAACCTCTGCTATACATATGCAAGGTG-CACGCGTTCCGTCTCCATCGTTCCCCTGCA TAT-TATGCACATTTGGCAGCTTTCCGTGCTCGATTTTAT-ATGGAGCCGGAGACATCTGACGGTGGTTCA GTAACAAGTGGGGCTGCTGGTGGCAGAGGGGGTG-GTGCAGGAGCTGCTGGAAGGAACACCCGAGCCC CAAGTGCTGGTGCTGCTGTTAGACCTCTTCCT-GCGCTCAAGGATAATGTGAAGAGGGTTATGTTC-TACT GC (SEQ ID NO:314) and CACCTAT-CACTCTCTTTCTCTCTACAAACATATCGTGCC-GTTTCTCTCTCGGCCTCTCTTCGTGTTTTA GGGCACCGTGGTGGTTGGTATCCAGGCGGCG-GTTTTGAGTTATTACCATGGTGCGGAAGAAGAG-GACT GATGTTCCTGGTGGTGCTGAGAGTTTT-GAGTCCCATGAAACTGGAGGGGCACGAGGTGGT-GCCCAACG CCCATCACAGCAGCAGCAACATCAG-CATCAGCAAGGCGGAGGAAGAGGCTGGGCAC-CTCAGCATGGA GGACATGGTGGCCGTGGTG-GTGGGGGAGCTCCACGTGGTGGAATGGCCCCTCA-ACAATCCTATGGTGG ACCTCCTGAATACTAC-CAACAGGGCAGGGGAACTCAACAGTATCAACGAG-GTGGAGGACAACCCCAG CGCCGTGGTG-GCATGGGGGCCGTGGGGCACGGCCACCAGTAC-CCGAGCTGCACCAAGCAACCCAGA CTCCACATCA-GCCTGTACCATATGGAAGACCATCAGAAACAT-ACTCAGAGGCTGGTTCCTCGTCTCAG CCACCT-GAACCAACGACACAGCAAGTGACTCAGCAATTC-CAGCAACTTGTTGTGCAGCCAGAAGCAGC TGCAACCCAAGCAATACAACCAGCATCGAG-CAAGTCGATGAGGTTCCACTCCGGCCAG-GAAAGGGT AGTACTGGTATTAGATGCATAGT-TAAGGCCAATCACTTCTTTGCCGAGTTACCTGAC-AAAGATCTGCAC CAGTATGATGTTTCAATTACTC-CTGAGGTCGCCTCTCGGGGTGTCAACCGGGCCGT-CATGGAGCAGCT GGTGAAGCTTTATAGAGAATC-CCATCTTGGGAAGAGGCTTCCAGCCTATGACGG- AAGAAAAAGTCTAT ACACAGCAGGGCCCCTC-
CCTTTTGTTCAAAAGGATTTTAAAATCACTCTAATT-
GATGATGATGATGGAC CTGGTGGTGCTAG-
GAGGGAAAGAGAGTTTAAAGTTGTGATCAAGCTG-
GCGGCTCGTGCTGATCTTCAT CACTTGGGGATGT-
TCTTACAAGGGAGACAGGCTGATGCACCG-
CAAGAAGCACTTCAGGTGCTGGATAT TGTGC-
TACGTGAGTTGCCAACATCTAGGTATTGTCCTGTG-
GGCCGCTCTTTCTATTCCCCTCATTTAGGA
CGAAGACAACCACTGGGTGAAGGTTTAGA-
GAGCTGGCGTGGCTTCTATCAAAGTATTCGTCCTA-
CACA GATGGGATTATCCCTGAATATTGATATGTCT-
TCCACGGCTTTCATTGAGCCACTGCCGATTATTGACTT
CGTGAGCCAGCTTCTGAATCGGGATATCTCTTCTA-
GACCACTGTCTGATGCTGACCGCGTTAAGATAAA
GAAGGCACTGAGAGGTGTAAAGGTGGGGGTCACT-
CATCGTGGAAATATGCGGAGGAAGTATCGCATT
TCTGGCTTGACGTCTCAAGCAACAAGAGAGTT-
GACTTTTCCTGTCGATGAAAGGGGTACGAT-
GAAAGC TGTTGTGGAATATTTTCGGGAAACCTATG-
GTTTTGTCATTCGGCATACCCAGTGGCCTTGTCTT-
CAAGT TGGAAATACGCAGAGGCCAAATTACTTGC-
CAATGGAAGTATGTAAGATTGTAGAGGGACAGA-
GATAC TCAAAGCGCTTGAATGAGAGGCAGA-
TAACAGCACTTCTAAAAGTGACCTGCCAACGTCC-
TCAAGAGA GAGAACGTGATATTCTTCAGACTGT-
TCATCACAATGCTTATGCTGATGACCCATATGC-
GAAGGAGTTTG GTATTAAGATCAGTGAGGAGCTT-
GCTCAAGTTGAGGCTCGCGTTTTGCCTGCACCTT-
GGCTTAAATACC ATGATACAGGTCGAGA-
GAAAGACTGTCTGCCACAAGTGGGCCAGTG-
GAATATGATGAATAAGAAAAT GGTTAATGGAG-
GAACAGTGAACAACTGGATCTGTGTAAACTTTT-
CTCGCAATGTGCAAGACACAGTTG CACGTG-
GATTTTGTTCCGAGCTTGCACAAATGTGCATGA-
TATCCGGAATGAACTTCAATCCCAATCCTG TTC-
TACCACCAGTGAGTGCTCGCCCTGATCAAGTTGA-
GAGAGTCTTGAAAACTCGATTTCACGATGCTA
TGACAAAGTTGCAGCCAAATGGGAGAGAGCTA-
GATCTTTTGATTGTGATATTACCAGACAATAACGGC
TCTCTTTATGGTGATCTAAAACGGATTTGTGAAACT-
GAACTTGGAATTGTCTCACAATGCTGCTTGACA
AAACATGTATTTAAGATGAGCAAGCAGTATT-
TAGCTAATGTATCCCTGAAGATAAATGTGAAGGT-
TGG AGGAAGAAATACTGTGCTGGTTGAT-
GCGCTCTCTAGACGAATTCCCCTTGTCAGCGAC-
CGCCCAACTA TCATTTTTGGTGCAGATGTCAC-
CCATCCCCACCCTGGGGAGGATTCTAGCCCGT-
CAATTGCTGCGGTGG TTGCTTCTCAAGATTGGCCT-
GAAATTACAAAGTATGCTGGTTTGGTTTCTGCTC-
AAGCGCATAGGCAAG AGCTTATACAAGATCTGTA-
CAAGACTTGGCAAGATCCAGTTAGAGGACCTGT-
GACTGGTGGCATGATA AAGGAATTACTTATTTCCT-
TCCGTCGAGCAACTGGACAGAAGCCGCAGAGA-
ATTATATTCTACAGAGA TGGTGTTAGTGAAGGA-
CAATTTTACCAAGTTCTTCTTTTTGAACTTGATG-
CAATCCGCAAGGCATGTGC ATCTTTAGAACCCAAC-
TATCAGCCCCGGTTACGTTTGTTGTGGTCCAGA-
AACGGCATCATACTAGGTT GTTTGCCAATAACCAC-
CACGACAGAAATGCAGTTGATCG-
GAGTGGGAACATTTTGCCTGGTACCGTTG TAGAT-
TCAAAGATATGCCACCCTACTGAATTTGATTTCT-
ATCTCTGTAGCCATGCCGGCATACAGGGTA CTAGC-
CGCCCAGCTCATTATCATGTTCTGTGGGAT-
GAGAACAATTTTACTGCTGACGCCCTGCAGTCTT
TGACTAACAATCTTTGCTATACATATGCTAGGTG-
TACTCGTTCTGTCTCCATTGTTCCACCAGCATATTA
TGCACATTTGGCAGCTTTCCGTGCTCGGTTTTA-
CATGGAGCCAGAGACATCTGATAATGGATCAGT-
CAC AAGCGCAGCTGCTTCAAACAGAGGAGGTT-
TAGGAGCTATGGGAAGGAGCACGCGAGCACCA-
GGTGCT GGTGCTGCTGTAAGGCCCCTTCCTGCTCT-
CAAGGAGAATGTTAAGAGGGTTATGTTTTATTGT
(SEQ ID NO:315).

Nicotiana benthamiana plants were treated using a procedure similar to that described in Example 12. Polynucleotide solution (or mixed polynucleotides in the case of AGO1) were prepared in 0.01% (v/v) SILWET L-77 and 2% (w/v) ammonium sulfate in 5 millimolar sodium phosphate, pH 6.8. Two fully expanded leaves per plant were dipped into 0.1% SILWET L-77 solution freshly made with ddH2O for a few seconds, and allowed to dry. About 30 minutes later, 20 microliters of polynucleotide solution was applied to each of the two pre-treated leaves. For PDS, each of 5 plants received 25 nanomoles of the PDS anti-sense polynucleotide (SEQ ID NO:34); for AGO1, each of 5 plants received 50 nanomoles of each of the 14 AGO1 anti-sense polynucleotides (SEQ ID NOS:300-313); for PDS and AGO combined treatments, each of 5 plants received 25 nanomoles of the PDS anti-sense polynucleotide (SEQ ID NO:34) and 50 nanomoles of each of the 14 AGO1 anti-sense polynucleotides (SEQ ID NOS:300-313) applied on separate leaves. Paired control plants were treated with buffer (0.01% (v/v) SILWET L-77 and 2% (w/v) ammonium sulfate in 5 millimolar sodium phosphate, pH 6.8). No difference was observed between plants treated with the AGO1 anti-sense polynucleotides and the plants treated with buffer alone. Plants treated with the PDS anti-sense polynucleotide displayed systemic bleaching. Plants treated with both the PDS anti-sense polynucleotide and the separately applied AGO1 anti-sense polynucleotides did not display systemic bleaching, indicating that suppression of AGO1 blocked the systemic spread of the silencing signal.

Example 34

This example illustrates a method for inducing systemic regulation of a target endogenous gene in a growing plant comprising topically coating onto leaves of said growing plant polynucleotides having sequence essentially identical to, or essentially complementary to, a sequence of 18 or more contiguous nucleotides in either said target endogenous gene or messenger RNA transcribed from said target endogenous gene, whereby said polynucleotides permeate the interior of said growing plant and induce systemic regulation of said target endogenous gene. More specifically this example illustrates use of a composition comprising surfactant and polynucleotides to at least transiently induce systemic regulation of the endogenous Zea mays 5-enolpyruvylshikimate-3-phosphate synthase (EPSPS) gene.

A genomic sequence of the endogenous Zea mays 5-enolpyruvylshikimate-3-phosphate synthase (EPSPS) gene was identified as ACCTACTTCCCCCTCGC-
CCCTCTCATGGTCTCTCTCGCGCCCAGATCTGC-
TACTAGACGGCACCGCTGC AGCGCGTCGT-
GTCGCGGGGTTGGTGGCAGGCAGCGAGAGCTT-
GCCGTTCCTCTCTCTCAGTTGTCAG GTCCTAGGCT-
CACCTCACCGGCTCCCAGCCCGCCTTCTATTTCTTC-
CTCCCCGACCCCGTGCAGGTGGCA GTCCAGTC-
CACGCCACCAACCGCGAGGCGAACCAAACCAAC-
CCACTCTCCCCAACCCCGCGCGCCCAG GCCGC-
CCGCCCTACCAACCATCGGCGTCGGCAATGGCG-
GCCATGGCGACCAAGGCCGCCGCGGGCAC CGT- GTCGCTGGACCTCGCCGCGCCGCCGGCGGCGGC-
AGCGGCGGCGGCGGTGCAGGCGGGTGCCGAG
GAGATCGTGCTGCAGCCCATCAAGGAGATCTCCG-
GCACCGTCAAGCTGCCGGGGTCCAAGTCGCTTTC
CAACCGGATCCTCCTGCTCGCCGCCCTGTCCGAG-
GTGAGCGATTTTGGTGCTTGCTGCGCTGCCCTGTC
TCACTGCTACCTAAATGTTTTGCCTGTCGAATAC-
CATGGATTCTCGGTGTAATCCATCTCACGATCAGA
TGCACCGCATGTCGCATGCCTAGCTCTCTCTAATTT-
GTCTAGTAGTTTGTATACGGATTAATATTGATA
AATCGGTACCGCAAAAGCTAGGTG-
TAAATAAACACTAGAAAATTGGATGTTC-
CCCTATCGGCCTGTAC TCGGCTACTCGTTCTTGT-
GATGGCATGCTGTCTCTTCTTGGTGTTTGGTGAA-
CAACCTTATGAAATTTGG GCGCAAAGAACTCGC-
CCTCAAGGGTTGATCTTATGCCATCGTCATGA-
TAAACAGTGGAGCACGGACGA TCCTTTACGTT-
GTTTTTAACAAACTTTGTCAGAAAACTAGCATCA-
TTAACTTCTTAATGACGATTTCACA
ACAAAAAAAGGTAACCTCGC-
TACTAACATAACAAAATACTTGTTGCTTATTAAT-
TATATGTTTTTTAAT CTTTGATCAGGGGACAACA-
GTGGTTGATAACCTGTTGAACAGTGAGGATGTC-
CACTACATGCTCGGGG CCTTGAGGACTCTTG-
GTCTCTCTGTCGAAGCGGACAAAGCTGC-
CAAAAGAGCTGTAGTTGTTGGCTGT GGTG-
GAAAGTTCCCAGTTGAGGATTCTAAAGAGGAAG-
TGCAGCTCTTCTTGGGGAATGCTGGAACTGC AAT-
GCGGCCATTGACAGCAGCTGTTACTGCTGCTGGTG-
GAAATGCAACGTATGTTCCTCTCTTTCTCT CTA-
CAATACTTGCTGGAGTTAGTATGAAACCCATGGGT-
ATGTCTAGTGGCTTATGGTGTATTGGTTTTT GAACT-
TCAGTTACGTGCTTGATGGAGTACCAAGAAT-
GAGGGAGAGACCCATTGGCGACTTGGTTGTCG
GATTGAAGCAGCTTGGTGCAGATGTTGATTGTTC-
CTTGGCACTGACTGCCCACCTGTTCGTGTCAATG
GAATCGGAGGGCTACCTGGTGGCAAGGTTAGC-
TACTAAGGGCCACATGTTACATTCTTCTGTAAATGG
TACAACTATTGTCGAGCTTTTGCATTTG-
TAAGGAAAGCATTGATTGATCTGAATTTGATGCTA-
CACCAC AAAATATCCTACAAATGGTCATC-
CCTAACTAGCAAACAATGAAGTAATACTTGGCAT-
GTGTTTATCAA ATTAATTTCCATCTTCTGGGGCATT-
GCCTGTTTTCTAGTCTAATAGCATTTGTTTTTAGCAT-
TAATTAGC TCTTACAATTGTTATGTTCTACAGGT-
CAAGCTGTCTGGCTCCATCAGCAGTCAGTACTTG-
AGTGCCTTG CTGATGGCTGCTCCTTTGGCTCT-
TGGGGATGTGGAGATTGAAATCATTGATAAAT-
TAATCTCCATTCCC TACGTCGAAATGACATTGAGAT-
TGATGGAGCGTTTTGGTGTGAAAGCAGAGCATT-
CTGATAGCTGGGA CAGATTCTACATTAAGGGAGGT-
CAAAAATACAAGTAAGCTCTGTAATGTATTTCAC-
TACTTTGATGCC AATGTTTCAGTTTTCAGTTTTC-
CAAACAGTCGCATCAATATTTGAATAGATGCACT-
GTAGAAAAAAAAT CATTGCAGGGAAAAACTAG-
TACTGAGTATTTTGACTGTAAATTATTTTACCA-
GTCGGAATATAGTCAGT CTATTGGAGT-
CAAGAGCGTGAACCGAAATAGCCAGTTAATTATC-
CCATTATACAGAGGACAACCATGT ATACTATT-
GAAACTTGGTTTATAAGAGAATCTAGGTAGCTG-
GACTCGTAGCTGCTTGGCATGGATACCT TCT-
TATCTTTAGGAAAAGACACTTGATTTTTTTTTCT-
GTGGCCCTCTATGATGTGTGAACCTGCTTCTC TATT-
GCTTTAGAAGGATATATCTATGTCGTTATGCAACAT-
GCTTCCCTTAGCCATTTGTACTGAAATCA
GTTTCATAAGTTCGTTAGTGGTTCCCTAAAC-
GAAACCTTGTTTTTCTTTGCAATCAACAGGTC-
CCCTAA AAATGCCTATGTTGAAGGTGATGCCT-
CAAGCGCAAGCTATTTCTTGGCTGGTGCTGCAAT-
TACTGGAG GGACTGTGACTGTGGAAGGTTGTG-
GCACCACCAGTTTGCAGGTAAAGATTTCTTGGCTG-
GTGCTACAA TAACTGCTTTTGTCTTTTTGGTTTCA-
GCATTGTTCTCAGAGTCACTAAATAACATTATCAT-
CTGCAAATG TCAAATAGACATACTTAGGTGAAT-
TCATGTAACCGTTTCCTTACAAATTTGCTGAAAC-
CTCAGGGTGAT GTGAAGTTTGCTGAGGTACTGGA-
GATGATGGGAGCGAAGGTTACATGGACCGAGAC-
TAGCGTAACTG TTACTGGCCCACCGCGGGAGC-
CATTTGGGAGGAAACACCTCAAGGCGATTGATGT-
CAACATGAACAA GATGCCTGATGTCGCCAT-
GACTCTTGCTGTGGTTGCCCTCTTTGCCGATGGC-
CCGACAGCCATCAGAGA CGGTAAAACATTCTCA-
GCCCTACAACCATGCCTCTTCTACATCACTACTT-
GACAAGACTAAAAACTATT GGCTCGTTGGCAGTG-
GCTTCCTGGAGAGTAAAGGAGACCGAGAGGATG-
GTTGCGATCCGGACGGAGC TAACCAAGGTAAGGC-
TACATACTTCACATGTCTCACGTCGTCTTTC-
CATAGCTCGCTGCCTCTTAGCGG CTTGCCTGCG-
GTCGCTCCATCCTCGGTTGCTGTCTGTGTTTTCCA-
CAGCTGGGAGCATCTGTTGAGGAA GGGCCGGAC-
TACTGCATCATCACGCCGCCGGAGAAGCTGAACGT-
GACGGCGATCGACACGTACGACG ACCACAGGATG-
GCCATGGCCTTCTCCCTTGCCGCCTGTGCCGAGG-
TCCCCGTGACCATCCGGGACCCT GGGTGCACCCG-
GAAGACCTTCCCCGACTACTTCGATGTGCTGAG-
CACTTTCGTCAAGAATTAATAAAG CGTGCGATAC-
TACCACGCAGCTTGATTGAAGTGATAGGCTTGTG-
CTGAGGAAATACATTTCTTTTGTTC
TGTTTTTTCTCTTTCACGGGATTAAGTTTTGAGTCT-
GTAACGTTAGTTGTTTGTAGCAAGTTTCTATTTC
GGATCTTAAGTTTGTGCACTGTAAGC-
CAAATTTCATTTCAAGAGTGGTTCGTTG-
GAATAATAAGAATA ATAAATTACGTTTCAGTGGCT-
GTCAAGCCTGCTGCTACGTTTTAGGAGATGGCA-
TTAGACATTCATCAT CAACAACAATAAAACCTTT-
TAGCCTCAAACAATAATAGTGAAGTTATTTTT-
TAGTCCTAAACAAGTTGC ATTAGGATATAGT-
TAAAACACAAAAGAAGCTAAAGTTAGGGTTTAG-
ACATGTGGATATTGTTTTCCAT (SEQ ID NO:316), with
a 5' untranslated region located at nucleotide positions 1-306
and a 3' untranslated region located at nucleotide positions
3490-3907. A EPSPS cDNA sequence was identified as
ACCTACTTCCCCCTCGCCCCTCTCATG-
GTCTCTCTCGCGCCCAGATCTGCTACTAGACG-
GCACCGCTGC AGCGCGTCGTGTCGCGGGGTTG-
GTGGCAGGCAGCGAGAGCTTGCCGTTCCTCTCTC-
TCAGTTGTCAG GTCCTAGGCTCACCTCACCG-
GCTCCCAGCCCGCTTCTATTTCTTCCTCCCCGAC-
CCCGTGCAGGTGGCA GTCCAGTCCACGCCAC-
CAACCGCGAGGCGAACCAAACCAACCCACTCTC-
CCCAACCCCGCGCGCCCAG GCCGCCCGCCCTAC-
CAACCATCGGCGTCGGCAATGGCGGCCATGGC-
GACCAAGGCCGCCGCGGGCAC CGTGTCGCTG-
GACCTCGCCGCGCCGCCGGCGGCGGCAGCGGCG-
GCGGCGGTGCAGGCGGGTGCCGAG GAGATCGT-
GCTGCAGCCCATCAAGGAGATCTCCGGCACCGT-
CAAGCTGCCGGGGTCCAAGTCGCTTTC CAACCG-
GATCCTCCTGCTCGCCGCCCTGTCCGAGGGGACA-
ACAGTGGTTGATAACCTGTTGAACAGTG AGGAT-
GTCCACTACATGCTCGGGGCCTTGAGGACTCTTG-
GTCTCTCTGTCGAAGCGGACAAAGCTGCC
AAAAGAGCTGTAGTTGTTGGCTGTGGTGGAAAGT-
TCCCAGTTGAGGATTCTAAAGAGGAAGTGCAGCT
CTTCTTGGGGAATGCTGGAACTGCAATGCGGCCAT-
TGACAGCAGCTGTTACTGCTGCTGGTGGAAATG CAACTTACGTGCTTGATGGAGTACCAAGAATGAGGGAGAGACCCATTGGCGACTTGGTTGTCGGATTG AAGCAGCTTGGTGCAGATGTTGATTGTTTCCTTGGCACTGACTGCCCACCTGTTCGTGTCAATGGAATC GGAGGGCTACCTGGTGGCAAGGTCAAGCTGTCTGGCTCCATCAGCAGTCAGTACTTGAGTGCCTTGCT GATGGCTGCTCCTTTGGCTCTTGGGGATGTGGAGATTGAAATCATTGATAAATTAATCTCCATTCCCTA CGTCGAAATGACATTGAGATTGATGGAGCGTTTTGGTGTGAAAGCAGAGCATTCTGATAGCTGGGACA GATTCTACATTAAGGGAGGTCAAAAATACAAGTCCCCTAAAAATGCCTATGTTGAAGGTGATGCCTCA AGCGCAAGCTATTTCTTGGCTGGTGCTGCAATTACTGGAGGGACTGTGACTGTGGAAGGTTGTGGCAC CACCAGTTTGCAGGGTGATGTGAAGTTTGCTGAGGTACTGGAGATGATGGGAGCGAAGGTTACATGGA CCGAGACTAGCGTAACTGTTACTGGCCCACCGCGGGAGCCATTTGGGAGGAAACACCTCAAGGCGATT GATGTCAACATGAACAAGATGCCTGATGTCGCCATGACTCTTGCTGTGGTTGCCCTCTTTGCCGATGGC CCGACAGCCATCAGAGACGTGGCTTCCTGGAGAGTAAAGGAGACCGAGAGGATGGTTGCGATCCGGA CGGAGCTAACCAAGCTGGGAGCATCTGTTGAGGAAGGGCCGGACTACTGCATCATCACGCCGCCGGA GAAGCTGAACGTGACGGCGATCGACACGTACGACGACCACAGGATGGCCATGGCCTTCTCCCTTGCCG CCTGTGCCGAGGTCCCCGTGACCATCCGGGACCCTGGGTGCACCCGGAAGACCTTCCCCGACTACTTC GATGTGCTGAGCACTTTCGTCAAGAATTAATAAAGCGTGCGATACTACCACGCAGCTTGATTGAAGTG ATAGGCTTGTGCTGAGGAAATACATTTCTTTTGTTCTGTTTTTTCTCTTTCACGGGATTAAGTTTTGAGT CTGTAACGTTAGTTGTTTGTAGCAAGTTTCTATTTCGGATCTTAAGTTTGTGCACTGTAAGCCAAATTTC ATTTCAAGAGTGGTTCGTTGGAATAATAAGAATAATAAATTACGTTTCAGTGGCTGTCAAGCCTGCTG CTACGTTTTAGGAGATGGCATTAGACATTCATCATCAACAACAATAAAACCTTTTAGCCTCAAACAAT AATAGTGAAGTTATTTTTAGTCCTAAACAAGTTGCATTAGGATATAGTTAAAACACAAAAGAAGCTA AAGTTAGGGTTTAGACATGTGGATATTGTTTTCCAT (SEQ ID NO:317). A 240 base pair double-stranded RNA polynucleotide was designed with one strand corresponding to the DNA sequence TACTTGAGTGCCTTGCTGATGGCTGCTCCTTTGGCTCTTGGGGATGTGGAGATTGAAATCATTGATAAA TTAATCTCCATTCCGTACGTCGAAATGACATTGAGATTGATGGAGCGTTTTGGTGTGAAAGCAGAGCA TTCTGATAGCTGGGACAGATTCTACATTAAGGGAGGTCAAAAATACAAGTCCCCTAAAAATGCCTATG TTGAAGGTGATGCCTCAAGCGCAAGCTATTTCTTG (SEQ ID NO:318) which corresponds to a 240 nucleotide segment located at nucleotide positions 937-1176 of the EPSPS cDNA sequence.

Figure 37:
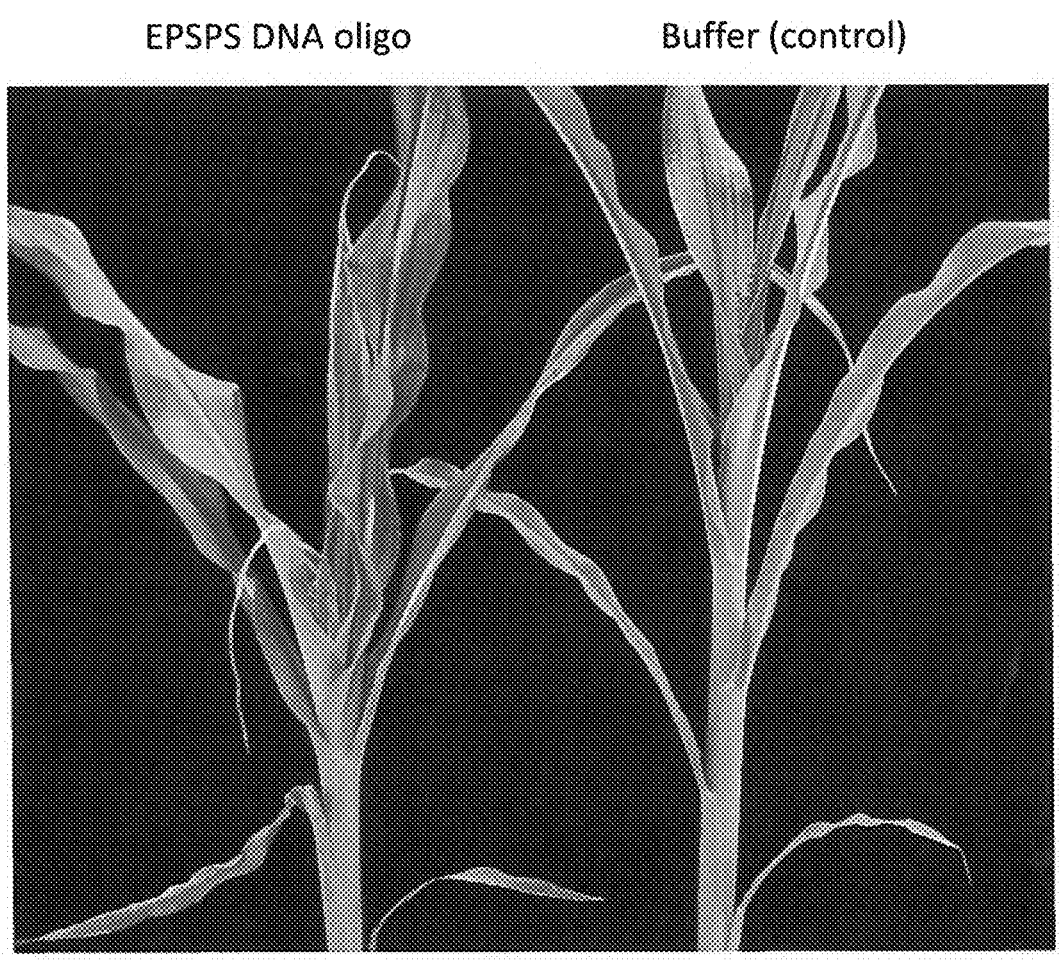
FIG. 37 illustrates the effect on *Zea mays* (Gaspe) monocot plants by topical treatment with dsRNA polynucleotides ("EPSPS DNA oligo") targeting the endogenous EPSPS gene, or with buffer alone as a control, as described in Example 34.

*Zea mays* (Gaspe) seeds were germinated on germination paper. Seedlings were transferred to 4 inch pots and plants were grown in a growth chamber. Three 17-day-old plants were topically treated with polynucleotides and three plants were used as controls. Two lower leaves of each plant were marked and then pre-treated by dipping in a solution of 0.1% SILWET L-77. About 30 minutes after the surfactant pre-treatment, 20 microliters of treatment solution was applied to the upper side of each of the two pre-treated leaves. Treatment solution consisted of a mixture of 100 microliters of 2× buffer solution, 90 microliters water, 10 microliters of a 4.6 micrograms/microliter solution of the EPSPS dsRNA (with one strand corresponding to SEQ ID NO:318); the 2× buffer solution was a mixture of 200 microliters of 0.1% SILWET L-77, 200 microliters 50 millimolar sodium phosphate, 146 microliters 34% ammonium phosphate, and 454 microliters water. At 8 days after treatment, two of the three polynucleotide-treated plants were stunted with damaged or dead apical leaves (similar to the phenotype observed in similarly EPSPS polynucleotide-treated *Nicotiana benthamiana* plants), whereas all three of the control plants had normal growth and morphology (FIG. 37).

Example 35

The efficacy of different substances (including salts, a chelating agent, a humectant, and polyamines) as polynucleotide transferring agents or as enhancers of a known polynucleotide transferring agent was investigated. Ammonium sulfate had previously been shown to enhance permeability of plants to polynucleotides (see, e. g., Example 13). Table 26 lists the effect on herbicidal activity (presented as percent of weed control/kill, and as plant height) of ammonium sulfate and EDTA as additives to 1% SILWET L-77 spray solutions of topically applied polynucleotides (RNA) on glyphosate-resistant Palmer amaranth plants. In this particular experiment, ethylenediaminetetraacetic acid (EDTA) at 0.004% was found to act similarly to 2% ammonium sulfate in the spray solution, enhancing the efficacy of the polynucleotides and potentiating the herbicidal activity of glyphosate.

TABLE 26

| Treatment | Palmer control (%) | Palmer height (cm) |
| --- | --- | --- |
| No addition | 0 | 7.5 |
| +2% ammonium sulfate | 43 | 1.8 |
| +0.004% EDTA | 45 | 1.0 |

Table 27 lists the effect on herbicidal activity (presented as percent of weed control/kill, and as plant height) of various salts including inorganic salts (sodium chloride, sodium sulfate, ammonium sulfate, ammonium chloride) and organic salts (tetramethylammonium chloride, tetraethylammonium chloride, tetrapropylammonium bromide, and tetrabutylphosphonium bromide) as additives to 1% SILWET L-77 spray solutions of topically applied polynucleotides (RNA) on glyphosate-resistant Palmer amaranth plants. In this particular experiment, ammonium chloride and tetrabutylphosphonium bromide were found to act similarly to ammonium sulfate in the spray solution, enhancing the efficacy of the polynucleotides and potentiating the herbicidal activity of glyphosate.

TABLE 27

| Treatment | Palmer control (%) | Palmer height (cm) |
| --- | --- | --- |
| No addition | 0 | 16.0 |
| +2% sodium chloride | 15 | 15.0 |
| +2% sodium sulfate | 7 | 17.0 |
| +2% ammonium sulfate | 54 | 9.3 |
| +2% ammonium chloride | 52 | 10.3 |
| +2% tetramethylammonium chloride | 19 | 15.0 |
| +2% tetraethylammonium chloride | 27 | 12.0 |
| +2% tetrapropylammonium bromide | 34 | 11.0 |
| +2% tetrabutylphosphonium bromide | 19 | 13.3 |

TABLE 27-continued

| Treatment | Palmer control (%) | Palmer height (cm) |
|---|---|---|
| +2% tetrabutylphosphonium bromide | 55 | 5.3 |

Table 28 lists the effect of the humectant glycerin on herbicidal activity (presented as percent of weed control/kill, and as plant height) of topically applied polynucleotides (RNA) on glyphosate-resistant Palmer amaranth plants. Glycerin was found to enhance the efficacy of the polynucleotides, potentiating the herbicidal activity of glyphosate.

TABLE 28

| Treatment | Palmer control (%) | Palmer height (cm) |
|---|---|---|
| No addition | 0 | 16.0 |
| Silwet L-77/AMS (no glycerin) | 54 | 9.3 |
| Silwet L-77/AMS + 0.5% glycerin | 57 | 6.3 |

Figure 38:
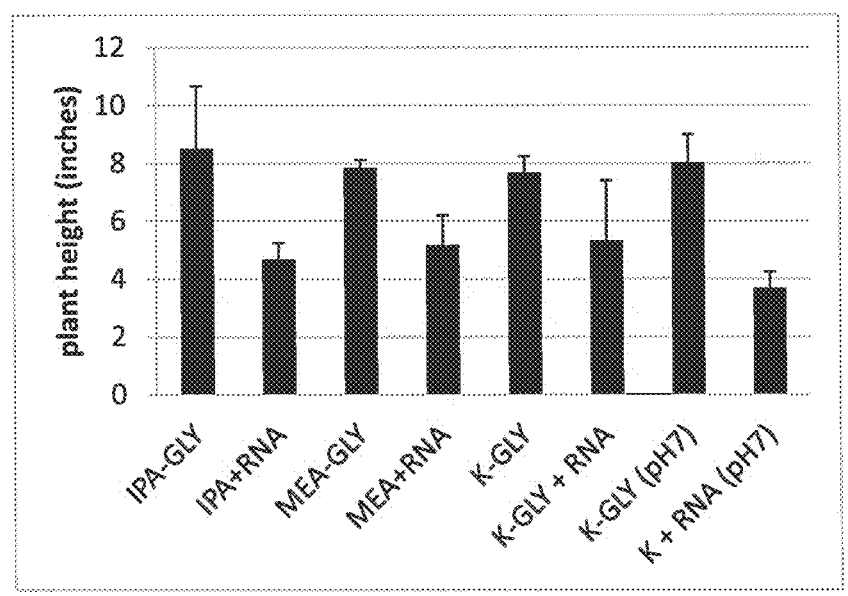
FIG. 38 illustrates the effect of varying glyphosate counter-ions on herbicidal activity on glyphosate-resistant Palmer amaranth plants, as described in Example 35.

FIG. 38 depicts the effect of varying glyphosate counter-ions on herbicidal activity (presented as percent of weed control/kill, and as plant height) of topically applied polynucleotides (RNA) on glyphosate-resistant Palmer amaranth plants. A mixture of EPSPS polynucleotides (IDT [1] (SEQ ID NO:83-84), IDT [2] (SEQ ID NO:85-86), IDT [3] (SEQ ID NO:87-88), and IDT [4] (SEQ ID NO:89-90)) in 0.5% SILWET L-77, 2% ammonium sulfate in 10 millimolar sodium phosphate buffer, pH 6.8 with 0.2% Roundup® WeatherMax® carrier (MON56151 tallowamine surfactant blend of tallowamine (16-18C) and cocoamine (12-14C) in the ratio of 55:45) and 1682 g acid equivalent per hectare of one of the glyphosate salts; K+ glyphosate, isopropylammonium+glyphosate or monoethanolammonium+glyphosate at 215 liters/acre by Milli spray on 3 replicates of 4-6 inch glyphosate-resistant Palmer amaranth containing 16 copies of EPSPS. Plant height was scored at 21 days after glyphosate treatment. Results (presented as percent of weed control/kill, and as plant height) are given in Table 29. The isopropylammonium and monoethanolammonium salts of glyphosate provided better herbicidal activity compared to the potassium salt.

TABLE 29

| Treatment | Palmer control (%) | Palmer height (cm) |
|---|---|---|
| No addition | 0 | 16 |
| K + glyphosate | 23 | 12.3 |
| K + glyphosate + EPSPS polynucleotides | 32 | 10.8 |
| IPA + glyphosate | 9 | 14.5 |
| IPA + glyphosate + EPSPS polynucleotides | 66 | 5.5 |
| MEA + glyphosate | 9 | 14.5 |
| MEA + glyphosate + EPSPS polynucleotides | 66 | 5.5 |

Figure 39:
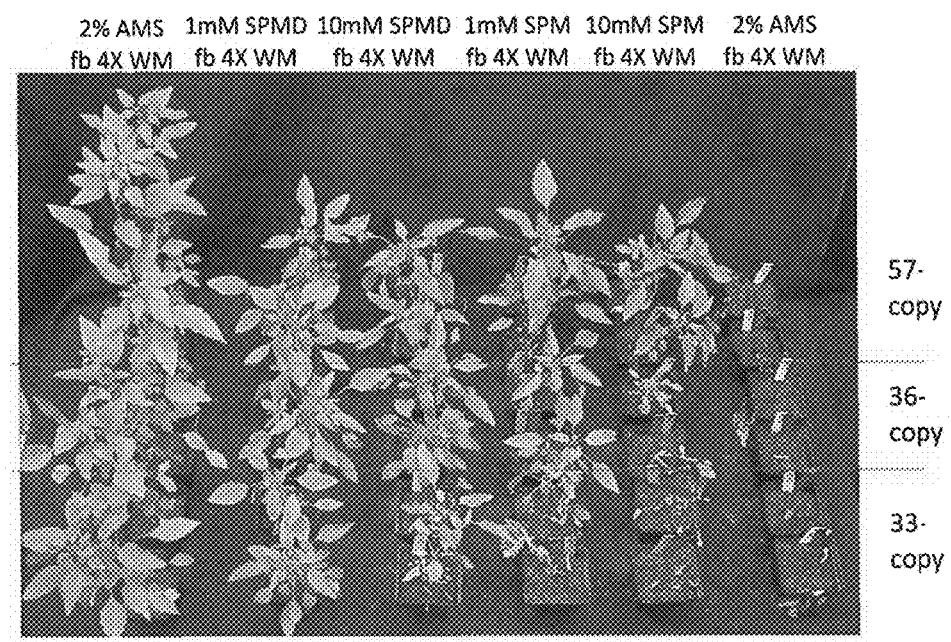
FIG. 39 illustrates the effect of the polyamines spermine ("SPM") and spermidine ("SPMD") or ammonium sulfate ("AMS") on glyphosate-resistant Palmer amaranth containing 33, 36, or 57 copies of EPSPS, as described in Example 35. "fb 4X WM" means "followed by treatment with glyphosate (3360 g acid equivalent per hectare of Roundup® WeatherMAX® brand herbicide)".

The effect of the polyamine cations spermine (N,N'-bis(3-aminopropyl)butane-1,4-diamine) and spermidine (N-(3-aminopropyl)butane-1,4-diamine) on herbicidal activity of topically applied polynucleotides (RNA) on glyphosate-resistant Palmer amaranth plants was investigated. Polynucleotide solutions were prepared using a mixture of equal amounts of the four oligonucleotide-size "short" dsRNA molecules described in Example 1, which have an anti-sense strand designed to hybridize to the mRNA transcribed from the Palmer amaranth EPSPS gene (SEQ ID NO:1) at positions 14-38 (short dsRNA-1), positions 153-177 (short dsRNA-2), 345-369 (short dsRNA-3), and 1105-1129 (short dsRNA-4), as indicated by underlined nucleotides in FIG. 1; the dsRNAs had a two nucleotide overhang at the 3' end of the anti-sense strand, and had two deoxynucleotides as the terminal nucleotides at the 3' end of the sense strand. The dsRNA polynucleotide solutions were prepared with either 1 or 10 millimolar spermine or spermidine or 2% ammonium sulfate, in a 10 millimolar sodium phosphate (pH 6.8) buffer. Control solutions (without polynucleotides) were prepared with either 1 or 10 millimolar spermine or spermidine or 2% ammonium sulfate, in a 10 millimolar sodium phosphate (pH 6.8) buffer. Glyphosate-resistant Palmer amaranth plants (33, 36, or 57 copies EPSPS) were pre-sprayed with 1% SILWET L-77. The dsRNA polynucleotide solutions (11.6 grams/acre) or buffer solutions were applied as drops on four lower fully expanded leaves of glyphosate resistant Palmer amaranth by pipetting. Two days following polynucleotide treatment the plants were sprayed with glyphosate (3360 g acid equivalent per hectare of Roundup® WeatherMAX® brand herbicide). Plants were photographed at 14 days after glyphosate treatment; results are shown in FIG. 39. Treatment with dsRNA and 10 millimolar spermine followed by glyphosate treatment killed glyphosate-resistant Palmer amaranth with 33-copy EPSPS and severely injured and stunted glyphosate-resistant Palmer amaranth with 36-copy EPSPS. Treatment with 10 mM spermidine alone stunted 33-copy glyphosate-resistant Palmer amaranth. In this particular experiment, neither spermine nor spermidine at 1 or 10 millimolar performed as well as 2% ammonium sulfate.

Example 36

The efficacy of different surfactants as polynucleotide transferring agents was tested in polynucleotide spray solutions applied to glyphosate-resistant Palmer amaranth. Break-Thru surfactants were obtained from Evonik Industries; SILWET surfactants were obtained from Momentive. Spray solutions were prepared the same day as spraying. A mixture of EPSPS polynucleotides (IDT [1] (SEQ ID NO:83-84), IDT [3] (SEQ ID NO:87-88), and IDT [4] (SEQ ID NO:89-90)) was added to spray solutions 15 to 50 minutes before spraying and 1- to 2-milliliters applied using a custom low-dead-volume ("milli") sprayer to one-to-four inch glyphosate-resistant (R-22) Palmer amaranth plants grown from cuttings. Between 10 and 225 micrograms total polynucleotides were applied to each plant, depending on the experiment; typically 23 micrograms total polynucleotides were applied per plant. Treated plants were placed in a greenhouse set for either a 26.7/21.1 degrees Celsius or 29.4/21.1 degrees Celsius 14/10 hour temperature and supplemental light schedule. After 2 to 3 days, the plants were sprayed with glyphosate ("2× Wmax" or 1682 g acid equivalent per hectare of Roundup® WeatherMAX® brand herbicide) by regular sprayer (10 gallons/acre) and returned to the greenhouse. The amount of control (visual injury) relative to unsprayed treatments, plant height and pictures of Palmer amaranth were collected at different time intervals up to 21 days after glyphosate treatment. Fresh weight of above-soil plant material was collected at the last time point. An overall plant injury score between 0 and 3 was given each treatment based on the combined analysis of Control, Height, Fresh Weight and Visual Plant Phenotype, where "3"

is strong herbicidal activity, "2" is moderate activity, "1" is mild activity and "0" is no activity observed after correction for any observed injury caused by treatment with glyphosate alone; results are shown in Table 30.

Physical properties of the different surfactants were also investigated and listed in Table 30. Seventy milliliters of surfactant solution (0.5% surfactant in aqueous solution containing 2% ammonium sulfate, buffer (20 millimolar potassium phosphate, pH 6.8), with or without an EPSPS polynucleotide (IDT [2] (SEQ ID NO:85-86), 0.09 milligrams/milliliter) added, were prepared on the same day as measurement. Dynamic surface tension was measured at ambient room temperature (22 to 23 degrees Celsius) on a Kruss BP100 tensiometer using the maximum bubble pressure method plotting surface tension versus surface age. The instrument was set to automatically detect the surface and immerse the capillary to a depth of 10 mm. Surface tension measurements for three surface ages (approximately 20, 500 and 1250 ms) were recorded. Surface tension in dynes per cm was reported at the 1250 ms interval as an approximation of static surface tension and the change between 20 and 500 ms was reported as an estimate of the dynamic surface tension. Hydrophile-lipophile balance (HLP) values for the surfactants were obtained from surfactant references and product information.

TABLE 30

| Surfactant name | CAS number | Chemistry | Surfactant Type | Surfactant Class | Palmer injury score | Surface tension literature | 1250 ms | delta 20-500 ms | HLB |
|---|---|---|---|---|---|---|---|---|---|
| Break-Thru S 321 | na | polyether-modified polysiloxane | organosilicone | nonionic | 3 | na | 22.7 | 27.1 | 40.0 |
| Break-Thru S 200 | 67674-67-3 | polyether-modified polysiloxane | organosilicone | nonionic | 3 | 22 | 26.9 | 23.0 | |
| Break-Thru OE 441 | 68937-55-3 | polyether-modified polysiloxane | organosilicone | nonionic | 1 | na | 43.8 | 2.9 | 40.0 |
| Break-Thru S 278 | 27306-78-1 | polyether-modified polysiloxane | organosilicone | nonionic | 2 | 21 | 24.2 | 23.4 | |
| Break-Thru S 243 | na | polyether-modified polysiloxane | organosilicone | nonionic | 2 | 47 | 50.3 | 7.7 | 16.7 |
| Silwet L-77 | 27306-78-1 | trisiloxane; polyalkylene oxide-modified polymethylsiloxane | organosilicone | nonionic | 3 | 20.5 | 26.4 | 23.4 | 13.5 |
| Silwet HS 429 | na | hydrolytically stable silicone | organosilicone | nonionic | 3 | 32-40 | 40.1 | 12.1 | |
| Silwet HS 312 | na | silicone | organosilicone | nonionic | 3 | 26.7 | 29.5 | 11.3 | |
| Break-Thru S 233 | 134180-76-0 | trisiloxane | organosilicone | nonionic | 3 | 23 | 26.1 | 10.0 | |

What is claimed is:

1. A method of delivering a double-stranded RNA (dsRNA) polynucleotide to the interior of a cell of a plant comprising: applying the dsRNA polynucleotide and a transferring agent selected from an organosilicone surfactant and a cationic lipid to an exterior surface of the plant,
   wherein the transferring agent facilitates permeation of the dsRNA polynucleotide from the exterior surface of the plant to the interior of the plant cell without the aid of a physical abrasive, and
   wherein the dsRNA polynucleotide is 21 to 700 base pairs in length and comprises a nucleotide sequence that is identical or complementary to at least 21 contiguous nucleotides of an endogenous gene or a transcribed RNA of the plant.

2. The method of claim 1, wherein the plant is growing in a field.

3. The method of claim 1, wherein the plant is a pigweed, velvetleaf, waterhemp, prickly lettuce, dandelion, alfalfa, corn, soybean, canola, cotton, sugar beet, sugarcane, wheat, or rice plant.

4. The method of claim 1, wherein the plant is a weed or volunteer plant.

5. The method of claim 1, wherein the plant is resistant to one or more of glyphosate, dicamba and sulfonylurea.

6. The method of claim 1, wherein the cell is a leaf cell.

7. The method of claim 1, wherein the dsRNA polynucleotide and the transferring agent are applied separately.

8. The method of claim 1, wherein the dsRNA polynucleotide and the transferring agent are applied concurrently.

9. The method of claim 1, wherein the organosilicone surfactant is a silicone polyether copolymer.

10. The method of claim 9, wherein the silicone polyether copolymer is a copolymer of polyalkylene oxide modified heptamethyl trisiloxane and allyloxypolypropylene glycol methylether.

11. The method of claim 1, further comprising applying an organic or an inorganic salt.

12. The method of claim 11, wherein the salt is an ammonium salt.

13. The method of claim 12, wherein the ammonium salt is ammonium sulfate.

14. The method of claim 1, wherein the dsRNA polynucleotide and the transferring agent are applied onto the exterior surface of the plant by a spray apparatus.

15. The method of claim 1, wherein the endogenous gene: (i) is an essential gene, (ii) encodes a protein that provides herbicide resistance, or (iii) transcribes to an RNA regulatory agent.

16. The method of claim 1, wherein the endogenous gene encodes a protein selected from the group consisting of a 5-enolpyruvylshikimate-3-phosphate synthase (EPSPS), an acetohydroxyacid synthase, an acetolactate synthase (ALS), an acetyl-coenzyme A carboxylase (ACCase), a dihydropteroate synthase, a phytoene desaturase (PDS), a protoporphyrin IX oxygenase (PPO), a hydroxyphenylpyruvate dioxygenase (HPPD), a para-aminobenzoate synthase, a glutamine synthase (GS), a glufosinate-tolerant glutamine synthase, a 1-deoxy-D-xylulose 5-phosphate (DOXP) synthase, a dihydropteroate (DHP) synthase, a phenylalanine ammonia lyase (PAL), a glutathione S-transferase (GST), a D1 protein of photosystem II, a mono-oxygenase, a cytochrome P450, a cellulose synthase, a beta-tubulin, and a serine hydroxymethyltransferase.

17. The method of claim 1, wherein the endogenous gene is a native gene or a recombinant transgene.

18. The method of claim 1, further comprising applying a non-polynucleotide herbicide.

19. The method of claim 18, wherein the non-polynucleotide herbicide is selected from the group consisting of glyphosate, dicamba, phosphinothricin, bromoxynil, ioxynil and chlorsulfuron.

* * * * *

SEQUENCE LISTING

<160> NUMBER OF SEQ ID NOS: 320

<210> SEQ ID NO 1
<211> LENGTH: 1557
<212> TYPE: DNA
<213> ORGANISM: Amaranthus palmeri

<400> SEQUENCE: 1

```
atggctcaag ctactaccat caacaatggt gtccatactg gtcaattgca ccatacttta      60
cccaaaaccc agttacccaa atcttcaaaa actcttaatt ttggatcaaa cttgagaatt     120
tctccaaagt tcatgtcttt aaccaataaa agagttggtg ggcaatcatc aattgttccc     180
aagattcaag cttctgttgc tgctgcagct gagaaacctt catctgtccc agaaattgtg     240
ttacaaccca tcaaagagat ctctggtact gttcaattgc ctgggtcaaa gtctttatcc     300
aatcgaatcc ttcttttagc tgctttgtct gagggcacaa cagtggtcga caacttgctg     360
tatagtgatg atattcttta tatgttggac gctctcagaa ctcttggttt aaaagtggag     420
gatgatagta cagccaaaag ggcagtcgta gagggttgtg gtggtctgtt tcctgttggt     480
aaagatggaa aggaagagat tcaacttttc cttggtaatg caggaacagc gatgcgccca     540
ttgacagctg cggttgccgt tgctggagga aattcaagtt atgtgcttga tggagtacca     600
```

```
agaatgaggg agcgccccat tggggatctg gtagcaggtc taaagcaact tggttcagat    660
gtagattgtt ttcttggcac aaattgccct cctgttcggg tcaatgctaa aggaggcctt    720
ccagggggca aggtcaagct ctctggatcg gttagtagcc aatatttaac tgcacttctc    780
atggctactc ctttgggtct tggagacgtg gagattgaga tagttgataa attgatttct    840
gtaccgtatg ttgaaatgac aataaagttg atggaacgct ttggagtatc cgtagaacat    900
agtgatagtt gggacaggtt ctacattcga ggtggtcaga aatacaaatc tcctggaaag    960
gcatatgttg agggtgatgc ttcaagtgct agctacttcc tagccggagc cgccgtcact   1020
ggtgggactg tcactgtcaa gggttgtgga acaagcagtt tacagggtga tgtaaaattt   1080
gccgaagttc ttgagaagat gggttgcaag gtcacctgga cagagaatag tgtaactgtt   1140
actggaccac ccagggattc atctggaaag aaacatctgc gtgctatcga cgtcaacatg   1200
aacaaaatgc cagatgttgc tatgactctt gcagttgttg ccttgtatgc agatgggccc   1260
accgccatca gagatgtggc tagctggaga gtgaaggaaa ccgaacggat gattgccatt   1320
tgcacagaac tgagaaagct tggggcaaca gttgaggaag gatctgatta ctgtgtgatc   1380
actccgcctg aaaagctaaa ccccaccgcc attgaaactt atgacgatca ccgaatggcc   1440
atggcattct ctcttgctgc ctgtgcagat gttcccgtca ctatccttga tccgggatgc   1500
acccgtaaaa ccttcccgga ctactttgat gttttagaaa agttcgccaa gcattga     1557

<210> SEQ ID NO 2
<211> LENGTH: 1761
<212> TYPE: DNA
<213> ORGANISM: Nicotiana benthamiana

<400> SEQUENCE: 2
atgccccaaa tcggacttgt atctgctgtt aatttgagag tccaaggtaa ttcagcttat     60
ctttggagct cgaggtcttc gttgggaact gaaagtcaag atgtttgctt gcaaaggaat    120
ttgttatgtt ttggtagtag cgactccatg gggcataagt taaggattcg tactccaagt    180
gccacgaccc gaagattgac aaaggacttt aatcctttaa aggtagtctg cattgattat    240
ccaagaccag agctagacaa tacagttaac tatttggagg cggcgttatt atcatcatcg    300
tttcgtactt cctcacgccc aactaaacca ttggagattg ttattgctgg tgcaggtttg    360
ggtggtttgt ctacagcaaa atatctggca gatgctggtc acaaaccgat attgctggag    420
gcaagagatg tcctaggtgg gaaggtagct gcatggaaag atgatgatgg agattggtac    480
gagactgggt tgcacatatt ctttggggct tacccaaata tgcagaacct gtttggagaa    540
ctagggattg atgatcggtt gcagtggaag gaacattcaa tgatatttgc gatgcctaac    600
aagccagggg agttcagccg ctttgatttt cctgaagctc ttcctgcgcc attaaatgga    660
attttggcca tactaaagaa caacgaaatg cttacgtggc ccgagaaagt caaatttgct    720
attggactct tgccagcaat gcttggaggg caatcttatg ttgaagctca agacggttta    780
agtgttaagg actggatgag aaagcaaggt gtgcctgata gggtgacaga tgaggtgttc    840
attgccatgt caaaggcact taacttcata aaccctgacg agctttcgat gcagtgcatt    900
ttgattgctt tgaacagatt tcttcaggag aaacatggtt caaaaatggc cttttttagat    960 ggtaacccct ctgagagact ttgcatgccg attgtggaac atattgagtc aaaaggtggc   1020
caagtcagac taaactcacg aataaaaaag atcgagctga atgaggatgg aagtgtcaaa   1080
tgttttatac tgaataatgg cagtacaatt aaaggagatg cttttgtgtt tgccactcca   1140
```

-continued

| | |
|---|---|
| gtggatatct tgaagcttct tttgcctgaa gactggaaag agatcccata tttccaaaag | 1200 |
| ttggagaagc tagtgggagt tcctgtgata aatgtccata tatggtttga cagaaaactg | 1260 |
| aagaacacat ctgataatct gctcttcagc agaagcccgt tgctcagtgt gtacgctgac | 1320 |
| atgtctgtta catgtaagga atattacaac cccaatcagt ctatgttgga attggtattt | 1380 |
| gcacccgcag aagagtggat aaatcgtagt gactcagaaa ttattgatgc tacaatgaag | 1440 |
| gaactagcga agcttttccc tgatgaaatt tcggcagatc agagcaaagc aaaaatattg | 1500 |
| aagtatcatg ttgtcaaaac cccaaggtct gtttataaaa ctgtgccagg ttgtgaaccc | 1560 |
| tgtcggccct tgcaaagatc ccctatagag ggttttatt tagctggtga ctacacgaaa | 1620 |
| cagaagtact tggcttcaat ggaaggtgct gtcttatcag gaaagctttg tgcacaagct | 1680 |
| attgtacagg attacgagtt acttcttggc cggagccaga agatgttggc agaagcaagc | 1740 |
| gtagttagca tagtgaacta a | 1761 |

<210> SEQ ID NO 3
<211> LENGTH: 559
<212> TYPE: DNA
<213> ORGANISM: artificial sequence
<220> FEATURE:
<223> OTHER INFORMATION: Synthetic Construct

<400> SEQUENCE: 3

| | |
|---|---|
| ggcccatagg ccttttttcta aataggccc atttaagcta ttaacaatct tcaaaagtac | 60 |
| cacatcgctt aggtaaagaa agcagctgag tttatatatg gttagagacg aagtagtgat | 120 |
| tgcgacgagc gacgtctcgc cctcatcgca atccacgcca ttgagcttga ggccattggc | 180 |
| gacggccgag aggcggtcgc ttaagattag catgtccttg acgcggagtt cttccagacc | 240 |
| gttcatcacg gtcgcccctt ccgcgaaggc ggcggcgaca gcgagaatcg gatattcgtc | 300 |
| gatcatcgaa ggcgcgcggt cttccggcac cgtgacgcat aaacacggtg ccggaagacc | 360 |
| gcgcgccttc gatgatcgac gaatatccga ttctcgctgt cgccgccgcc ttcgcggaag | 420 |
| gggcgaccgt gatgaacggt ctggaagaac tccgcgtcaa ggaaagcgac cgcctctcgg | 480 |
| ccgtcgccaa tggcctcaag ctcaatggcg tggattgcga tgagggcgag acgtcgctcg | 540 |
| tcgttttttt tggcaaaaa | 559 |

<210> SEQ ID NO 4
<211> LENGTH: 10
<212> TYPE: DNA
<213> ORGANISM: artificial sequence
<220> FEATURE:
<223> OTHER INFORMATION: Synthetic Construct

<400> SEQUENCE: 4

| | |
|---|---|
| tcccacatcg | 10 |

<210> SEQ ID NO 5
<211> LENGTH: 13
<212> TYPE: DNA
<213> ORGANISM: artificial sequence
<220> FEATURE:
<223> OTHER INFORMATION: Synthetic Construct

<400> SEQUENCE: 5

| | |
|---|---|
| aagattagca cgg | 13 |

<210> SEQ ID NO 6
<211> LENGTH: 11

-continued

<212> TYPE: DNA
<213> ORGANISM: artificial sequence
<220> FEATURE:
<223> OTHER INFORMATION: Synthetic Construct

<400> SEQUENCE: 6
acgcataaaa t                                                              11

<210> SEQ ID NO 7
<211> LENGTH: 6
<212> TYPE: DNA
<213> ORGANISM: artificial sequence
<220> FEATURE:
<223> OTHER INFORMATION: Synthetic Construct

<400> SEQUENCE: 7 tttttt                                                                     6

<210> SEQ ID NO 8
<211> LENGTH: 20
<212> TYPE: DNA
<213> ORGANISM: Amaranthus palmeri

<400> SEQUENCE: 8
accctccacg actgcccttt                                                     20

<210> SEQ ID NO 9
<211> LENGTH: 19
<212> TYPE: DNA
<213> ORGANISM: Amaranthus palmeri

<400> SEQUENCE: 9
gtttccttca ctctccagc                                                      19

<210> SEQ ID NO 10
<211> LENGTH: 20
<212> TYPE: DNA
<213> ORGANISM: Amaranthus palmeri

<400> SEQUENCE: 10
gtagcttgag ccattattgt                                                     20

<210> SEQ ID NO 11
<211> LENGTH: 20
<212> TYPE: DNA
<213> ORGANISM: Amaranthus palmeri

<400> SEQUENCE: 11
gttgatggta gtagcttgag                                                     20

<210> SEQ ID NO 12
<211> LENGTH: 20
<212> TYPE: DNA
<213> ORGANISM: Amaranthus palmeri

<400> SEQUENCE: 12
accctccacg actgcccttt                                                     20

<210> SEQ ID NO 13
<211> LENGTH: 19
<212> TYPE: DNA
<213> ORGANISM: Amaranthus palmeri

<400> SEQUENCE: 13
gtttccttca ctctccagc                                              19

<210> SEQ ID NO 14
<211> LENGTH: 18
<212> TYPE: DNA
<213> ORGANISM: Hordeum vulgare

<400> SEQUENCE: 14
aagcggttga gcactgaa                                               18

<210> SEQ ID NO 15
<211> LENGTH: 20
<212> TYPE: DNA
<213> ORGANISM: Amaranthus palmeri

<400> SEQUENCE: 15
accctccacg actgcccttt                                             20

<210> SEQ ID NO 16
<211> LENGTH: 40
<212> TYPE: DNA
<213> ORGANISM: artificial sequence
<220> FEATURE:
<223> OTHER INFORMATION: Synthetic Construct

<400> SEQUENCE: 16
taatacgact cactataggg caagagatgt cctaggtggg                        40

<210> SEQ ID NO 17
<211> LENGTH: 44
<212> TYPE: DNA
<213> ORGANISM: artificial sequence
<220> FEATURE:
<223> OTHER INFORMATION: Synthetic Construct

<400> SEQUENCE: 17
taatacgact cactatagga cagatttctt caggagaaac atgg                   44

<210> SEQ ID NO 18
<211> LENGTH: 21
<212> TYPE: DNA
<213> ORGANISM: artificial sequence
<220> FEATURE:
<223> OTHER INFORMATION: Synthetic Construct

<400> SEQUENCE: 18
gcaagagatg tcctaggtgg g                                           21

<210> SEQ ID NO 19
<211> LENGTH: 25
<212> TYPE: DNA
<213> ORGANISM: artificial sequence
<220> FEATURE:
<223> OTHER INFORMATION: Synthetic Construct

<400> SEQUENCE: 19
acagatttct tcaggagaaa catgg                                       25

<210> SEQ ID NO 20
<211> LENGTH: 41
<212> TYPE: DNA
<213> ORGANISM: artificial sequence
<220> FEATURE:
<223> OTHER INFORMATION: Synthetic Construct

<400> SEQUENCE: 20

```
taatacgact cactataggc atctccttta attgtactgc c        41

<210> SEQ ID NO 21
<211> LENGTH: 41
<212> TYPE: DNA
<213> ORGANISM: artificial sequence
<220> FEATURE:
<223> OTHER INFORMATION: Synthetic Construct

<400> SEQUENCE: 21
taatacgact cactataggt ttaattgtac tgccattatt c        41

<210> SEQ ID NO 22
<211> LENGTH: 22
<212> TYPE: DNA
<213> ORGANISM: artificial sequence
<220> FEATURE:
<223> OTHER INFORMATION: Synthetic Construct

<400> SEQUENCE: 22
catctccttt aattgtactg cc                             22

<210> SEQ ID NO 23
<211> LENGTH: 22
<212> TYPE: DNA
<213> ORGANISM: artificial sequence
<220> FEATURE:
<223> OTHER INFORMATION: Synthetic Construct

<400> SEQUENCE: 23
tttaattgta ctgccattat tc                             22

<210> SEQ ID NO 24
<211> LENGTH: 25
<212> TYPE: DNA
<213> ORGANISM: artificial sequence
<220> FEATURE:
<223> OTHER INFORMATION: Synthetic Construct

<400> SEQUENCE: 24
cacttccatc ctcattcagc tcgat                          25

<210> SEQ ID NO 25
<211> LENGTH: 24
<212> TYPE: DNA
<213> ORGANISM: artificial sequence
<220> FEATURE:
<223> OTHER INFORMATION: Synthetic Construct

<400> SEQUENCE: 25
acacctcatc tgtcaccta tcag                            24

<210> SEQ ID NO 26
<211> LENGTH: 24
<212> TYPE: DNA
<213> ORGANISM: artificial sequence
<220> FEATURE:
<223> OTHER INFORMATION: Synthetic Construct

<400> SEQUENCE: 26
cagtctcgta ccaatctcca tcat                           24

<210> SEQ ID NO 27
<211> LENGTH: 41
<212> TYPE: DNA
```

```
<213> ORGANISM: artificial sequence
<220> FEATURE:
<223> OTHER INFORMATION: Synthetic Construct

<400> SEQUENCE: 27
taatacgact cactataggg atccatgata tcgtgaacat c         41

<210> SEQ ID NO 28
<211> LENGTH: 38
<212> TYPE: DNA
<213> ORGANISM: artificial sequence
<220> FEATURE:
<223> OTHER INFORMATION: Synthetic Construct

<400> SEQUENCE: 28
taatacgact cactataggg gcaaagaaaa atgcgtcg            38

<210> SEQ ID NO 29
<211> LENGTH: 21
<212> TYPE: DNA
<213> ORGANISM: artificial sequence
<220> FEATURE:
<223> OTHER INFORMATION: Synthetic Construct

<400> SEQUENCE: 29
atccatgata tcgtgaacat c                              21

<210> SEQ ID NO 30
<211> LENGTH: 18
<212> TYPE: DNA
<213> ORGANISM: artificial sequence
<220> FEATURE:
<223> OTHER INFORMATION: Synthetic Construct

<400> SEQUENCE: 30
gcaaagaaaa atgcgtcg                                  18

<210> SEQ ID NO 31
<211> LENGTH: 40
<212> TYPE: DNA
<213> ORGANISM: artificial sequence
<220> FEATURE:
<223> OTHER INFORMATION: Synthetic Construct

<400> SEQUENCE: 31
tgttttatac tgaataatgg cagtacaatt aaaggagatg          40

<210> SEQ ID NO 32
<211> LENGTH: 15
<212> TYPE: DNA
<213> ORGANISM: artificial sequence
<220> FEATURE:
<223> OTHER INFORMATION: Synthetic Construct

<400> SEQUENCE: 32
catctccttt aattg                                     15

<210> SEQ ID NO 33
<211> LENGTH: 18
<212> TYPE: DNA
<213> ORGANISM: artificial sequence
<220> FEATURE:
<223> OTHER INFORMATION: Synthetic Construct

<400> SEQUENCE: 33
catctccttt aattgtac                                  18
```

<210> SEQ ID NO 34
<211> LENGTH: 21
<212> TYPE: DNA
<213> ORGANISM: artificial sequence
<220> FEATURE:
<223> OTHER INFORMATION: Synthetic Construct

<400> SEQUENCE: 34
catctccttt aattgtactg c                                              21

<210> SEQ ID NO 35
<211> LENGTH: 33
<212> TYPE: DNA
<213> ORGANISM: artificial sequence
<220> FEATURE:
<223> OTHER INFORMATION: Synthetic Construct

<400> SEQUENCE: 35
catctccttt aattgtactg ccattattca gta                                 33

<210> SEQ ID NO 36
<211> LENGTH: 21
<212> TYPE: DNA
<213> ORGANISM: artificial sequence
<220> FEATURE:
<223> OTHER INFORMATION: Synthetic Construct

<400> SEQUENCE: 36
gcagtacaat taaaggagat g                                              21

<210> SEQ ID NO 37
<211> LENGTH: 1614
<212> TYPE: DNA
<213> ORGANISM: Amaranthus palmeri

<400> SEQUENCE: 37
tcaatttcat ctattggaag tgattttttg ggtcattctg tgagaaattt cagtgttagt      60
aaagtttatg gagcaaagca agaaatggg cactgcccctt taaaggttgt ttgtatagat    120
tatcctaggc cagagcttga agtacatcc aatttcttgg aagccgccta cttatcttct     180
acttttcgga attcgcctcg tcctcagaag ccattagaag ttgtaattgc tggagcaggt    240
ttggctggtc tatccacggc aaagtattta gctgatgcag tcacaaaacc catattgttg    300
gaagcacgag atgttttagg aggaaaggtt gcagcgtgga aggatgagga tggtgactgg    360
tatgagactg gctacatat attctttggg gcatatccaa atgtccaaaa tctatttgga    420
gaacttggta taaatgaccg actgcaatgg aaggagcact ctatgatttt gcaatgccc    480 agcaagcccg gtgaattcag tcgctttgat tttcccgaaa tcctgcctgc accattaaat    540
ggcatatggg caatcctaag aaataatgaa atgctaacct ggccagaaaa aatcaagttt    600
gccattggct tgttgcctgc tatggcaggc ggacagtcat atgttgaagc acaagatggt    660
ttgagtgtcc aagagtggat gagaaaacaa ggagtacccg atcgtgtaac tgatgatgtg    720
tttattgcca tgtcaaaggc actgaacttc ataaatcccg atgaacttc aatgcagtgc    780 atcttgattg ctctgaaccg attcctgcag gagaaacatg ttctaagat ggccttccta    840 gacggaaacc ctccagagag gctgtgcatg cctattgtta aacacatcga gtcactaggt    900
ggtgaagtta aacttaactc tcgtatacaa aagattcagt ggaccagag tggaagcgtg    960 aagagttttt tgctaaataa cgggagggaa atacgaggag atgcctatgt ttttgccacc   1020

| | |
|---|---|
| ccagttgaca tcttgaagct gttactacct gatacttgga aggaaatctc atacttcaaa | 1080 |
| aaacttgaga aattagtggg cgttcctgtg attaatgttc acatatggtt tgacagaaaa | 1140 |
| ttaaagaata catatgacca tctactcttc agcaggagtc ctcttttgag tgtctatgct | 1200 |
| gatatgtcgg agacatgcaa ggaatataag gatccaaata gatccatgct ggaattggtt | 1260 |
| tttgcacccg cggaggaatg gatttcacga agcgacactg atattataga ggcaacaatg | 1320 |
| aaagagcttg ccaagctttt cccggatgaa atcgctgccg atggaagcaa ggccaagatc | 1380 |
| ctcaaatatc atgtcgtcaa actccaagg tcggtttata agactgtacc ggattgtgaa | 1440 |
| ccttgtcggc cgctgcaaag atcaccaata gagggtttct atttagctgg tgattacaca | 1500 |
| aaacaaaaat atttggcttc tatggaaggt gctgtcttat ctgggaagct tgtgcacag | 1560 |
| gctatcgtac aggattatga tctgctgagt tctcgagcac aaagagaatt ggcg | 1614 |

<210> SEQ ID NO 38
<211> LENGTH: 1761
<212> TYPE: DNA
<213> ORGANISM: Nicotiana benthamiana

<400> SEQUENCE: 38

| | |
|---|---|
| atgccccaaa tcggacttgt atctgctgtt aatttgagag tccaaggtaa ttcagcttat | 60 |
| ctttggagct cgaggtcttc gttgggaact gaaagtcaag atgtttgctt gcaaaggaat | 120 |
| ttgttatgtt ttggtagtag cgactccatg gggcataagt taaggattcg tactccaagt | 180 |
| gccacgaccc gaagattgac aaaggacttt aatcctttaa aggtagtctg cattgattat | 240 |
| ccaagaccag agctagacaa tacagttaac tatttggagg cggcgttatt atcatcatcg | 300 |
| tttcgtactt cctcacgccc aactaaacca ttggagattg ttattgctgg tgcaggtttg | 360 |
| ggtggtttgt ctacagcaaa atatctggca gatgctggtc acaaaccgat attgctggag | 420 |
| gcaagagatg tcctaggtgg aaggtagct gcatggaaag atgatgatgg agattggtac | 480 |
| gagactgggt tgcacatatt ctttggggct tacccaaata tgcagaacct gtttggagaa | 540 |
| ctagggattg atgatcggtt gcagtggaag gaacattcaa tgatatttgc gatgcctaac | 600 |
| aagccagggg agttcagccg ctttgatttt cctgaagctc ttcctgcgcc attaaatgga | 660 |
| attttggcca tactaaagaa caacgaaatg cttacgtggc ccgagaaagt caaatttgct | 720 |
| attggactct tgccagcaat gcttggaggg caatcttatg ttgaagctca agacggttta | 780 |
| agtgttaagg actggatgag aaagcaaggt gtgcctgata gggtgacaga tgaggtgttc | 840 |
| attgccatgt caaaggcact taacttcata aaccctgacg agctttcgat gcagtgcatt | 900 |
| ttgattgctt tgaacagatt tcttcaggag aaacatggtt caaaaatggc ctttttagat | 960 |
| ggtaaccctc ctgagagact ttgcatgccg attgtggaac atattgagtc aaaaggtggc | 1020 |
| caagtcagac taaactcacg aataaaaaag atcgagctga atgaggatgg aagtgtcaaa | 1080 |
| tgttttatac tgaataatgg cagtacaatt aaaggagatg cttttgtgtt tgccactcca | 1140 |
| gtggatatct tgaagcttct tttgcctgaa gactggaaag agatcccata tttccaaaag | 1200 |
| ttggagaagc tagtgggagt tcctgtgata aatgtccata tatggtttga cagaaaactg | 1260 |
| aagaacacat ctgataatct gctcttcagc agaagcccgt tgctcagtgt gtacgctgac | 1320 |
| atgtctgtta catgtaagga atattacaac cccaatcagt ctatgttgga attggtatt | 1380 |
| gcacccgcag aagagtggat aaatcgtagt gactcagaaa ttattgatgc tacaatgaag | 1440 |
| gaactagcga agcttttccc tgatgaaatt tcggcagatc agagcaaagc aaaaatattg | 1500 |
| aagtatcatg ttgtcaaaac cccaaggtct gtttataaaa ctgtgccagg ttgtgaaccc | 1560 |

```
tgtcggccct tgcaaagatc ccctatagag ggttttatt tagctggtga ctacacgaaa    1620
cagaagtact tggcttcaat ggaaggtgct gtcttatcag gaaagctttg tgcacaagct    1680
attgtacagg attacgagtt acttcttggc cggagccaga agatgttggc agaagcaagc    1740
gtagttagca tagtgaacta a                                              1761

<210> SEQ ID NO 39
<211> LENGTH: 22
<212> TYPE: DNA
<213> ORGANISM: Nicotiana benthamiana

<400> SEQUENCE: 39
ggcagtacaa ttaaaggaga tg                                             22

<210> SEQ ID NO 40
<211> LENGTH: 1557
<212> TYPE: DNA
<213> ORGANISM: Amaranthus palmeri

<400> SEQUENCE: 40
atggctcaag ctactaccat caacaatggt gtccatactg gtcaattgca ccatacttta    60
cccaaaaccc agttacccaa atcttcaaaa actcttaatt ttggatcaaa cttgagaatt    120
tctccaaagt tcatgtcttt aaccaataaa agagttggtg ggcaatcatc aattgttccc    180
aagattcaag cttctgttgc tgctgcagct gagaaaccct catctgtccc agaaattgtg    240
ttacaaccca tcaaagagat ctctggtact gttcaattgc ctgggtcaaa gtctttatcc    300
aatcgaatcc ttcttttagc tgctttgtct gagggcacaa cagtggtcga caacttgctg    360
tatagtgatg atattcttta tatgttggac gctctcagaa ctcttggttt aaaagtggag    420
gatgatagta cagccaaaag gcagtcgta gagggttgtg gtggtctgtt tcctgttggt    480
aaagatggaa aggaagagat tcaacttttc cttggtaatg caggaacagc gatgcgccca    540
ttgacagctg cggttgccgt tgctggagga aattcaagtt atgtgcttga tggagtacca    600
agaatgaggg agcgccccat tggggatctg gtagcaggtc taaagcaact tggttcagat    660
gtagattgtt ttcttggcac aaaattgccct cctgttcggg tcaatgctaa aggaggcctt    720
ccagggggca aggtcaagct ctctggatcg gttagtagcc aatatttaac tgcacttctc    780
atggctactc ctttgggtct tggagacgtg agattgaga tagttgataa attgatttct    840
gtaccgtatg ttgaaatgac aataaagttg atggaacgct tggagtatc cgtagaacat    900 agtgatagtt gggacaggtt ctacattcga ggtggtcaga aatacaaatc tcctggaaag    960
gcatatgttg agggtgatgc ttcaagtgct agctacttcc tagccggagc gccgtcact    1020 ggtgggactg tcactgtcaa gggtgtgga acaagcagtt acagggtga gtaaaatt    1080 gccgaagttc ttgagaagat gggttgcaag gtcacctgga cagagaatag tgtaactgtt    1140 actgaccac ccaggattc atctggaaag aaacatctgc gtgctatcga cgtcaacatg    1200
aacaaaatgc agatgttgc tatgactctt gcagttgttg ccttgtatgc agatgggccc    1260
accgccatca gagatgtggc tagctggaga gtgaaggaaa ccgaacggat gattgccatt    1320
tgcacagaac tgagaaagct tggggcaaca gttgaggaag atctgattaa ctgtgtgatc    1380
actccgcctg aaaagctaaa ccccaccgcc attgaaactt atgacgatca ccgaatggcc    1440
atggcattct ctcttgctgc ctgtgcagat gttcccgtca ctatccttga tccgggatgc    1500
acccgtaaaa ccttcccgga ctactttgat gttttagaaa agttcgccaa gcattga      1557
```

<210> SEQ ID NO 41
<211> LENGTH: 250
<212> TYPE: DNA
<213> ORGANISM: Amaranthus palmeri
<220> FEATURE:
<221> NAME/KEY: misc_feature
<222> LOCATION: (27)..(27)
<223> OTHER INFORMATION: n is a, c, g, or t

<400> SEQUENCE: 41

```
cgccagggct gcagacgcgt tacgtantcg gatccagaat tcgtgattaa cgtcacagca    60
tgtcatgtaa acacgcgaa tcagaccggt ccactcttgt tttaatttga gacaattttg   120
atgttgagtc atcccacacc aaccccaaaa aattcaacaa caaactctta taatgattcc   180
ctctactcta ctagagtcta caccaaccca cttctctttt gcccaccaaa actttggttt   240
ggtaagaact                                                         250
```

<210> SEQ ID NO 42
<211> LENGTH: 244
<212> TYPE: DNA
<213> ORGANISM: Amaranthus palmeri

<400> SEQUENCE: 42

```
caccaaccca cttctctttt gcccaccaaa actttggttt ggtaagaact aagccctctt    60
cttcccttc tctctcttaa agcctaaaa tccacctaac tttttcagcc aacaaacaac    120
gccaaattca aggaagaat aatgatggct caagctacta ccatcaacaa tggtgtccat    180
actggtcaat tgcaccatac tttacccaaa acccagttac ccaaatcttc aaaaactctt   240
aatt                                                               244
```

<210> SEQ ID NO 43
<211> LENGTH: 250
<212> TYPE: DNA
<213> ORGANISM: Amaranthus palmeri

<400> SEQUENCE: 43

```
ccatacttta cccaaaaccc agttacccaa atcttcaaaa actcttaatt ttggatcaaa    60
cttgagaatt tctccaaagt tcatgtcttt aaccaataaa agagttggtg ggcaatcatc   120
aattgttccc aagattcaag cttctgttgc tgctgcagct gagaaaccctt catctgtccc   180
agaaattgtg ttacaaccca tcaaagagat ctctggtact gttcaattgc ctgggtcaaa   240
gtctttatcc                                                         250
```

<210> SEQ ID NO 44
<211> LENGTH: 250
<212> TYPE: DNA
<213> ORGANISM: Amaranthus palmeri

<400> SEQUENCE: 44

```
tcaaagagat ctctggtact gttcaattgc ctgggtcaaa gtctttatcc aatcgaatcc    60
ttcttttagc tgctttgtct gagggcacaa cagtggtcga caacttgctg tatagtgatg   120
atattctta tatgttggac gctctcagaa ctcttggttt aaaagtggag gatgatagta   180
cagccaaaag ggcagtcgta gagggttgtg gtggtctgtt tcctgttggt aaagatggaa   240
aggaagagat                                                         250
```

<210> SEQ ID NO 45
<211> LENGTH: 250

```
<212> TYPE: DNA
<213> ORGANISM: Amaranthus palmeri

<400> SEQUENCE: 45
gagggttgtg gtggtctgtt tcctgttggt aaagatggaa aggaagagat tcaacttttc        60
cttggtaatg caggaacagc gatgcgccca ttgacagctg cggttgccgt tgctggagga       120
aattcaagtt atgtgcttga tggagtacca agaatgaggg agcgccccat tggggatctg       180
gtagcaggtc taaagcaact tggttcagat gtagattgtt tcttggcac aaattgccct        240 cctgttcggg                                                              250

<210> SEQ ID NO 46
<211> LENGTH: 250
<212> TYPE: DNA
<213> ORGANISM: Amaranthus palmeri

<400> SEQUENCE: 46
tggttcagat gtagattgtt tcttggcac aaattgccct cctgttcggg tcaatgctaa         60
aggaggcctt ccaggggca aggtcaagct ctctggatcg gttagtagcc aatatttaac       120
tgcacttctc atggctactc ctttgggtct tggagacgtg gagattgaga tagttgataa      180
attgatttct gtaccgtatg ttgaaatgac aataaagttg atggaacgct ttggagtatc      240
cgtagaacat                                                              250

<210> SEQ ID NO 47
<211> LENGTH: 250
<212> TYPE: DNA
<213> ORGANISM: Amaranthus palmeri

<400> SEQUENCE: 47
ttgaaatgac aataaagttg atggaacgct ttggagtatc cgtagaacat agtgatagtt       60
gggacaggtt ctacattcga ggtggtcaga aatacaaatc tcctggaaag gcatatgttg      120
agggtgatgc ttcaagtgct agctacttcc tagccggagc cgccgtcact ggtgggactg      180
tcactgtcaa gggttgtgga acaagcagtt tacagggtga tgtaaaattt gccgaagttc      240
ttgagaagat                                                              250

<210> SEQ ID NO 48
<211> LENGTH: 250
<212> TYPE: DNA
<213> ORGANISM: Amaranthus palmeri

<400> SEQUENCE: 48
acaagcagtt tacagggtga tgtaaaattt gccgaagttc ttgagaagat gggttgcaag       60
gtcacctgga cagagaatag tgtaactgtt actggaccac ccagggattc atctggaaag      120
aaacatctgc gtgctatcga cgtcaacatg aacaaaatgc cagatgttgc tatgactctt      180
gcagttgttg ccttgtatgc agatgggccc accgccatca gagatgtggc tagctggaga      240
gtgaaggaaa                                                              250

<210> SEQ ID NO 49
<211> LENGTH: 250
<212> TYPE: DNA
<213> ORGANISM: Amaranthus palmeri

<400> SEQUENCE: 49
agatgggccc accgccatca gagatgtggc tagctggaga gtgaaggaaa ccgaacggat       60
```

```
gattgccatt tgcacagaac tgagaaagct tggggcaaca gttgaggaag gatctgatta    120
ctgtgtgatc actccgcctg aaaagctaaa ccccaccgcc attgaaactt atgacgatca    180
ccgaatggcc atggcattct ctcttgctgc ctgtgcagat gttcccgtca ctatccttga    240
tccgggatgc                                                          250

<210> SEQ ID NO 50
<211> LENGTH: 257
<212> TYPE: DNA
<213> ORGANISM: Amaranthus palmeri

<400> SEQUENCE: 50
ctcttgctgc ctgtgcagat gttcccgtca ctatccttga tccgggatgc acccgtaaaa     60
ccttcccgga ctactttgat gttttagaaa agttcgccaa gcattgatga gtagctatat    120
acgagatcct taaattgtac gccgaaggtt ttgatttgag tctaatagta gataaaaggc    180
tataaataaa ctggctttct gcttgagtaa ttatgaaatt ctttgtatta tgtttgtgag    240
atttgaagta gcttata                                                  257

<210> SEQ ID NO 51
<211> LENGTH: 273
<212> TYPE: DNA
<213> ORGANISM: Amaranthus palmeri

<400> SEQUENCE: 51
taattatgaa attctttgta ttatgtttgt gagatttgaa gtagcttata aattacaatg     60
tactaaagtc tagaaataag ttatgtatct tttaaatcaa tgagaaatgc atacttgaaa    120
ggcttgacct tgtatttgtg acctaaagag tactaacttt ggagtttcca actcatttgt    180
ttatctcatt ttttttaat ttttgattta aattgtttat tttatgagt aatcatgtat      240 ctttcttatt ctaaccaaat gtaatactcc ttc                                273

<210> SEQ ID NO 52
<211> LENGTH: 301
<212> TYPE: DNA
<213> ORGANISM: Amaranthus palmeri

<400> SEQUENCE: 52
tatgagtaat catgtatctt tcttattcta accaaatgta atactccttc caactctctt     60
taaacgtcca cactctgggc acagagtgta atagtgtggt ggttggagtc ttttaagtga    120
ttataataat tgtaaatgtg gtagttagaa tattttaagt aatgtaggtg gggtattatg    180
gtcttgttga acataggata tttaggtaaa aaatctatgc aaaaaaagga aagtaagcaa    240
ataaagcgaa ttgacctgaa agaaaagtg gacatgtata gtgagttgga ggaagtatttt    300 t                                                                   301

<210> SEQ ID NO 53
<211> LENGTH: 1710
<212> TYPE: DNA
<213> ORGANISM: Lactuca sativa

<400> SEQUENCE: 53
atgtctctgt ttggaaatgt ttctgccatt aactcaagtg gaaagtgtat agtaatgaat     60
ctttcaagca cacaaatcac ttcaagagat tgtttcaaga ttacctcagg gcaaaaagat    120
gttttgtcat ttggatgctg tgatgctatg gtaacagatt gcaattccc aagtgctcgt    180 tctttttacac caagatcaaa gaagaatgtc tcccctctaa aggtagtttg tgttgattat    240
```

```
ccaagaccag atcttgataa cacatctaat ttcttggaag ctgctcactt gtcttcaacc    300
ttcagaactt ccccacgccc atctaagcca ttgaagattg taattgctgg tgcaggttta    360
gctggtttat caactgctaa gtatttagct gatgcaggtc acaagccaat tttactagaa    420
gcaagagatg ttcttggtgg aaaggtggca gcttggaaag atgatgatgg agattggtat    480
gagacaggtt tacacatatt ctttggagct tacccaaatg tacaaaattt atttggagag    540
ctaggaatta atgatagatt acagtggaag gagcattcta tgatatttgc aatgccaaat    600
aagcctggag aatttagtag gtttgacttc ccagatgttt tacctgcacc attgaatgga    660 attttttgcta tattgaggaa caatgaaatg ctgacgtggc ctgagaaagt gaagtttgca    720
attgggctgt tgcctgcaat gttaggtgga caggcttatg ttgaggccca agatgggctt    780
agtgttcagg actggatgag aaagcaaggt atacctgatc gagttactac tgaagtgttt    840
attgcaatgt caaaagcatt aaactttata aatccagatg aactttcaat gcaatgtatt    900
ctcattgctc taaaccgttt tcttcaggaa agcatggtt ccaagatggc attttttagat    960 gggagcccac cagaaagact ttgcaagcca attgttgacc acatcgagtc actcggtggc   1020
caagtcagag tcaactcacg aatacaaaaa attgagttaa acaaagacgg aactgtccgg   1080
aactttctat tgagtgatgg gaatgttcta gaagctgatg cttatgtttt cgctacccct   1140
gttgacattc tcaagcttct tttacccgaa gaatggaaac caattccata tttcaaaaaa   1200
ttagagaagt tagtcggtgt tcctgttata aacgttcata tatggtttga cagaaagctg   1260
aaaaacacat atgatcactt acttttcagt aggtcacctc tgctgagtgt gtatgctgac   1320
atgtcagtga catgtaagga atattatgat ccgaataagt caatgttgga gttggttctt   1380
gctccagctg aggaatggat ttcaagaagt gacactgata ttattgatgc aacaatgagt   1440
gaactttcaa ggcttttttcc tgatgaaatt gcagctgatc aaagtaaagc aaaaatcttg   1500
aaatataaag ttgttaaaac accaaggtct gtttataaaa ctgttccaga ttgtgaacca   1560
tgtcgacccc tacaaagatc tccaattcaa ggatttttatt tatctggtga ttatactaaa   1620
caaaagtatt tggcttcaat gggggggtgct gttttatctg gaaaaatttg tgcacaagct   1680
attttacaag attatgagat gcttgctaca                                    1710

<210> SEQ ID NO 54
<211> LENGTH: 42
<212> TYPE: DNA
<213> ORGANISM: artificial sequence
<220> FEATURE:
<223> OTHER INFORMATION: Synthetic Construct

<400> SEQUENCE: 54
taatacgact cactataggg tttggagctt acccaaatgt ac                        42

<210> SEQ ID NO 55
<211> LENGTH: 45
<212> TYPE: DNA
<213> ORGANISM: artificial sequence
<220> FEATURE:
<223> OTHER INFORMATION: Synthetic Construct

<400> SEQUENCE: 55
taatacgact cactataggg aggccacgtc agcatttcat tgttc                     45

<210> SEQ ID NO 56
<211> LENGTH: 23
<212> TYPE: DNA
```

```
<213> ORGANISM: artificial sequence
<220> FEATURE:
<223> OTHER INFORMATION: Synthetic Construct

<400> SEQUENCE: 56
ccattcaatg gtgcaggtaa aac                                                  23

<210> SEQ ID NO 57
<211> LENGTH: 21
<212> TYPE: DNA
<213> ORGANISM: artificial sequence
<220> FEATURE:
<223> OTHER INFORMATION: Synthetic Construct

<400> SEQUENCE: 57
catagaatgc tccttccact g                                                    21

<210> SEQ ID NO 58
<211> LENGTH: 33
<212> TYPE: DNA
<213> ORGANISM: artificial sequence
<220> FEATURE:
<223> OTHER INFORMATION: Synthetic Construct

<400> SEQUENCE: 58
caaataaatt ttgtacattt gggtaagctc caa                                       33

<210> SEQ ID NO 59
<211> LENGTH: 2349
<212> TYPE: DNA
<213> ORGANISM: Solanum lycopersicum

<400> SEQUENCE: 59
gggtttatct cgcaagtgtg gctatggtgg gacgtgtcaa attttggatt gtagccaaac          60
atgagatttg atttaaaggg aattggccaa atcaccgaaa gcaggcatct tcatcataaa         120
ttagtttgtt tatttataca gaattatacg cttttactag ttatagcatt cggtatcttt         180
ttctgggtaa ctgccaaacc accacaaatt tcaagtttcc atttaactct tcaacttcaa         240
cccaaccaaa tttatttgct taattgtgca gaaccactcc ctatatcttc taggtgcttt         300
cattcgttcc gagtaaaatg cctcaaattg gacttgtttc tgctgttaac ttgagagtcc         360
aaggtagttc agcttatctt tggagctcga ggtcgtcttc tttgggaact gaaagtcgag         420
atggttgctt gcaaaggaat tcgttatgtt ttgctggtag cgaatcaatg ggtcataagt         480
taaagattcg tactccccat gccacgacca gaagattggt taaggacttg gggcctttaa         540
aggtcgtatg cattgattat ccaagaccag agctggacaa tacagttaac tatttggagg         600
ctgcattttt atcatcaacg ttccgtgctt ctccgcgccc aactaaacca ttggagattg         660
ttattgctgg tgcaggtttg ggtggtttgt ctacagcaaa atatttggca gatgctggtc         720
acaaaccgat actgctggag gcaagggatg ttctaggtgg aaaggtagct gcatggaaag         780
atgatgatgg agattggtac gagactggtt tgcatatatt ctttgggggct acccaaaata         840 ttcagaacct gtttggagaa ttagggatta cgatcgatt gcaatggaag gaacattcaa         900
tgatatttgc aatgccaagc aagccaggag aattcagccg ctttgatttc tccgaagctt         960
tacccgctcc tttaaatgga attttagcca tcttaaagaa taacgaaatg cttacatggc        1020
cagagaaagt caaatttgca attggactct gccagcaat gcttggaggg caatcttatg        1080
ttgaagctca agatgggata agtgttaagg actggatgag aaagcaaggt gtgccggaca        1140
gggtgacaga tgaggtgttc attgctatgt caaaggcact caacttttata aaccctgacg        1200
```

```
aactttcaat gcagtgcatt ttgatcgcat tgaacaggtt tcttcaggag aaacatggtt   1260
caaaaatggc ctttttagat ggtaatcctc ctgagagact ttgcatgccg attgttgaac   1320
acattgagtc aaaaggtggc caagtcagac tgaactcacg aataaaaaag attgagctga   1380
atgaggatgg aagtgtcaag agtttttatac tgagtgacgg tagtgcaatc gagggagatg   1440
cttttgtgtt tgccgctcca gtggatattt tcaagcttct attgcctgaa gactggaaag   1500
agattccata tttccaaaag ttggagaagt tagtcggagt acctgtgata aatgtacata   1560
tatggtttga cagaaaactg aagaacacat atgatcattt gctcttcagc agaagctcac   1620
tgctcagtgt gtatgctgac atgtctgtta catgtaagga atattacaac cccaatcagt   1680
ctatgttgga attggttttt gcacctgcag aagagtggat atctcgcagc gactcagaaa   1740
ttattgatgc aacgatgaag gaactagcaa cgcttttttcc tgatgaaatt tcagcagatc   1800
aaagcaaagc aaaaatattg aagtaccatg ttgtcaaaac tccgaggtct gtttataaaa   1860
ctgtgccagg ttgtgaaccc tgtcggcctt tacaaagatc cccaatagag gggtttttatt   1920 tagccggtga ctacacgaaa cagaaatact tggcttcaat ggaaggcgct gtcttatcag   1980
gaaagctttg tgctcaagct attgtacagg attatgagtt acttgttgga cgtagccaaa   2040
agaagttgtc ggaagcaagc gtagtttagc tttgtggtta ttatttagct tctgtacact   2100
aaatttatga tgcaagaagc gttgtacaca acatatagaa gaagagtgcg aggtgaagca   2160
agtaggagaa atgttaggaa agctcctata caaaaggatg gcatgttgaa gattagcatc   2220
tttttaatcc caagtttaaa tataaagcat atttttatgta ccactttctt tatctggggt   2280
ttgtaatccc tttatatctt tatgcaatct ttacgttagt taaaaaaaaa aaaaaaaaaa   2340
aaaactcga                                                            2349

<210> SEQ ID NO 60
<211> LENGTH: 200
<212> TYPE: DNA
<213> ORGANISM: artificial sequence
<220> FEATURE:
<223> OTHER INFORMATION: Synthetic Construct

<400> SEQUENCE: 60
tcgcagcgac tcagaaatta ttgatgcaac gatgaaggaa ctagcaacgc ttttccctga     60
tgaaatttca gcagatcaaa gcaaagcaaa aatattgaag taccatgttg tcaaaactcc    120
gaggtctgtt tataaaactg tgccaggttg tgaaccctgt cggcctttac aaagatcccc    180
aatagagggg ttttatttag                                                 200

<210> SEQ ID NO 61
<211> LENGTH: 43
<212> TYPE: DNA
<213> ORGANISM: artificial sequence
<220> FEATURE:
<223> OTHER INFORMATION: Synthetic Construct

<400> SEQUENCE: 61
taatacgact cactataggg tcgcagcgac tcagaaatta ttg                        43

<210> SEQ ID NO 62
<211> LENGTH: 45
<212> TYPE: DNA
<213> ORGANISM: artificial sequence
<220> FEATURE:
<223> OTHER INFORMATION: Synthetic Construct
```

<400> SEQUENCE: 62
taatacgact cactataggg gtaaaggccg acagggttca caacc     45

<210> SEQ ID NO 63
<211> LENGTH: 21
<212> TYPE: RNA
<213> ORGANISM: artificial sequence
<220> FEATURE:
<223> OTHER INFORMATION: Synthetic Construct

<400> SEQUENCE: 63
cuaccaucaa caaugguguc c     21

<210> SEQ ID NO 64
<211> LENGTH: 21
<212> TYPE: RNA
<213> ORGANISM: artificial sequence
<220> FEATURE:
<223> OTHER INFORMATION: Synthetic Construct

<400> SEQUENCE: 64
ggacaccauu guugauggua g     21

<210> SEQ ID NO 65
<211> LENGTH: 21
<212> TYPE: RNA
<213> ORGANISM: artificial sequence
<220> FEATURE:
<223> OTHER INFORMATION: Synthetic Construct

<400> SEQUENCE: 65
gucgacaacu ugcuguauag u     21

<210> SEQ ID NO 66
<211> LENGTH: 21
<212> TYPE: RNA
<213> ORGANISM: artificial sequence
<220> FEATURE:
<223> OTHER INFORMATION: Synthetic Construct

<400> SEQUENCE: 66
acuauacagc aaguugucga c     21

<210> SEQ ID NO 67
<211> LENGTH: 21
<212> TYPE: RNA
<213> ORGANISM: artificial sequence
<220> FEATURE:
<223> OTHER INFORMATION: Synthetic Construct

<400> SEQUENCE: 67
ggucaccugg acagagaaua g     21

<210> SEQ ID NO 68
<211> LENGTH: 21
<212> TYPE: RNA
<213> ORGANISM: artificial sequence
<220> FEATURE:
<223> OTHER INFORMATION: Synthetic Construct

<400> SEQUENCE: 68
cuauucucug uccaggugac c     21

<210> SEQ ID NO 69
<211> LENGTH: 21

```
<212> TYPE: RNA
<213> ORGANISM: artificial sequence
<220> FEATURE:
<223> OTHER INFORMATION: Synthetic Construct

<400> SEQUENCE: 69
aaugccagau guugcuauga c                                              21

<210> SEQ ID NO 70
<211> LENGTH: 21
<212> TYPE: RNA
<213> ORGANISM: artificial sequence
<220> FEATURE:
<223> OTHER INFORMATION: Synthetic Construct

<400> SEQUENCE: 70
gucauagcaa caucuggcau u                                              21

<210> SEQ ID NO 71
<211> LENGTH: 2827
<212> TYPE: DNA
<213> ORGANISM: Amaranthus palmeri

<400> SEQUENCE: 71
atggcaacaa tggcttccct agtgagtttg ggaagctctg gagcaacttg ctcagggcaa      60
ttggaggttt ccttttcatt ggttaagaaa attacattgc ctagaagaaa ttgtagttgc     120
aattttaggc aattaggagg ggggaggaga tggcgttacg tttcggtgtg tagactttct     180
gtcactactg attatgtttc tgagcaagga aatgctgttt ctcttgaaaa tgcatatagt     240
gagagtaaag aagagggtct catcttgaag ccttctccta gccggtttt gaaatccggg      300 tctgatggaa atcggaaatt tggggagagt tcggtggcgt tttcgagtaa tgggaaattg     360
gataatgtag aggagaggaa gaaggttatt gattcattgg atgaggtatt agaaaaggcc     420
gagagattag aaacggcgaa cttacaagca gataatagaa aggatagcac aaatgtaaat     480
aaaccgtctc cgagtgtaag tagttcaacc aatggtaaac ctgtaaataa tttgaacaaa     540
gggaagccta agctgcgaa gagcgttttgg agaaagggaa atccagtttc tactgtgcaa     600
aaagtagtgc aagaatctcc gaagattgaa aaggttgaga gagtggaagc tcgaacgacc     660
agccaatcgt ctgaaacgat aagacccca gtgccactac agaggcctga gattaagttg      720
caggcaaagc cttctactgc tcctccaccc atgcctaaga gccggtttt gaaggatgtg      780 gggatgtcct ccagagctga tgggaaggac cagtctgtga atctaaaga gaggaagcct     840 attctagtgg acaaatttgc caccaagaag gcatcagttg atccgtcgat tgctcaagca     900
gtaattgccc caccaaaacc tgctaaattt ccttctggaa agtttaaaga tgattatcgg     960
aagaagggtc ttgcagctgg tgggccgaag aggcgtatgg tcaatgatga tgatattgaa    1020
atgcatgaag acacttcaga gctcggtctt tctattcctg gtgctgctac ggctcggaaa    1080
ggcaggaaat ggagtaaggc aagtcgcaag gctgccagac gccaagcagc tagagatgcc    1140
gctcctgtta agtggaaat cttagaggtt gaagaaaagg gcatgtcgac cgaagaatta    1200
gcatacaact ggctctattag cgaaggtgaa attcttgggt acctgtattc taaggggata    1260
aaaccagatg gtgtgcaaac tcttgacaag gcaatggtaa agatgatatg tgaaagatat    1320
gacgtggagg ttttggacgc actttctgaa caaatggaag aaatggctcg aagaaggaa     1380 attttcgacg aagatgacct tgacaagctt gaagataggc ctcctgtgct tactataatg    1440
ggtcatgtag atcatggcaa gacgaccctt ctggattata tacggaagag caaggttgct    1500
```

```
gcttctgaag ctggtgggat tacacaaggt attggtgctt ataaagtgga agtaccggtt    1560
gatggcaagt tgctgccttg tgtctttctt gacactcccg gacacgaggc gttcggggca    1620
atgagggctc gtggagcaag agtgacagat attgctatta tagttgtagc tgctgacgat    1680
gggatccgtc ctcaaacaaa tgaagccata gcacatgcaa aagcagctgg tgtacctatt    1740
gtggttgcaa ttaataagat tgacaaggat ggggctaatc cggaccgtgt gatgcaagag    1800
ctttcatcaa ttggtctaat gccagaggat tggggtggtg ataccccaat ggtcaagata    1860
agtgctctaa aaggtgaaaa tgtggacgag ttactcgaga cagccatgct tgtcgccgag    1920
ttgcaagagt taaaggctaa tcctcagagg aacgctaagg gcactgtaat tgaggctggt    1980
cttcataaat caaaaggacc cattgccact tttattgtgc agaatggtac cctcaaacaa    2040
ggggatactg tagtttgtgg ggaagcattt gggaaggttc gtgccctatt tgatcacgga    2100
gggaatcgcg ttgatgaagc tggtccatct attcccgtgc aggttattgg attgaataat    2160
gttccttttg ccggtgatga gttcgaggta gtgagttccc ttgatatagc tcgtgaaaag    2220
gcagaggtcc gtgcagagtc tttacgaaat gagcgtatag ctgctaaggc cggagacgga    2280
aaggttacgc tgtcatcctt ggcatcggct gtttcttcag ggaagatggc tggtttggat    2340
ttgcaccagt taaatatcat tttgaaggtt gatgttcagg gatcaatcga ggcattgagg    2400
caagctctag aagttcttcc tcaagataac gtcactttga agtttctctt acaagcgacc    2460
ggagatgtta ctacaagtga tgttgatctt gcagttgcta gtaaagctat tatcttgggg    2520
ttcaatgtga aggcaccagg ttctgtcgaa aaattagcag ataacaaagg tgttgaaatt    2580
cggctttata aagtcattta tgatctaatt gacgacatgc ggagtgcaat ggaaggaatg    2640
ctagatcccg ttgaggaaca agttgcaatt ggttcagccg aagtgcgggc tacattcagt    2700
agtggtagtg gccgtgtcgc tggatgcatg gtgaccgagg gaaagattac caaaggctgt    2760
gggattcgag tgatacggaa gggaaaaact gtccacgttg gagttcttga ttcgttgcgt    2820
cgagtaa                                                              2827

<210> SEQ ID NO 72
<211> LENGTH: 200
<212> TYPE: DNA
<213> ORGANISM: artificial sequence
<220> FEATURE:
<223> OTHER INFORMATION: Synthetic Construct

<400> SEQUENCE: 72
tttcgagtaa tgggaaattg gataatgtag aggagaggaa gaaggttatt gattcattgg     60
atgaggtatt agaaaaggcc gagagattag aaacggcgaa cttacaagca gataatagaa    120
aggatagcac aaatgtaaat aaaccgtctc cgagtgtaag tagttcaacc aatggtaaac    180 ctgtaaaataa tttgaacaaa                                               200

<210> SEQ ID NO 73
<211> LENGTH: 160
<212> TYPE: RNA
<213> ORGANISM: artificial sequence
<220> FEATURE:
<223> OTHER INFORMATION: Synthetic Construct

<400> SEQUENCE: 73
uucgaguaau gggaaauugg auaauguaga ggagaggaag aagguuauug auucauugga     60
ugagguauua gaaaaggccg agagauuaga aacggcgaac uuacaagcag auaauagaaa    120
ggauagcaca aauguaaaua aaccgucucc gagguguaagu                         160
```

<210> SEQ ID NO 74
<211> LENGTH: 160
<212> TYPE: RNA
<213> ORGANISM: artificial sequence
<220> FEATURE:
<223> OTHER INFORMATION: Synthetic Construct

<400> SEQUENCE: 74
acuuacacuc ggagacgguu uauuuacauu ugugcuaucc uuucuauuau cugcuuguaa    60
guucgccguu ucuaaucucu cggccuuuuc uaauaccuca uccaaugaau caauaaccuu   120
cuuccucucc ucuacauuau ccaauuuccc auuacucgaa                        160

<210> SEQ ID NO 75
<211> LENGTH: 22
<212> TYPE: DNA
<213> ORGANISM: artificial sequence
<220> FEATURE:
<223> OTHER INFORMATION: Synthetic Construct

<400> SEQUENCE: 75
atttctccaa acgctcttcg ca                                            22

<210> SEQ ID NO 76
<211> LENGTH: 22
<212> TYPE: DNA
<213> ORGANISM: artificial sequence
<220> FEATURE:
<223> OTHER INFORMATION: Synthetic Construct

<400> SEQUENCE: 76
atccaatttc ccattactcg aa                                            22

<210> SEQ ID NO 77
<211> LENGTH: 22
<212> TYPE: DNA
<213> ORGANISM: artificial sequence
<220> FEATURE:
<223> OTHER INFORMATION: Synthetic Construct

<400> SEQUENCE: 77
gtttctaatc tctcggcctt tt                                            22

<210> SEQ ID NO 78
<211> LENGTH: 21
<212> TYPE: DNA
<213> ORGANISM: artificial sequence
<220> FEATURE:
<223> OTHER INFORMATION: Synthetic Construct

<400> SEQUENCE: 78
ttgaactact tacactcgga g                                             21

<210> SEQ ID NO 79
<211> LENGTH: 21
<212> TYPE: DNA
<213> ORGANISM: artificial sequence
<220> FEATURE:
<223> OTHER INFORMATION: Synthetic Construct

<400> SEQUENCE: 79
taaccttctt cctctcctct a                                             21

<210> SEQ ID NO 80

```
<211> LENGTH: 21
<212> TYPE: DNA
<213> ORGANISM: artificial sequence
<220> FEATURE:
<223> OTHER INFORMATION: Synthetic Construct

<400> SEQUENCE: 80
gtccttccca tcagctctgg a                                               21

<210> SEQ ID NO 81
<211> LENGTH: 20
<212> TYPE: DNA
<213> ORGANISM: artificial sequence
<220> FEATURE:
<223> OTHER INFORMATION: Synthetic Construct

<400> SEQUENCE: 81
cgtagcagca ccaggaatag                                                 20

<210> SEQ ID NO 82
<211> LENGTH: 21
<212> TYPE: DNA
<213> ORGANISM: artificial sequence
<220> FEATURE:
<223> OTHER INFORMATION: Synthetic Construct

<400> SEQUENCE: 82
cagcagctac aactataata g                                               21

<210> SEQ ID NO 83
<211> LENGTH: 25
<212> TYPE: RNA
<213> ORGANISM: artificial sequence
<220> FEATURE:
<223> OTHER INFORMATION: Synthetic Construct

<400> SEQUENCE: 83
cuaccaucaa caauguguc cauac                                            25

<210> SEQ ID NO 84
<211> LENGTH: 27
<212> TYPE: RNA
<213> ORGANISM: artificial sequence
<220> FEATURE:
<223> OTHER INFORMATION: Synthetic Construct

<400> SEQUENCE: 84
guauggacac cauuguugau gguagua                                         27

<210> SEQ ID NO 85
<211> LENGTH: 23
<212> TYPE: RNA
<213> ORGANISM: artificial sequence
<220> FEATURE:
<223> OTHER INFORMATION: Synthetic Construct

<400> SEQUENCE: 85
aguugguggg caaucaucaa uug                                             23

<210> SEQ ID NO 86
<211> LENGTH: 27
<212> TYPE: RNA
<213> ORGANISM: artificial sequence
<220> FEATURE:
<223> OTHER INFORMATION: Synthetic Construct

<400> SEQUENCE: 86
```

```
aacaauugau gauugcccac caacucu                                              27

<210> SEQ ID NO 87
<211> LENGTH: 24
<212> TYPE: RNA
<213> ORGANISM: artificial sequence
<220> FEATURE:
<223> OTHER INFORMATION: Synthetic Construct

<400> SEQUENCE: 87
ggucgacaac uugcuguaua guga                                                 24

<210> SEQ ID NO 88
<211> LENGTH: 27
<212> TYPE: RNA
<213> ORGANISM: artificial sequence
<220> FEATURE:
<223> OTHER INFORMATION: Synthetic Construct

<400> SEQUENCE: 88
aucacuauac agcaaguugu cgaccuc                                              27

<210> SEQ ID NO 89
<211> LENGTH: 24
<212> TYPE: RNA
<213> ORGANISM: artificial sequence
<220> FEATURE:
<223> OTHER INFORMATION: Synthetic Construct

<400> SEQUENCE: 89
ugcaagguca ccuggacaga gaaa                                                 24

<210> SEQ ID NO 90
<211> LENGTH: 27
<212> TYPE: RNA
<213> ORGANISM: artificial sequence
<220> FEATURE:
<223> OTHER INFORMATION: Synthetic Construct

<400> SEQUENCE: 90
uauucucugu ccaggugacc uugcaac                                              27

<210> SEQ ID NO 91
<211> LENGTH: 21
<212> TYPE: RNA
<213> ORGANISM: artificial sequence
<220> FEATURE:
<223> OTHER INFORMATION: Synthetic Construct

<400> SEQUENCE: 91
aacaugaaca aaaugccaga u                                                    21

<210> SEQ ID NO 92
<211> LENGTH: 21
<212> TYPE: RNA
<213> ORGANISM: artificial sequence
<220> FEATURE:
<223> OTHER INFORMATION: Synthetic Construct

<400> SEQUENCE: 92
aucuggcauu uuguucaugu u                                                    21

<210> SEQ ID NO 93
<211> LENGTH: 27
<212> TYPE: RNA
```

```
<213> ORGANISM: artificial sequence
<220> FEATURE:
<223> OTHER INFORMATION: Synthetic Construct

<400> SEQUENCE: 93
guauggacac cauuguugau gguagua                                              27

<210> SEQ ID NO 94
<211> LENGTH: 27
<212> TYPE: RNA
<213> ORGANISM: artificial sequence
<220> FEATURE:
<223> OTHER INFORMATION: Synthetic Construct

<400> SEQUENCE: 94
uacuaccauc aacaauggug uccauac                                              27

<210> SEQ ID NO 95
<211> LENGTH: 27
<212> TYPE: RNA
<213> ORGANISM: artificial sequence
<220> FEATURE:
<223> OTHER INFORMATION: Synthetic Construct

<400> SEQUENCE: 95
aauaauugau gauugcccac caacucu                                              27

<210> SEQ ID NO 96
<211> LENGTH: 27
<212> TYPE: RNA
<213> ORGANISM: artificial sequence
<220> FEATURE:
<223> OTHER INFORMATION: Synthetic Construct

<400> SEQUENCE: 96
agaguuggug ggcaaucauc aauuauu                                              27

<210> SEQ ID NO 97
<211> LENGTH: 27
<212> TYPE: RNA
<213> ORGANISM: artificial sequence
<220> FEATURE:
<223> OTHER INFORMATION: Synthetic Construct

<400> SEQUENCE: 97
aucacuauac agcaaguugu cgaccac                                              27

<210> SEQ ID NO 98
<211> LENGTH: 27
<212> TYPE: RNA
<213> ORGANISM: artificial sequence
<220> FEATURE:
<223> OTHER INFORMATION: Synthetic Construct

<400> SEQUENCE: 98
guggucgaca acuugcugua uagugau                                              27

<210> SEQ ID NO 99
<211> LENGTH: 27
<212> TYPE: RNA
<213> ORGANISM: artificial sequence
<220> FEATURE:
<223> OTHER INFORMATION: Synthetic Construct

<400> SEQUENCE: 99
uauucucugu ccaggugacc uugcaac                                              27
```

<210> SEQ ID NO 100
<211> LENGTH: 27
<212> TYPE: RNA
<213> ORGANISM: artificial sequence
<220> FEATURE:
<223> OTHER INFORMATION: Synthetic Construct

<400> SEQUENCE: 100
guugcaaggu caccuggaca gagaaua                                           27

<210> SEQ ID NO 101
<211> LENGTH: 29
<212> TYPE: RNA
<213> ORGANISM: artificial sequence
<220> FEATURE:
<223> OTHER INFORMATION: Synthetic Construct

<400> SEQUENCE: 101
gguauggaca ccauuguuga ugguaguac                                         29

<210> SEQ ID NO 102
<211> LENGTH: 29
<212> TYPE: RNA
<213> ORGANISM: artificial sequence
<220> FEATURE:
<223> OTHER INFORMATION: Synthetic Construct

<400> SEQUENCE: 102
gcuaccauca acaauggugu ccauaccac                                         29

<210> SEQ ID NO 103
<211> LENGTH: 29
<212> TYPE: RNA
<213> ORGANISM: artificial sequence
<220> FEATURE:
<223> OTHER INFORMATION: Synthetic Construct

<400> SEQUENCE: 103
gaagaauuga ugauugccca ccaacucac                                         29

<210> SEQ ID NO 104
<211> LENGTH: 29
<212> TYPE: RNA
<213> ORGANISM: artificial sequence
<220> FEATURE:
<223> OTHER INFORMATION: Synthetic Construct

<400> SEQUENCE: 104
gaguuggugg gcaaucauca auuauucac                                         29

<210> SEQ ID NO 105
<211> LENGTH: 27
<212> TYPE: RNA
<213> ORGANISM: artificial sequence
<220> FEATURE:
<223> OTHER INFORMATION: Synthetic Construct

<400> SEQUENCE: 105
gaucacuaua cagcaaguug ucgacac                                           27

<210> SEQ ID NO 106
<211> LENGTH: 27
<212> TYPE: RNA
<213> ORGANISM: artificial sequence
<220> FEATURE:

<223> OTHER INFORMATION: Synthetic Construct

<400> SEQUENCE: 106
gucgacaacu ugcuguauag ugaucac         27

<210> SEQ ID NO 107
<211> LENGTH: 29
<212> TYPE: RNA
<213> ORGANISM: artificial sequence
<220> FEATURE:
<223> OTHER INFORMATION: Synthetic Construct

<400> SEQUENCE: 107
guauucucug uccaggugac cuugcacac         29

<210> SEQ ID NO 108
<211> LENGTH: 29
<212> TYPE: RNA
<213> ORGANISM: artificial sequence
<220> FEATURE:
<223> OTHER INFORMATION: Synthetic Construct

<400> SEQUENCE: 108
gugcaagguc accuggacag agaauacac         29

<210> SEQ ID NO 109
<211> LENGTH: 58
<212> TYPE: RNA
<213> ORGANISM: artificial sequence
<220> FEATURE:
<223> OTHER INFORMATION: Synthetic Construct

<400> SEQUENCE: 109
guauggacac cauuguugau gguaguagaa auacuaccau caacaauggu guccauac         58

<210> SEQ ID NO 110
<211> LENGTH: 58
<212> TYPE: RNA
<213> ORGANISM: artificial sequence
<220> FEATURE:
<223> OTHER INFORMATION: Synthetic Construct

<400> SEQUENCE: 110
aauaauugau gauugcccac caacucugaa aagaguuggu gggcaaucau caauuauu         58

<210> SEQ ID NO 111
<211> LENGTH: 58
<212> TYPE: RNA
<213> ORGANISM: artificial sequence
<220> FEATURE:
<223> OTHER INFORMATION: Synthetic Construct

<400> SEQUENCE: 111
aucacuauac agcaaguugu cgaccacgaa aguggucgac aacuugcugu auagugau         58

<210> SEQ ID NO 112
<211> LENGTH: 58
<212> TYPE: RNA
<213> ORGANISM: artificial sequence
<220> FEATURE:
<223> OTHER INFORMATION: Synthetic Construct

<400> SEQUENCE: 112
uauucucugu ccaggugacc uugcaacgaa aguugcaagg ucaccuggac agagaaua         58

```
<210> SEQ ID NO 113
<211> LENGTH: 168
<212> TYPE: RNA
<213> ORGANISM: artificial sequence
<220> FEATURE:
<223> OTHER INFORMATION: Synthetic Construct

<400> SEQUENCE: 113
gaucacaaau uugccgguuu augaucaaau acggaacaua agacagauac acuugaacac      60
caugauucgc auuggggug ugguuacucg ucguucugga guauucccuc aguugaugca       120
ggugaaguau gacugcaaua aaugggggc uauccugggu cccuuuuu                    168

<210> SEQ ID NO 114
<211> LENGTH: 168
<212> TYPE: RNA
<213> ORGANISM: artificial sequence
<220> FEATURE:
<223> OTHER INFORMATION: Synthetic Construct

<400> SEQUENCE: 114
aaaaagggac ccaggauagc cccacauuua uugcagucau acuucaccug caucaacuga      60
gggaauacuc cagaacgacg aguaaccaca cccccaaugc gaaucauggu guucaagugu      120 aucugcuua uguuccguau uugaucauaa accggcaaau uugugauc                    168

<210> SEQ ID NO 115
<211> LENGTH: 25
<212> TYPE: RNA
<213> ORGANISM: artificial sequence
<220> FEATURE:
<223> OTHER INFORMATION: Synthetic Construct

<400> SEQUENCE: 115
uuuucuaaua ccucauccaa ugaau                                            25

<210> SEQ ID NO 116
<211> LENGTH: 25
<212> TYPE: RNA
<213> ORGANISM: artificial sequence
<220> FEATURE:
<223> OTHER INFORMATION: Synthetic Construct

<400> SEQUENCE: 116
auucauugga ugagguauua gaaaa                                            25

<210> SEQ ID NO 117
<211> LENGTH: 25
<212> TYPE: RNA
<213> ORGANISM: artificial sequence
<220> FEATURE:
<223> OTHER INFORMATION: Synthetic Construct

<400> SEQUENCE: 117
uaucugcuug uaaguucgcc guuuc                                            25

<210> SEQ ID NO 118
<211> LENGTH: 25
<212> TYPE: RNA
<213> ORGANISM: artificial sequence
<220> FEATURE:
<223> OTHER INFORMATION: Synthetic Construct

<400> SEQUENCE: 118
gaaacggcga acuuacaagc agaua                                            25
```

```
<210> SEQ ID NO 119
<211> LENGTH: 25
<212> TYPE: RNA
<213> ORGANISM: artificial sequence
<220> FEATURE:
<223> OTHER INFORMATION: Synthetic Construct

<400> SEQUENCE: 119
ggagacgguu uauuuacauu ugugc                                          25

<210> SEQ ID NO 120
<211> LENGTH: 25
<212> TYPE: RNA
<213> ORGANISM: artificial sequence
<220> FEATURE:
<223> OTHER INFORMATION: Synthetic Construct

<400> SEQUENCE: 120
gcacaaaugu aaauaaaccg ucucc                                          25

<210> SEQ ID NO 121
<211> LENGTH: 25
<212> TYPE: RNA
<213> ORGANISM: artificial sequence
<220> FEATURE:
<223> OTHER INFORMATION: Synthetic Construct

<400> SEQUENCE: 121
uauuuacagg uuuaccaug guuga                                           25

<210> SEQ ID NO 122
<211> LENGTH: 25
<212> TYPE: RNA
<213> ORGANISM: artificial sequence
<220> FEATURE:
<223> OTHER INFORMATION: Synthetic Construct

<400> SEQUENCE: 122
ucaaccaaug guaaaccugu aaaua                                          25

<210> SEQ ID NO 123
<211> LENGTH: 185
<212> TYPE: RNA
<213> ORGANISM: artificial sequence
<220> FEATURE:
<223> OTHER INFORMATION: Synthetic Construct

<400> SEQUENCE: 123
gacggaaacc cuccagagag gcugugcaug ccuauuguua aacacaucga gucacuaggu    60
ggugaaguua aacuuaacuc ucguauacaa aagauucagu uggaccagag uggaagcgug   120
aagaguuuuu ugcuaaauaa cgggagggaa auacgaggag augccuaugu uuuugccacc   180
ccagu                                                               185

<210> SEQ ID NO 124
<211> LENGTH: 185
<212> TYPE: RNA
<213> ORGANISM: artificial sequence
<220> FEATURE:
<223> OTHER INFORMATION: Synthetic Construct

<400> SEQUENCE: 124
acuggggugg caaaaacaua ggcaucuccu cguauuccc ucccguuauu uagcaaaaaa     60
cucuucacgc uuccacucug guccaacuga aucuuuugua uacgagaguu aaguuuaacu   120
```
ucaccaccua gugacucgau guguuuaaca auaggcaugc acagccucuc uggagggbuu    180
ccguc    185

<210> SEQ ID NO 125
<211> LENGTH: 22
<212> TYPE: DNA
<213> ORGANISM: artificial sequence
<220> FEATURE:
<223> OTHER INFORMATION: Synthetic Construct

<400> SEQUENCE: 125
gtgatattac ctccaacacg at    22

<210> SEQ ID NO 126
<211> LENGTH: 21
<212> TYPE: DNA
<213> ORGANISM: artificial sequence
<220> FEATURE:
<223> OTHER INFORMATION: Synthetic Construct

<400> SEQUENCE: 126
atagtaagca caggatcgga g    21

<210> SEQ ID NO 127
<211> LENGTH: 21
<212> TYPE: DNA
<213> ORGANISM: artificial sequence
<220> FEATURE:
<223> OTHER INFORMATION: Synthetic Construct

<400> SEQUENCE: 127
ctttcaatcc actgtcaacc g    21

<210> SEQ ID NO 128
<211> LENGTH: 22
<212> TYPE: DNA
<213> ORGANISM: artificial sequence
<220> FEATURE:
<223> OTHER INFORMATION: Synthetic Construct

<400> SEQUENCE: 128
atcaagcgtt cgaagacctc at    22

<210> SEQ ID NO 129
<211> LENGTH: 21
<212> TYPE: DNA
<213> ORGANISM: artificial sequence
<220> FEATURE:
<223> OTHER INFORMATION: Synthetic Construct

<400> SEQUENCE: 129
cagcaatggc ggtaggtaac a    21

<210> SEQ ID NO 130
<211> LENGTH: 21
<212> TYPE: DNA
<213> ORGANISM: artificial sequence
<220> FEATURE:
<223> OTHER INFORMATION: Synthetic Construct

<400> SEQUENCE: 130
gcaattgccc gaatcctttt a    21

<210> SEQ ID NO 131

-continued

<211> LENGTH: 21
<212> TYPE: DNA
<213> ORGANISM: artificial sequence
<220> FEATURE:
<223> OTHER INFORMATION: Synthetic Construct

<400> SEQUENCE: 131
tagctcaata tcaaggtcct a        21

<210> SEQ ID NO 132
<211> LENGTH: 21
<212> TYPE: DNA
<213> ORGANISM: artificial sequence
<220> FEATURE:
<223> OTHER INFORMATION: Synthetic Construct

<400> SEQUENCE: 132
tcataagcac cctctataca c        21

<210> SEQ ID NO 133
<211> LENGTH: 20
<212> TYPE: DNA
<213> ORGANISM: artificial sequence
<220> FEATURE:
<223> OTHER INFORMATION: Synthetic Construct

<400> SEQUENCE: 133
ttcttaacct cgtcgagatg          20

<210> SEQ ID NO 134
<211> LENGTH: 21
<212> TYPE: DNA
<213> ORGANISM: artificial sequence
<220> FEATURE:
<223> OTHER INFORMATION: Synthetic Construct

<400> SEQUENCE: 134
atacccgagt atccttgcaa a        21

<210> SEQ ID NO 135
<211> LENGTH: 21
<212> TYPE: DNA
<213> ORGANISM: artificial sequence
<220> FEATURE:
<223> OTHER INFORMATION: Synthetic Construct

<400> SEQUENCE: 135
tagggcccac ggccttggag t        21

<210> SEQ ID NO 136
<211> LENGTH: 21
<212> TYPE: DNA
<213> ORGANISM: artificial sequence
<220> FEATURE:
<223> OTHER INFORMATION: Synthetic Construct

<400> SEQUENCE: 136
agcggatata acctcagcta g        21

<210> SEQ ID NO 137
<211> LENGTH: 21
<212> TYPE: DNA
<213> ORGANISM: artificial sequence
<220> FEATURE:
<223> OTHER INFORMATION: Synthetic Construct

<400> SEQUENCE: 137
cttcgtggcc aacgaatga c                                               21

<210> SEQ ID NO 138
<211> LENGTH: 21
<212> TYPE: DNA
<213> ORGANISM: artificial sequence
<220> FEATURE:
<223> OTHER INFORMATION: Synthetic Construct

<400> SEQUENCE: 138
caagctcggg tccctgcttg c                                              21

<210> SEQ ID NO 139
<211> LENGTH: 21
<212> TYPE: DNA
<213> ORGANISM: artificial sequence
<220> FEATURE:
<223> OTHER INFORMATION: Synthetic Construct

<400> SEQUENCE: 139
ggaaggtaga tgacatgagt t                                              21

<210> SEQ ID NO 140
<211> LENGTH: 21
<212> TYPE: DNA
<213> ORGANISM: artificial sequence
<220> FEATURE:
<223> OTHER INFORMATION: Synthetic Construct

<400> SEQUENCE: 140
gatggcatag ttaccactgt c                                              21

<210> SEQ ID NO 141
<211> LENGTH: 21
<212> TYPE: DNA
<213> ORGANISM: artificial sequence
<220> FEATURE:
<223> OTHER INFORMATION: Synthetic Construct

<400> SEQUENCE: 141
tccgtagctt acataccgaa g                                              21

<210> SEQ ID NO 142
<211> LENGTH: 21
<212> TYPE: DNA
<213> ORGANISM: artificial sequence
<220> FEATURE:
<223> OTHER INFORMATION: Synthetic Construct

<400> SEQUENCE: 142
tccaagtgaa taggagaaac a                                              21

<210> SEQ ID NO 143
<211> LENGTH: 21
<212> TYPE: DNA
<213> ORGANISM: artificial sequence
<220> FEATURE:
<223> OTHER INFORMATION: Synthetic Construct

<400> SEQUENCE: 143
agcagcttct gcgtcttcta c                                              21

<210> SEQ ID NO 144
<211> LENGTH: 21
<212> TYPE: DNA

```
<213> ORGANISM: artificial sequence
<220> FEATURE:
<223> OTHER INFORMATION: Synthetic Construct

<400> SEQUENCE: 144
acagcacgca cgccaagacc g                                              21

<210> SEQ ID NO 145
<211> LENGTH: 21
<212> TYPE: DNA
<213> ORGANISM: artificial sequence
<220> FEATURE:
<223> OTHER INFORMATION: Synthetic Construct

<400> SEQUENCE: 145
cgatgtaagg aatttggtaa a                                              21

<210> SEQ ID NO 146
<211> LENGTH: 21
<212> TYPE: DNA
<213> ORGANISM: artificial sequence
<220> FEATURE:
<223> OTHER INFORMATION: Synthetic Construct

<400> SEQUENCE: 146 cgagggatt gcagcagaag a                                               21

<210> SEQ ID NO 147
<211> LENGTH: 21
<212> TYPE: DNA
<213> ORGANISM: artificial sequence
<220> FEATURE:
<223> OTHER INFORMATION: Synthetic Construct

<400> SEQUENCE: 147
gtaggagaat acggtgaagt a                                              21

<210> SEQ ID NO 148
<211> LENGTH: 21
<212> TYPE: DNA
<213> ORGANISM: artificial sequence
<220> FEATURE:
<223> OTHER INFORMATION: Synthetic Construct

<400> SEQUENCE: 148
gaccccaaga aaatcgtctg c                                              21

<210> SEQ ID NO 149
<211> LENGTH: 19
<212> TYPE: DNA
<213> ORGANISM: artificial sequence
<220> FEATURE:
<223> OTHER INFORMATION: Synthetic Construct

<400> SEQUENCE: 149
gtcttacaag ggttctcaa                                                 19

<210> SEQ ID NO 150
<211> LENGTH: 21
<212> TYPE: DNA
<213> ORGANISM: artificial sequence
<220> FEATURE:
<223> OTHER INFORMATION: Synthetic Construct

<400> SEQUENCE: 150
atctatgttc acctccctgt g                                              21
```

<210> SEQ ID NO 151
<211> LENGTH: 21
<212> TYPE: DNA
<213> ORGANISM: artificial sequence
<220> FEATURE:
<223> OTHER INFORMATION: Synthetic Construct

<400> SEQUENCE: 151
ataaaccatt agctttcccg g				21

<210> SEQ ID NO 152
<211> LENGTH: 21
<212> TYPE: DNA
<213> ORGANISM: artificial sequence
<220> FEATURE:
<223> OTHER INFORMATION: Synthetic Construct

<400> SEQUENCE: 152
tttattggaa caagcggagt t				21

<210> SEQ ID NO 153
<211> LENGTH: 21
<212> TYPE: DNA
<213> ORGANISM: artificial sequence
<220> FEATURE:
<223> OTHER INFORMATION: Synthetic Construct

<400> SEQUENCE: 153
tatagcacca cttcccgata g				21

<210> SEQ ID NO 154
<211> LENGTH: 21
<212> TYPE: DNA
<213> ORGANISM: artificial sequence
<220> FEATURE:
<223> OTHER INFORMATION: Synthetic Construct

<400> SEQUENCE: 154
gcaccacgag gatcacaaga a				21

<210> SEQ ID NO 155
<211> LENGTH: 21
<212> TYPE: DNA
<213> ORGANISM: artificial sequence
<220> FEATURE:
<223> OTHER INFORMATION: Synthetic Construct

<400> SEQUENCE: 155
ccacccgaga aacctctcca a				21

<210> SEQ ID NO 156
<211> LENGTH: 21
<212> TYPE: DNA
<213> ORGANISM: artificial sequence
<220> FEATURE:
<223> OTHER INFORMATION: Synthetic Construct

<400> SEQUENCE: 156
cagtcttgac gagtgattcc t				21

<210> SEQ ID NO 157
<211> LENGTH: 22
<212> TYPE: DNA
<213> ORGANISM: artificial sequence
<220> FEATURE:

```
<223> OTHER INFORMATION: Synthetic Construct

<400> SEQUENCE: 157
gttcttcagg gctaaatcgg ga                                              22

<210> SEQ ID NO 158
<211> LENGTH: 22
<212> TYPE: DNA
<213> ORGANISM: artificial sequence
<220> FEATURE:
<223> OTHER INFORMATION: Synthetic Construct

<400> SEQUENCE: 158
gttcaagagc ttcaacgaga ac                                              22

<210> SEQ ID NO 159
<211> LENGTH: 22
<212> TYPE: DNA
<213> ORGANISM: artificial sequence
<220> FEATURE:
<223> OTHER INFORMATION: Synthetic Construct

<400> SEQUENCE: 159
atacaaactc caacgcgtcc ag                                              22

<210> SEQ ID NO 160
<211> LENGTH: 22
<212> TYPE: DNA
<213> ORGANISM: artificial sequence
<220> FEATURE:
<223> OTHER INFORMATION: Synthetic Construct

<400> SEQUENCE: 160
ctcttggaaa gcatcagtac ca                                              22

<210> SEQ ID NO 161
<211> LENGTH: 22
<212> TYPE: DNA
<213> ORGANISM: artificial sequence
<220> FEATURE:
<223> OTHER INFORMATION: Synthetic Construct

<400> SEQUENCE: 161
ctagaaagat acccacccaa tt                                              22

<210> SEQ ID NO 162
<211> LENGTH: 22
<212> TYPE: DNA
<213> ORGANISM: artificial sequence
<220> FEATURE:
<223> OTHER INFORMATION: Synthetic Construct

<400> SEQUENCE: 162
actagaattc aaacacccac cc                                              22

<210> SEQ ID NO 163
<211> LENGTH: 22
<212> TYPE: DNA
<213> ORGANISM: artificial sequence
<220> FEATURE:
<223> OTHER INFORMATION: Synthetic Construct

<400> SEQUENCE: 163
tttctgctca ttcaactcct cc                                              22
```

```
<210> SEQ ID NO 164
<211> LENGTH: 22
<212> TYPE: DNA
<213> ORGANISM: artificial sequence
<220> FEATURE:
<223> OTHER INFORMATION: Synthetic Construct

<400> SEQUENCE: 164
tatgtatgtg cccggttagc tt                                          22

<210> SEQ ID NO 165
<211> LENGTH: 21
<212> TYPE: DNA
<213> ORGANISM: artificial sequence
<220> FEATURE:
<223> OTHER INFORMATION: Synthetic Construct

<400> SEQUENCE: 165
tcatatccaa gccagatcct c                                           21

<210> SEQ ID NO 166
<211> LENGTH: 21
<212> TYPE: DNA
<213> ORGANISM: artificial sequence
<220> FEATURE:
<223> OTHER INFORMATION: Synthetic Construct

<400> SEQUENCE: 166
tgcatcacac atcaccaaga t                                           21

<210> SEQ ID NO 167
<211> LENGTH: 21
<212> TYPE: DNA
<213> ORGANISM: artificial sequence
<220> FEATURE:
<223> OTHER INFORMATION: Synthetic Construct

<400> SEQUENCE: 167
gtactcctgt tcaatgccat a                                           21

<210> SEQ ID NO 168
<211> LENGTH: 21
<212> TYPE: DNA
<213> ORGANISM: artificial sequence
<220> FEATURE:
<223> OTHER INFORMATION: Synthetic Construct

<400> SEQUENCE: 168
attgatacca gcatagagac a                                           21

<210> SEQ ID NO 169
<211> LENGTH: 21
<212> TYPE: DNA
<213> ORGANISM: artificial sequence
<220> FEATURE:
<223> OTHER INFORMATION: Synthetic Construct

<400> SEQUENCE: 169
agcaattctc tctagaatgt a                                           21

<210> SEQ ID NO 170
<211> LENGTH: 21
<212> TYPE: DNA
<213> ORGANISM: artificial sequence
<220> FEATURE:
<223> OTHER INFORMATION: Synthetic Construct
```

```
<400> SEQUENCE: 170
catcattcct catcgactta g                                          21

<210> SEQ ID NO 171
<211> LENGTH: 21
<212> TYPE: DNA
<213> ORGANISM: artificial sequence
<220> FEATURE:
<223> OTHER INFORMATION: Synthetic Construct

<400> SEQUENCE: 171
ctctcgttgc cctctccata a                                          21

<210> SEQ ID NO 172
<211> LENGTH: 21
<212> TYPE: DNA
<213> ORGANISM: artificial sequence
<220> FEATURE:
<223> OTHER INFORMATION: Synthetic Construct

<400> SEQUENCE: 172
caacgcccca ggagaaagtt c                                          21

<210> SEQ ID NO 173
<211> LENGTH: 195
<212> TYPE: RNA
<213> ORGANISM: artificial sequence
<220> FEATURE:
<223> OTHER INFORMATION: Synthetic Construct

<400> SEQUENCE: 173
cugaagcugg ugaaggugaa gauggacgaa ugaaaucugc gauuggaauu gggacccuuc    60
uucaggaugg cuugggagau acgaucaggg ugucucuaac agaaccacca gaagaggaga   120
uagacccuug cagaagguug gcaaaucuug gaacaaaagc agcugaaauu cagcaaggag   180
uggcaccauu ugaag                                                  195

<210> SEQ ID NO 174
<211> LENGTH: 195
<212> TYPE: RNA
<213> ORGANISM: artificial sequence
<220> FEATURE:
<223> OTHER INFORMATION: Synthetic Construct

<400> SEQUENCE: 174
cuucaaaugg ugccacuccu ugcugaauuu cagcugcuuu uguuccaaga uuugccaacc    60
uucugcaagg gucuaucucc ucuucgggug guucuguuag agacacccug aucguaucuc   120
ccaagccauc cugaagaagg gucccaauuc caaucgcaga uuucauucgu ccaucuucac   180
cuucaccagc uucag                                                  195

<210> SEQ ID NO 175
<211> LENGTH: 183
<212> TYPE: RNA
<213> ORGANISM: artificial sequence
<220> FEATURE:
<223> OTHER INFORMATION: Synthetic Construct

<400> SEQUENCE: 175
ucccaucaaa gucccuaca aaauaugugc aguuccuau cuuccuugcc gccauucaua     60
caaacuaugu ugauuguaca aggggcuug gugauuugu cuuucuaag aguuugaca      120 augagauugu acugugggag ccaauuauga aggagcaauc uccggagag gguucaguug   180
``` aca                                                                          183

<210> SEQ ID NO 176
<211> LENGTH: 183
<212> TYPE: RNA
<213> ORGANISM: artificial sequence
<220> FEATURE:
<223> OTHER INFORMATION: Synthetic Construct

<400> SEQUENCE: 176
ugucaacuga acccucucca ggagauugcu ccuucauaau uggcucccac aguacaaucu    60
cauugucaac acucuuagaa agaacaaaau caccaagcca ccuugacaa ucaacauagu   120 uuguaugaau ggcggcaagg aagauaggaa acugcacaua uuuuguaggg aacuuugaug   180
gga                                                                          183

<210> SEQ ID NO 177
<211> LENGTH: 143
<212> TYPE: RNA
<213> ORGANISM: artificial sequence
<220> FEATURE:
<223> OTHER INFORMATION: Synthetic Construct

<400> SEQUENCE: 177
uugugcuuaa aacaucgacc agacagacaa uauuucuucc uguuguugga cuaguugauc    60
cugauacgcu gaaaccuggu gauuuaguug gugucaacaa agauaguuau cuuauccugg   120
acacucugcc gucggaauau gau                                                    143

<210> SEQ ID NO 178
<211> LENGTH: 143
<212> TYPE: RNA
<213> ORGANISM: artificial sequence
<220> FEATURE:
<223> OTHER INFORMATION: Synthetic Construct

<400> SEQUENCE: 178
aucauauucc gacggcagag uguccaggau aagauaacua ucuuuguuga caccaacuaa    60
aucaccaggu uucagcguau caggaucaac uaguccaaca acaggaagaa auauugucug   120 ucggucgau guuuuaagca caa                                                     143

<210> SEQ ID NO 179
<211> LENGTH: 159
<212> TYPE: RNA
<213> ORGANISM: artificial sequence
<220> FEATURE:
<223> OTHER INFORMATION: Synthetic Construct

<400> SEQUENCE: 179
cgcugcaguu ggugaaguag aucccggcaa ggggauuuca cuccguuuc cacgucuggu    60 ucguauccga gaggauaaau cuccagagga cgccacauca ucugagcagg uggcggauau   120
guacagaucu caagcaaaca auccacaccg caaaaagag                                   159

<210> SEQ ID NO 180
<211> LENGTH: 159
<212> TYPE: RNA
<213> ORGANISM: artificial sequence
<220> FEATURE:
<223> OTHER INFORMATION: Synthetic Construct

<400> SEQUENCE: 180
cucuuuuugc gguguggauu guuugcuuga gaucuguaca uauccgccac cugcucagau    60
gauguggcgu ccucuggaga uuuauccucu cggauacgaa ccagacgugg aaaccggagu   120
gaaauccccu ugccgggauc uacuucacca acugcagcg                         159

<210> SEQ ID NO 181
<211> LENGTH: 159
<212> TYPE: RNA
<213> ORGANISM: artificial sequence
<220> FEATURE:
<223> OTHER INFORMATION: Synthetic Construct

<400> SEQUENCE: 181
uaaagauggc ggaaaaaucg acuaugauaa auugauugac aaauucggcu gucagcgacu    60
ugauuuaucg cucauucaga gaauugagcg caucacugcu cguccugcuc auguauuucu   120
ucgccgcaac guuucuucg cucaccguga uuugaauga                          159

<210> SEQ ID NO 182
<211> LENGTH: 159
<212> TYPE: RNA
<213> ORGANISM: artificial sequence
<220> FEATURE:
<223> OTHER INFORMATION: Synthetic Construct

<400> SEQUENCE: 182
ucauucaaau cacggugagc gaagaaaacg uugcggcgaa gaaauacaug agcaggacga    60
gcagugaugc gcucaauucu cugaaugagc gauaaaucaa gucgcugaca gccgaauuug   120
ucaaucaauu uaucauaguc gauuuuccg ccaucuuua                          159

<210> SEQ ID NO 183
<211> LENGTH: 150
<212> TYPE: RNA
<213> ORGANISM: artificial sequence
<220> FEATURE:
<223> OTHER INFORMATION: Synthetic Construct

<400> SEQUENCE: 183
ugaagcugau gcugaaggaa aggauauuga ugcuagugaa guaguucgcc caagggugcc    60
auuagaagcu ugccuagcua gcuacucagc uccggaggag gugauggacu ucuacagcac   120
ugcauugaag gcaaaggcaa cugcuacaaa                                   150

<210> SEQ ID NO 184
<211> LENGTH: 150
<212> TYPE: RNA
<213> ORGANISM: artificial sequence
<220> FEATURE:
<223> OTHER INFORMATION: Synthetic Construct

<400> SEQUENCE: 184
uuuguagcag uugccuuugc cuucaaugca gugcuguaga aguccaucac cuccuccgga    60
gcugaguagc uagcuaggca agcuucuaau ggcacccuug ggcgaacuac uucacuagca   120
ucaauauccu uuccuucagc aucagcuuca                                   150

<210> SEQ ID NO 185
<211> LENGTH: 155
<212> TYPE: RNA
<213> ORGANISM: artificial sequence
<220> FEATURE:
<223> OTHER INFORMATION: Synthetic Construct

<400> SEQUENCE: 185
acaccugccc uaacaucucg ggguuuucuc gaagaagauu uuguuaaagu ggccgaguau    60
uuugaugcug cuguuaagcu ggcucuaaaa aucaaggcug acacaaaagg aacaaaguug   120
aaggacuucg uugccaccuu gcagucuggu guuuu                              155

<210> SEQ ID NO 186
<211> LENGTH: 155
<212> TYPE: RNA
<213> ORGANISM: artificial sequence
<220> FEATURE:
<223> OTHER INFORMATION: Synthetic Construct

<400> SEQUENCE: 186
aaaacaccag acugcaaggu ggcaacgaag uccuucaacu uuguccuuu ugugucagcc    60 uugauuuuua gagccagcuu aacagcagca ucaaaauacu cggccacuuu aacaaaaucu   120
ucuucgagaa aaccccgaga guuagggca ggugu                               155

<210> SEQ ID NO 187
<211> LENGTH: 159
<212> TYPE: RNA
<213> ORGANISM: artificial sequence
<220> FEATURE:
<223> OTHER INFORMATION: Synthetic Construct

<400> SEQUENCE: 187
ugaacuacga agcaggcaaa uucuccaaaa guaaaggcau uggaguuuuu gggaaugacg    60
ccaagaauuc uaauauaccu guagaagugu ggagauacua ucugcuaaca aacaggccug   120
agguaucaga cacauuguuc acuugggcgg aucuucaag                          159

<210> SEQ ID NO 188
<211> LENGTH: 159
<212> TYPE: RNA
<213> ORGANISM: artificial sequence
<220> FEATURE:
<223> OTHER INFORMATION: Synthetic Construct

<400> SEQUENCE: 188
cuugaagauc cgcccaagug aacaaugugu cugauaccuc aggccuguuu guuagcagau    60
aguaucucca cacuucuaca gguauauuag aauucuuggc gucauuccca aaaacuccaa   120
ugccuuuacu uuuggagaau uugccugcuu cguaguuca                          159

<210> SEQ ID NO 189
<211> LENGTH: 24
<212> TYPE: DNA
<213> ORGANISM: artificial sequence
<220> FEATURE:
<223> OTHER INFORMATION: Synthetic Construct

<400> SEQUENCE: 189
tcccatctcc cacatgggtt actg                                           24

<210> SEQ ID NO 190
<211> LENGTH: 24
<212> TYPE: DNA
<213> ORGANISM: artificial sequence
<220> FEATURE:
<223> OTHER INFORMATION: Synthetic Construct

<400> SEQUENCE: 190
cagtaaccca tgtgggagat ggga                                           24

<210> SEQ ID NO 191
<211> LENGTH: 22
<212> TYPE: DNA
<213> ORGANISM: artificial sequence
<220> FEATURE:
<223> OTHER INFORMATION: Synthetic Construct

<400> SEQUENCE: 191
ggctgatgaa attcaagtgc ta                                              22

<210> SEQ ID NO 192
<211> LENGTH: 21
<212> TYPE: DNA
<213> ORGANISM: artificial sequence
<220> FEATURE:
<223> OTHER INFORMATION: Synthetic Construct

<400> SEQUENCE: 192
aaactgagct tggaaataat c                                               21

<210> SEQ ID NO 193
<211> LENGTH: 22
<212> TYPE: DNA
<213> ORGANISM: artificial sequence
<220> FEATURE:
<223> OTHER INFORMATION: Synthetic Construct

<400> SEQUENCE: 193
gaacccaaaa ttgtcacttt tt                                              22

<210> SEQ ID NO 194
<211> LENGTH: 24
<212> TYPE: DNA
<213> ORGANISM: artificial sequence
<220> FEATURE:
<223> OTHER INFORMATION: Synthetic Construct

<400> SEQUENCE: 194
atgcacttgt ttatactctt gtca                                            24

<210> SEQ ID NO 195
<211> LENGTH: 21
<212> TYPE: DNA
<213> ORGANISM: artificial sequence
<220> FEATURE:
<223> OTHER INFORMATION: Synthetic Construct

<400> SEQUENCE: 195
atttattagt gttctaaaga a                                               21

<210> SEQ ID NO 196
<211> LENGTH: 24
<212> TYPE: DNA
<213> ORGANISM: artificial sequence
<220> FEATURE:
<223> OTHER INFORMATION: Synthetic Construct

<400> SEQUENCE: 196
tgtagtagct tataagatta gctt                                            24

<210> SEQ ID NO 197
<211> LENGTH: 22
<212> TYPE: DNA
<213> ORGANISM: artificial sequence
<220> FEATURE:
<223> OTHER INFORMATION: Synthetic Construct

```
<400> SEQUENCE: 197
gttgtccctt ttatgggtct tt                                              22

<210> SEQ ID NO 198
<211> LENGTH: 21
<212> TYPE: DNA
<213> ORGANISM: artificial sequence
<220> FEATURE:
<223> OTHER INFORMATION: Synthetic Construct

<400> SEQUENCE: 198
cccgtgcaat ttctgggaag c                                               21

<210> SEQ ID NO 199
<211> LENGTH: 24
<212> TYPE: DNA
<213> ORGANISM: artificial sequence
<220> FEATURE:
<223> OTHER INFORMATION: Synthetic Construct

<400> SEQUENCE: 199
attagttttt tatacacgaa agat                                            24

<210> SEQ ID NO 200
<211> LENGTH: 24
<212> TYPE: DNA
<213> ORGANISM: artificial sequence
<220> FEATURE:
<223> OTHER INFORMATION: Synthetic Construct

<400> SEQUENCE: 200
atctttcgtg tataaaaaac taat                                            24

<210> SEQ ID NO 201
<211> LENGTH: 22
<212> TYPE: DNA
<213> ORGANISM: artificial sequence
<220> FEATURE:
<223> OTHER INFORMATION: Synthetic Construct

<400> SEQUENCE: 201
ttggtggttt ggccacttcc gt                                              22

<210> SEQ ID NO 202
<211> LENGTH: 21
<212> TYPE: DNA
<213> ORGANISM: artificial sequence
<220> FEATURE:
<223> OTHER INFORMATION: Synthetic Construct

<400> SEQUENCE: 202
tttgtttgct atttagctgg a                                               21

<210> SEQ ID NO 203
<211> LENGTH: 24
<212> TYPE: DNA
<213> ORGANISM: artificial sequence
<220> FEATURE:
<223> OTHER INFORMATION: Synthetic Construct

<400> SEQUENCE: 203
caatttgcag caactcgcac tgga                                            24

<210> SEQ ID NO 204
```

```
<211> LENGTH: 22
<212> TYPE: DNA
<213> ORGANISM: artificial sequence
<220> FEATURE:
<223> OTHER INFORMATION: Synthetic Construct

<400> SEQUENCE: 204
tcccaccatt ggctattccg ac                                              22

<210> SEQ ID NO 205
<211> LENGTH: 21
<212> TYPE: DNA
<213> ORGANISM: artificial sequence
<220> FEATURE:
<223> OTHER INFORMATION: Synthetic Construct

<400> SEQUENCE: 205
ctgtctctct ttttaatttc t                                               21

<210> SEQ ID NO 206
<211> LENGTH: 24
<212> TYPE: DNA
<213> ORGANISM: artificial sequence
<220> FEATURE:
<223> OTHER INFORMATION: Synthetic Construct

<400> SEQUENCE: 206
ccactttgca cacatctccc actt                                            24

<210> SEQ ID NO 207
<211> LENGTH: 22
<212> TYPE: DNA
<213> ORGANISM: artificial sequence
<220> FEATURE:
<223> OTHER INFORMATION: Synthetic Construct

<400> SEQUENCE: 207
gaggatccac gtatagtagt ag                                              22

<210> SEQ ID NO 208
<211> LENGTH: 21
<212> TYPE: DNA
<213> ORGANISM: artificial sequence
<220> FEATURE:
<223> OTHER INFORMATION: Synthetic Construct

<400> SEQUENCE: 208
tttaaataaa gaaattattt a                                               21

<210> SEQ ID NO 209
<211> LENGTH: 40
<212> TYPE: DNA
<213> ORGANISM: artificial sequence
<220> FEATURE:
<223> OTHER INFORMATION: Synthetic Construct

<400> SEQUENCE: 209
taatacgact cactataggg cttgagttta taacgaagct                           40

<210> SEQ ID NO 210
<211> LENGTH: 39
<212> TYPE: DNA
<213> ORGANISM: artificial sequence
<220> FEATURE:
<223> OTHER INFORMATION: Synthetic Construct

<400> SEQUENCE: 210
```

```
taatacgact cactataggg cttctaattt tcaaggacg                                39

<210> SEQ ID NO 211
<211> LENGTH: 24
<212> TYPE: DNA
<213> ORGANISM: artificial sequence
<220> FEATURE:
<223> OTHER INFORMATION: Synthetic Construct

<400> SEQUENCE: 211
agcttctaat tttcaaggac gata                                               24

<210> SEQ ID NO 212
<211> LENGTH: 25
<212> TYPE: DNA
<213> ORGANISM: artificial sequence
<220> FEATURE:
<223> OTHER INFORMATION: Synthetic Construct

<400> SEQUENCE: 212
gtcatgtgac tccactttga ttttg                                              25

<210> SEQ ID NO 213
<211> LENGTH: 25
<212> TYPE: DNA
<213> ORGANISM: artificial sequence
<220> FEATURE:
<223> OTHER INFORMATION: Synthetic Construct

<400> SEQUENCE: 213
ctcaattccg ataaatttaa gaaat                                              25

<210> SEQ ID NO 214
<211> LENGTH: 26
<212> TYPE: DNA
<213> ORGANISM: artificial sequence
<220> FEATURE:
<223> OTHER INFORMATION: Synthetic Construct

<400> SEQUENCE: 214
cgaagctatt ggaccgacct aatttc                                             26

<210> SEQ ID NO 215
<211> LENGTH: 26
<212> TYPE: DNA
<213> ORGANISM: artificial sequence
<220> FEATURE:
<223> OTHER INFORMATION: Synthetic Construct

<400> SEQUENCE: 215
ggaattgagg gcttcccaga aattgc                                             26

<210> SEQ ID NO 216
<211> LENGTH: 25
<212> TYPE: DNA
<213> ORGANISM: artificial sequence
<220> FEATURE:
<223> OTHER INFORMATION: Synthetic Construct

<400> SEQUENCE: 216 atgactttt gattggtgaa actaa                                               25

<210> SEQ ID NO 217
<211> LENGTH: 45
<212> TYPE: DNA
```

```
<213> ORGANISM: artificial sequence
<220> FEATURE:
<223> OTHER INFORMATION: Synthetic Construct

<400> SEQUENCE: 217
taatacgact cactataggt ggaactccaa cacacaaaaa atttc            45

<210> SEQ ID NO 218
<211> LENGTH: 41
<212> TYPE: DNA
<213> ORGANISM: artificial sequence
<220> FEATURE:
<223> OTHER INFORMATION: Synthetic Construct

<400> SEQUENCE: 218
taatacgact cactataggt tgaaaaataa tcataatttt a                41

<210> SEQ ID NO 219
<211> LENGTH: 22
<212> TYPE: DNA
<213> ORGANISM: artificial sequence
<220> FEATURE:
<223> OTHER INFORMATION: Synthetic Construct

<400> SEQUENCE: 219
gcataatata ttgatccggt at                                     22

<210> SEQ ID NO 220
<211> LENGTH: 24
<212> TYPE: DNA
<213> ORGANISM: artificial sequence
<220> FEATURE:
<223> OTHER INFORMATION: Synthetic Construct

<400> SEQUENCE: 220
ctgaaagttc atacataggt actc                                   24

<210> SEQ ID NO 221
<211> LENGTH: 22
<212> TYPE: DNA
<213> ORGANISM: artificial sequence
<220> FEATURE:
<223> OTHER INFORMATION: Synthetic Construct

<400> SEQUENCE: 221
ggtactccaa ttttcagtat at                                     22

<210> SEQ ID NO 222
<211> LENGTH: 24
<212> TYPE: DNA
<213> ORGANISM: artificial sequence
<220> FEATURE:
<223> OTHER INFORMATION: Synthetic Construct

<400> SEQUENCE: 222
ctgaaaattg gagtacctat gtat                                   24

<210> SEQ ID NO 223
<211> LENGTH: 27
<212> TYPE: DNA
<213> ORGANISM: artificial sequence
<220> FEATURE:
<223> OTHER INFORMATION: Synthetic Construct

<400> SEQUENCE: 223
atgtatgaac tttcagaata ttatacc                                27
```

<210> SEQ ID NO 224
<211> LENGTH: 22
<212> TYPE: DNA
<213> ORGANISM: artificial sequence
<220> FEATURE:
<223> OTHER INFORMATION: Synthetic Construct

<400> SEQUENCE: 224
taccggatca atatattatg ct                                              22

<210> SEQ ID NO 225
<211> LENGTH: 647
<212> TYPE: DNA
<213> ORGANISM: Amaranthus palmeri

<400> SEQUENCE: 225
ttcaaaatga atttaaaatt ataaaaaat caatatggac acaagaccgg atatcaatcc      60
gacccgaaat agttgacttg aaatcaacct gatgacccga atgaacacct ctagttatca   120
ctaacaaggg tcagattgcg tacatcaaac ccctcaaatc ctgcttaggt gggagcttgt   180
caatggctta ggggtaacgg gaatgtgtgt gctatgtaca ttgtgcatct attcttatgc   240
ttatttatgt tgagttagtt ttttttttgg atcaaatata aagagcttaa cttttgtatt   300
ttcttgatgt ggtgtagtgg tgatgaagat caggctgaga gaatctaaat tggccaaaat   360
tctgagagaa caagaagtga gttcagccct tcgtgctgct ggtgttggtg tgattagttg   420
catcatacag agagatgaag gcgaactcc gatgaggcat tcattctatt ggtcagcaga    480
aaaacaatat tatagtgagg agcctttact acgtcatttg gaaccccctc tatctatgta   540
tctcgagctg gtactagtct ctgaaccgat tgcctttctt ctgctttgtt attttgtgtg   600
atatttcgac ttaagtctaa tttacatcgt tttgtacatt tgttatc                 647

<210> SEQ ID NO 226
<211> LENGTH: 738
<212> TYPE: DNA
<213> ORGANISM: Amaranthus palmeri

<400> SEQUENCE: 226
ttttgctttt ttactattat ttccttcttt tcaaggattt gagttgttta ttgctgactg     60
cttcctatgt attacccata tgtctctgta taggcattac gggagctgta cctacatcta   120
actcctatac aacgtgtgaa tattgcccgg catcctaatc gccccacttt tcttgaccac   180
gtattcagca tcacagaaaa ggtttctgat ttattataat ttttgtcatt tgtattcact   240
cttcaataaa gtacatccat tatcaatctt tacggaggtt gttcacacaa cttcttgttt   300
cattttgcat aattagtttg tggaactaca tggagatcgt gctggttatg atgaccctgc   360
tatagttact ggccttggta cgatagatgg taggcgttat atgttcattg gtcatcaaaa   420
gggaagaaat acgaaggaaa atattgcacg gaatttcggg atgcctactc ctcatgggta   480
aatgctttac tataatgttt tactttaatt taattaccta tgttatttag gatgaaaatg   540 aatactttc ttattactat tacttaggtt cctaatgcac aaaaaccgta attattaatg    600
taccctaatg gaattaacac atggtaatta agctctccgc tttgtgtaat taatccaatt   660
ttttagagag tcaaatagtt caggttaaac tagagctttt catacccaaa taataaaacc   720
aagggtaaat ttccaaaa                                                 738

<210> SEQ ID NO 227

```
<211> LENGTH: 880
<212> TYPE: DNA
<213> ORGANISM: Amaranthus palmeri

<400> SEQUENCE: 227
atgtgatcaa ttaaagaaaa agtctaatta tatgagcccg tctcacagtg acggagctat      60
catagagccc atggggtcac gtgcccttcg gggttttttag aaaaaattca agtatacttt    120
ttctattaat aagagtaaaa atgtaaaatt aatattaaac tcttttgata ataaatactc    180
tctcactta gtaattttgt cttatttatt tattttatct catgtgttta ataaggtcag    240
ttgacttatt ttgttccatt ttcttttatg gtatgccgta tttaaaattt tagcaagtaa    300
agataaaata gttgttaatc ttacaaataa aactctatcg aaatttcatc cattagttaa    360
tgtccccaaa aagtccgaac tacaaatcga ccactgtcat cacatggtga gatagtctca    420
tataaaacga gttcagttat taaaggaaaa taggaaacac gaaacagtta atttaggcgg    480
ggcctatgta ttatccaaat gtgatactcc agtccacatt actcagtcct tccaattgaa    540
cagttggctt aatctaccaa gcgcgtggcc ataaatgcct ctaacacttt tcaatctctc    600
agataactct cacaccactt atcatcacaa ttcacaatta ctctaattct ttttattcct    660
ttccatgtcg ctaattttct actgattcag gttttattct cagcttttat caattttatt    720
tcatgctttt tatgtcaatt tcttgtttcg cattttgtct tccacttgct gtctgtttta    780
ttaatcaatt ttgtatgatt gttggaataa ttgtatgtat ttttcatgat tttcctctta    840
tggaggttca taatgtattg ctagatttgt ttactttcac                          880

<210> SEQ ID NO 228
<211> LENGTH: 453
<212> TYPE: DNA
<213> ORGANISM: Amaranthus palmeri

<400> SEQUENCE: 228
aatttgagcg ggaaaatttt aatatcatta aatagtcttt gctttagtat atagaatagt      60
taaaattaat agtcaaactt attgtaatag catgcactaa tctataataa tcttatcctg    120
aaagctataa taaaattata aaaaaatata tgtgaaaaac taatttgagc gggaaaattt    180
taaccaaggg ctaacacgta tcattaaata gtctttactt tagtatatag aatgataatt    240
aacgatcata aaacaaaatt gtcactttca gtagcaaact tacaaaatga gcagagtacc    300
tcatatcata aaattgcttc tttctcattt gttgtgttgc tctcatttta ggagttcatc    360
gtttatatcg tcgtcttacc actcaatcac ttttagattt attagtagca cttcctcaat    420
ctacagcagc aatttctaca gttcaacaac ctc                                 453

<210> SEQ ID NO 229
<211> LENGTH: 3953
<212> TYPE: DNA
<213> ORGANISM: Amaranthus palmeri

<400> SEQUENCE: 229
ggaaaattta cctagaataa tccaatttat tcgtgatttt tctacaaatt ccaacttcaa      60
ggggtatttg cctaaagtaa ttaaacttgg atacccgat gacctgctat agtagataat     120
ttaccagaaa attaaaaatg aaaattaatt taaaattaga gaaaaatttt gaaatttcat    180
ataaaaaatt ttaaataata aaaaaaatat aaatttttt gaacatttta ttttaatcta    240
tcttttttga aaaaataaaa cttagttata gcaagtgatc tggtcaccgg gtttactcta    300
ggaaaatatc cctcaaagtt gagattattc atggttaata aataggtgag attattatag    360
```

-continued

```
aaaaattacg aataaattgg attattgttg gtaattttttt tttcaaaact atccctagga     420
aggaccttat tagtgattct ccctctactt tggaggagta tattgtggac ttcccatctt     480
ccttaattgt attgtaactt ttaactattg attctttaaa aaaagaact tataaaattg      540 taggttaat aaaatctaag attttatcta atttcactt gattattccg attttgtatt       600
cacattattt taaatgacat tcgtcaaata aaaaaaaata gtttcattgc attccaattt     660
tgttgactag ggggattaaa gaaagaatag tatcaataat cgtaatgtag caagtagtac     720
aaaagaagta tatttcaata tgtcaaactt tgatctcgtt gtaacttgta atttgtacga    780
tgcggtgtga atgacatact tcacctttttt cattatttta tactggtagt gacatgggat   840
tattattgcg atatttgcag taatgaaaat ttttttggtt gttgctttta caaacaaaaa    900
ttctaccgaa ttttttattaa atttaattca acacgttggt gttacccatg atttataggt   960
ctgggtccgc cactgctagc taacattaaa caatttaaca aactcaatac accaacctaa   1020
aaataaaatt ttttttggcca taatttttag aattttagtt tttaaacatt atatttggga   1080
attttttttc cttttatata tataaaataa aaaaaaatcc aaaaaagggg acacacatta    1140
atacacactt gaaagcatcg atgatatcga agaaaaacca gatggggtgc ccaattatct    1200
tcgtctcctt cgatattatc gaattcatta acaacattat atcaaaaacc aaccaaatta    1260
ccaactttcg aaaccaatat tcgccgtatt tttctctatt caacaatccc tacaatggcg    1320
gcattgccag cttcttcttc tcctgcaatt tcggaatcac ccacttgcaa tttttcttcct  1380 attcaaaaaa tcactaccac tcgctttcta aggtttcatt cggttttact cccaagccta    1440
aatttggcct tttctccaag gtttatttttc tatctctttt ttaattggtt aatcaattgg   1500
attgttgaat ttttcagggt ttaacggtat aatatttgtg ggtttttttcg agtacattct   1560 gggtttgtag tattggattt ggcattgctt ttaattttttg agattgggtt ttttgggttt   1620
tatttggttc ttgtgattca aggttattga tttgctgcat taaactgtat ttatggaatg   1680
atgtcaatta actgttacat tacattgctt tatggttttc atcatgctga ttagtgatta    1740
ctgtgtttga atctcttgct tctctatgta ctatttaatc tgatacaaca agtacaacct    1800
agaaaacagg ttaaagggaa atctataagc ttagtaaatt aacacttgaa agaagctaat    1860
gacggagaga ggggtctttt tggagaaggc agttttcata ttattgctca gttctctagt    1920
gcagctttac ttcacttaga cactcttaag tagaggtcat aggtgttcag aatagatcca    1980
aagacccgat atttaccgga ctttgtaaac aacttaaccc gacttcaaaa tgaatttaca    2040
atcatataaa agcaatatgg acttaaaccg attttgaacc gaccttgacc ggttgatccg    2100
aatgaatgcc tctactctta agcatgtcaa ctgtaatatg aaatagaatt ataatataaa    2160
ctaagttcat gttttcttca actacaaatg aaatttatg acccaaataa tgtgtgaata    2220
cccccagcaa taggttgaat ggcatttagt tcagttgatt ttagcagacc acatctgccc    2280
tcatattcca ttgttcagtt tagttgttag tagctgtaca taatagacta attaagttgt    2340
cattttgatc catgttatgg ttgtctggga taaacggatt ggaattgtat aataaaagtt    2400
tgggttagtt tattttgctc taggaggggt tatgtcatat gtgcactctg ttggcaaccc    2460
gacaatgcaa aacattttca tacttggtac gttgttgcgt gttttgtgcc cttcgtattt    2520
tgtaactgtt gatgaatgtg taaaaatata ctacatgatc atatgctagt aggtcttctt    2580
cacctagtaa agaaattttt ctaacacgag aagttcaaaa catattccca ttaccattat    2640
ccaacatcag tacccgagtc caagtaacat agggtgtccc tttatgatag tataagaatt    2700
```

```
ggtgcatgaa aaacgcgtga ttgtagcgag gatagtaggc gggagaggta caggatttga   2760
aaattttgaa ttgctaaaac gctatcagga tcttgttttt cttactttga tgttgctttt   2820
ttgaaatttg atccaaattg ttaaattatt gagactaatt cctgttgatc ctgtcgtgaa   2880
ctttgtagaa tctttcaggc cgcattctca cagtgaaggc tcaattaaac aaggtgagtc   2940 ttttttttgtc ttaactctta tgcagttcat tatctcttct actgatgaga aaaccactat   3000
ttggcctaat tctaatttcc ttctaggttg cttttggatgg ttcaaatcat gctccatcac   3060
cttcgcacga aaaatctggg ctaccagccc aagaaaagaa gaacgatgag ccgtctagtg   3120
aatcttctcc tgcagcatca gtgtctgaag aacgagtctc cgaattcttg agccaagttg   3180
ccggtcttgt caagtatgta acattcttta ttttcattct tccacacact cgcaatttgg   3240
ataacgagat gtctttagag acgtctgggg aacaagggag aaatgagtct agaggttgct   3300
agagagaacg agataaatac taatatatat gaatatttca taatccacat taaaaaaata   3360
caattgaatt tgcattatgg tgaactacca aagaatcgaa tatttttttaa tactccatgt   3420 tttgtggtct agacttgtgg attctagaga cattgtagag ttgcaattaa aacaactgga   3480
ctgtgagata ttgatccgca agcaggaagc tattcctcaa ccacaaattc ctaatcctac   3540
acatgtcgtt gcaatgcaac caccaccacc tgctgtagcg tctgcccag ctcccgtctc   3600 ttcaccagcc actcctcgtc ctgcgttacc tgcccagcg cctgctgcca cgtcagctaa   3660
gccatcactt ccacctctca agagcccat gtcaggcaca ttctaccgta gtccagctcc   3720
tggcgagccg ccttttcgtga aggtaagtgt atacccctt tttagtgttg tatttctgtg   3780
ttatatcaat ttttgcattt tgtgaagctg aaaataaatc tttcatttc cataggttgg   3840 agataaagtt aagaaaggac aagtcatatg cattatcgag gctatgaagt tgatgaatga   3900
aatcgaggta cgtatgttat tgcttttaaac ttcatgcctt aggccgtgaa gtt         3953

<210> SEQ ID NO 230
<211> LENGTH: 595
<212> TYPE: DNA
<213> ORGANISM: Amaranthus palmeri

<400> SEQUENCE: 230
acaaaaagca caaattcaat aatatactct ttaagtttgt ttatcttcta attagttcgg    60
ttaaaacggt tccccacttt cttctccgac tctcacaatt atcttcccct attcattttt    120
cttccaccct ctcaatggc ggctgtttcc ttcaatatca atggtggaaa gattggaact    180
ttatgttcaa gacacgaatt cgtttgtggg tttgtaagaa aatttcattt tagaactcat    240
acttctatat ttgaaaaaca tatgccaaaa acttcaaggt ttaaagcaat ggaagtttct    300
gcaaatgcaa cagtaaatat agttcctgtt tcagctcatt ctaggtaatt ttatttctcg    360
aaaatttccg atttacaatt aaattaatct tgttttgtag gtaatgaatt gcagaagaaa    420
tagatggatt cttatttgtt tattggtatt tgttatataa ttttttgttta tattagtttc    480 tgaattgtga ttattctgat tgtatgtcaa ggtttaggtt gttattaata aatgtaaatt    540
ggattgattg aagttgcaat aaggtgatgg cgtgatgctg attgttgtaa atttt          595

<210> SEQ ID NO 231
<211> LENGTH: 667
<212> TYPE: DNA
<213> ORGANISM: Amaranthus palmeri

<400> SEQUENCE: 231
caacaatgag aatttagaat ccatatcaat cttgatattc aagggtatt aagtaattaa     60
```

```
agaacaacca ttgttaagcg cctccactat cttcttcctt ctcattctcc attctcgctt      120
agctttcctc tcgcactaat tacctccatt tgcaacctttt caagctttca acaatggcgt     180
ccacttcttc aaacccacca ttttcctcct ttactaaacc taacaaaatc cctaatctgc      240
aatcatccat ttacgctatc cctttgtcca attctcttaa acccacttct tcttcttcaa      300
tcctccgccg ccccctttcaa atctcatcat cttcttctca atcacctaaa cctaaacctc     360
cttccgctac tataactcaa tcaccttcat ctctcaccga tgataaaccc tcttcttttg      420
tttcccgatt tagccctgaa gaacccagaa aaggttgcga tgttctcgtt gaagctcttg      480
aacgtgaagg tgttaccgat gttttttgctt accctggtgg agcatccatg gaaatccatc     540
aagctcttac tcgttctaat atcattagaa atgttcttcc tcgacatgaa caaggtgggg      600
ttttcgctgc tgaaggctac gctcgtgcta ctggacgcgt tggagtttgt attgccactt      660
ctggtcc                                                                667
```

```
<210> SEQ ID NO 232
<211> LENGTH: 2415
<212> TYPE: DNA
<213> ORGANISM: Amaranthus palmeri

<400> SEQUENCE: 232
```

```
atttggataa cttttcctt tgattcgaat cggattattt ttaatacagt attatgaact        60
gatttaatga aagtggagga agtttcaatt tttaaagttg taggtgtaat gttttctcat      120
tttggatatg aaagtggagg aagtttcaat ttcgaatcat gttgccagt tgattcaatg      180 aatgctcttg gaaatgacca agagttcaag gcttcttgtt ataaaacatt tcaattttga     240
tctaagaatg aactatttag aacttaaagt aattaaatta ttagttataa cttataaaaa      300
aattcaattt taaccttaaa tttataaatt atgacccttaa aaagatcaag tattgaacgc     360
atatttagaa aaattataat tcggcttatc agtctcatat tgagacggtc tcgtccaaga     420
caagttgtat catttatata atcaaatata attatgagtg tattcatgta ggtttcaact     480
ttaaagccta ggtgaaagat atgttgtagc atctttgtga aagtcagcct ataacttggt     540
tctaaaattt tgaagcataa ccatatagtc cctcgaattc attcaagttg tccaattac     600 ttttttatac ttgccgagac aacatttaaa cccttaatat ttctaattaa tcttaattaa     660
aaattatgaa aatttgatat taataatctt tgtattgaaa cgaattttaac aagatctcac    720 atgactatgt tttaacttat agattaaaaa aaaatacaaa ttaagagtga taagtgaata     780
gtgccccaaa acaaatggga caacttagat gaattggagg taatattagg tagcaagtga     840
tcactttaac atcaaaattg atcacttata ggttcaaatt gaacttttta ctttaattga     900
tatgtttaaa tactacttta aattgaaatt gatatttta aggtcaaaat tgaaaccttt     960
aagattataa ttgaaaattg gcagaagaaa acaaagaga aagaatataa gacacgcaaa     1020
ttgtaccgat ctactcttat ttcaatttga cggtctcg cccaagacta gatgttcggt     1080
catcctacac caaccccaaa aaattcaaca acaaagtctt ataatgattc cctctaatct    1140
actacagtct acaccaaccc actttctctt tgcccaccaa aactttggtt tggtaagaac    1200
taagccctct tctttccctt ctctctctct taaaagcctg aaaaatccac ctaactttt    1260 tttaagccaa caaacaacgc caaattcaga gaaagaataa tggctcaagc tactaccatc    1320
aacaatggtg tccaaactgg tcaattgcac catactttac ccaaatccca gttacccaaa    1380
tcttcaaaaa ctcttaattt tggatcaaac ttgagaattt ctccaaagtt catgtctta    1440
```

```
accaataaaa aagagttggt gggcaatcat tcaattgttc ccaagattca agcttctgtt    1500
gctgctgcag ctgagaaacc ttcatctgtc ccagaaattg tgttacaacc catcaaagag    1560
atctctggta ctgttcaatt gcctgggtca aagtctttat ccaatcgaat ccttcttta     1620 gctgctttgt ctgaggtatt tatttctcaa ctgcgaaaac aatctctatt tgatattgga    1680
atttatatta catactccat cttgttgtaa ttgcattagt agatacttat gttttgacct    1740
ttgttcattt gtttgttgaa ttggtagtgt gagaatttg aatgtaatta tttgtttttc    1800
catgtgaatt taatctgatt aaatccactt cttatttatg ttaagttgca atgatgtttg    1860
ccaaatggtt atcattgaag ataagtttg cctacttttg accctcccaa cttcgcggtg    1920
gtagagccat tttatgttat tgggggaaat tagaaagatt tatttgtttt gcctttcgaa    1980
atagtagcgt tcgtgattct gatttgggtg tctttataga tatgatatat gggttattca    2040
tgtaatgtgt aggtttatgc attatgttgg atgcatgtct ggtgttattg ctgtaaatgg    2100
atgaatgttg ttatttggag acattttttc attcattttt tcccttttta attggaactg    2160
gaagagggaa agttattggg agtaattaaa aggttgtgag ttcgatacac tgcatcaaag    2220
acgaagaact tgacatagat gttgaaggct aatccttatc actgcttgaa ttcaatatgt    2280
atctgaaaat tttacccctc tatatgcatc tgttttgct aataaagtgt ttttggacta    2340
tcatgttttg tgatgcttaa gagggtgata ttactgagat aaatggaaat atcaaaataa    2400
catctattgt gaagt                                                    2415

<210> SEQ ID NO 233
<211> LENGTH: 3049
<212> TYPE: DNA
<213> ORGANISM: Amaranthus palmeri

<400> SEQUENCE: 233
caagcttcaa ttatcgtttt caaaataagt atttcaaagt ctataaagat attgtataag      60
ttttagttca aatttaataa gtttttttt ttttttttt ttttttttg aaaatccaaa        120 ttgaataagt taatarttaa attatgacat ataattatga catataaattt gaccatgata     180 ttttacaatc taacttaatt ttgaacttat tatttctaat attcaattat cgttctaaaa     240
ataagtattt aaattgtata gatatattgt ataacattta gttcaaattt aattattgat     300
agttttattg actatttatt tggkgtttga aattcatcca tagaatgata gaataacacc     360
attttttata taacttcgtt ctaaaatttt gaagcataac catatactcc ctccaattca     420
tccaagttgt ccaatttact ttttcatact tgccgaggca acatttaaac ccttaatatt     480
tctaattaat gttaattaaa aattatgaaa atttgatatt aataatcctt gtattgaaac     540
aaatctaaca agatcccaca tgactatgtt ttaacttata gattaagaat aaaatacaaa     600
ttaagagtaa taagtgaata gtgtcccaaa acaaatagga caacttggat gaattggagg     660
tagtattagg tagcaagtga tcactttaac atcaaaattg atcagttaca ggttcaaatt     720 gaaacttta ctttaattga tatgtttaaa tactacttta aattgaaatt gatattctta     780
aggtcaaaat tgaaaacttt aagattataa ttgaaaaatg cccagaagat gaaaaaacag     840
agagaaagca tgtaagacac gcaaattgaa ccagtctact cttgtttcaa tttgagacgg     900
tctcgcccaa gaccagatgt tcagtcatcc tacaccaacc ccaaaaaatt caacaacaaa     960 ctcttatat gattccctct aatctactag agtctacacc aacccacttt ctctttgccc    1020
accaaaactt tggtttggtg agaactaagc cctcttcttt cccttctctc tcttaaaagc    1080 ctaaaacca ccaactttt cagccaagaa acaacgcgaa attcagagga agaataatgg    1140
```

```
ctcaagctac taccatcaac aatggtgtcc atactggtca attgcaccat actttaccca      1200
aaacccagtt acccaaatct tcaaaaactc ttaattttgg atcaaacttg agaatttctc      1260
caaagttcat gtctttaacc aataaaagag ttggtgggca atcatcaatt gttcccaaga      1320
ttcaagcttc tgttgctgct gcagctgaga aaccttcatc tgtcccagaa attgtgttac      1380
aacccatcaa agagatctct ggtactgttc aattgcctgg gtcaaagtct ttatccaatc      1440
gaatccttct tttagctgct ttgtctgagg cacaacagt ggtcgacaac ttgctgtata       1500
gtgatgatat tctttatatg ttggacgctc tcagaactct tggttttaaaa gtggaggatg     1560 atagtacagc caaagggca gtcgtagagg gttgtggtgg tctgtttcct gttggtaaag       1620
atggaaagga agagattcaa cttttccttg gtaatgcagg aacagcgatg cgcccattga      1680
cagctgcggt tgccgttgct ggaggaaatt caagttatgt gcttgatgga gtaccaagaa      1740
tgagggagcg ccccattggg gatctggtag caggtctaaa gcaacttggt tcagatgtag      1800
attgttttct tggcacaaat tgccctcctg ttcgggtcaa tgctaaagga ggccttccag      1860
ggggcaaggt caagctctct ggatcggtta gtagccaata tttaactgca cttctcatgg      1920
ctactccttt gggtcttgga gacgtggaga ttgagatagt tgataaattg atttctgtac      1980
cgtatgttga aatgacaata aagttgatgg aacgctttgg agtatccgta gaacatagtg      2040
atagttggga caggttctac attcgaggtg gtcagaaata caaatctcct ggaaaggcat      2100
atgttgaggg tgatgcttca agtgctagct acttcctagc cggagccgcc gtcactggtg      2160
ggactgtcac tgtcaagggt tgtggaacaa gcagtttaca ggtataatgt taacccttac      2220
ccttcacatt gttctgctaa attctagagg acccctttcaa ttctgggtgg ataagcacg      2280 gcaatttgac cgcaaaaaaa ttgcaaaatt attctgctga tagaacatct cgagatgaga      2340
tcatattgag ttttggcgtc aacataaacc taatcaaata atgaaaaata caaacatcat      2400
atggtttctt ttgtctttat gactagacac tctctattat tccttgattg ggatcttatt      2460
tgaaattgct gtgtagccta cacctcatgt tcagattttg ttcgtatacc agactttct       2520 tgattgggat cttatttgtc ccctggattt tgcatagggt gatgtaaaat ttgccgaagt      2580
tcttgagaag atgggttgca aggtcacctg gacagagaat agtgtaactg ttactggacc      2640
acccagggat tcatctggaa agaaacatct gcgtgctatc gacgtcaaca tgaacaaaat      2700
gccagatgtt gctatgactc ttgcagttgt tgccttgtat gcagatgggc ccaccgccat      2760
cagagatgtg gctagctgga gagtgaagga aaccgaacgg atgattgcca tttgcacaga      2820
actgagaaag cttggggcaa cagttgagga aggatctgat tactgtgtga tcactccgcc      2880
tgaaaagcta accccaccg ccattgaaac ttatgacgat caccgaatgg ccatggcatt       2940
ctctcttgct gcctgtgcag atgttcccgt cactatcctt gatccgggat gcacccgtaa      3000
aaccttcccg gactactttg atgttttaga aaagttcgcc aagcattga                 3049
```

<210> SEQ ID NO 234
<211> LENGTH: 1113
<212> TYPE: DNA
<213> ORGANISM: Amaranthus palmeri

<400> SEQUENCE: 234

```
tcttaatttg tattttatta ttaatctata agttaaaaca tagtcaagtg agatcttgtt        60
tgattcgtct ctatgcaagg attttcatat caacttttca taattttttga ttatacacaa      120 ttacaaatat taacgaacga ataagtgcat taaaaagagt gcaaaaagca aatgggacac       180
```

```
ttgtgttgaa taggagggag tatacattaa gatgaatcta acgagatctc acatggatat      240
aatttgtctt ctatatatgt ctaaaaaatc ttgatcaaat ttctctttcc aaaatagaat      300
attctaaatg gaagaacat taagaaacgg agggagtact tataagttaa gatagttggg       360
ggtatttagg taaaaaaatc tatgccaaaa gtagaaagtg gacaattaga gtgactttac      420
taaataagga aagtggacat ttaaaatgaa tcggagggag catattaact ttattttcaa      480
agtgtgaaac ataatcatat ttaggtaaaa aaattatcaa tttaacgtca aaattgatca      540
caaataggtt aaaattgaaa tttttatgt taattgatct attgttcact ttaaattgaa       600
attgatatcc tttaaggtta aaattaatac ctctaaaatt aaaattatta aaggcccaga     660
aaataaaaaa aaagaagac aggctattag taaaattatt aagtatgtaa ggttgataca      720
cgcgcgaatt gagccggccc acttttagtt tcaatttgaa acagtctcaa tcaagaccaa     780
ttatttatta ttttattatt ttattgtttt aagctcaatg ggttggactt gataaattat     840
attttgagga gacgggctat tagtaaaatt aatagttgga atcttttttg atatactata     900
aaaagaggta tctggtggag ccttaaatct gcgcaattga agtcctcaat acacatctcg     960
ctcttcttat tctctttcat ctatttcctc ctttgatcaa actacgccat gtctctctta    1020
aatgatctcg ttaaccttaa tctctctgaa actaccgata agattatcgc tgaatacata    1080
tggtaataca acaatccttc ctcttttttca ttt                                 1113
```

<210> SEQ ID NO 235  
<211> LENGTH: 882  
<212> TYPE: DNA  
<213> ORGANISM: Amaranthus palmeri  
<220> FEATURE:  
<221> NAME/KEY: misc_feature  
<222> LOCATION: (451)..(459)  
<223> OTHER INFORMATION: n is a, c, g, or t

<400> SEQUENCE: 235

```
aaaaaaccgt cttatttgta gaaaataaaa aactaaaaag tagtatcaac ttttagacta       60
gtcataagtg agtggcatca aacttgttct ataaaaaggg aagagttcct caacttgaga      120
ttcatatttt ttgtgatttc taaatagaag aacatactca tcttccactt ctcttattca     180
tcaaatttta tttgttcccc aaaaaaacat gtctcttctt acagatctca tcaatcttaa     240
tctttctgac tccactgaga agatcattgc tgaatacata tggtcagttt tcatcccttt     300
tttttacctt taatcccact ttttgttttt acccaccatt tttttcatct attttctctt     360
aaagatttta acttttact ttttttgtgta tataacattc atttttttcaa ttgggtaggt    420 tagaaaattt ctataaataa ataaataaat nnnnnnnnnt accttaatcc cactttttgt     480
ttctacccac cattttttttc atcaattttt cttaaagatt ttaactttttt ttaacttttt   540 cttggttttt gtgtatatac caatcattta ttttcactag tgtaggttaa aaaatatcta    600
aaaataaata aaatagaata aaaatgtaat cactagatta acccatgaat tatttccctt    660 gttttttactc aaacttttta ccccttgttaa aaaaataatg atataaataa attttttgagg  720 gtttgttaaa cccatatgta atctatatcg aaaaaattag atagcgggtt tgttgtgga     780 caaactaaat aacaaattta ggaataaact tttgagggtt tattgaaaaa ataacccata    840
tttaatctat atcgaaaaaa tgatagcgag ctttgtatag at                      882
```

<210> SEQ ID NO 236  
<211> LENGTH: 1083  
<212> TYPE: DNA  
<213> ORGANISM: Amaranthus palmeri

<400> SEQUENCE: 236

```
cgtcgaagta gaagacgcgg aagctgcttt taacatcagc gtttcgcatg gggctattcc      60
ctgtgtttct cctattcaat tggaaaacgg tgtcgtttta tctgaggttc atttatatgg     120
ggatgttgtg cttcggtatg taagctacgg aaatgaatgt ggggatgtgt tttttcttcc     180
tgggtttgag gaaatgccgg aggaatcatc gtttagagga cttgattttg cattcgaag     240
gttggatcat gctgtaggga atgtccctga gttggctcct gcaattgctt atttgaagaa     300
gtttactggg tttcatgagt ttgctgagtt tacagctgaa gatgttggga cgagtgaaag     360
tggattgaat tcagccgtat tggcaaacaa tgatgaaatg tgttgtttc cgatgaatga     420
acctgtgtat gggacaaaaa ggaagagcca aattcaaact tatttggagc ataatgaagg     480
ggctggtgta cagcatttgg ctttgatgag tgaagacata ttttggactt aagggagat     540
gaggaagaga agtgttcttg gtgggtttga gtttatgccg tcgccgcctc cgacttatta     600
ccggaatttg aggaacagag ctgctgatgt attgagtgag gagcagatga aggagtgtga     660
agagttgggg attttggtgg ataaagatga tcagggcact ttgcttcaaa tcttcaccaa     720
acctattgga gacaggtaaa ttttaatctt gctttcaatt gcttttgctt gatggattga     780
ctagcaaatt tgatcgcatt tgttgcttaa tatgacttga tgatacttcc tctgtttcga     840
aatactcgct acattcgcta cattttgttt tgtgcactat tcatcgttca agcttatttt     900
acatattgcg actaatgtgt aactaaaaat atagtcaagt gggatcttgt ttgaatcgtc     960
taatggcata ctttcatcat attaaatttt tataattttt agattagtgt agtttaagat    1020
attaatgctc aaaattgtgc attggattgc gtaaaaaagt gaaatgtagc aagtattatg    1080
aaa                                                                  1083
```

<210> SEQ ID NO 237
<211> LENGTH: 788
<212> TYPE: DNA
<213> ORGANISM: Amaranthus palmeri

<400> SEQUENCE: 237

```
aaaaccaaag gaaataagtt ataggtagga aaaattgtta ttgaagttaa tgtagtaaac      60
tagtaactta aactgtgata ccccggattt agcttaaaaa gagattgata gactactcat     120
atcaacaagg tgcatcttct tttctaggga gcccatttgc taagaactct acagttaagc     180
gtgcttggtg gggagcaatc ttaggatggg tgacctcctg ggaagttttc ctgggtgcgc     240
acgggtgagg ccaaagtgcg ttaaaaagac ttgtgttggt ctgtggggct tgtctacagt     300
ctccatgagt agtcaccggc ggtacgagag gccggggtgt tacataaaca gactcaaagg     360
cgctaagcca agtagccaat agcaacatgt gtggcctgcg gacagtcaca aaaacacaca     420
atttcttatt tttactctct tttatctctt ttaggcttta gccatcaaca ataaaacaac     480
atgataaagc aattcattta ctgctaaatt ccaacaattt ggtcccttttt tcctgttctt     540
tcagtttcac ataccctctt atcaatctat atccaaaact atttcatttt ccaaactctt     600
ttaaacccaa aaatcaaaac ttttgattga agaacaaact tgggggtttt tggaaaatga     660
gtcattttgg atatgcttgt gctactcaat ccacatcaag atatgttctt ttaggaaatt     720
caaataaccc cacttcaatt tcatctattg gaagtgattt tttgggtcat tctgtgagaa     780
atttcagt                                                             788
```

<210> SEQ ID NO 238

<211> LENGTH: 2631
<212> TYPE: DNA
<213> ORGANISM: Amaranthus palmeri

<400> SEQUENCE: 238

```
tggtacctac cctgtttaca ttttcaattt ccccctttt  tctctactac tcctacttta      60
ttgattctta tccatgtgtg ttctatggga attgacatta attgttcagg tgtgtatgct     120
ggtgatcctt ctaagttgag tatgaaagct gcatttggaa aggtctggac cttagagcaa     180
aagggtggta gtatcattgc cggtacactc aaaactattc aggaaaggaa gaataatcct     240
ccaccgcctc gagacccgtc cgtaatcacc attactcatt gctttccttc accttgtatc     300
ttaccttaat atacatgtat ttaattgata atgtcacatt gcctcatttg cagccgcctt     360
cctaaaccta agggccagac tgttggatcc tttaggaaag ggctcattat gttacctacc     420
gccattgctg ctaggtatct tttgactctc aaatcttaaa tatttctcat cttctccttc     480
tgctaatact agtatgttta ccatcttttt attttttag  gcttggcagt aaagtcaaac     540
tatcgtggac actttctaat attgataagt cgctcaatgg tgaatacaat ctcacttatc     600
aaacacccga tggaccggtt tctgttagga ccaaagcggt tgtcatgact gtcccttcat     660
acattgcaag tagcctgctt cgtccgctct cagtgagtat cattctttcc ttcatttctt     720
ttcgtttatt gttgtccaat gtcttgttaa acaccagttt ggccttgtgc tcgtgaatta     780
tggctacaat gttaactgat tcaggcactg tgggagatgc ctaagtttct aaaacctctg     840
cgcataatgt ttgtttggat gttaggaatt gcattgaaaa attgcttttg tgatgttgat     900
gttaatacca attacaagtg tgttcttcaa cttctgcaat accttgttcg agtgagcttg     960
agggggttta gattagtgtc caatgtgaaa ctagcaaatg aactccaagc gctgggatag    1020
gtccttggga tggagcccct gatacccaag acagtattca aaccctctaa gtagagtgag    1080
agatcaagga aagaaactgg gtggttcctc aaatcgtaaa aaatgaatac agtgtcatga    1140
ttgctaatct tatcacaaat cgtaaaaaat gaattatggt cgattttgga ctattttgg    1200
gtcattttga gtgaatctcg aacttaaaaa gcgagtcttc tagcagttct tgttacagcg    1260
gggcatacat aggtaggaat ttggtttttt actatttgag ccttttgact gttgtggccg    1320
gtaatatgga atagtctagc acttctgcgt gtgtacaact agtatttatt gtaattatgt    1380
gatcgcactt aactctcaga taaaacctta agcactaaca ttttgttttg gttgaaggaa    1440
tcaggaggaa agaaaattga gggatttgtt ggtatataga ttccttttgtt tggataacaa    1500
aattggagtg gagagatttg gaaggaagaa ttttataggg attagttccc attacactta    1560
tgttgattac aaaatttctc caaagtggaa agattttga gtgaaaatgt ttttttatttc   1620
tcttcctctc cctttctttc cctcttaaac aaacaaggaa agttaatctt atcattccgt    1680
accttcccct tctgttcttt ttttctctc  caaaattctt atcctaacgt agtgttattg    1740
tcactgtctt atgaacgaga attcttttct tcctaatact gcttgtgttg cacagtcaat    1800
gatttagcta gatcatcttt ggttagctac tcaaaatatt tacataaaat acttgtagaa    1860
ataaatacca ataggtcttg tcaagaagta gtttcaatgc tataagtttt aaccaatcct    1920
caaaatttac accatggaga tatctgcgga taagaactag taactgtagc agctgtaact    1980
gttgcaatca gttttatggt ttgccttgca aatcaaactt tggatgttgt ttgccttaca    2040
atttgttact attacgtgaa gttagtgtt  cgcccttcac attgtacttt ggttttgtt    2100
ttccttgcaa tttgctcttt gaagtataaa gtgctgagtg ctgagtgctg agtgctgacc    2160
tttcctgctc aggatgttgc tgcagattct ctttctcaat tttactatcc accagtcgca    2220
```

-continued

```
gcagtgtccc tttcttatcc caaagaagca attagaccag aatgcttgat cgatggagaa    2280
ctaaaaggat tcgggcaatt gcatcctcgc agccagggtg tggaaacctt gggtatatgc    2340
tcccattcaa ctatatctca atttttatga gtattttttct ttctctgaat tattcaattt    2400
ggtgacgtta aattttgatt gtactcgaca ggaacaattt atagttcatc tcttttccct    2460
ggtcgagcac cacctggtag gaccttgatc ttgagctaca ttggaggtgc tacaaatgtt    2520
ggcatattac aaaaggcaag tcatttatac aattatatct gttgtatcct caaataagtg    2580
ggtatcaatc ctgacgacat gcttgcttgt atcgatgcag agtgaagatg a             2631
```

<210> SEQ ID NO 239
<211> LENGTH: 23
<212> TYPE: DNA
<213> ORGANISM: Euphorbia heterophylla

<400> SEQUENCE: 239
agtttacagg gagatgtaaa gtt                                              23

<210> SEQ ID NO 240
<211> LENGTH: 23
<212> TYPE: DNA
<213> ORGANISM: Euphorbia heterophylla

<400> SEQUENCE: 240
agtttgcagg gagatgtgaa att                                              23

<210> SEQ ID NO 241
<211> LENGTH: 23
<212> TYPE: DNA
<213> ORGANISM: Ambrosia trifida

<400> SEQUENCE: 241
agtttacagg gggatgtaaa gtt                                              23

<210> SEQ ID NO 242
<211> LENGTH: 23
<212> TYPE: DNA
<213> ORGANISM: Abutilon theophrasti

<400> SEQUENCE: 242
agtttgcagg gtgatgtaaa att                                              23

<210> SEQ ID NO 243
<211> LENGTH: 23
<212> TYPE: DNA
<213> ORGANISM: Xanthium strumarium

<400> SEQUENCE: 243
agtttgcagg gtgatgtgaa att                                              23

<210> SEQ ID NO 244
<211> LENGTH: 23
<212> TYPE: DNA
<213> ORGANISM: Ipomoea hederacea

<400> SEQUENCE: 244
agtttacagg gggatgttaa gtt                                              23

<210> SEQ ID NO 245
<211> LENGTH: 23
<212> TYPE: DNA

```
<213> ORGANISM: Chenopodium album

<400> SEQUENCE: 245
agtttacagg gtgatgtaaa att                                           23

<210> SEQ ID NO 246
<211> LENGTH: 23
<212> TYPE: DNA
<213> ORGANISM: Digitaria sanguinalis

<400> SEQUENCE: 246
agtttgcagg gtgatgtgaa att                                           23

<210> SEQ ID NO 247
<211> LENGTH: 23
<212> TYPE: DNA
<213> ORGANISM: Senna obtusifolia

<400> SEQUENCE: 247
agtttacagg gagatgtaaa att                                           23

<210> SEQ ID NO 248
<211> LENGTH: 23
<212> TYPE: DNA
<213> ORGANISM: Amaranthus rudis/tuberculatus

<400> SEQUENCE: 248
agtttacagg gtgatgtaaa att                                           23

<210> SEQ ID NO 249
<211> LENGTH: 23
<212> TYPE: DNA
<213> ORGANISM: Amaranthus palmeri

<400> SEQUENCE: 249
agtttacagg gtgatgtaaa att                                           23

<210> SEQ ID NO 250
<211> LENGTH: 23
<212> TYPE: DNA
<213> ORGANISM: Amaranthus palmeri

<400> SEQUENCE: 250
agtttacagg gtgatgtaaa att                                           23

<210> SEQ ID NO 251
<211> LENGTH: 54
<212> TYPE: DNA
<213> ORGANISM: Euphorbia heterophylla

<400> SEQUENCE: 251
tcgatgtgaa catgaacaaa atgccagatg tcgctatgac attggctgtg gttg         54

<210> SEQ ID NO 252
<211> LENGTH: 55
<212> TYPE: DNA
<213> ORGANISM: Euphorbia heterophylla

<400> SEQUENCE: 252
tcgatgtgaa tatgaacaaa atgccagatg ttgctatgac attagctgtg gttgc        55

<210> SEQ ID NO 253
<211> LENGTH: 55
```

```
<212> TYPE: DNA
<213> ORGANISM: Ambrosia trifida

<400> SEQUENCE: 253
tcgatgttaa catgaacaaa atgccagatg ttgccatgac gcttgcagtc gttgc          55

<210> SEQ ID NO 254
<211> LENGTH: 55
<212> TYPE: DNA
<213> ORGANISM: Abutilon theophrasti

<400> SEQUENCE: 254
ttgatgtcaa catgaacaaa atgccagatg ttgccatgac tctcgctgtt gttgc          55

<210> SEQ ID NO 255
<211> LENGTH: 55
<212> TYPE: DNA
<213> ORGANISM: Xanthium strumarium

<400> SEQUENCE: 255
ttgatgtcaa catgaacaaa atgcctgatg tcgcaatgac tcttgctgtg gttgc          55

<210> SEQ ID NO 256
<211> LENGTH: 55
<212> TYPE: DNA
<213> ORGANISM: Ipomoea hederacea

<400> SEQUENCE: 256
ttgatgtcaa catgaacaaa atgccagatg ttgccatgac tcttgctgta gttgc          55

<210> SEQ ID NO 257
<211> LENGTH: 55
<212> TYPE: DNA
<213> ORGANISM: Chenopodium album

<400> SEQUENCE: 257
ttgatgtcaa catgaacaaa atgccagatg tcgcaatgac tcttgctgtt gttgc          55

<210> SEQ ID NO 258
<211> LENGTH: 55
<212> TYPE: DNA
<213> ORGANISM: Digitaria sanguinalis

<400> SEQUENCE: 258
ttgacgtcaa catgaacaaa atgcctgatg tcgcaatgac tcttgctgtg gttgc          55

<210> SEQ ID NO 259
<211> LENGTH: 55
<212> TYPE: DNA
<213> ORGANISM: Senna obtusifolia

<400> SEQUENCE: 259
ttgatgtcaa catgaacaag atgccagatg ttgccatgac gcttgctgta gttgc          55

<210> SEQ ID NO 260
<211> LENGTH: 55
<212> TYPE: DNA
<213> ORGANISM: Amaranthus rudis/tuberculatus

<400> SEQUENCE: 260
tcgacgtcaa catgaataaa atgccagatg ttgctatgac tcttgcagtt gttgc          55

<210> SEQ ID NO 261
```

```
<211> LENGTH: 55
<212> TYPE: DNA
<213> ORGANISM: Amaranthus palmeri

<400> SEQUENCE: 261
tcgacgtcaa catgaacaaa atgccagatg ttgctatgac tcttgcagtt gttgc        55

<210> SEQ ID NO 262
<211> LENGTH: 55
<212> TYPE: DNA
<213> ORGANISM: Amaranthus palmeri

<400> SEQUENCE: 262
tcgacgtcaa catgaacaaa atgccagatg ttgctatgac tcttgcagtt gttgc        55

<210> SEQ ID NO 263
<211> LENGTH: 55
<212> TYPE: DNA
<213> ORGANISM: artificial sequence
<220> FEATURE:
<223> OTHER INFORMATION: Synthetic Construct
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (35)..(35)
<223> OTHER INFORMATION: n is a, c, g, or t
<220> FEATURE:
<221> NAME/KEY: misc_feature
<222> LOCATION: (41)..(41)
<223> OTHER INFORMATION: n is a, c, g, or t
<220> FEATURE:
<221> NAME/KEY: misc_feature
<222> LOCATION: (47)..(47)
<223> OTHER INFORMATION: n is a, c, g, or t
<220> FEATURE:
<221> NAME/KEY: misc_feature
<222> LOCATION: (50)..(50)
<223> OTHER INFORMATION: n is a, c, g, or t

<400> SEQUENCE: 263
tngangtcaa catgaacaaa atgccagatg tngcnatgac ncttgcngtn gttgc        55

<210> SEQ ID NO 264
<211> LENGTH: 21
<212> TYPE: RNA
<213> ORGANISM: artificial sequence
<220> FEATURE:
<223> OTHER INFORMATION: Synthetic Construct

<400> SEQUENCE: 264
aacaugaaca aaaugccaga u                                             21

<210> SEQ ID NO 265
<211> LENGTH: 21
<212> TYPE: RNA
<213> ORGANISM: artificial sequence
<220> FEATURE:
<223> OTHER INFORMATION: Synthetic Construct

<400> SEQUENCE: 265
```

-continued aucuggcauu uguucaugu u                                              21

<210> SEQ ID NO 266
<211> LENGTH: 22
<212> TYPE: RNA
<213> ORGANISM: artificial sequence
<220> FEATURE:
<223> OTHER INFORMATION: Synthetic Construct

<400> SEQUENCE: 266
aacaugaaca aaaugccaga ug                                            22

<210> SEQ ID NO 267
<211> LENGTH: 22
<212> TYPE: RNA
<213> ORGANISM: artificial sequence
<220> FEATURE:
<223> OTHER INFORMATION: Synthetic Construct

<400> SEQUENCE: 267
caucuggcau uuuguucaug uu                                            22

<210> SEQ ID NO 268
<211> LENGTH: 24
<212> TYPE: RNA
<213> ORGANISM: artificial sequence
<220> FEATURE:
<223> OTHER INFORMATION: Synthetic Construct

<400> SEQUENCE: 268
caacaugaac aaaaugccag augu                                          24

<210> SEQ ID NO 269
<211> LENGTH: 24
<212> TYPE: RNA
<213> ORGANISM: artificial sequence
<220> FEATURE:
<223> OTHER INFORMATION: Synthetic Construct

<400> SEQUENCE: 269
acaucuggca uuuuguucau guug                                          24

<210> SEQ ID NO 270
<211> LENGTH: 35
<212> TYPE: RNA
<213> ORGANISM: artificial sequence
<220> FEATURE:
<223> OTHER INFORMATION: Synthetic Construct

<400> SEQUENCE: 270
ucgacgucaa caugaacaaa augccagaug uugcu                              35

<210> SEQ ID NO 271
<211> LENGTH: 35
<212> TYPE: RNA
<213> ORGANISM: artificial sequence
<220> FEATURE:
<223> OTHER INFORMATION: Synthetic Construct

<400> SEQUENCE: 271
agcaacaucu ggcauuuugu ucauguugac gucga                              35

<210> SEQ ID NO 272
<211> LENGTH: 45
<212> TYPE: RNA

<213> ORGANISM: artificial sequence
<220> FEATURE:
<223> OTHER INFORMATION: Synthetic Construct

<400> SEQUENCE: 272
ucgacgucaa caugaacaaa augccagaug uugcuaugac ucuug            45

<210> SEQ ID NO 273
<211> LENGTH: 45
<212> TYPE: RNA
<213> ORGANISM: artificial sequence
<220> FEATURE:
<223> OTHER INFORMATION: Synthetic Construct

<400> SEQUENCE: 273
caagagucau agcaacaucu ggcauuuugu ucauguugac gucga            45

<210> SEQ ID NO 274
<211> LENGTH: 55
<212> TYPE: RNA
<213> ORGANISM: artificial sequence
<220> FEATURE:
<223> OTHER INFORMATION: Synthetic Construct

<400> SEQUENCE: 274
ucgacgucaa caugaacaaa augccagaug uugcuaugac ucuugcaguu guugc     55

<210> SEQ ID NO 275
<211> LENGTH: 55
<212> TYPE: RNA
<213> ORGANISM: artificial sequence
<220> FEATURE:
<223> OTHER INFORMATION: Synthetic Construct

<400> SEQUENCE: 275
gcaacaacug caagagucau agcaacaucu ggcauuuugu ucauguugac gucga     55

<210> SEQ ID NO 276
<211> LENGTH: 45
<212> TYPE: DNA
<213> ORGANISM: artificial sequence
<220> FEATURE:
<223> OTHER INFORMATION: Synthetic Construct

<400> SEQUENCE: 276
taatacgact cactataggg ctttattgaa tttagctatg taatc            45

<210> SEQ ID NO 277
<211> LENGTH: 41
<212> TYPE: DNA
<213> ORGANISM: artificial sequence
<220> FEATURE:
<223> OTHER INFORMATION: Synthetic Construct

<400> SEQUENCE: 277
taatacgact cactataggg tttatcaacc aaatgtgcag c                41

<210> SEQ ID NO 278
<211> LENGTH: 49
<212> TYPE: DNA
<213> ORGANISM: artificial sequence
<220> FEATURE:
<223> OTHER INFORMATION: Synthetic Construct

<400> SEQUENCE: 278
taatacgact cactataggg ttgtctgtac ataattgtga gatttgtgg         49

<210> SEQ ID NO 279
<211> LENGTH: 21
<212> TYPE: DNA
<213> ORGANISM: artificial sequence
<220> FEATURE:
<223> OTHER INFORMATION: Synthetic Construct

<400> SEQUENCE: 279
ctgtgatcat catatgtatc a                                           21

<210> SEQ ID NO 280
<211> LENGTH: 21
<212> TYPE: DNA
<213> ORGANISM: artificial sequence
<220> FEATURE:
<223> OTHER INFORMATION: Synthetic Construct

<400> SEQUENCE: 280
ccttaactct ccagctagca a                                           21

<210> SEQ ID NO 281
<211> LENGTH: 21
<212> TYPE: DNA
<213> ORGANISM: artificial sequence
<220> FEATURE:
<223> OTHER INFORMATION: Synthetic Construct

<400> SEQUENCE: 281
cagcccgcaa atgtttcatt c                                           21

<210> SEQ ID NO 282
<211> LENGTH: 21
<212> TYPE: DNA
<213> ORGANISM: artificial sequence
<220> FEATURE:
<223> OTHER INFORMATION: Synthetic Construct

<400> SEQUENCE: 282
gccgtcaatg gccgcattgc t                                           21

<210> SEQ ID NO 283
<211> LENGTH: 21
<212> TYPE: DNA
<213> ORGANISM: artificial sequence
<220> FEATURE:
<223> OTHER INFORMATION: Synthetic Construct

<400> SEQUENCE: 283
tccttccctc agaaagggca g                                           21

<210> SEQ ID NO 284
<211> LENGTH: 21
<212> TYPE: DNA
<213> ORGANISM: artificial sequence
<220> FEATURE:
<223> OTHER INFORMATION: Synthetic Construct

<400> SEQUENCE: 284
ttgcctcatg ctgctaatct g                                           21

<210> SEQ ID NO 285
<211> LENGTH: 789
<212> TYPE: DNA
<213> ORGANISM: Nicotiana benthamiana

<400> SEQUENCE: 285

| | | | | | |
|---|---|---|---|---|---|
| cttatatgtg | cttaagccta | acgtgcaccc | ggcccCttaa | ccccagcagt | tttcaatcta | 60 |
| cctaccgtct | ctaccatttt | cttctagttg | gtgaaaattt | ctaactttga | gaaaacaagc | 120 |
| caaagttttt | gtttctaaga | acgcaaaatg | agtgaaattt | tttgcagcaa | tggcacagat | 180 |
| tagcagcatg | aggcaaggga | tacagacccc | taatcttaat | tcctattttc | ctaaaaccca | 240 |
| aaaggttcct | ctttttttcgc | attctatctt | ctttggatca | aagaaaataa | cccaaaattc | 300 |
| agcaaaatct | ttgtgggtgt | gtaagaaaga | ttcagttttg | agggtggcaa | agtcaccttt | 360 |
| taggatttgt | gcatcagtgg | ccactgcaca | gaagcccaac | gagattgtgc | tgcaacccat | 420 |
| caaagatata | tcaggcactg | ttaaattgcc | tggttctaaa | tccctttcca | accgtattct | 480 |
| ccttcttgct | gcccttttctg | agggaaggac | tgttgttgac | aatttactga | gtagtgatga | 540 |
| cattcattac | atgcttggtg | cgttgaaaac | acttggactt | catgtagaag | atgacaatga | 600 |
| aaaccaacga | gcaattgtgg | aaggttgtgg | tgggcagttt | cctgtcggcg | agaagtctga | 660 |
| ggaagaaatc | caactattcc | ttggaaatgc | aggaacagca | atgcggccat | tgacggcagc | 720 |
| agttactgta | gctggaggac | attcaagata | tgtacttgat | ggagttccta | ggatgagaga | 780 |
| gagaccgat | | | | | | 789 |

<210> SEQ ID NO 286
<211> LENGTH: 799
<212> TYPE: DNA
<213> ORGANISM: Nicotiana benthamiana

<400> SEQUENCE: 286

| | | | | | |
|---|---|---|---|---|---|
| cactgacgtt | ggattagagg | taggctcctt | atatgtgctt | aagcctaacg | tgcagccggc | 60 |
| ccccaacccc | agcagttttc | aatctaccta | ccgtctctac | catttttctta | tagtagttga | 120 |
| aaatttctaa | ctttgagaaa | acaagccaaa | gttttgtttc | taagaacaca | aagggagtga | 180 |
| aattttttgc | agcaatggca | cagattagca | gcatgaggca | agggatacag | accCctaatc | 240 |
| ttaattccta | ttttcctaaa | acccaaaagg | ttcctctttt | ttcgcattct | atcttcattg | 300 |
| gatcaaagaa | ataacccaa | aattcagcaa | aatctttgtg | ggtgtgtaag | aaagattcag | 360 |
| ttttgagggt | ggcaaagtca | cctttttagga | tttgtgcatc | agtggccact | gcacagaagc | 420 |
| ctaacgagat | tgtgctgcaa | cctatcaaag | atatatcagg | cactgttaaa | ttacctggtt | 480 |
| ctaaatccct | ttccaatcgt | attctccttc | ttgctgccct | ttctgaggga | aggactgttg | 540 |
| ttgcaatttt | actgagtagt | gatgacattc | attacatgct | tggtgcattg | aaaacacttg | 600 |
| gacttcatgt | agaagatgac | aatgaaaacc | aacgagcaat | cgtagaaggt | tgtggtgggc | 660 |
| agttcctgt | cggcaagaag | tctgaggaag | aaatccaact | attccttgga | aatgcaggaa | 720 |
| cagcaatgcg | gccattgacg | gcagcagtta | ctgtagctgg | tggacattct | agatatgtac | 780 |
| ttgatggagt | tcctaggat | | | | | 799 |

<210> SEQ ID NO 287
<211> LENGTH: 845
<212> TYPE: DNA
<213> ORGANISM: Nicotiana benthamiana

<400> SEQUENCE: 287

| | | | | | |
|---|---|---|---|---|---|
| aaattcttgg | ttcgaggagg | tcagaagtac | aagtctcctg | gaaaagcata | tgttgaagga | 60 |
| gatgcctcaa | gtgctagcta | cttttttggcg | ggtgcagctc | tcacaggtgg | aactgtcact | 120 |
| gttgaaggtt | gtggaacaag | cagtttacag | ggggatgtta | agtttgctga | ggtcctcgaa | 180 |

```
aagatggggg cagaagttac atggacagag aacagtgtca cggttaaagg acctccaagg    240
aactcttctg gaatgaaaca tttgcgggct gttgacgtta acatgaacaa aatgccagat    300
gttgccatga ctcttgctgt agttgcactt tttgctgata gtcctactgc cataagagat    360
gttgctagct ggagagttaa ggaaactgag cggatgattg ccatatgcac agaacttagg    420
aagttgggtg caacagttgt agaagggcca gactactgca taatcactcc acctgaaaag    480
ttaaaagtag cggaaattga tacatatgat gatcacagaa tggccatggc tttctctctt    540
gcggcttgtg ctgatgttcc agtcaccatt aaggaccccg gttgtactcg caaaaccttc    600
cccaactact ttgacgttct ccagcagtat tccaagcatt aaaccacttt ccattaagaa    660
ttttgaaaaa gagagacttt gacaacaatg gtgtcatacc ggaagagaaa agctttgatc    720
caagctttca actccttttc atttgtcatg tgatgatcat tgtatttgtt gaagttgagc    780
tgcttttctt ttgtccagaa gacatgtatg gatactatta ctatatagtt aaggtgaact    840
cagca                                                                845
```

<210> SEQ ID NO 288
<211> LENGTH: 21
<212> TYPE: DNA
<213> ORGANISM: artificial sequence
<220> FEATURE:
<223> OTHER INFORMATION: Synthetic Construct

<400> SEQUENCE: 288
ccacatggtc cagtatctgc c                                               21

<210> SEQ ID NO 289
<211> LENGTH: 21
<212> TYPE: DNA
<213> ORGANISM: artificial sequence
<220> FEATURE:
<223> OTHER INFORMATION: Synthetic Construct

<400> SEQUENCE: 289
caagcaagga acccatccat t                                               21

<210> SEQ ID NO 290
<211> LENGTH: 21
<212> TYPE: DNA
<213> ORGANISM: artificial sequence
<220> FEATURE:
<223> OTHER INFORMATION: Synthetic Construct

<400> SEQUENCE: 290
ggccacacct gcatgcattg c                                               21

<210> SEQ ID NO 291
<211> LENGTH: 21
<212> TYPE: DNA
<213> ORGANISM: artificial sequence
<220> FEATURE:
<223> OTHER INFORMATION: Synthetic Construct

<400> SEQUENCE: 291
gtgttcacgg tagacaaatc c                                               21

<210> SEQ ID NO 292
<211> LENGTH: 21
<212> TYPE: DNA
<213> ORGANISM: artificial sequence
<220> FEATURE:

<223> OTHER INFORMATION: Synthetic Construct

<400> SEQUENCE: 292
tgcactgcac ttgacgcacg t                                              21

<210> SEQ ID NO 293
<211> LENGTH: 21
<212> TYPE: DNA
<213> ORGANISM: artificial sequence
<220> FEATURE:
<223> OTHER INFORMATION: Synthetic Construct

<400> SEQUENCE: 293
aactgatgca ttgcacttga c                                              21

<210> SEQ ID NO 294
<211> LENGTH: 21
<212> TYPE: DNA
<213> ORGANISM: artificial sequence
<220> FEATURE:
<223> OTHER INFORMATION: Synthetic Construct

<400> SEQUENCE: 294
caaatcagga aggtatgaga g                                              21

<210> SEQ ID NO 295
<211> LENGTH: 21
<212> TYPE: DNA
<213> ORGANISM: artificial sequence
<220> FEATURE:
<223> OTHER INFORMATION: Synthetic Construct

<400> SEQUENCE: 295
tgtcaaggtt ttgtttcctg g                                              21

<210> SEQ ID NO 296
<211> LENGTH: 543
<212> TYPE: DNA
<213> ORGANISM: Nicotiana benthamiana

<400> SEQUENCE: 296
gcaatggctt cctcagttct ttcctcagca gcagttgcca cccgcagcaa tgttgctcaa     60
gctaacatgg ttgcaccttt cacaggtctt aagtctgctg cctcattccc tgtttcaaga   120
aagcaaaacc ttgacatcac ttccattgcc agcaacggcg gaagagtgca atgcatgcag   180
gtgtggccac caattaacat gaagaagtat gagactctct cataccttcc cgatttgagc   240
caggagcaat tgctctccga aattgagtac cttttgaaga atggatgggt tccttgcttg   300
gaattcgaga ctgagaaagg atttgtctac cgtgaacacc acaagtcacc aggatactat   360
gatggcagat actggaccat gtggaagcta cctatgttcg gatgcactga tgccacccaa   420
gtgttggctg aggtgggaga ggcgaagaag gaatacccac aggcctgggt ccgtatcatt   480
ggatttgaca acgtgcgtca agtgcagtgc atcagtttca ttgcctccaa gcctgacggc   540
tac                                                                 543

<210> SEQ ID NO 297
<211> LENGTH: 543
<212> TYPE: DNA
<213> ORGANISM: Nicotiana benthamiana

<400> SEQUENCE: 297
acaatggctt cctcagttct ttcctcagca gcagttgcca cccgcagcaa tgttgctcaa     60

-continued

```
gctaacatgg ttgcacccttt cactggtctt aagtcagctg ccttttttccc tgtttcaagg      120 aagcaaaacc ttgacatcac ttccattgcc agcaacggcg aaagagtgca atgcatgcag      180
gtgtggccac caattaacaa gaagaagtac gagactctct cataccttcc tgatctgagc      240
gtggagcaat tgcttagcga aattgagtac ctcttgaaaa atggatgggt tccttgcttg      300
gaattcgaga ctgagcgcgg atttgtctac cgtgaacacc acaagtcacc gggatactat      360
gacggcagat actggaccat gtggaagttg cctatgttcg gatgcactga tgccacccaa      420
gtgttggccg aggtggaaga ggcgaagaag gcatacccac aggcctggat ccgtattatt      480
ggattcgaca acgtgcgtca agtgcagtgc atcagtttca ttgcctacaa gccagaaggc      540
tac                                                                    543
```

<210> SEQ ID NO 298
<211> LENGTH: 486
<212> TYPE: DNA
<213> ORGANISM: Nicotiana benthamiana

<400> SEQUENCE: 298

```
caagccaaca tggttgcacc cttcactggc ctcaagtccg cctcctcctt ccctgttacc      60
aggaaacaaa accttgacat tacctccatt gctagcaatg gtggaagagt tcaatgcatg      120
caggtgtggc caccaattaa catgaagaag tacgagacac tctcataccct tcctgatttg      180 agccaggagc aattgcttag tgaagttgag tacctttttga aaaatggatg ggttccttgc      240
ttggaattcg agactgagcg tggattcgtc taccgtgaac accacaactc accaggatac      300
tacgatggca gatactggac catgtggaag ttgcccatgt tcgggtgcac tgatgccact      360
caggtgttgg ctgaggtcga ggaggcaaag aaggcttacc acaagcctg gttagaatc      420 attggattcg acaacgtccg tcaagtgcaa tgcatcagtt ttatcgcctc caagccagaa      480
ggctac                                                                 486
```

<210> SEQ ID NO 299
<211> LENGTH: 537
<212> TYPE: DNA
<213> ORGANISM: Nicotiana benthamiana

<400> SEQUENCE: 299

```
ggctcagtta tgtcctcagc tgccgctgtt tccaccggcg ccaatgctgt tcaagccagc      60
atggtcgcac ccttcactgg cctcaaggcc gcctcctcct tcccggtttc aggaaacaa      120 aaccttgaca ttacttccat tgctagaaat ggtggaagag tccaatgcat gcaggtgtgg      180
ccgccaatta acaagaagaa gtacgagaca ctctcatacc ttcctgattt gagcgtggag      240
caattgctta gcgaaattga gtaccttttg aaaaatggat gggttccttg cttggaattc      300
gagactgagc atggattcgt ctaccgtgaa caccaccact caccaggata ctacgatggc      360
agatactgga cgatgtggaa gttgcccatg ttcgggtgca ccgatgccac tcaggtcttg      420
gctgaggtag aggaggccaa gaaggcttac cacaagcct gggtcagaat cattggattc      480
gacaacgtcc gtcaagtgca atgcatcagt ttcatcgcct acaagcccga aggctat      537
```

<210> SEQ ID NO 300
<211> LENGTH: 21
<212> TYPE: DNA
<213> ORGANISM: artificial sequence
<220> FEATURE:
<223> OTHER INFORMATION: Synthetic Construct

<400> SEQUENCE: 300
ggaggcaaaa tacgagcctc a    21

<210> SEQ ID NO 301
<211> LENGTH: 21
<212> TYPE: DNA
<213> ORGANISM: artificial sequence
<220> FEATURE:
<223> OTHER INFORMATION: Synthetic Construct

<400> SEQUENCE: 301
cactaatctt aataccaaac t    21

<210> SEQ ID NO 302
<211> LENGTH: 25
<212> TYPE: DNA
<213> ORGANISM: artificial sequence
<220> FEATURE:
<223> OTHER INFORMATION: Synthetic Construct

<400> SEQUENCE: 302
tatgggtcat tagcataggc attat    25

<210> SEQ ID NO 303
<211> LENGTH: 21
<212> TYPE: DNA
<213> ORGANISM: artificial sequence
<220> FEATURE:
<223> OTHER INFORMATION: Synthetic Construct

<400> SEQUENCE: 303
tctcaagaat atcacgctcc c    21

<210> SEQ ID NO 304
<211> LENGTH: 24
<212> TYPE: DNA
<213> ORGANISM: artificial sequence
<220> FEATURE:
<223> OTHER INFORMATION: Synthetic Construct

<400> SEQUENCE: 304
cccttgggga cgctggcagg tcac    24

<210> SEQ ID NO 305
<211> LENGTH: 40
<212> TYPE: DNA
<213> ORGANISM: artificial sequence
<220> FEATURE:
<223> OTHER INFORMATION: Synthetic Construct

<400> SEQUENCE: 305
taatacgact cactataggg ggagagagct agatcttttg    40

<210> SEQ ID NO 306
<211> LENGTH: 41
<212> TYPE: DNA
<213> ORGANISM: artificial sequence
<220> FEATURE:
<223> OTHER INFORMATION: Synthetic Construct

<400> SEQUENCE: 306
taatacgact cactataggc acagtatttc ttcctccaac c    41

<210> SEQ ID NO 307
<211> LENGTH: 21

```
<212> TYPE: DNA
<213> ORGANISM: artificial sequence
<220> FEATURE:
<223> OTHER INFORMATION: Synthetic Construct

<400> SEQUENCE: 307
ttgctcatct aaatacatg t                                          21

<210> SEQ ID NO 308
<211> LENGTH: 24
<212> TYPE: DNA
<213> ORGANISM: artificial sequence
<220> FEATURE:
<223> OTHER INFORMATION: Synthetic Construct

<400> SEQUENCE: 308
tcatcttaaa tacatgtttt gtca                                      24

<210> SEQ ID NO 309
<211> LENGTH: 22
<212> TYPE: DNA
<213> ORGANISM: artificial sequence
<220> FEATURE:
<223> OTHER INFORMATION: Synthetic Construct

<400> SEQUENCE: 309
ttatcttcag ggatacatta gc                                        22

<210> SEQ ID NO 310
<211> LENGTH: 24
<212> TYPE: DNA
<213> ORGANISM: artificial sequence
<220> FEATURE:
<223> OTHER INFORMATION: Synthetic Construct

<400> SEQUENCE: 310
aatactgctt gctcatctta aata                                      24

<210> SEQ ID NO 311
<211> LENGTH: 21
<212> TYPE: DNA
<213> ORGANISM: artificial sequence
<220> FEATURE:
<223> OTHER INFORMATION: Synthetic Construct

<400> SEQUENCE: 311
gacaattcca agttcagttt c                                         21

<210> SEQ ID NO 312
<211> LENGTH: 24
<212> TYPE: DNA
<213> ORGANISM: artificial sequence
<220> FEATURE:
<223> OTHER INFORMATION: Synthetic Construct

<400> SEQUENCE: 312
ccgttttaga tcaccataaa gaga                                      24

<210> SEQ ID NO 313
<211> LENGTH: 21
<212> TYPE: DNA
<213> ORGANISM: artificial sequence
<220> FEATURE:
<223> OTHER INFORMATION: Synthetic Construct

<400> SEQUENCE: 313
```
ttgtctggta atatcacaat c                                              21

<210> SEQ ID NO 314
<211> LENGTH: 2937
<212> TYPE: DNA
<213> ORGANISM: Nicotiana benthamiana

<400> SEQUENCE: 314

| | | | | |
|---|---|---|---|---|
| atggtgagga | agaggagaac | tgagttacct | ggttctggtg | agagctctgg gtctcaagaa | 60 |
| actggcggac | agggtcgtgg | ccagcatcca | cagcagctgc | accaagctac ctcccagact | 120 |
| ccatatcaaa | ctgcaatgac | tactcagcca | ataccttatg | caagaccaac tgaaacatcc | 180 |
| tccgaagctg | gttcctcatc | tcagccacct | gagcaggcag | ctctacaagt gacacaacag | 240 |
| ttccagcaac | ttgctttgca | caagaagcg | gctacaacgc | aagcagttcc acctgcatca | 300 |
| agcaaattac | taaggtttcc | cctgcgtcca | gggaagggga | gcaatggtat gagatgcata | 360 |
| gtcaaagcca | atcacttctt | cgcagagctg | cctgacaaag | acttgcacca gtatgatgtc | 420 |
| acaatttctc | cagaggtgtc | atcacgtggc | gtcaaccgtg | ctgtcatggc gcaactggtg | 480 |
| aagctgtacc | aagaatctca | tcttgggaag | agacttccag | catatgatgg aaggaaaagt | 540 |
| ctatacactg | cagggcccct | tccatttgtt | caaaaagact | tcaaaataac tcttattgat | 600 |
| gatgaggatg | ggcctggtgg | tgctagaagg | gaaagggaat | ttaaagttgt gatcaaattg | 660 |
| gctgcccgtg | ctgatcttca | tcacttggga | atgtttttag | aagggaaaca ggctgatgca | 720 |
| cctcaagagg | cgcttcaagt | tctggatatt | gttctgcgtg | agttgccaac atctaggttt | 780 |
| tgtcctgtgg | gtcgttcttt | ctattcccgt | gatttagggc | gaaagcaacc attgggtgaa | 840 |
| ggtttagaaa | gttggcgtgg | gttctatcaa | agcattcgcc | ccacacaaat gggcttatca | 900 |
| ctgaacatcg | atatgtcttc | cactgcattc | attgagccac | tgccagtcat tgattttgtg | 960 |
| acacagcttc | tgaaccgaga | tgtgccatct | agaccactgt | ctgatgctgg ccgtgtaaag | 1020 |
| ataaaaaaag | ctctgagagg | tgtgaaggtg | gaggttactc | atcgtggaaa tatgcggagg | 1080 |
| aagtaccgca | tttcgggttt | aacatctcaa | gcaacaagag | agttgacctt ccctgttgat | 1140 |
| gaaaatggta | cagtgaaatc | tgtaattgag | tattttcgag | aaacatatgg gtttgtaatt | 1200 |
| cagcatactc | agtggccttg | tctacaagtt | ggaaatcagc | agagacctaa ttacttgcca | 1260 |
| atggaagtct | gcaagattgt | ggagggacaa | aggtactcaa | agcgcttgaa tgagagacag | 1320 |
| attactgcac | ttctgaaagt | gacctgccag | cgtccccaag | ggagggagcg tgatattctt | 1380 |
| gagaccgtac | atcataatgc | ctatgctaat | gacccatatg | ccaaggagtt tggtattaag | 1440 |
| attagtgaca | agttggcaca | agttgaggct | cgtatttttgc | ctccacctcg gcttaaatat | 1500 |
| catgataacg | tcgagaaaaa | ggactgcctg | ccacaagttg | gccaatggaa tatgatgaat | 1560 |
| aagaaaatgg | taaatggagg | gacggtgaac | aattggatct | gcataaactt ctctcgcaat | 1620 |
| gtgcaagata | gtgttgctca | tgggttttgc | tctgagcttg | cacaaatgtg ccagatatct | 1680 |
| ggcatgaatt | tcaatccaaa | tcctgttctg | ccaccttcga | gtgcacgccc tgatcaggtc | 1740 |
| gaaagagtat | tgaaaactcg | atttcatgat | gctatgacta | agttgcagct gcatgggaga | 1800 |
| gagcttgatt | tgctagttgt | catcttgcca | gacaataatg | gatctcttta tggtgatctg | 1860 |
| aagcgcattt | gtgagactga | actaggagtc | gtctcacagt | gctgtttgac aaaacatgta | 1920 |
| tttaagatga | gcaaacagta | tctagccaat | gtagcgctga | aaatcaatgt gaaggtggga | 1980 |
| gggagaaaca | ctgtgcttgt | tgatgcaata | tcgaggcgaa | ttcctcttgt cagcgaccgg | 2040 |
| cctaccatca | tttttggtgc | agatgtcacc | caccctcacc | ctggggagga ctctagccca | 2100 |

```
tccattgccg cggtggttgc ttctcaagat tggcctgaga ttacaaagta tgctggtcta    2160
gtttctgctc aagcccatag gcaagagctt attcaggatc tgtacacgac taggcaagat    2220
cctgttaagg ggacagttgc tggtggaatg attaaggact tacttatatc cttccgaaga    2280
gctactggac aaaagcccca gagaataatt ttctataggg atggtgttag tgaaggacaa    2340
ttttatcaag tgcttctgtt cgaacttgat gcgatccgca aagcatgtgc gtctttggag    2400
ccaaattatc agccccagt cacatttgtt gtggttcaga aacgacatca cacaaggctt     2460
tttgccaata accaccgtga cagaaatgca gttgacagga gcgggaacat tatacctggt    2520
actgttgtag attcaaagat atgccacccg acagagtttg atttctatct ttgtagccat    2580
gccggcatac agggtacgag ccgtccagct cactaccatg ttctatggga cgagaacaaa    2640
ttcacagccg atgcgctgca gtctttgacc aacaacctct gctatacata tgcaaggtgc    2700
acgcgttccg tctccatcgt tcccctgca tattatgcac atttggcagc tttccgtgct     2760 cgatttttata tggagccgga gacatctgac ggtggttcag taacaagtgg ggctgctggt    2820
ggcagagggg gtggtgcagg agctgctgga aggaacaccc gagccccaag tgctggtgct    2880
gctgttagac tcttcctgc gctcaaggat aatgtgaaga gggttatgtt ctactgc        2937
```

<210> SEQ ID NO 315
<211> LENGTH: 3274
<212> TYPE: DNA
<213> ORGANISM: Nicotiana benthamiana

<400> SEQUENCE: 315

```
cacctatcac tctctttctc tctctacaaa catatcgtgc cgtttctctc tcggcctctc      60
ttcgtgtttt agggcaccgt ggtggttggt atccaggcgg cggttttgag ttattaccat    120
ggtgcggaag aagaggactg atgttcctgg tggtgctgag agttttgagt cccatgaaac    180
tggaggggca cgaggtggtg cccaacgccc atcacagcag cagcaacatc agcatcagca    240
aggcggagga agaggctggg cacctcagca tggaggacat ggtggccgtg gtggtggggg    300
agctccacgt ggtggaatgg cccctcaaca atcctatggt ggacctcctg aatactacca    360
acagggcagg ggaactcaac agtatcaacg aggtggagga caaccccagc gccgtggtgg    420 catgggggc cgtggggcac ggccaccagt acccgagctg caccaagcaa cccagactcc      480
acatcagcct gtaccatatg gaagaccatc agaaacatac tcagaggctg gttcctcgtc    540
tcagccacct gaaccaacga cacagcaagt gactcagcaa ttccagcaac ttgttgtgca    600
gccagaagca gctgcaaccc aagcaataca accagcatcg agcaagtcga tgaggtttcc    660
actccggcca ggaaagggta gtactggtat tagatgcata gttaaggcca atcacttctt    720
tgccgagtta cctgacaaag atctgcacca gtatgatgtt tcaattactc ctgaggtcgc    780
ctctcggggt gtcaaccggg ccgtcatgga gcagctggtg aagctttata gagaatccca    840
tcttgggaag aggcttccag cctatgacgg aagaaaaagt ctatacacag cagggcccct    900
cccttttgtt caaaaggatt ttaaaatcac tctaattgat gatgatgatg gacctggtgg    960
tgctaggagg gaaagagagt ttaaagttgt gatcaagctg gcggctcgtg ctgatcttca   1020
tcacttgggg atgttcttac aagggagaca ggctgatgca ccgcaagaag cacttcaggt   1080
gctggatatt gtgctacgtg agttgccaac atctaggtat tgtcctgtgg gccgctcttt   1140
ctattcccct catttaggac gaagacaacc actgggtgaa ggtttagaga gctgcgtgg    1200 cttctatcaa agtattcgtc ctacacagat gggattatcc ctgaatattg atatgtcttc   1260
```

```
cacggctttc attgagccac tgccgattat tgacttcgtg agccagcttc tgaatcggga    1320
tatctcttct agaccactgt ctgatgctga ccgcgttaag ataaagaagg cactgagagg    1380
tgtaaaggtg ggggtcactc atcgtggaaa tatgcggagg aagtatcgca tttctggctt    1440
gacgtctcaa gcaacaagag agttgacttt tcctgtcgat gaaggggta cgatgaaagc     1500
tgttgtggaa tattttcggg aaacctatgg ttttgtcatt cggcataccc agtggccttg    1560
tcttcaagtt ggaaatacgc agaggccaaa ttacttgcca atggaagtat gtaagattgt    1620
agagggacag agatactcaa agcgcttgaa tgagaggcag ataacagcac ttctaaaagt    1680
gacctgccaa cgtcctcaag agagagaacg tgatattctt cagactgttc atcacaatgc    1740
ttatgctgat gacccatatg cgaaggagtt tggtattaag atcagtgagg agcttgctca    1800
agttgaggct cgcgttttgc ctgcaccttg gcttaaatac catgatacag tcgagagaa     1860
agactgtctg ccacaagtgg gccagtggaa tatgatgaat aagaaaatgg ttaatggagg    1920
aacagtgaac aactggatct gtgtaaactt ttctcgcaat gtgcaagaca cagttgcacg    1980
tggattttgt tccgagcttg cacaaatgtg catgatatcc ggaatgaact tcaatcccaa    2040
tcctgttcta ccaccagtga gtgctcgccc tgatcaagtt gagagagtct tgaaaactcg    2100
atttcacgat gctatgacaa agttgcagcc aaatgggaga gagctagatc ttttgattgt    2160
gatattacca gacaataacg gctctctttta tggtgatcta aaacggattt gtgaaactga    2220
acttggaatt gtctcacaat gctgcttgac aaaacatgta tttaagatga gcaagcagta    2280
tttagctaat gtatccctga agataaatgt gaaggttgga ggaagaaata ctgtgctggt    2340
tgatgcgctc tctagacgaa ttccccttgt cagcgaccgc ccaactatca tttttggtgc    2400
agatgtcacc catccccacc ctggggagga ttctagcccg tcaattgctg cggtggttgc    2460
ttctcaagat tggcctgaaa ttacaaagta tgctggtttg gtttctgctc aagcgcatag    2520
gcaagagctt atacaagatc tgtacaagac ttggcaagat ccagttagag gacctgtgac    2580
tggtggcatg ataaaggaat tacttatttc cttccgtcga gcaactggac agaagccgca    2640
gagaattata ttctacagag atggtgttag tgaaggacaa ttttaccaag ttcttctttt    2700
tgaacttgat gcaatccgca aggcatgtgc atctttagaa cccaactatc agccccggt    2760
tacgtttgtt gtggtccaga aacggcatca tactaggttg tttgccaata ccaccacga    2820
cagaaatgca gttgatcgga gtgggaacat tttgcctggt accgttgtag attcaaagat    2880
atgccaccct actgaatttg atttctatct ctgtagccat gccggcatac agggtactag    2940
ccgcccagct cattatcatg ttctgtggga tgagaacaat tttactgctg acgccctgca    3000
gtctttgact aacaatcttt gctatacata tgctaggtgt actcgttctg tctccattgt    3060
tccaccagca tattatgcac atttggcagc tttccgtgct cggttttaca tggagccaga    3120
gacatctgat aatggatcag tcacaagcgc agctgcttca aacagaggag gtttaggagc    3180
tatgggaagg agcacgcgag caccaggtgc tggtgctgct gtaaggcccc ttcctgctct    3240
caaggagaat gttaagaggg ttatgtttta ttgt                                3274
```

<210> SEQ ID NO 316
<211> LENGTH: 3907
<212> TYPE: DNA
<213> ORGANISM: Zea mays
<400> SEQUENCE: 316

```
acctacttcc ccctcgcccc tctcatggtc tctctcgcgc ccagatctgc tactagacgg      60
caccgctgca gcgcgtcgtg tcgcgggggt tggtggcagg cagcgagagc ttgccgttcc     120
```

```
tctctctcag ttgtcaggtc ctaggctcac ctcaccggct cccagcccgc ttctatttct    180
tcctccccga ccccgtgcag gtggcagtcc agtccacgcc accaaccgcg aggcgaacca    240
aaccaaccca ctctccccaa ccccgcgcgc ccaggccgcc cgccctacca accatcggcg    300
tcggcaatgg cggccatggc gaccaaggcc gccgcgggca ccgtgtcgct ggacctcgcc    360
gcgccgccgg cggcggcagc ggcggcggcg gtgcaggcgg gtgccgagga gatcgtgctg    420
cagcccatca aggagatctc cggcaccgtc aagctgccgg ggtccaagtc gctttccaac    480
cggatcctcc tgctcgccgc cctgtccgag gtgagcgatt ttggtgcttg ctgcgctgcc    540
ctgtctcact gctacctaaa tgttttgcct gtcgaatacc atggattctc ggtgtaatcc    600
atctcacgat cagatgcacc gcatgtcgca tgcctagctc tctctaattt gtctagtagt    660
ttgtatacgg attaatattg ataaatcggt accgcaaaag ctaggtgtaa ataaacacta    720
gaaaattgga tgttccccta tcggcctgta ctcggctact cgttcttgtg atggcatgct    780
gtctcttctt ggtgtttggt gaacaacctt atgaaatttg ggcgcaaaga actcgccctc    840
aagggttgat cttatgccat cgtcatgata aacagtggag cacggacgat cctttacgtt    900
gtttttaaca aactttgtca gaaaactagc atcattaact tcttaatgac gatttcacaa    960
caaaaaaagg taacctcgct actaacataa caaaatactt gttgcttatt aattatatgt   1020
tttttaatct ttgatcaggg gacaacagtg gttgataacc tgttgaacag tgaggatgtc   1080
cactacatgc tcggggcctt gaggactctt ggtctctctg tcgaagcgga caaagctgcc   1140
aaaagagctg tagttgttgg ctgtggtgga aagttcccag ttgaggattc taaagaggaa   1200
gtgcagctct tcttggggaa tgctggaact gcaatgcggc cattgacagc agctgttact   1260
gctgctggtg gaaatgcaac gtatgttttcc tctctttctc tctacaatac ttgctggagt   1320
tagtatgaaa cccatgggta tgtctagtgg cttatggtgt attggttttt gaacttcagt   1380
tacgtgcttg atggagtacc aagaatgagg gagagaccca ttggcgactt ggttgtcgga   1440
ttgaagcagc ttggtgcaga tgttgattgt ttccttggca ctgactgccc acctgttcgt   1500
gtcaatggaa tcggagggct acctggtggc aaggttagct actaagggcc acatgttaca   1560
ttcttctgta aatggtacaa ctattgtcga gcttttgcat ttgtaaggaa agcattgatt   1620
gatctgaatt tgatgctaca ccacaaaata tcctacaaat ggtcatccct aactagcaaa   1680
caatgaagta atacttggca tgtgtttatc aaattaattt ccatcttctg gggcattgcc   1740
tgttttctag tctaatagca tttgttttta gcattaatta gctcttacaa ttgttatgtt   1800
ctacaggtca agctgtctgg ctccatcagc agtcagtact tgagtgcctt gctgatggct   1860
gctcctttgg ctcttgggga tgtggagatt gaaatcattg ataaattaat ctccattccc   1920
tacgtcgaaa tgacattgag attgatggag cgttttggtg tgaaagcaga gcattctgat   1980
agctgggaca gattctacat taagggaggt caaaaataca gtaagctct gtaatgtatt    2040 tcactacttt gatgccaatg tttcagtttt cagttttcca aacagtcgca tcaatatttg   2100
aatagatgca ctgtagaaaa aaaatcattg cagggaaaaa ctagtactga gtattttgac   2160
tgtaaattat tttaccagtc ggaatatagt cagtctattg gagtcaagag cgtgaaccga   2220
aatagccagt taattatccc attatacaga ggacaaccat gtatactatt gaaacttggt   2280
ttataagaga atctaggtag ctggactcgt agctgcttgg catggatacc ttcttatctt   2340
taggaaaaga cacttgattt ttttttttctg tggccctcta tgatgtgtga acctgcttct   2400
ctattgcttt agaaggatat atctatgtcg ttatgcaaca tgcttccctt agccatttgt   2460
```

| | |
|---|---|
| actgaaatca gtttcataag ttcgttagtg gttccctaaa cgaaaccttg ttttctttg | 2520 |
| caatcaacag gtcccctaaa aatgcctatg ttgaaggtga tgcctcaagc gcaagctatt | 2580 |
| tcttggctgg tgctgcaatt actggaggga ctgtgactgt ggaaggttgt ggcaccacca | 2640 |
| gtttgcaggt aaagatttct tggctggtgc tacaataact gcttttgtct ttttggtttc | 2700 |
| agcattgttc tcagagtcac taaataacat tatcatctgc aaatgtcaaa tagacatact | 2760 |
| taggtgaatt catgtaaccg tttccttaca aatttgctga aacctcaggg tgatgtgaag | 2820 |
| tttgctgagg tactggagat gatgggagcg aaggttacat ggaccgagac tagcgtaact | 2880 |
| gttactggcc caccgcggga gccatttggg aggaaacacc tcaaggcgat tgatgtcaac | 2940 |
| atgaacaaga tgcctgatgt cgccatgact cttgctgtgg ttgccctctt tgccgatggc | 3000 |
| ccgacagcca tcagagacgg taaaacattc tcagccctac aaccatgcct cttctacatc | 3060 |
| actacttgac aagactaaaa actattggct cgttggcagt ggcttcctgg agagtaaagg | 3120 |
| agaccgagag gatggttgcg atccggacgg agctaaccaa ggtaaggcta catacttcac | 3180 |
| atgtctcacg tcgtctttcc atagctcgct gcctcttagc ggcttgcctg cggtcgctcc | 3240 |
| atcctcggtt gctgtctgtg ttttccacag ctgggagcat ctgttgagga agggccggac | 3300 |
| tactgcatca tcacgccgcc ggagaagctg aacgtgacgg cgatcgacac gtacgacgac | 3360 |
| cacaggatgg ccatggcctt ctcccttgcc gcctgtgccg aggtccccgt gaccatccgg | 3420 |
| gaccctgggt gcacccggaa gaccttcccc gactacttcg atgtgctgag cactttcgtc | 3480 |
| aagaattaat aaagcgtgcg atactaccac gcagcttgat tgaagtgata ggcttgtgct | 3540 |
| gaggaaatac atttctttg ttctgttttt tctctttcac gggattaagt tttgagtctg | 3600 |
| taacgttagt tgtttgtagc aagtttctat ttcggatctt aagtttgtgc actgtaagcc | 3660 |
| aaatttcatt tcaagagtgg ttcgttggaa taataagaat aataaattac gtttcagtgg | 3720 |
| ctgtcaagcc tgctgctacg ttttaggaga tggcattaga cattcatcat caacaacaat | 3780 |
| aaaacctttt agcctcaaac aataatagtg aagttatttt ttagtcctaa acaagttgca | 3840 |
| ttaggatata gttaaaacac aaaagaagct aaagttaggg tttagacatg tggatattgt | 3900 |
| tttccat | 3907 |

<210> SEQ ID NO 317
<211> LENGTH: 2149
<212> TYPE: DNA
<213> ORGANISM: Zea mays

<400> SEQUENCE: 317

| | |
|---|---|
| acctacttcc ccctcgcccc tctcatggtc tctctcgcgc ccagatctgc tactagacgg | 60 |
| caccgctgca gcgcgtcgtg tcgcgggggt tggtggcagg cagcgagagc ttgccgttcc | 120 |
| tctctctcag ttgtcaggtc ctaggctcac ctcaccggct cccagcccgc ttctatttct | 180 |
| tcctccccga ccccgtgcag gtggcagtcc agtccacgcc accaaccgcg aggcgaacca | 240 |
| aaccaaccca ctctcccaa ccccgcgcgc ccaggccgcc cgccctacca accatcggcg | 300 |
| tcggcaatgg cggccatggc gaccaaggcc gccgcgggca ccgtgtcgct ggacctcgcc | 360 |
| gcgccgccgg cggcggcagc ggcggcggcg gtgcaggcgg gtgccgagga gatcgtgctg | 420 |
| cagcccatca aggagatctc cggcaccgtc aagctgccgg ggtccaagtc gctttccaac | 480 |
| cggatcctcc tgctcgccgc cctgtccgag gggacaacag tggttgataa cctgttgaac | 540 |
| agtgaggatg tccactacat gctcgggcc ttgaggactc ttggtctctc tgtcgaagcg | 600 |
| gacaaagctg ccaaaagagc tgtagttgtt ggctgtggtg gaaagttccc agttgaggat | 660 |

```
tctaaagagg aagtgcagct cttcttgggg aatgctggaa ctgcaatgcg gccattgaca    720
gcagctgtta ctgctgctgg tggaaatgca acttacgtgc ttgatggagt accaagaatg    780
agggagagac ccattggcga cttggttgtc ggattgaagc agcttggtgc agatgttgat    840
tgtttccttg gcactgactg cccacctgtt cgtgtcaatg aatcggagg ctacctggt     900 ggcaaggtca agctgtctgg ctccatcagc agtcagtact tgagtgcctt gctgatggct    960
gctcctttgg ctcttgggga tgtggagatt gaaatcattg ataaattaat ctccattccc   1020
tacgtcgaaa tgacattgag attgatggag cgttttggtg tgaaagcaga gcattctgat   1080
agctgggaca gattctacat taagggaggt caaaaataca agtcccctaa aaatgcctat   1140
gttgaaggtg atgcctcaag cgcaagctat ttcttggctg gtgctgcaat tactggaggg   1200
actgtgactg tggaaggttg tggcaccacc agtttgcagg gtgatgtgaa gtttgctgag   1260
gtactggaga tgatgggagc gaaggttaca tggaccgaga ctagcgtaac tgttactggc   1320
ccaccgcggg agccatttgg gaggaaacac ctcaaggcga ttgatgtcaa catgaacaag   1380
atgcctgatg tcgccatgac tcttgctgtg gttgccctct tgccgatgg cccgacagcc   1440 atcagagacg tggcttcctg gagagtaaag gagaccgaga ggatggttgc gatccggacg   1500
gagctaacca agctgggagc atctgttgag gaagggccgg actactgcat catcacgccg   1560
ccggagaagc tgaacgtgac ggcgatcgac acgtacgacg accacaggat ggccatggcc   1620
ttctcccttg ccgcctgtgc cgaggtcccc gtgaccatcc gggaccctgg gtgcacccgg   1680
aagaccttcc ccgactactt cgatgtgctg agcactttcg tcaagaatta ataaagcgtg   1740
cgatactacc acgcagcttg attgaagtga taggcttgtg ctgaggaaat acatttcttt   1800
tgttctgttt tttctctttc acgggattaa gttttgagtc tgtaacgtta gttgtttgta   1860
gcaagtttct atttcggatc ttaagtttgt gcactgtaag ccaaatttca tttcaagagt   1920
ggttcgttgg aataataaga ataataaatt acgtttcagt ggctgtcaag cctgctgcta   1980
cgttttagga gatggcatta gacattcatc atcaacaaca ataaaacctt ttagcctcaa   2040
acaataatag tgaagttatt ttttagtcct aaacaagttg cattaggata tagttaaaac   2100
acaaaagaag ctaaagttag ggtttagaca tgtggatatt gttttccat               2149

<210> SEQ ID NO 318
<211> LENGTH: 240
<212> TYPE: DNA
<213> ORGANISM: Zea mays

<400> SEQUENCE: 318
tacttgagtg ccttgctgat ggctgctcct ttggctcttg gggatgtgga gattgaaatc     60
attgataaat taatctccat tccgtacgtc gaaatgacat tgagattgat ggagcgtttt    120
ggtgtgaaag cagagcattc tgatagctgg acagattct acattaaggg aggtcaaaaa    180
tacaagtccc ctaaaaatgc ctatgttgaa ggtgatgcct caagcgcaag ctatttcttg    240

<210> SEQ ID NO 319
<211> LENGTH: 297
<212> TYPE: DNA
<213> ORGANISM: Nicotiana benthamiana

<400> SEQUENCE: 319
gctgtatcat atcttcttct ttagaacact aataaattaa acttcgagat aatgatttct     60
gacaagagta taaacaagtg catctatgaa gatttgaggt tgtccaaaaa agtgacaatt    120
```

```
ttgggttcct ataaactgta tttacattat tgttatttgc aactataaaa attttagatt      180
atttccaagc tcagtttctt caacttaaat gaaggtagca cttgaatttc atcagcctct      240
atgacccagt aacccatgtg ggagatggga gcaaagtggt caaactttag aaggaat         297

<210> SEQ ID NO 320
<211> LENGTH: 269
<212> TYPE: DNA
<213> ORGANISM: Nicotiana benthamiana

<400> SEQUENCE: 320
gtatgaactt tcagaatatt ataccggatc aatatattat gctgaaatat ttttcggact       60
ttaaataatt tctttattta aatttatttt tatacaaaaa taactaaatt tcaattactt      120
ttaaaattat gattattttt caattaccac ttatacatcc tgctattttg aatttcaccc      180
gaaagaacta ctactatacg tggatcctca atgacccagt aacccaagtg ggagatgtgt      240
gcaaagtggt caaatcttag aaggaatga                                        269
```